US008956844B2

(12) United States Patent
Agard et al.

(10) Patent No.: US 8,956,844 B2
(45) Date of Patent: Feb. 17, 2015

(54) FUNGAL XYLANASES AND XYLOSIDASES

(71) Applicant: Codexis, Inc., Redwood City, CA (US)

(72) Inventors: Nicholas John Agard, San Francisco, CA (US); David Elgart, San Mateo, CA (US); Jie Yang, Foster City, CA (US); Goutami Banerjee, Redwood City, CA (US); Jeanne Bonomo Benoit, Menlo Park, CA (US); Dipnath Baidyaroy, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 13/914,475

(22) Filed: Jun. 10, 2013

(65) Prior Publication Data

US 2014/0017733 A1 Jan. 16, 2014

Related U.S. Application Data

(60) Provisional application No. 61/774,695, filed on Mar. 8, 2013, provisional application No. 61/774,706, filed on Mar. 8, 2013, provisional application No. 61/673,358, filed on Jul. 19, 2012, provisional application No. 61/658,166, filed on Jun. 11, 2012.

(51) Int. Cl.
C12N 1/00 (2006.01)
C12N 9/24 (2006.01)
C07H 21/04 (2006.01)
C12P 19/14 (2006.01)

(52) U.S. Cl.
CPC ............... *C12N 9/2482* (2013.01); *C12P 19/14* (2013.01)
USPC . 435/200; 435/209; 435/254.11; 435/254.21; 435/254.3; 435/254.6; 536/23.1; 536/23.2

(58) Field of Classification Search
None
See application file for complete search history.

(56) References Cited

U.S. PATENT DOCUMENTS

| | | |
|---|---|---|
| 3,990,944 A | 11/1976 | Gauss et al. |
| 3,990,945 A | 11/1976 | Huff et al. |
| 4,356,196 A | 10/1982 | Hultquist |
| 4,461,648 A | 7/1984 | Foody |
| 4,486,553 A | 12/1984 | Wesch |
| 4,556,430 A | 12/1985 | Converse et al. |
| 4,600,590 A | 7/1986 | Dale |
| 5,037,663 A | 8/1991 | Dale |
| 5,171,592 A | 12/1992 | Holtzapple et al. |
| 5,605,793 A | 2/1997 | Stemmer |
| 5,811,238 A | 9/1998 | Stemmer et al. |
| 5,811,381 A | 9/1998 | Emalfarb et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 5,939,544 A | 8/1999 | Karstens et al. |
| 6,015,707 A | 1/2000 | Emalfarb et al. |
| 6,090,595 A | 7/2000 | Foody et al. |
| 6,096,548 A | 8/2000 | Stemmer |
| 6,106,888 A | 8/2000 | Dale et al. |
| 6,117,679 A | 9/2000 | Stemmer |
| 6,132,970 A | 10/2000 | Stemmer |
| 6,165,793 A | 12/2000 | Stemmer |
| 6,176,176 B1 | 1/2001 | Dale et al. |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |

(Continued)

FOREIGN PATENT DOCUMENTS

| | | |
|---|---|---|
| EP | 0137280 B1 | 3/1992 |
| WO | 95/22625 A1 | 8/1995 |

(Continued)

OTHER PUBLICATIONS

Berka et al. NCBI, Accession No. 016477 (Jan. 4, 2012).*
Loginova et al. (Abstract) Microbiologiia (Jul.-Aug. 1983) vol. 52 (4) pp. 605-608.*
Altschul, S.F., et al., "Gapped BLAST and PSI-BLAST: a new generation af protein database search programs,"Nucleic Acids Res., 25(17):3389-3402 [1997].
Berka, et al., "Comparative genomic analysis of the thermophilic biomass-degrading fungi *Myceliophthora thermophila* and *Thielavia terrestris*," Nat. Biotechnol., 29:922-927 [2011].
Blaiseau, P-L., et al., "Prmary stucue of a chitinase-encoding gene (chi1) fom the filamentous fungus *Aphanociadium album*: similarity to bacterial chitinases," Gene, 120(2):243-248 [1992].

(Continued)

*Primary Examiner* — Nashaat Nashed
(74) *Attorney, Agent, or Firm* — Codexis, Inc.

(57) ABSTRACT

The present invention provides fungal xylanase and/or xylosidase enzymes suitable for use in saccharification reactions. The present invention provides xylanase and xylosidase enzymes suitable for use in saccharification reactions. The present application further provides genetically modified fungal organisms that produce xylanase(s) and/or xylosidase(s), as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures. In some embodiments, the xylanase and xylosidase enzyme(s) are *M. thermophila* enzymes.

14 Claims, 5 Drawing Sheets

(56) References Cited

U.S. PATENT DOCUMENTS

| | | | |
|---|---|---|---|
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,086 B1 | 6/2003 | Emalfrab et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,399,627 B2 | 7/2008 | Emalfarb et al. |
| 7,419,809 B2 | 9/2008 | Foody et al. |
| 7,421,347 B2 | 9/2008 | Selfinov et al. |
| 7,430,477 B2 | 9/2008 | Selfinov et al. |
| 7,465,791 B1 | 12/2008 | Hallberg et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,754,457 B2 | 7/2010 | Foody et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 2007/0031953 A1 | 2/2007 | Dunson, Jr. et al. |
| 2007/0238155 A1 | 10/2007 | Gusakov et al. |
| 2008/0057541 A1 | 3/2008 | Hill et al. |
| 2008/0104724 A1 | 5/2008 | Sticklen et al. |
| 2008/0194005 A1 | 8/2008 | Emalfarb et al. |
| 2009/0061484 A1 | 3/2009 | Scott et al. |
| 2009/0099079 A1 | 4/2009 | Emalfarb et al. |
| 2009/0209009 A1 | 8/2009 | Tolan et al. |
| 2010/0267089 A1 | 10/2010 | Yang et al. |
| 2011/0287515 A1 | 11/2011 | Asenjo et al. |

FOREIGN PATENT DOCUMENTS

| | | |
|---|---|---|
| WO | 96/00787 A1 | 1/1996 |
| WO | 97/00078 | 1/1997 |
| WO | 97/35966 A1 | 10/1997 |
| WO | 98/15633 A1 | 4/1998 |
| WO | 98/27230 A1 | 6/1998 |
| WO | 00/42651 A1 | 7/2000 |
| WO | 01/75767 A2 | 10/2001 |
| WO | 2008/073914 A2 | 6/2008 |
| WO | 2009/045651 A2 | 4/2009 |
| WO | 2009/152336 A1 | 12/2009 |
| WO | 2010/022511 A1 | 3/2010 |
| WO | 2010/107303 A2 | 9/2010 |
| WO | 2012/027374 A2 | 3/2012 |

OTHER PUBLICATIONS

Boel, E., et al., "Two different types of intervening sequences in the glucoamylase gene from *Aspergillus niger*," EMBO J., 3(7):1581-1585 [1984].

Botstein, D., et al., "Strategies and Applications ofin Vitro Mutagenesis," Science, 229(4719):1193-1201 [1985].

Brigham, J.S., et al., "Hemicellulases: Diversity and Applications," in Handbook on Bioethanol (C. Wyman ed.) pp. 119-141, Taylor and Francis, Washington DC, (1995).

Carter, P., "Site-directed mutagenesis," Biochem. J., 237:1-7 [1986].

Case, M.E, et al., "Efficient transformation of *Neurospora crassa* by utilizing hybrid plasmid DNA," Proc. Natl. Acad. Sci. USA, 76(10):5259-5263 [1979].

Chaveroche, M., et al., "A rapid method for efficient gene replacement in the filamentous fungus *Aspergillus nidulans*," Nucl. Acids Res., 28:22 e97 [2000].

Cho, Y., et al., "A high throughput targeted gene disruption method for *Alternaria brassicicola* functional genomics using linear minimal element (LME) constructs," Mol Plant Microbe Interact,19(1):7-15 [2006].

Christians, F.C., et al., "Directed evolution of thymidine kinase for AZT phosphorylation using DNA family shuffling," Nat. Biotechnol., 17:259-264 [1999].

Combier, J.-P., et al., "*Agrobacterium tumefaciens*-mediated transformation as a tool for insertional mutagenesis in the symbiotic ectomycorrhizal fungus *Hebeloma cylindrosporum*," FEMS Microbiol Lett., 220:141-8 [2003].

Crameri A., et al., "DNA shuffling of a family of genes from diverse species accelerates directed evolution," Nature, 391:288-291 [1998].

Crameri, A., et al., "Improved green fluorescent protein by molecular evolution using DNA shuffling," Nat. Biotechnol., 14:315-319 [1996].

Crameri, A., et al., "Molecular evolution of an arsenate detoxification pathway by DNA shuffling," Nat. Biotechnol., 15:436-438 [1997 ].

Dale, S.J., et al., "Oligonucleotide-Directed Random Mutagenesis Using the Phosphorothioate Method," Meth. Mol. Biol., 57:369-74 [1996].

Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.

Drissen, R.E.T., et al., "Modelling ethanol production from cellulose: separate hydrolysis and fermentation versus simultaneous saccharification and fermentation," Biocat. Biotransform., 27:27-35 [2009].

Firon, A., et al., "Identification of Essential Genes in the Human Fungal Pathogen *Aspergillus fumigatus* by Transposon Mutagenesis," Eukaryot. Cell, 2(2):247-55 [2003].

Foreman, P.K., et al., "Transcriptional Regulation of Biomass-degrading Enzymes in the Filamentous Fungus *Trichoderma reesei*," J. Biol. Chem., 278(34):31988-31997 [2003].

Garg. A.K., "An addition to the genus *Chrysosporium corda*," Mycopathologia, 30(3-4):221-224 [1966].

(56) References Cited

OTHER PUBLICATIONS

Glenn, J.K., et al., "Mn(II) Oxidtion Is the Principal Functon of the Extrelular Mn-Peoxidase from Phanerochaete chrysosporium'," Arch. Biochem. Biophys., 251(2):688-696 [1986].

Guo, Z., et al., "3'-End-Forming Signals of Yeast mRNA," Mol. Cell. Biol., 15(11):5983-5990 [1995].

Harris, P.V., et al., "Stimulation of Lignocellulosic Biomass Hydrolysis by Proteins of Glycoside Hydrolase Family 61: Structure and Function of a Large, Enigmatic Family," Biochem., 49:3305-3316 [2010].

Harvey, P.J., et al., "Veratryl alcohol as a mediaor and the role of radical cations in lignin biodegradation by *Phanerochaete chrysosporium*," FEBS Lett., 195(1,2):242-246 [1986].

Henikoff, S., et al. "Amino acid substitution matrices from protein blocks," Proc. Natl. Acad. Sci. USA, 89:10915-10919 [1992].

Hong, J., et al., "Cloning and functional expression of thermostable beta-glucosidase gene from *Thermoascus aurantiacus*," Appl. Microbiol. Biotechnol, 73:1331-1339 [2007].

Johnstone, I.L., et al., "Cloning an *Aspergillus nidulans* developmental gene by transformation," EMBO J.,4 (5):1307-1311 [1985].

Kelly, J.M., et al., "Tansformation of *Aspergillus niger* by the amdS gene of *Aspergillus nidulans*," EMBO J., 4 (2):475-479 [1985].

Kinsey, J.A., et al., "Transformation of *Neurospora crassa* with the Cloned am (Glutamate Dehydrogenase) Gene," Mol. Cell. Biol., 4:117-122 [1984].

Kramer, B., et al., "Dfferent base/base mismatches are corrected with different efficiencies by the methyl-directed, DNA mismatch-repair system of *E. coli*," Cell, 38:897-887 [1984].

Limon, C., et al., "Primary structure and expession pattern of the 3-kDa chitinase gene from the nucoparasitic fungus *Trichocherma harzianum*," Curr. Genet., 28:478-83 [1995].

Ling, M.M., et al., "Approaches to DNA Mutagenesis: An Overview," Anal. Biochem., 254(2):157-78 [1997].

Maruyama, J., "Multiple gene disruptions by marker recycling with highly efficient gene-targeting background (delta-ligD) in *Aspergillus oryzae*," Biotechnol Lett., 30:1811-1817 [2008].

Minshull, J., et al., "Protein evolution by molecular breeding," Curr. Op. Chem. Biol., 3:284-290 [1999].

Nunberg, J.H., et al., "Molecular Cloning and Characterization of the Glucoamylase Gene of *Aspergillus awamori*," Mol. Cell Biol., 4(11):2306-2315 [1984].

Parry, N.J., et al., "Biochemical characterization and mechanism of action of a thermostable beta-glucosidase purified from *Thermoascus aurantiacus*," Biochem. J., 353:117-127 [2001].

Porath, J., "Immobilized metal ion affinity chromatography," Protein Expression and Purification, 3:263-281 [1992].

Romanos, M.A., et al., "Foreign gene expression in yeast: a review," Yeast 8:423-488 [1992].

Rothstein, R.J., "One-step gene disruption in Yeast," Meth. Enzymol., 101:202-211 [1983].

Rotsaert, F.A.J., et al., "Site-directed mutagenesis of the heme axial ligands in the hemoflavoenzyme cellobiose dehydrogenase," Arch. Biochem. Biophys., 390(2):206-14 [2001].

Saloheimo, M., et al., "Swollenin, a *Trichoderma reesei* protein with sequence similarity to the plant expansins, exhibits disruption activity on cellulosic materials," Eur. J. Biochem., 269:4202-4211 [2002].

Sheir-Neiss, G., et al., "Characterization of the secreted cellulases of *Trichoderma reesei* wild type and mutants during controlled fermentations," Appl. Microbiol. Biotechnol., 20:46-53 [1984].

Simonen, M., et al., "Protein Secretion in *Bacillus* Species," Microbiological Reviews, 57:109-137 [1993].

Smith, M., "In Vitro Mutagenesis," Ann. Rev. Genet., 19:423-462 [1985].

Stemmer, W.P.C., "DNA shuffling by random fragmentation and reassembly: In vitro recombination for molecular evolution," Proc. Nat. Acad. Sci. USA, 91:10747-10751 [1994].

Stemmer. W.P.C., "Rapid evolution of a protein in vitro by DNA shuffling," Nature, 370:389-391 [1994].

Takahashi, T., et al., "Efficient gene disruption in the koji-mold *Aspergillus sojae* using a novel variation of the positive-negative method," Mol. Gen. Genom., 272: 344-352 [2004].

Taussig, R., et al., "Nucleotide sequence of the yeast SUC2 gene for invertase," Nucl. Acids Res., 11(6):1943-54 [1983].

Tilburn, J., et al., "Transformation by integration in *Aspergillus nidulans*," Gene 26:205-221 [1983].

Viikari, L., et al., "Thermostable enzymes in lignocellulose hyrolysis," Adv. Biochem. Eng. Biotechnol., 108:121-45 [2007]

Weil, J., et al., "Pretreatment of Yellow Poplar Sawdust by Pressure Cooking in Water," Appl. Biochem. Biotechnol., 68(1-2): 21-40 [1997].

Wells, J.A., et al., "Cassette muatagenesis: an efficient method for generation of multiple mutations at defined sites" Gene, 34:315-323 [1985].

Wilson, I.A., et al., "The structure of antigenic determinant in a protein," Cell, 37:767-778 [1984].

Yelton, M.M., et al., "Transformation of *Asperillus nidulans* by using a trpC plasmid" Proc. Natl. Acad. Sci. USA, 81:1480-1474 [1984].

You, B., et al., "Gene-specife disruption in the fillamentous fungus *Cercospora nicotianae* using a split-marker approach," Arch Micriobiol., 191:615-622 [2009].

Zhang, J.-H., et al., "Directed evolution of a fucosidase fom a galactosidase by DNA shuffling and screening" Proc. Nat. Acad. Sci. U.S.A., ,94:4504-4509 [1997].

Genbank Accession No. CP003007 dated Oct. 26, 2011.

SwissProt Accession No. P00724 dated Feb. 22, 2012.

UniProtKT/TrEMBL Accession No. G2QKP9 dated Nov. 16, 2011.

\* cited by examiner

FUNGAL XYLANASES AND XYLOSIDASES

CROSS-REFERENCE TO RELATED APPLICATIONS

This application claims benefit of priority to U.S. provisional application No. 61/774,695, filed Mar. 8, 2013; U.S. provisional application No. 61/774,706 filed Mar. 8, 2103; U.S. provisional application No. 61/673,358, filed Jul. 19, 2012; and U.S. provisional application No. 61/658,166, filed Jun. 11, 2012, the entire contents of each of which are incorporated by reference for all purposes.

REFERENCE TO A SEQUENCE LISTING APPENDIX SUBMITTED AS AN ASCII TEXT FILE

The Sequence Listing written in file 90834-877292_ST25.TXT, created on Jun. 5, 2013, 211,593 bytes, machine format IBM-PC, MS-Windows operating system, is hereby incorporated by reference.

FIELD OF THE INVENTION

The present invention provides xylanase and xylosidase enzymes suitable for use in saccharification reactions. The present application further provides genetically modified fungal organisms that produce xylanase(s) and/or xylosidase(s), as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures.

BACKGROUND

Interest has arisen in fermentation of carbohydrate-rich biomass to provide alternatives to petrochemical sources for fuels and organic chemical precursors. There is great interest in using lignocellulosic feedstocks where the plant cellulose is broken down to sugars and subsequently converted to desired end products, such as organic chemical precursors. Lignocellulosic biomass is primarily composed of cellulose, hemicelluloses, and lignin. Cellulose and hemicellulose can be hydrolyzed in a saccharification process to sugars that can be subsequently converted to various products via fermentation. The major fermentable sugars obtained from lignocelluloses are glucose and xylose. For economical product yields, a process that can effectively convert all the major sugars present in cellulosic feedstock would be highly desirable.

SUMMARY OF THE INVENTION

The present invention provides xylanase and xylosidase enzymes suitable for use in saccharification reactions. The present application further provides genetically modified fungal organisms that produce xylanases and/or xylosidases, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures. The present application further provides genetically modified fungal organisms that produce xylanases and/or xylosidases, as well as enzyme mixtures exhibiting enhanced hydrolysis of cellulosic material to fermentable sugars, enzyme mixtures produced by the geneti-cally modified fungal organisms, and methods for producing fermentable sugars from cellulose using such enzyme mixtures. In some embodiments, the xylanase and/or xylosidase is obtained from *Myceliophthora thermophila*.

The present invention provides an isolated xylanase and/or beta-xylosidase or biologically active xylanase and/or beta-xylosidase fragment comprising (a) an amino acid sequence comprising at least about 70%, at least about 71%, at least about 72%, at least about 73%, at least about 74%, at least about 75%, at least about 76%, at least about 77%, at least about 78%, at least about 79%, at least about 80%, at least about 81%, at least 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to a SEQ ID NO:2, 3, 5, 6, 8 and/or 9. The present invention further provides an isolated xylanase and/or beta-xylosidase or biologically active xylanase and/or beta-xylosidase fragment comprising (a) an amino acid sequence comprising at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a SEQ ID NO:2, 3, 5, 6, 8 and/or 9. In some embodiments, the isolated xylanase and/or beta-xylosidase or biologically active xylanase and/or beta-xylosidase fragment comprises at least one sequence selected from SEQ ID NO:2, 3, 5, 6, 8 and/or 9. In some embodiments, the isolated xylanase and/or beta-xylosidase or biologically active xylanase and/or beta-xylosidase fragment is a *Myceliophthora thermophila* xylanase and/or beta-xylosidase, and/or biologically active xylanase and/or beta-xylosidase fragment.

The present invention also provides enzyme compositions comprising the xylanase and/or beta-xylosidases provided herein, as well as biologically active xylanase and/or beta-xylosidase fragment(s). In some embodiments, the enzyme compositions further comprise at least one additional enzyme. In some further embodiments, the enzyme compositions comprise one or more enzymes selected from cellulases, hemicellulases, xylanases, amylases, glucoamylases, proteases, esterases, xylanases, beta-xylosidases, arabinofuranosidases, alpha-glucuronidases, acetylxylan esterases, feruloyl esterases, alpha-glucuronyl esterases, GH61 enzymes, and lipases. In some additional embodiments, the enzyme compositions further comprise one or more enzyme(s) selected from endoglucanases (EG), β-glucosidases (BGL), Type 1 cellobiohydrolases (CBH1), and/or Type 2 cellobiohydrolases (CBH2). In some embodiments, the EG is EG2, while in some additional embodiments, the EG is EG1 (e.g., EG1b). In some embodiments, the CBH1 is CBH1a, while in some additional embodiments, the CBH1 is CBH1b. In some further embodiments, the CBH2 is CBH2a, while in some additional embodiments, the CBH2 is CBH2b.

The present invention also provides an isolated polynucleotide comprising a nucleic acid sequence encoding the xylanase and/or beta-xylosidases provided herein, and/or a polynucleotide that hybridizes under stringent hybridization conditions to the polynucleotide and/or a complement of a polynucleotide that encodes a polypeptide comprising the amino acid sequence of the xylanase and/or beta-xylosidases and/or biologically active xylanase and/or beta-xylosidase fragments provided herein. In some embodiments, the polynucleotide comprises a sequence that has least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identity to SEQ ID NOS:1, 4 and/or 7. In some embodiments, the polynucleotide comprises a sequence that has least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to SEQ ID NOS:1, 4 and/or 7. In some additional embodiments, the polynucleotide comprises at least one sequence selected from SEQ ID NOS:1, 4, and/or 7.

The present invention also provides a recombinant nucleic acid construct comprising at least one polynucleotide sequence, wherein the polynucleotide is selected from: a polynucleotide that encodes a polypeptide comprising an amino acid sequence comprising at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NOS:2, 3, 5, 6, 8 and/or 9; a polynucleotide that hybridizes under stringent hybridization conditions to at least a fragment of a polynucleotide that encodes a polypeptide comprising the amino acid sequence of SEQ ID NOS:2, 3, 5, 6, 8, and/or 9; and/or a polynucleotide that hybridizes under stringent hybridization conditions to the complement of at least a fragment of a polynucleotide that encodes a polypeptide comprising the amino acid sequence of SEQ ID NOS:2, 3, 5, 6, 8, and/or 9. In some embodiments, the recombinant nucleic acid construct comprises at least one sequence selected from SEQ ID NOS:2, 3, 5, 6, 8, and/or 9.

In some embodiments, the present invention further provides a recombinant nucleic acid construct comprising at least one polynucleotide sequence, wherein the polynucleotide is selected from: a polynucleotide that encodes a polypeptide comprising an amino acid sequence comprising at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identity to SEQ ID NOS:2, 3, 5, 6, 8 and/or 9; a polynucleotide that hybridizes under stringent hybridization conditions to at least a fragment of a polynucleotide that encodes a polypeptide comprising the amino acid sequence of SEQ ID NOS:2, 3, 5, 6, 8, and/or 9; and/or a polynucleotide that hybridizes under stringent hybridization conditions to the complement of at least a fragment of a polynucleotide that encodes a polypeptide comprising the amino acid sequence of SEQ ID NOS:2, 3, 5, 6, 8, and/or 9. In some embodiments, the polypeptide sequence comprises SEQ ID NOS:2, 3, 5, 6, 8, and/or 9.

In some embodiments, the polynucleotide sequence is at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identical to SEQ ID NOS:1, 4, and/or 7. In some additional embodiments, the polynucleotide sequence is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NOS:1, 4, and/or 7. In some further embodiments, the polynucleotide sequence comprises SEQ ID NOS:1, 4, and/or 7. In some embodiments, the polynucleotide sequence is operably linked to a promoter. In some further embodiments, the promoter is a heterologous promoter. In some additional embodiments, the nucleic acid sequence is operably linked to at least one additional regulatory sequence.

The present invention also provides recombinant host cells that express at least one polynucleotide sequence encoding at least one xylanase and/or beta-xylosidase and/or at least one biologically active xylanase and/or beta-xylosidase fragment. In some embodiments, the host cell comprises at least one nucleic acid construct as provided herein. In some embodiments, the host cell comprises at least one polypeptide sequence set forth in SEQ ID NOS:2, 3, 5, 6, 8, and/or 9. In some additional embodiments, the host cell comprises at least one polynucleotide sequence set forth in SEQ ID NOS:1, 4, and/or 7. In some further embodiments, at least one xylanase and/or beta-xylosidase and/or at least one biologically active xylanase and/or beta-xylosidase is produced by said cell. In some additional embodiments, the produced xylanase and/or beta-xylosidase is secreted from the host cell. In some further embodiments, at least one xylanase and/or beta-xylosidase and/or at least one biologically active xylanase and/or beta-xylosidase is produced by said cell. In some additional embodiments, the produced xylanase and/or beta-xylosidase is secreted from the host cell. In some embodiments, the host cell further produces one or more enzymes selected from cellulases, hemicellulases, xylanases, amylases, glucoamylases, proteases, esterases, xylanases, beta-xylosidases, arabinofuranosidases, alpha-glucuronidases, acetylxylan esterases, feruloyl esterases, alpha-glucuronyl esterases, GH61 enzymes, and lipases. In some additional embodiments, the host cells further comprise one or more enzyme(s) selected from endoglucanases (EG), β-glucosidases (BGL), Type 1 cellobiohydrolases (CBH1), and/or Type 2 cellobiohydrolases (CBH2). In some embodiments, the EG is EG2, while in some additional embodiments, the EG is EG1 (e.g., EG1b). In some additional embodiments, the CBH1 is CBH1a, while in some additional embodiments, the CBH1 is CBH1b. In some further embodiments, the CBH2 is CBH2a, while in some additional embodiments, the CBH2 is CBH2b. In some further embodiments, the host cell produces at least two recombinant cellulases, while in some other embodiments, the host cell produces at least three, at least four or at least five recombinant cellulases. In some additional embodiments, the cell is a prokaryotic or eukaryotic cell. In some embodiments, the host cell is a yeast cell or filamentous fungal cell. In some further embodiments, the filamentous fungal cell is a *Myceliophthora*, a *Thielavia*, a *Trichoderma*, or an *Aspergillus* cell. In some alternative embodiments, the host cell is selected from *Saccharomyces* and *Myceliophthora*. In some embodiments, the filamentous fungal cell is a *Myceliophthora thermophila* cell. In some additional embodiments, the host cell is a yeast cell. In some embodiments, the yeast cell is *Saccharomyces cerevisiae*.

The present invention also provides methods for producing at least one fermentable sugar from a feedstock, comprising contacting the feedstock with at least one enzyme composition provided herein, under culture conditions whereby fermentable sugars are produced. In some embodiments, the enzyme compositions of the methods further comprise at least one additional enzyme. In some further embodiments of the methods, the enzyme compositions comprise one or more enzymes selected from cellulases, hemicellulases, xylanases, amylases, glucoamylases, proteases, esterases, xylanases, beta-xylosidases, arabinofuranosidases, alpha-glucuronidases, acetylxylan esterases, feruloyl esterases, alpha-glucuronyl esterases, GH61 enzymes, and lipases. In some additional embodiments of the methods, the enzyme compositions further comprise one or more enzyme(s) selected from endoglucanases (EG), β-glucosidases (BGL), Type 1 cellobiohydrolases (CBH1), and/or Type 2 cellobiohydrolases (CBH2). In some embodiments of the methods, the EG is EG2, while in some additional embodiments, the EG is EG1 (e.g., EG1b). In some embodiments of the methods, the CBH1 is CBH1a, while in some additional embodiments, the CBH1 is CBH1b. In some further embodiments of the methods, the CBH2 is CBH2a, while in some additional embodiments, the CBH2 is CBH2b. In some embodiments, the methods further comprise pretreating the feedstock prior to contacting the enzyme composition and feedstock. In some embodiments of the methods, the feedstock comprises wheat grass, wheat straw, barley straw, sorghum, rice grass, sugarcane, sugar beet, bagasse, tops, leaves, seed pods, fruit, switchgrass, corn stover, corn fiber, grains, and/or a combination thereof. In some embodiments, the fermentable sugar comprises glucose and/or xylose. In some additional embodiments, the methods further comprise recovering at least one fermentable sugar. In some further embodiments, the methods further comprise contacting at least one fermentable sugar with a microorganism under conditions such that said microorganism produces at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some embodiments, the fermentation product is an alcohol selected from ethanol and butanol. In some further embodiments of the methods, the alcohol is ethanol. In some additional embodiments, the feedstock is a cellulosic and/or lignocellulosic feedstock.

The present invention also provides methods of producing an end product from a feedstock, comprising: contacting the feedstock with a composition according to any of Claims 3 to 6, under conditions whereby at least one fermentable sugar is produced from the substrate; and contacting the fermentable sugar with a microorganism under conditions such that the microorganism uses the fermentable sugar to produce an end-product. In some embodiments, the methods comprise simultaneous saccharification and fermentation reactions (SSF). In some alternative embodiments, the methods comprise separate saccharification and fermentation reactions (SHF). In some embodiments, the feedstock is a cellulosic and/or lignocellulosic feedstock.

The present invention also provides methods of producing a fermentation end product from a feedstock, comprising: obtaining at least one fermentable sugar produced according to at least one method provided herein; and contacting the fermentable sugar with a microorganism in a fermentation to produce at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some embodiments, the fermentation end product is at least one alcohol selected from ethanol and butanol. In some additional embodiments, the microorganism is a yeast. In some further embodiments, the yeast cell is *Saccharomyces cerevisiae*. In some further embodiments, the methods further comprise recovering the fermentation end product.

The present invention also provides recombinant organisms comprising a xylanase and/or beta-xylosidase and/or biologically active xylanase and/or beta-xylosidase fragment comprising (a) an amino acid sequence comprising at least about 70%, at least about 75%, at least about 80%, at least about 81%, at least 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to a SEQ ID NO:2, 3, 5, 6, 8 and/or 9. In some embodiments, the recombinant organisms comprise a xylanase and/or beta-xylosidase and/or biologically active xylanase and/or beta-xylosidase fragment comprising (a) an amino acid sequence comprising at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a SEQ ID NO:2, 3, 5, 6, 8 and/or 9.

The present invention further provides methods for producing at least one fermentable sugar from a feedstock, comprising contacting the feedstock with the recombinant organism and/or the recombinant host cell set forth herein, under culture conditions whereby fermentable sugars are produced. In some embodiments, the recombinant organism and/or recombinant host cell further comprises at least one enzyme selected from endoglucanases (EG), β-glucosidases (BGL), Type 1 cellobiohydrolases (CBH1), Type 2 cellobiohydrolases (CBH2), and GH61 enzymes. In some additional embodiments, at least one enzyme is a recombinant enzyme. In some additional embodiments, at least one enzyme is a heterologous enzyme. In some further embodiments, the methods further comprise pretreating the feedstock prior to contacting the feedstock with the recombinant organism. In some further embodiments, the feedstock comprises wheat grass, wheat straw, barley straw, sorghum, rice grass, sugarcane, sugar beet, bagasse, switchgrass, corn stover, corn fiber, grains, or a combination thereof. In some additional embodiments, the fermentable sugar comprises glucose and/or xylose. In some embodiments, the methods further comprise recovering at least one fermentable sugar. In some embodiments, the methods further comprise contacting at least one fermentable sugar with a microorganism under conditions such that the microorganism produces at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some embodiments, the fermentation product is an alcohol selected from ethanol and butanol. In some additional embodiments, the alcohol is ethanol. In some further embodiments, the feedstock is a cellulosic and/or lignocellulosic feedstock.

The present invention also provides methods of producing an end product from a feedstock, comprising: a) contacting the feedstock with a recombinant organism and/or recombinant host cell under conditions whereby at least one fermentable sugar is produced from the substrate; and b) contacting the fermentable sugar with a microorganism under conditions such that the microorganism uses the fermentable sugar to produce an end-product. In some embodiments, the recombinant organism and/or recombinant host cell further comprises at least one enzyme selected from endoglucanases (EG), β-glucosidases (BGL), Type 1 cellobiohydrolases (CBH1), and Type 2 cellobiohydrolases (CBH2). In some additional embodiments, at least one enzyme is a recombinant enzyme. In some further embodiments, at least one enzyme is a heterologous enzyme. In some embodiments, the methods comprise a simultaneous saccharification and fermentation reactions (SSF), while in some additional embodiments, the methods comprise separate saccharification and fermentation reactions (SHF). In some embodiments, the feedstock is a cellulosic and/or lignocellulosic feedstock.

The present invention also provides methods of producing a fermentation end product from a feedstock, comprising: a) obtaining at least one fermentable sugar produced according to any of the methods provided herein; and b) contacting the fermentable sugar with a microorganism in a fermentation to produce at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some additional embodiments, the fermentation end product is at least one alcohol selected from ethanol and butanol. In some embodiments, the microorganism is a yeast. In some embodiments, the methods further comprise recovering the fermentation end product.

The present invention also provides an isolated xylanase and/or xylosidase and/or biologically active xylanase and/or xylosidase fragment comprising (a) an amino acid sequence comprising at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, the isolated xylanase and/or xylosidase or biologically active xylanase and/or xylosidase fragment is a *Myceliophthora thermophila* xylanase and/or xylosidase. In some embodiments, the present invention also provides an isolated xylanase and/or xylosidase and/or biologically active xylanase and/or xylosidase fragment comprising (a) an amino acid sequence comprising at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, the isolated xylanase and/or xylosidase or biologically active xylanase and/or xylosidase fragment is a *Myceliophthora thermophila* xylanase and/or xylosidase.

The present invention also provides enzyme compositions comprising the xylanase and/or xylosidase and/or biologically active xylanase and/or xylosidase fragment(s). The present invention also provides enzyme compositions comprising the xylanase and/or xylosidases. In some additional embodiments, the enzyme compositions of Claim 3, further comprise: (i) at least one additional enzyme; wherein said at least one additional enzyme is selected from: (ii) one or more enzymes selected from cellulases, hemicellulases, xylanases, amylases, glucoamylases, proteases, esterases, and/or lipases; and/or (iii) one or more enzyme(s) selected from endoglucanases (EG), β-glucosidases (BGL), Type 1 cellobiohydrolases (CBH1), Type 2 cellobiohydrolases (CBH2), and/or GH61 enzymes.

The present invention also provides a recombinant fungal organism comprising at least one xylanase and/or xylosidase and/or biologically active xylanase and/or xylosidase fragment as provided herein. The present invention further provides a recombinant fungal organism comprising at least one polynucleotide comprising at least one nucleic acid sequence encoding the xylanase and/or xylosidase of provided herein, or a polynucleotide that hybridizes under stringent hybridization conditions to the polynucleotide and/or a complement of a polynucleotide that encodes a polypeptide comprising the amino acid sequence provided herein, optionally wherein said polynucleotide comprises a sequence that has least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to SEQ ID NO:1, 4, 7, 10, 12, 14, 17, 20, 23, 26, 29, 32, 35, 38, 41, 44, 47, 50, 53, 56, 58, 60, 62, and/or 64. In some embodiments, the present invention further provides a recombinant fungal organism comprising at least one polynucleotide comprising at least one nucleic acid sequence encoding the xylanase and/or xylosidase of provided herein, or a polynucleotide that hybridizes under stringent hybridization conditions to the polynucleotide and/or a complement of a polynucleotide that encodes a polypeptide comprising the amino acid sequence provided herein, optionally wherein said polynucleotide comprises a sequence that has least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identity to SEQ ID NO:1, 4, 7, 10, 12, 14, 17, 20, 23, 26, 29, 32, 35, 38, 41, 44, 47, 50, 53, 56, 58, 60, 62, and/or 64. In some additional embodiments, the present invention further provides a recombinant fungal organism comprising at least one polynucleotide comprising at least one nucleic acid sequence encoding the xylanase and/or xylosidase of provided herein, or a polynucleotide that hybridizes under stringent hybridization conditions to the polynucleotide and/or a complement of a polynucleotide that encodes a polypeptide comprising the amino acid sequence provided herein, optionally wherein said polynucleotide comprises SEQ ID NO:1, 4, 7, 10, 12, 14, 17, 20, 23, 26, 29, 32, 35, 38, 41, 44, 47, 50, 53, 56, 58, 60, 62, and/or 64.

The present invention also provides recombinant nucleic acid constructs comprising at least one polynucleotide sequence, wherein the polynucleotide is selected from: (a) a polynucleotide that encodes a polypeptide comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; (b) a polynucleotide that hybridizes under stringent hybridization conditions to at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; and/or (c) a polynucleotide that hybridizes under stringent hybridization conditions to the complement of at least a fragment of a polynucleotide that encodes a polypeptide comprising the amino acid sequence of SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, (i) the polynucleotide sequence is at least about 70%, at least about 75%, at least about 80%, at least about 85%, at least about 90%, at least about 91%, at least about 92%, at least 93%, at least 94%, at least 95%, at least 96%, at least 97%, at least 98%, at least 99%, or 100% identical to SEQ ID NO:1, 4, 7, 10, 12, 14, 17, 20, 23, 26, 29, 32, 35, 38, 41, 44, 47, 50, 53, 56, 58, 60, 62, and/or 64; (ii) the polynucleotide sequence is operably linked to a promoter, optionally wherein said promoter is a heterologous promoter; and/or (iii) the polynucleotide sequence is operably linked to at least one additional regulatory sequence. The present invention also provides recombinant nucleic acid constructs comprising at least one polynucleotide sequence, wherein the polynucleotide is selected from: (a) a polynucleotide that encodes a polypeptide comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; (b) a polynucleotide that hybridizes under stringent hybridization conditions to at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; and/or (c) a polynucleotide that hybridizes under stringent hybridization conditions to the complement of at least a fragment of a polynucleotide that encodes a polypeptide comprising the amino acid sequence of SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, (i) the polynucleotide sequence is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:1, 4, 7, 10, 12, 14, 17, 20, 23, 26, 29, 32, 35, 38, 41, 44, 47, 50, 53, 56, 58, 60, 62, and/or 64; (ii) the polynucleotide sequence is operably linked to a promoter, optionally wherein said promoter is a heterologous promoter; and/or (iii) the polynucleotide sequence is operably linked to at least one additional regulatory sequence.

The present invention further provides a recombinant host cell that expresses at least one polynucleotide sequence encoding at least one xylanase and/or xylosidase as provided herein. In some embodiments, the host cell comprises at least one nucleic acid construct as provided herein; (ii) said host cell comprises the polypeptide sequence set forth in SEQ ID NOS: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; (iii) said host cell comprises the polynucleotide sequence set forth in SEQ ID NOS: 1, 4, 7, 10, 12, 14, 17, 20, 23, 26, 29, 32, 35, 38, 41, 44, 47, 50, 53, 56, 58, 60, 62, and/or 64; (iv) at least one xylanase and/or xylosidase is produced by said cell; (v) the produced xylanase and/or xylosidase is secreted from the host cell; (vi) said host cell further produces at least one enzyme selected from endoglucanases (EG), β-glucosidases (BGL), Type 1 cellobiohydrolases (CBH1), Type 2 cellobiohydrolases (CBH2), and GH61 enzymes; (vii) said cell produces at least two recombinant cellulases; (vii) said cell produces at least three, at least four or at least five recombinant cellulases; (viii) said cell is a prokaryotic or eukaryotic cell, such as wherein said cell is a yeast cell or filamentous fungal cell, for example wherein the filamentous fungal cell is a *Myceliophthora*, a *Thielavia*, a *Trichoderma*, or an *Aspergillus* cell; and/or (ix) said cell is selected from *Saccharomyces* and *Myceliophthora*, such as wherein the filamentous fungal cell is a *Myceliophthora thermophila* or wherein the yeast cell is *Saccharomyces cerevisiae*.

The present invention also provides methods for producing at least one fermentable sugar from a feedstock, comprising contacting the feedstock with the xylanase(s) and/or xylosidase(s) provided herein, the enzyme composition provided herein, the recombinant organism provided herein, and/or the host cell provided herein, under culture conditions whereby fermentable sugars are produced. In some embodiments of the methods, (i) the enzyme composition comprises at least one enzyme selected from endoglucanases (EG), β-glucosidases (BGL), Type 1 cellobiohydrolases (CBH1), Type 2 cellobiohydrolases (CBH2), and GH61 enzymes, or said at least one enzyme is a recombinant enzyme; (ii) further comprising pretreating the feedstock prior to said contacting; (iii) wherein the feedstock comprises wheat grass, wheat straw, barley straw, sorghum, rice grass, sugarcane, sugar beet, bagasse, switchgrass, corn stover, corn fiber, grains, or a combination thereof; (iv) wherein the fermentable sugar comprises glucose and/or xylose; (v) further comprising recovering at least one fermentable sugar; (vi) further comprising contacting the at least one fermentable sugar with a microorganism under conditions such that said microorganism produces at least one fermentation end product, optionally wherein said fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams, such as wherein said fermentation product is an alcohol selected from ethanol and butanol, for example wherein said alcohol is ethanol; and/or (vii) the feedstock is a cellulosic and/or lignocellulosic feedstock.

The present invention further provides methods of producing an end product from a feedstock, comprising: a) contacting the feedstock with at least one xylanase and/or xylosidase enzyme as provided herein, an enzyme composition as provided herein, the recombinant organism as provided herein, and/or the host cell as provided herein, under conditions whereby at least one fermentable sugar is produced from the substrate; and b) contacting the fermentable sugar with a microorganism under conditions such that the microorganism uses the fermentable sugar to produce an end-product. In some embodiments, (i) the recombinant host cell further comprises at least one enzyme selected from endoglucanases (EG), β-glucosidases (BGL), Type 1 cellobiohydrolases (CBH1), Type 2 cellobiohydrolases (CBH2), and GH61 enzymes, such as wherein said at least one enzyme is a recombinant enzyme and/or wherein said at least one enzyme is a heterologous enzyme; (ii) the method comprises a simultaneous saccharification and fermentation reactions (SSF); or comprises separate saccharification and fermentation reactions (SHF); and/or (iii) the feedstock is a cellulosic and/or lignocellulosic feedstock.

The present invention also provides methods of producing a fermentation end product from a feedstock, comprising: a) obtaining at least one fermentable sugar produced according to a method provided herein; and b) contacting the fermentable sugar with a microorganism in a fermentation to produce at least one fermentation end product, optionally: (i) wherein said fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams, such as wherein said fermentation end product is at least one alcohol selected from ethanol and butanol; (ii) wherein the microorganism is a yeast; and/or (iii) further comprising recovering the fermentation end product.

The present invention also provides a recombinant organisms comprising at least one xylanase and/or xylosidase and/or biologically active xylanase and/or xylosidase fragment comprising (a) an amino acid sequence comprising at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. The present invention also provides recombinant organisms comprising a xylanase and/or xylosidase and/or biologically active xylanase and/or xylosidase fragment comprising (a) an amino acid sequence comprising at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, the present invention also provides recombinant organisms comprising a xylanase and/or xylosidase and/or biologically active xylanase and/or xylosidase fragment comprising (a) an amino acid sequence comprising SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, the xylanase and/or xylosidase or biologically active xylanase and/or xylosidase fragment is a *Myceliophthora thermophila* xylanase and/or xylosidase. The present invention also provides enzyme compositions comprising xylanase and/or xylosidase or biologically active xylanase and/or xylosidase fragment(s). In some further embodiments, the enzyme compositions comprise at least one additional enzyme and/or additional component (e.g., stabilizer(s), preservative(s), builder(s), etc.). In some additional embodiments, the additional enzyme is selected from cellulases, hemicellulases, xylanases, amylases, glucoamylases, proteases, esterases, and lipases. In some embodiments, the enzyme compositions comprise one or more enzyme(s) selected from endoglucanases (EG), β-glucosidases (BGL), Type 1 cellobiohydrolases (CBH1), Type 2 cellobiohydrolases (CBH2), and/or GH61 enzymes.

The present invention further provides recombinant organisms comprising at least one polynucleotide comprising at least one nucleic acid sequence, wherein said polynucleotide comprises a sequence that has least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:1, 4, 7, 10, 12, 14, 17, 20, 23, 26, 29, 32, 35, 38, 41, 44, 47, 50, 53, 56, 58, 60, 62, and/or 64. In some embodiments, the polynucleotide comprises a sequence that has least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to SEQ ID NO:1, 4, 7, 10, 12, 14, 17, 20, 23, 26, 29, 32, 35, 38, 41, 44, 47, 50, 53, 56, 58, 60, 62, and/or 64. In some embodiments, the recombinant organism comprises at least one polynucleotide comprising at least one nucleic acid sequence encoding the xylanase and/or xylosidase, wherein said polynucleotide comprises SEQ ID NO:1, 4, 7, 10, 12, 14, 17, 20, 23, 26, 29, 32, 35, 38, 41, 44, 47, 50, 53, 56, 58, 60, 62, and/or 64.

The present invention also provides recombinant nucleic acid constructs comprising at least one polynucleotide sequence, wherein the polynucleotide is selected from: (a) a polynucleotide that encodes a polypeptide comprising an amino acid sequence comprising at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identity to SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; (b) a polynucleotide that hybridizes under stringent hybridization conditions to at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; and/or (c) a polynucleotide that hybridizes under stringent hybridization conditions to the complement of at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some embodiments, the recombinant nucleic acid constructs comprise at least one polynucleotide sequence, wherein the polynucleotide is selected from: (a) a polynucleotide that encodes a polypeptide comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; (b) a polynucleotide that hybridizes under stringent hybridization conditions to at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; and/or (c) a polynucleotide that hybridizes under stringent hybridization conditions to the complement of at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some additional embodiments, the recombinant nucleic acid constructs comprise at least one polynucleotide sequence, wherein the polynucleotide is selected from: (a) a polynucleotide that encodes a polypeptide comprising an amino acid sequence comprising SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; (b) a polynucleotide that hybridizes under stringent hybridization conditions to at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65; and/or (c) a polynucleotide that hybridizes under stringent hybridization conditions to the complement of at least a fragment of a polynucleotide that encodes a polypeptide comprising the amino acid sequence of SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some further embodiments of the recombinant nucleic acid constructs the polynucleotide sequence is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identical to SEQ ID NO: 1, 4, 7, 10, 12, 14, 17, 20, 23, 26, 29, 32, 35, 38, 41, 44, 47, 50, 53, 56, 58, 60, 62, and/or 64. In some additional embodiments, the polynucleotide sequence is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 1, 4, 7, 10, 12, 14, 17, 20, 23, 26, 29, 32, 35, 38, 41, 44, 47, 50, 53, 56, 58, 60, 62, and/or 64. In still some additional embodiments, the polynucleotide sequence comprises SEQ ID NO: 1, 4, 7, 10, 12, 14, 17, 20, 23, 26, 29, 32, 35, 38, 41, 44, 47, 50, 53, 56, 58, 60, 62, and/or 64. In some further embodiments, the polynucleotide sequence is operably linked to a promoter. In some additional embodiments, the promoter is a heterologous promoter. In some additional embodiments, the nucleic acid sequence is operably linked to at least one additional regulatory sequence.

The present invention also provides recombinant host cells that express at least one polynucleotide sequence encoding at least one xylanase, xylosidase, xylanase fragment, and/or xylosidase fragment, as provided herein. In some embodiments, the recombinant host cell comprises at least one nucleic acid construct as provided herein. In some embodiments, the recombinant host cell comprises the polypeptide sequence set forth in SEQ ID NO:2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65. In some further embodiments, the recombinant host cell comprises the polynucleotide sequence set forth in SEQ ID NO: 1, 4, 7, 10, 12, 14, 17, 20, 23, 26, 29, 32, 35, 38, 41, 44, 47, 50, 53, 56, 58, 60, 62, and/or 64. In some additional embodiments, at least one xylanase and/or xylosidase is produced by the recombinant host cell. In some further embodiments, the produced xylanase and/or xylosidase is secreted from the host cell. In some additional embodiments, the recombinant host cell further produces at least one enzyme selected from endoglucanases (EG), β-glucosidases (BGL), Type 1 cellobiohydrolases (CBH1), Type 2 cellobiohydrolases (CBH2), and GH61 enzymes. In some embodiments, the recombinant host cell produces at least two recombinant cellulases, while in some other embodiments, the recombinant host cell produces at least three, at least four, or at least five recombinant cellulases. In some embodiments, the recombinant host cell is a prokaryotic or eukaryotic cell. In some further embodiments, the recombinant host cell is a yeast cell or filamentous fungal cell. In some embodiments, the filamentous fungal cell is a *Myceliophthora*, a *Thielavia*, a *Trichoderma*, an *Aspergillus* or a *Saccharomyces* cell. In some other embodiments, the filamentous fungal cell is a *Myceliophthora thermophila*, while in some alternative embodiments, the yeast cell is *Saccharomyces cerevisiae*.

The present invention also provides methods for producing at least one fermentable sugar from a feedstock, comprising contacting the feedstock with any of the enzyme composition(s) comprising at least one xylanase, xylosidase, xylanase fragment, and/or xylosidase fragment, as provided herein, under culture conditions whereby fermentable sugars are produced. In some embodiments, the enzyme composition further comprises at least one enzyme selected from endoglucanases (EG), β-glucosidases (BGL), Type 1 cellobiohydrolases (CBH1), Type 2 cellobiohydrolases (CBH2), and GI-161 enzymes. In some embodiments, at least one enzyme in the enzyme composition is a recombinant enzyme. In some additional embodiments, the methods further comprise pretreating the feedstock prior to said contacting the enzyme composition with the feedstock. In some further embodiments, the feedstock is a cellulosic and/or lignocellulosic feedstock. In some other embodiments, the feedstock comprises wheat grass, wheat straw, barley straw, sorghum, rice grass, sugarcane, sugar beet, bagasse, switchgrass, corn stover, corn fiber, grains, or a combination thereof. In some additional embodiments, the fermentable sugar comprises glucose and/or xylose. In some embodiments, the methods further comprise the step of recovering at least one fermentable sugar. In still some further embodiments, the methods further comprise the step of contacting at least one fermentable sugar with a microorganism under conditions such that said microorganism produces at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some additional embodiments, the fermentation product is an alcohol selected from ethanol and butanol. In some embodiments, the alcohol is ethanol.

The present invention also provides methods of producing an end product from a feedstock, comprising: contacting the feedstock with at least one enzyme composition comprising at least one xylanase, xylosidase, xylanase fragment, and/or xylosidase fragment, as provided herein, under conditions whereby at least one fermentable sugar is produced from the feedstock; and b) contacting the fermentable sugar with a microorganism under conditions such that the microorganism uses the fermentable sugar to produce an end-product. In some embodiments, the methods comprise a simultaneous saccharification and fermentation reactions (SSF), while in some other embodiments, the method comprises separate saccharification and fermentation reactions (SHF). In some further embodiments, the feedstock is a cellulosic and/or lignocellulosic feedstock. In some embodiments, the feedstock comprises wheat grass, wheat straw, barley straw, sorghum, rice grass, sugarcane, sugar beet, bagasse, switchgrass, corn stover, corn fiber, grains, or a combination thereof. In some additional embodiments, the methods comprise contacting the fermentable sugar with a microorganism in a fermentation to produce at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some additional embodiments, the fermentation product is an alcohol selected from ethanol and butanol. In some embodiments, the alcohol is ethanol. In some embodiments, the microorganism is a yeast. In some embodiments, the yeast is *Saccharomyces*, while in some further embodiments, the yeast is *S. cerevisiae*. In some embodiments, the methods further comprise the step of recovering the fermentation end product.

The present invention also provides methods for producing at least one fermentable sugar from a feedstock, comprising contacting the feedstock with the recombinant organism provided herein and/or the recombinant host cell provided herein, wherein the recombinant organism and/or recombinant host cell comprise at least one xylanase, xylosidase, xylanase fragment and/or xylosidase fragment, and wherein the contact occurs under culture conditions whereby fermentable sugars are produced. In some embodiments, the recombinant organism and/or recombinant host cell further comprises at least one enzyme selected from endoglucanases (EG), β-glucosidases (BGL), Type 1 cellobiohydrolases (CBH1), Type 2 cellobiohydrolases (CBH2), and/or GH61 enzymes. In some embodiments, at least one enzyme is a recombinant enzyme. In some further embodiments, at least one enzyme is a heterologous enzyme. In some additional embodiments, the methods further comprise pretreating the feedstock prior to said contacting. In some embodiments, the feedstock is a cellulosic and/or lignocellulosic feedstock. In some further embodiments, the feedstock comprises wheat grass, wheat straw, barley straw, sorghum, rice grass, sugarcane, sugar beet, bagasse, switchgrass, corn stover, corn fiber, grains, or a combination thereof. In some embodiments, the fermentable sugar comprises glucose and/or xylose. In some further embodiments, the methods further comprise the step of recovering at least one fermentable sugar. In some additional embodiments, the methods further comprise the step of contacting at least one fermentable sugar with a microorganism under conditions such that said microorganism produces at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some additional embodiments, the fermentation product is an alcohol selected from ethanol and butanol. In some embodiments, the alcohol is ethanol. In some embodiments, the microorganism is a yeast. In some embodiments, the yeast is *Saccharomyces*, while in some further embodiments, the yeast is *S. cerevisiae*. In some embodiments, the methods further comprise the step of recovering the fermentation end product.

The present invention also provides methods of producing a fermentation end product from a feedstock, comprising: a) obtaining at least one fermentable sugar produced according to any of the methods provided herein, and b) contacting the fermentable sugar with a microorganism in a fermentation to produce at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams. In some embodiments, the alcohol is ethanol. In some embodiments, the microorganism is a yeast. In some embodiments, the yeast is *Saccharomyces*, while in some further embodiments, the yeast is *S. cerevisiae*. In some embodiments, the methods further comprise the step of recovering the fermentation end product.

The present invention also provides the following further Embodiments:

1. A recombinant organism comprising a xylanase and/or beta-xylosidase and/or biologically active xylanase and/or beta-xylosidase fragment comprising (a) an amino acid sequence comprising at least about 70%, at least about 75%, at least about 80%, at least about 81%, at least 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to a SEQ ID NO:2, 3, 5, 6, 8 and/or 9.

2. The isolated xylanase and/or beta-xylosidase or biologically active xylanase and/or beta-xylosidase fragment of Embodiment 1, wherein said xylanase and/or beta-xylosidase is a *Myceliophthora thermophila* xylanase and/or beta-xylosidase.

3. An enzyme composition comprising the xylanase and/or beta-xylosidase of Embodiment 1 or 2.

4. The enzyme composition of Embodiment 3, further comprising at least one additional enzyme.

5. The enzyme composition of Embodiment 3 and/or 4, further comprising one or more enzymes selected from cellulases, hemicellulases, xylanases, amylases, glucoamylases, proteases, esterases, and lipases.

6. The enzyme composition of Embodiment 3, 4, and/or 5, further comprising one or more enzyme(s) selected from endoglucanases (EG), β-glucosidases (BGL), Type 1 cellobiohydrolases (CBH1), and/or Type 2 cellobiohydrolases (CBH2).

7. A recombinant fungal organism comprising at least one polynucleotide comprising at least one nucleic acid sequence encoding the xylanase and/or beta-xylosidase of Embodiment 1 and/or 2, or a polynucleotide that hybridizes under stringent hybridization conditions to the polynucleotide and/or a complement of a polynucleotide that encodes a polypeptide comprising the amino acid sequence provided in Embodiment 1 and/or 2.

8. The polynucleotide of Embodiment 7, wherein said polynucleotide comprises a sequence that has least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NOS:1, 4 and/or 7.

9. A recombinant nucleic acid construct comprising at least one polynucleotide sequence, wherein the polynucleotide is selected from: (a) a polynucleotide that encodes a polypeptide comprising an amino acid sequence comprising at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NOS:2, 3, 5, 6, 8 and/or 9; (b) a polynucleotide that hybridizes under stringent hybridization conditions to at least a fragment of a polynucleotide that encodes a polypeptide comprising the amino acid sequence of SEQ ID NOS:2, 3, 5, 6, 8, and/or 9; and/or (c) a polynucleotide that hybridizes under stringent hybridization conditions to the complement of at least a fragment of a polynucleotide that encodes a polypeptide comprising the amino acid sequence of SEQ ID NOS:2, 3, 5, 6, 8, and/or 9.

10. The recombinant nucleic acid construct of Embodiment 9, wherein the polynucleotide sequence is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NOS:1, 4, and/or 7.

11. The nucleic acid construct of Embodiment 8 and/or 9, wherein the polynucleotide sequence is operably linked to a promoter.

12. The nucleic acid construct of Embodiment 11, wherein said promoter is a heterologous promoter.

13. The nucleic acid construct of any of Embodiments 8-12, wherein said nucleic acid sequence is operably linked to at least one additional regulatory sequence.

14. A recombinant host cell that expresses at least one polynucleotide sequence encoding at least one xylanase and/or beta-xylosidase of Embodiment 1 and/or 2.

15. The recombinant host cell of Embodiment 14, wherein said host cell comprises at least one nucleic acid construct as provided in any of Embodiments 9-13.

16. The recombinant host cell of Embodiment 14 or 15, wherein said host cell comprises the polypeptide sequence set forth in SEQ ID NOS:2, 3, 5, 6, 8, and/or 9.

17. The recombinant host cell of any of Embodiments 14-16, wherein said host cell comprises the polynucleotide sequence set forth in SEQ ID NOS:1, 4, and/or 7.

18. The recombinant host cell of any of Embodiments 14-17, wherein at least one xylanase and/or beta-xylosidase is expressed by said cell.

19. The recombinant host cell of Embodiment 18, wherein the expressed xylanase and/or beta-xylosidase is secreted from the host cell.

20. The recombinant host cell of any of Embodiments 14-19, wherein said host cell further produces at least one enzyme selected from endoglucanases (EG), β-glucosidases (BGL), Type 1 cellobiohydrolases (CBH1), Type 2 cellobiohydrolases (CBH2), and GH61s.

21. The recombinant host cell of any of Embodiments 14-20, wherein said cell produces at least two recombinant cellulases.

22. The recombinant cell of any of Embodiments 14-21, wherein said cell produces at least three, at least four or at least five recombinant cellulases.

23. The recombinant cell of any of Embodiments 14-22, wherein said cell is a prokaryotic or eukaryotic cell.

24. The recombinant cell of Embodiment 23, wherein said cell is a yeast cell or filamentous fungal cell.

25. The recombinant host cell of Embodiment 23 or 24, wherein the filamentous fungal cell is a *Myceliophthora*, a *Thielavia*, a *Trichoderma*, or an *Aspergillus* cell.

26. The recombinant host cell of any of Embodiments 14-24, wherein said cell is selected from *Saccharomyces* and *Myceliophthora*.

27. The recombinant host cell of Embodiment 26, wherein the filamentous fungal cell is a *Myceliophthora thermophila*.

28. The recombinant host cell of Embodiment 26, wherein the yeast cell is *Saccharomyces cerevisiae*.

29. A method for producing at least one fermentable sugar from a feedstock, comprising contacting the feedstock with the enzyme composition according to any of Embodiments 3 to 6, under culture conditions whereby fermentable sugars are produced.

30. The method of Embodiment 29, wherein the enzyme composition comprises at least one enzyme selected from endoglucanases (EG), β-glucosidases (BGL), Type 1 cellobiohydrolases (CBH1), and Type 2 cellobiohydrolases (CBH2).

31. The method of Embodiment 29, wherein said at least one enzyme is a recombinant enzyme.

32. The method of any of Embodiments 29-31, further comprising pretreating the feedstock prior to said contacting.

33. The method of any of Embodiments 29 to 32, wherein the feedstock comprises wheat grass, wheat straw, barley straw, sorghum, rice grass, sugarcane, sugar beet, bagasse, switchgrass, corn stover, corn fiber, grains, or a combination thereof.

34. The method of any of Embodiments 29 to 33, wherein the fermentable sugar comprises glucose and/or xylose.

35. The method of any of Embodiments 29 to 34, further comprising recovering at least one fermentable sugar.

36. The method of any of Embodiments 29 to 35, further comprising contacting the at least one fermentable sugar with a microorganism under conditions such that said microorganism produces at least one fermentation end product.

37. The method of Embodiment 36, wherein said fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams.

38. The method of Embodiment 37, wherein said fermentation product is an alcohol selected from ethanol and butanol.

39. The method of Embodiment 38, wherein said alcohol is ethanol.

40. The method of any of Embodiments 29-39, wherein the feedstock is a cellulosic and/or lignocellulosic feedstock.

41. A method of producing an end product from a feedstock, comprising: a) contacting the feedstock with at least one enzyme composition according to any of Embodiments 3 to 6, under conditions whereby at least one fermentable sugar is produced from the substrate; and b) contacting the fermentable sugar with a microorganism under conditions such that the microorganism uses the fermentable sugar to produce an end-product.

42. The method of Embodiment 41, wherein the method comprises a simultaneous saccharification and fermentation reactions (SSF).

43. The method of Embodiment 41, wherein the method comprises separate saccharification and fermentation reactions (SHF).

44. The method of any of Embodiments 41 to 43, wherein the feedstock is a cellulosic and/or lignocellulosic feedstock.

45. A method of producing a fermentation end product from a feedstock, comprising: a) obtaining at least one fermentable sugar produced according to the method of any of Embodiments 29 to 44; and b) contacting the fermentable sugar with a microorganism in a fermentation to produce at least one fermentation end product.

46. The method of Embodiment 45, wherein said fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams.

47. The method of Embodiment 45 and/or 46, wherein said fermentation end product is at least one alcohol selected from ethanol and butanol.

48. The method of any of Embodiments 45 to 47, wherein the microorganism is a yeast.

49. The method of any of Embodiments 45 to 48, further comprising recovering the fermentation end product.

50. A method for producing at least one fermentable sugar from a feedstock, comprising contacting the feedstock with the recombinant organism of Embodiment 1 and/or the recombinant host cell set forth in any of Embodiments 14 to 28, under culture conditions whereby fermentable sugars are produced.

51. The method of Embodiment 50, wherein the recombinant organism and/or recombinant host cell further comprises at least one enzyme selected from endoglucanases (EG), β-glucosidases (BGL), Type 1 cellobiohydrolases (CBH1), and Type 2 cellobiohydrolases (CBH2).

52. The method of Embodiment 51, wherein said at least one enzyme is a recombinant enzyme.

53. The method of Embodiment 51 and/or 52, wherein said at least one enzyme is a heterologous enzyme.

54. The method of any of Embodiments 50-53, further comprising pretreating the feedstock prior to said contacting.

55. The method of any of Embodiments 50 to 54, wherein the feedstock comprises wheat grass, wheat straw, barley straw, sorghum, rice grass, sugarcane, sugar beet, bagasse, switchgrass, corn stover, corn fiber, grains, or a combination thereof.

56. The method of any of Embodiments 50 to 55, wherein the fermentable sugar comprises glucose and/or xylose.

57. The method of any of Embodiments 50 to 56, further comprising recovering at least one fermentable sugar.

58. The method of any of Embodiments 50 to 57, further comprising contacting the at least one fermentable sugar with a microorganism under conditions such that said microorganism produces at least one fermentation end product.

59. The method of Embodiment 58, wherein said fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams.

60. The method of Embodiment 59, wherein said fermentation product is an alcohol selected from ethanol and butanol.

61. The method of Embodiment 60, wherein said alcohol is ethanol.

62. The method of any of Embodiments 50-61, wherein the feedstock is a cellulosic and/or lignocellulosic feedstock.

63. A method of producing an end product from a feedstock, comprising: a) contacting the feedstock with the recombinant organism of Embodiment 1 and/or the recombinant host cell set forth in any of Embodiments 14 to 28, under conditions whereby at least one fermentable sugar is produced from the substrate; and b) contacting the fermentable sugar with a microorganism under conditions such that the microorganism uses the fermentable sugar to produce an end-product.

64. The method of Embodiment 63, wherein the recombinant organism and/or recombinant host cell further comprises at least one enzyme selected from endoglucanases (EG), β-glucosidases (BGL), Type 1 cellobiohydrolases (CBH1), and Type 2 cellobiohydrolases (CBH2).

65. The method of Embodiment 64, wherein said at least one enzyme is a recombinant enzyme.

66. The method of Embodiment 63 and/or 64, wherein said at least one enzyme is a heterologous enzyme.

67. The method of any of Embodiment 63-66, wherein the method comprises a simultaneous saccharification and fermentation reactions (SSF).

68. The method of any of Embodiments 63-66, wherein the method comprises separate saccharification and fermentation reactions (SHF).

69. The method of any of Embodiments 63 to 68, wherein the feedstock is a cellulosic and/or lignocellulosic feedstock.

70. A method of producing a fermentation end product from a feedstock, comprising: a) obtaining at least one fermentable sugar produced according to the method of any of Embodiments 63-69; and b) contacting the fermentable sugar with a microorganism in a fermentation to produce at least one fermentation end product.

71. The method of Embodiment 70, wherein said fermentation end product is selected from alcohols, fatty acids, lactic acid, acetic acid, 3-hydroxypropionic acid, acrylic acid, succinic acid, citric acid, malic acid, fumaric acid, succinic acid, amino acids, 1,3-propanediol, ethylene, glycerol, and β-lactams.

72. The method of Embodiment 70 and/or 71, wherein said fermentation end product is at least one alcohol selected from ethanol and butanol.

73. The method of any of Embodiments 70 to 72, wherein the microorganism is a yeast.

74. The method of any of Embodiments 70-73, further comprising recovering the fermentation end product.

DESCRIPTION OF THE INVENTION

Figure 1:
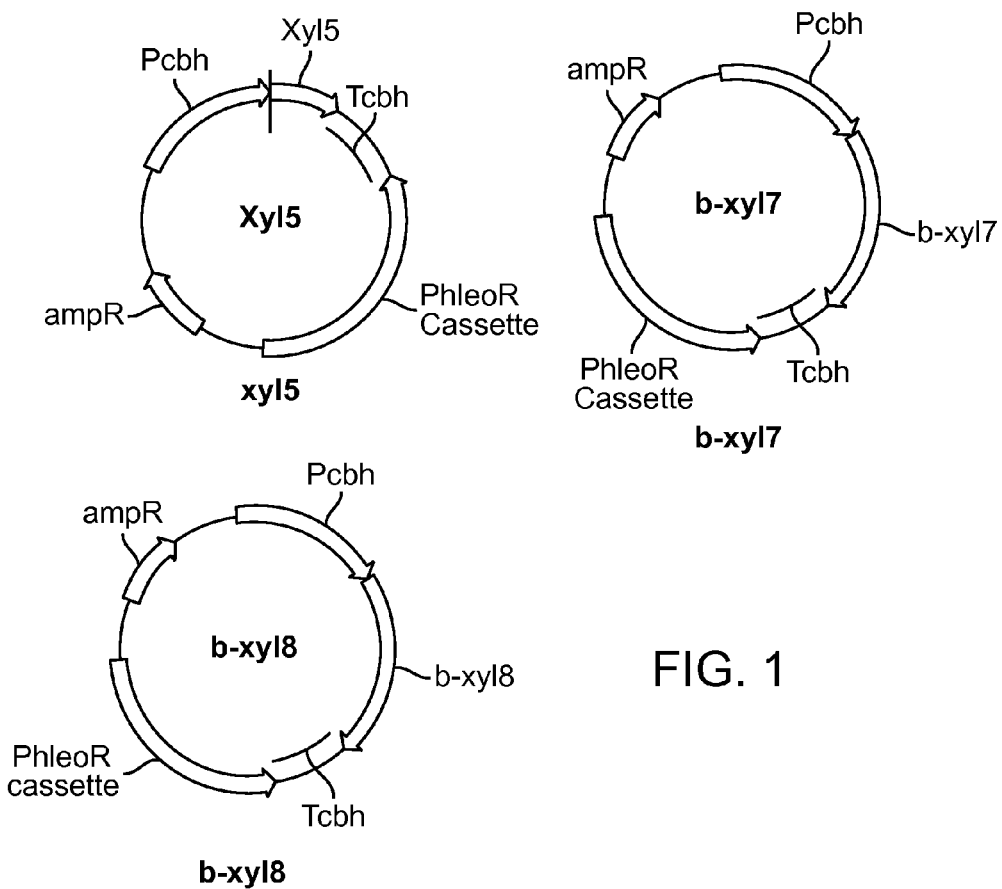
FIG. 1 provides the maps of the constructs used to transform *M. thermophile* with the xylanase (Xyl5) (SEQ ID NO:1) and beta-xylosidases (BXyl7 and BXyl8; SEQ ID NOS:4 and SEQ ID NO:7, 19, or 12, respectively) provided herein.

The present invention provides xylanase and xylosidase enzymes suitable for use in saccharification reactions. The present application further provides genetically modified fungal organisms that produce xylanase(s) and/or xylosidase(s), as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures. The present application further provides genetically modified fungal organisms that produce xylanase and xylosidases, as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures. In some embodiments, the xylanase and xylosidase is obtained from Myceliophthora thermophila.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the some methods and materials are described herein. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the term "cellulase" refers to any enzyme that is capable of degrading cellulose. Thus, the term encompasses enzymes capable of hydrolyzing cellulose (β-1,4-glucan or β-D-glucosidic linkages) to shorter cellulose chains, oligosaccharides, cellobiose and/or glucose. "Cellulases" are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," "BG," or "BGL"). These enzymes act in concert to catalyze the hydrolysis of cellulose-containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers.

As used herein, the term "xylanase" refers to enzymes within EC 3.2.1.8, that catalyze the hydrolysis of 1,4-beta-D-xylans, to cleave polymers or oligomers of xylose-containing xylans or hemicellulose into shorter chains. This enzyme may also be referred to as endo-1,4-beta-xylanase, 4-beta-D-xylan xylanohydrolase, endo-xylanase, or beta-xylanase.

As used herein, the term "xylanase polynucleotide" refers to a polynucleotide encoding a polypeptide comprising beta-xylanase activity.

As used herein, the term "xylanase activity" refers to the enzymatic activity of xylanase (i.e., hydrolyzing a cellulose-containing substrate).

As used herein, the terms "wild-type xylanase polynucleotide," "wild-type xylanase DNA," and "wild-type xylanase nucleic acid" refer to SEQ ID NO:1 of Xyl5, expressed by a naturally occurring Myceliophthora thermophila strain. This is sequence encoding the pre-mature peptide (i.e., containing the signal peptide).

As used herein, the term "xylosidase" refers to a group of enzymes that catalyze the hydrolysis of alpha- or beta-xylosidic linkages. Enzymes in class EC 3.2.1.8 catalyze the endo-hydrolysis of 1,4-beta-D-xylosidic linkages; while those in class EC 3.2.1.32 catalyze the endo-hydrolysis of 1,3-beta-D-xylosidic linkages; those in class EC 3.2.1.37 catalyze the exo-hydrolysis of 1,4-beta-D-linkages from the non-reducing termini of xylans; and those in class EC 3.2.1.72 catalyze the exo-hydrolysis of 1,3-beta-D-linkages from the non-reducing termini of xylans. Additional xylosidases have been identified that catalyze the hydrolysis of alpha-xylosidic bonds. As used herein, the term encompasses alpha-xylosidases and beta-xylosidases, as well as any other enzymes that have xylosidase activity (e.g., gamma-xylosidases).

As used herein the term "xylosidase polynucleotide" refers to a polynucleotide encoding a polypeptide comprising xylosidase activity.

As used herein, the term "xylosidase activity" refers to the enzymatic activity of xylosidase (i.e., hydrolyzing a cellulose-containing substrate).

As used herein, the term "alpha-xylosidase" refers to enzymes within EC 3.2.1 that remove the alpha-1,6-linked xylose residue from xyloglucan. In some embodiments, the removal of the alpha-1,6-linked xylose residue from xyloglucan facilitates the breakdown of xyloglucan to monomeric sugars (e.g., glucose and xylose).

As used herein the term "alpha-xylosidase polynucleotide" refers to a polynucleotide encoding a polypeptide comprising alpha-xylosidase activity.

As used herein, the term "alpha-xylosidase activity" refers to the enzymatic activity of alpha-xylosidase (i.e., removing the alpha-1,6-linked xylose residues from xyloglucan).

As used herein, the term "beta-xylosidase" refers to enzymes within EC 3.2.1.37, that catalyze the hydrolysis of 1,4-beta-D-xylans, to remove successive D-xylose residues from the non-reducing termini. This enzyme may also be referred to as xylan 1, beta-β-xylosidase, 1,4-beta-D-xylan xylohydrolase, exo-1,4-beta-xylosidase or xylobiase.

As used herein, the term "beta-xylosidase polynucleotide" refers to a polynucleotide encoding a polypeptide comprising beta-xylosidase activity.

As used herein, the term "beta-xylosidase activity" refers to the enzymatic activity of beta-xylosidase (i.e., hydrolyzing a cellulose-containing substrate).

As used herein, in some embodiments, the terms "wild-type beta-xylosidase polynucleotide," "wild-type beta-xylosidase DNA," and "wild-type beta-xylosidase nucleic acid" refer to SEQ ID NO:4, 7, and/or SEQ ID NO:10; these sequences encode the pre-mature peptide sequences (i.e., containing a signal peptide) of BXyl7 (also referred to herein and in the Figures as "b-xyl7"), and BXyl8 (also referred to herein and in the Figures as "b-xyl8"), respectively expressed by a naturally occurring *Myceliophthora thermophila* strain.

As used herein, the terms "endoglucanase" and "EG" refer to a category of cellulases (EC 3.2.1.4) that catalyze the hydrolysis of internal β-1,4 glucosidic bonds of cellulose.

As used herein, the term "xylosidase polypeptide" refers to a polypeptide comprising xylosidase activity. In some embodiments, the xylosidase is a "C1 xylosidase" derived from a strain C1 of *M. thermophila*.

As used herein, the term "alpha-xylosidase polypeptide" refers to a polypeptide comprising alpha-xylosidase activity. In some embodiments, the alpha-xylosidase is a "C1 alpha-xylosidase" derived from a strain C1 of *M. thermophila* (e.g., AXyl267 and AXyl6158).

As used herein, the term "beta-xylosidase polypeptide" refers to a polypeptide comprising beta-xylosidase activity. In some embodiments, the beta-xylosidase is a "C1 beta-xylosidase" derived from a strain C1 of *M. thermophile* (e.g., BXyl7 [SEQ ID NO:5] and BXyl8 [SEQ ID NOS:8, 11, and 13]).

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

As used herein, "combinatorial variant" refers to any variant that has a combination of two or more mutations (e.g., substitutions). In some embodiments, the combination of mutations results in changes in enzyme activity (e.g., improved thermostability, improved thermoactivity, improved specific activity, etc.).

The terms "improved" or "improved properties," as used herein in the context of describing the properties of a xylanase and/or xylosidase, refers to a xylanase and/or xylosidase polypeptide that exhibits an improvement in a property or properties as compared to another xylanase, xylosidase and/or a specified reference polypeptide. Improved properties include, but are not limited to such properties as increased protein expression, increased thermoactivity, increased thermostability, increased pH activity, increased stability (e.g., increased pH stability), increased product specificity, increased specific activity, increased substrate specificity, increased resistance to substrate or end-product inhibition, increased chemical stability, reduced inhibition by glucose, increased resistance to inhibitors (e.g., acetic acid, lectins, tannic acids, and phenolic compounds), and altered pH/temperature profile.

As used herein, the phrase "improved thermoactivity" or "increased thermoactivity" refers to an enzyme displaying an increase, relative to a reference enzyme, in the amount of xylanase or xylosidase enzymatic activity (e.g., substrate hydrolysis) in a specified time under specified reaction conditions, for example, elevated temperature. Exemplary methods for measuring xylanase and xylosidase activity are provided in the Examples herein. In addition, cells expressing and secreting the recombinant proteins can be cultured under the same conditions and the xylanase or xylosidase activity per volume culture medium can be compared.

As used herein, the term "improved thermostability" or "increased thermostability" refers to an enzyme displaying an increase in "residual activity" relative to a reference enzyme. Residual activity is determined by (1) exposing the test enzyme or reference enzyme to stress conditions of elevated temperature, optionally at lowered pH, for a period of time and then determining xylanase or xylosidase activity; (2) exposing the test enzyme or reference enzyme to unstressed conditions for the same period of time and then determining xylanase or xylosidase activity; and (3) calculating residual activity as the ratio of activity obtained under stress conditions (1) over the activity obtained under unstressed conditions (2). For example, the xylanase or xylosidase activity of the enzyme exposed to stress conditions ("a") is compared to that of a control in which the enzyme is not exposed to the stress conditions ("b"), and residual activity is equal to the ratio a/b. An enzyme with increased thermostability will have greater residual activity than the reference enzyme. In some embodiments, the enzymes are exposed to stress conditions of 55° C. at pH 5.0 for 1 hr, but other cultivation conditions, such as conditions described herein, can be used. Exemplary methods for measuring residual xylosidase activity are provided in the Examples herein.

As used herein, "EG 1" refers to a carbohydrate active enzyme expressed from a nucleic acid sequence coding for a glycohydrolase (GH) Family 7 catalytic domain classified under EC 3.2.1.4 or any protein, polypeptide or catalytically active fragment thereof. In some embodiments, the EG1 is functionally linked to a carbohydrate binding module (CBM), such as a Family 1 cellulose binding domain. As used herein, the term "EG1b polypeptide" refers to a polypeptide comprising EG1b activity.

As used herein, the term "EG2" refers to a carbohydrate active enzyme expressed from a nucleic acid sequence coding for a glycohydrolase (GH) Family 5 catalytic domain classified under EC 3.2.1.4 or any protein, polypeptide or catalytically active fragment thereof. In some embodiments, the EG2 is functionally linked to a carbohydrate binding module (CBM), such as a Family 1 cellulose binding domain.

As used herein, the term "EG3" refers to a carbohydrate active enzyme expressed from a nucleic acid sequence coding for a glycohydrolase (GH) Family 12 catalytic domain classified under EC 3.2.1.4 or any protein, polypeptide or catalytically active fragment thereof. In some embodiments, the EG3 is functionally linked to a carbohydrate binding module (CBM), such as a Family 1 cellulose binding domain.

As used herein, the term "EG4" refers to a carbohydrate active enzyme expressed from a nucleic acid sequence coding for a glycohydrolase (GH) Family 61 catalytic domain classified under EC 3.2.1.4 or any protein, polypeptide or fragment thereof. In some embodiments, the EG4 is functionally linked to a carbohydrate binding module (CBM), such as a Family 1 cellulose binding domain.

As used herein, the term "EG5" refers to a carbohydrate active enzyme expressed from a nucleic acid sequence coding for a glycohydrolase (GH) Family 45 catalytic domain classified under EC 3.2.1.4 or any protein, polypeptide or fragment thereof. In some embodiments, the EG5 is functionally linked to a carbohydrate binding module (CBM), such as a Family 1 cellulose binding domain.

As used herein, the term "EG6" refers to a carbohydrate active enzyme expressed from a nucleic acid sequence coding for a glycohydrolase (GH) Family 6 catalytic domain classified under EC 3.2.1.4 or any protein, polypeptide or fragment thereof. In some embodiments, the EG6 is functionally linked to a carbohydrate binding module (CBM), such as a Family 1 cellulose binding domain.

As used herein, the terms "cellobiohydrolase" and "CBH" refer to a category of cellulases (EC 3.2.1.91) that hydrolyze glycosidic bonds in cellulose.

As used herein, the terms "CBH1" and "type 1 cellobiohydrolase" refer to a carbohydrate active enzyme expressed from a nucleic acid sequence coding for a glycohydrolase (GH) Family 7 catalytic domain classified under EC 3.2.1.91 or any protein, polypeptide or catalytically active fragment thereof. In some embodiments, the CBH1 is functionally linked to a carbohydrate binding module (CBM), such as a Family 1 cellulose binding domain.

As used herein, the terms "CBH2" and "type 2 cellobiohydrolase" refer to a carbohydrate active enzyme expressed from a nucleic sequence coding for a glycohydrolase (GH) Family 6 catalytic domain classified under EC 3.2.1.91 or any protein, polypeptide or catalytically active fragment thereof. Type 2 cellobiohydrolases are also commonly referred to as "the Cel6 family." The CBH2 may be functionally linked to a carbohydrate binding module (CBM), such as a Family 1 cellulose binding domain.

As used herein, the terms "β-glucosidase," "cellobiase," and "BGL" refers to a category of cellulases (EC 3.2.1.21) that catalyze the hydrolysis of cellobiose to glucose.

As used herein, the term "glycoside hydrolase 61" and "GH61" refers to a category of cellulases that enhance cellulose hydrolysis when used in conjunction with one or more additional cellulases. The GH61 family of cellulases is described, for example, in the Carbohydrate Active Enzymes (CAZY) database (See e.g., Harris et al., Biochem., 49(15): 3305-16 [2010]).

A "hemicellulose" as used herein, refers to a polypeptide that can catalyze hydrolysis of hemicellulose into small polysaccharides such as oligosaccharides, or monomeric saccharides. Hemicelluloses include xylan, glucuonoxylan, arabinoxylan, glucomannan and xyloglucan. In some embodiments, hemicelluloses constitute major fractions of plant cell walls, including xyloglucan, glucuronarabinoxylan, mannan, galactan, arabinan, mixed-linked glucan, and/or glucuronarabinoyxlan. In some embodiments, the major hemicellulose in the primary walls of herbaceous dicotyledons is xyloglucan, comprising a backbone of beta-1,4-glucose substituted with an alpha-1,6-linked xylose, beta-linked galactose, and in some embodiments, alpha-linked fucose. In some embodiments, alpha-linked xylose is a major component of xyloglucans in the cell walls of higher plants that find use as feedstock in the methods of the present invention. Hemicellulases include, for example, the following: endoxylanases, b-xylosidases, a-L-arabinofuranosidases, a-D-glucuronidases, feruloyl esterases, coumaroyl esterases, a-galactosidases, b-galactosidases, b-mannanases, and b-mannosidases. In some embodiments, the present invention provides enzyme mixtures that comprise at least one xylanase and/or at least one xylosidase and one or more hemicellulases.

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include but are not limited to, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

As used herein, the terms "isolated" and "purified" are used to refer to a molecule (e.g., an isolated nucleic acid, polypeptide, etc.) or other component that is removed from at least one other component with which it is naturally associated.

As used herein, "polynucleotide" refers to a polymer of deoxyribonucleotides or ribonucleotides in either single- or double-stranded form, and complements thereof.

The terms "protein" and "polypeptide" are used interchangeably herein to refer to a polymer of amino acid residues.

The term "xylosidase polynucleotide" refers to a polynucleotide that encodes a xylosidase polypeptide.

In addition, the terms "amino acid" "polypeptide," and "peptide" encompass naturally-occurring and synthetic amino acids, as well as amino acid analogs. Naturally occurring amino acids are those encoded by the genetic code, as well as those amino acids that are later modified (e.g., hydroxyproline, γ-carboxyglutamate, and O-phosphoserine). As used herein, the term "amino acid analogs" refers to compounds that have the same basic chemical structure as a naturally occurring amino acid (i.e., an α-carbon that is bound to a hydrogen, a carboxyl group, an amino group, and an R group, including but not limited to homoserine, norleucine, methionine sulfoxide, and methionine methyl sulfonium). In some embodiments, these analogs have modified R groups (e.g., norleucine) and/or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a test sequence has a deletion relative to an aligned reference sequence, there will be no amino acid in the variant that corresponds to a position in the reference sequence at the site of deletion. Where there is an insertion in an aligned test sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. The following nomenclature may be used to describe substitutions in a test sequence relative to a reference sequence polypeptide or nucleic acid sequence: "R-#-V," where # refers to the position in the reference sequence, R refers to the amino acid (or base) at that position in the reference sequence, and V refers to the amino acid (or base) at that position in the test sequence. In some embodiments, an amino acid (or base) may be called "X," by which is meant any amino acid (or base).

As used herein, the term "reference enzyme" refers to an enzyme to which another enzyme of the present invention (e.g., a "test" enzyme, such as a xylanase or xylosidase) is compared in order to determine the presence of an improved property in the other enzyme being evaluated. In some embodiments, a reference enzyme is a wild-type enzyme (e.g., a wild-type xylanase or xylosidase). In some embodiments, the reference enzyme is an enzyme to which a test enzyme of the present invention is compared in order to determine the presence of an improved property in the test enzyme being evaluated, including but not limited to improved thermoactivity, improved thermostability, and/or improved stability. In some embodiments, a reference enzyme is a wild-type enzyme (e.g., a wild-type xylanase or xylosidase).

As used herein, the terms "biologically active fragment" and "fragment" refer to a polypeptide that has an amino-terminal and/or carboxy-terminal deletion(s) and/or internal deletion(s), but where the remaining amino acid sequence is identical to the corresponding positions in the sequence to which it is being compared (e.g., a full-length xylanase or xylosidase of the present invention) and that retains substantially all of the activity of the full-length polypeptide. In some embodiments, the biologically active fragment is a biologically active xylanase or xylosidase fragment. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length xylanase or xylosidase polypeptide. In some embodiments, the biologically active fragments comprise about 20%, about 21%, about 22%, about 23%, about 24%, about 25%, about 26%, about 27%, about 28%, about 29%, about 30%, about 35%, about 40%, about 45%, about 50%, or about 55% of a full-length xylosidase (e.g., BXyl8 [SEQ ID NO:5, 6, 8, 9, 11, or 13]).

As used herein, the term "overexpress" is intended to encompass increasing the expression of a protein to a level greater than the cell normally produces. It is intended that the term encompass overexpression of endogenous, as well as heterologous proteins.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. As used herein, "recombinant cells," as well as recombinant host cells," "recombinant microorganisms," and "recombinant fungal cells," contain at least one recombinant polynucleotide or polypeptide.

As used herein, "recombinant" used in reference to a cell or vector, refers to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. Thus, "recombinant" or "engineered" or "non-naturally occurring" when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level. "Recombination," "recombining" and generating a "recombined" nucleic acid generally encompass the assembly of at least two nucleic acid fragments. In some embodiments, "Recombination," "recombining," and generating a "recombined" nucleic acid also encompass the assembly of two or more nucleic acid fragments wherein the assembly gives rise to a chimeric gene.

As used herein, when used with reference to a nucleic acid or polypeptide, the term "heterologous" refers to a sequence that is not normally expressed and secreted by an organism (e.g., a wild-type organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

A nucleic acid construct, nucleic acid (e.g., a polynucleotide), polypeptide, or host cell is referred to herein as "recombinant" when it is non-naturally occurring, artificial or engineered. The present invention also provides recombinant nucleic acid constructs comprising a xylanase and/or xylosidase polynucleotide sequence that hybridizes under stringent hybridization conditions to the complement of a polynucleotide which encodes a polypeptide comprising the amino acid sequence of SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

As used herein, "identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

In some embodiments, the terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/more accurate pairwise optimal alignments—DNA/Protein Gap Open Penalty:15/10; DNA/Protein Gap Extension Penalty:6.66/0.1; Protein weight matrix: Gonnet series; DNA weight matrix: Identity.

As used herein the term "comparison window," includes reference to a segment of any one of a number of contiguous positions from about 20 to about 464 (e.g., about 50 to about 300 contiguous positions, about 50 to 250 contiguous positions, or also about 100 to about 200 contiguous positions), in which a sequence may be compared to a reference sequence of the same number of contiguous positions after the two sequences are optimally aligned. As noted, in some embodiments the comparison is between the entire length of the two sequences, or, if one sequence is a fragment of the other, the entire length of the shorter of the two sequences. Optimal alignment of sequences for comparison and determination of sequence identity can be determined by a sequence comparison algorithm or by visual inspection, as well-known in the art. When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure,"* Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising at least one xylanase and/or xylosidase polynucleotide sequence that hybridizes under stringent hybridization conditions to the complement of a polynucleotide which encodes a polypeptide comprising the amino acid sequence of SEQ ID NO: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65, wherein the polypeptide is capable of catalyzing the degradation of cellulose. Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, or greater sequence identity as determined using the methods described herein, such as BLAST using standard parameters.

As used herein, the term "pre-protein" refers to a protein including an amino-terminal signal peptide (or leader sequence) region attached. The signal peptide is cleaved from the pre-protein by a signal peptidase prior to secretion to result in the "mature" or "secreted" protein.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. An "expression vector" has a promoter sequence operably linked to the DNA sequence (e.g., transgene) to drive expression in a host cell, and in some embodiments a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, the term "operably linked" refers to a configuration in which a control sequence is appropriately placed at a position relative to the coding sequence of the DNA sequence such that the control sequence influences the expression of a polypeptide.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein. In some embodiments, the host cells are prokaryotic or eukaryotic cells that have been transformed or transfected with vectors constructed using recombinant DNA techniques as known in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In some embodiments, host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by any suitable genetic engineering techniques and/or classical microbiological techniques (e.g., chemical or UV mutagenesis and subsequent selection). Using recombinant technology, nucleic acid molecules can be introduced, deleted, inhibited or modified, in a manner that results in increased yields of xylanase and/or xylosidase within the organism or in the culture. For example, knockout of Alp1 function results in a cell that is protease deficient. Knockout of pyr5 function results in a cell with a pyrimidine deficient phenotype. In some genetic engineering approaches, homologous recombination is used to induce targeted gene modifications by specifically targeting a gene in vivo to suppress expression of the encoded protein. In an alternative approach, siRNA, antisense, and/or ribozyme technology finds use in inhibiting gene expression.

As used herein, the term "introduced" used in the context of inserting a nucleic acid sequence into a cell, means transformation, transduction, conjugation, transfection, and/or any other suitable method(s) known in the art for inserting nucleic acid sequences into host cells. Any suitable means for the introduction of nucleic acid into host cells find use in the present invention.

As used herein, the terms "transformed" and "transformation" used in reference to a cell refer to a cell that has a non-native nucleic acid sequence integrated into its genome or has an episomal plasmid that is maintained through multiple generations.

As used herein, the term "C1" refers to strains of *Myceliophthora thermophila*, including the fungal strain described by Garg (See, Garg, Mycopathol., 30: 3-4 [1966]). As used herein, "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV18#100f Δalp1, UV18#100f Δpyr5 Δalp1, UV18#100.fΔAalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO2008073914 and WO2010107303, each of which is incorporated herein by reference.

As used herein, the terms "improved thermoactivity" and "increased thermoactivity" refer to an enzyme (e.g., a "test" enzyme of interest) displaying an increase, relative to a reference enzyme, in the amount of enzymatic activity (e.g., substrate hydrolysis) in a specified time under specified reaction conditions, for example, elevated temperature.

As used herein, the terms "improved thermostability" and "increased thermostability" refer to an enzyme (e.g., a "test" enzyme of interest) displaying an increase in "residual activity" relative to a reference enzyme. Residual activity is determined by (1) exposing the test enzyme or reference enzyme to stress conditions of elevated temperature, optionally at lowered pH, for a period of time and then determining xylanase or xylosidase activity; (2) exposing the test enzyme or reference enzyme to unstressed conditions for the same period of time and then determining xylanase or xylosidase activity; and (3)

calculating residual activity as the ratio of activity obtained under stress conditions (1) over the activity obtained under unstressed conditions (2). For example, the xylanase or xylosidase activity of the enzyme exposed to stress conditions ("a") is compared to that of a control in which the enzyme is not exposed to the stress conditions ("b"), and residual activity is equal to the ratio a/b. A test enzyme with increased thermostability will have greater residual activity than the reference enzyme. In some embodiments, the enzymes are exposed to stress conditions of 55° C. at pH 5.0 for 1 hr, but other cultivation conditions can be used.

As used herein, the term "culturing" refers to growing a population of microbial cells under suitable conditions in a liquid or solid medium.

As used herein, the term "saccharification" refers to the process in which substrates (e.g., cellulosic biomass) are broken down via the action of cellulases to produce fermentable sugars (e.g. monosaccharides such as but not limited to glucose).

As used herein, the term "fermentable sugars" refers to simple sugars (e.g., monosaccharides, disaccharides and short oligosaccharides), including but not limited to glucose, xylose, galactose, arabinose, mannose and sucrose. Indeed, a fermentable sugar is any sugar that a microorganism can utilize or ferment.

As used herein the term "soluble sugars" refers to water-soluble hexose monomers and oligomers of up to about six monomer units.

As used herein, the term "fermentation" is used broadly to refer to the cultivation of a microorganism or a culture of microorganisms that use simple sugars, such as fermentable sugars, as an energy source to obtain a desired product.

As used herein, the term "feedstock" refers to any material that is suitable for use in production of an end product. It is intended that the term encompass any material suitable for use in saccharification reactions. In some embodiments, the term encompasses material obtained from nature that is in an unprocessed or minimally processed state, although it is not intended that the term be limited to these embodiments. In some embodiments, the term encompasses biomass and biomass substrates comprising any suitable compositions for use in production of fermentable sugars. In some embodiments, the feedstock is "pre-treated" before and/or while it is being used as a substrate in a saccharification reaction.

The terms "biomass," and "biomass substrate," encompass any suitable materials for use in saccharification reactions. The terms encompass, but are not limited to materials that comprise cellulose (i.e., "cellulosic biomass," "cellulosic feedstock," and "cellulosic substrate"). Biomass can be derived from plants, animals, or microorganisms, and may include, but is not limited to agricultural, industrial, and forestry residues, industrial and municipal wastes, and terrestrial and aquatic crops grown for energy purposes. Examples of biomass substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, tops, wood chips, sawdust, shrubs, bushes, seed pods, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, tops, stems, leaves, seed pods, fruit pods, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass may also comprise transgenic plants that express ligninase and/or cellulase enzymes (See e.g., US 2008/0104724 A1).

A biomass substrate is said to be "pretreated" when it has been processed by some physical and/or chemical means to facilitate saccharification. As described further herein, in some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. Thus, the term "biomass" encompasses any living or dead biological material that contains a polysaccharide substrate, including but not limited to cellulose, starch, other forms of long-chain carbohydrate polymers, and mixtures of such sources. It may or may not be assembled entirely or primarily from glucose or xylose, and may optionally also contain various other pentose or hexose monomers. Xylose is an aldopentose containing five carbon atoms and an aldehyde group. It is the precursor to hemicellulose, and is often a main constituent of biomass. In some embodiments, the substrate is slurried prior to pretreatment. In some embodiments, the consistency of the slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

In some embodiments, the pretreatment is carried out to hydrolyze hemicellulose, and/or a portion thereof present in the cellulosic substrate to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461, 648). Another method of pretreating the slurry involves continuous pretreatment (i.e., the cellulosic biomass is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the biomass. Rather, the alkali reacts with acidic groups present on the hemicellulose to open up the surface of the substrate. In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663 and 5,171,592). During this process, the cellulosic substrate is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In some alternative methods, dilute ammonia pretreatment is utilized. The dilute ammonia pretreatment method utilizes more dilute solutions of ammonia or ammonium hydroxide than AFEX (See e.g., WO2009/045651 and US 2007/0031953). This pretreatment process may or may not produce any monosaccharides.

An additional pretreatment process for use in the present invention includes chemical treatment of the cellulosic substrate with organic solvents, in methods such as those utilizing organic liquids in pretreatment systems (See e.g., U.S. Pat. No. 4,556,430; incorporated herein by reference). These methods have the advantage that the low boiling point liquids easily can be recovered and reused. Other pretreatments, such as the Organosolv™ process, also use organic liquids (See e.g., U.S. Pat. No. 7,465,791, which is also incorporated herein by reference). Subjecting the substrate to pressurized water may also be a suitable pretreatment method (See e.g., Weil et al. (1997) Appl. Biochem. Biotechnol., 68(1-2): 21-40 [1997], which is incorporated herein by reference). In some embodiments, the pretreated cellulosic biomass is processed after pretreatment by any of several steps, such as dilution with water, washing with water, buffering, filtration, or centrifugation, or any combination of these processes, prior to enzymatic hydrolysis, as is familiar to those skilled in the art. The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction. In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock. Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. In some embodiments, the pretreated cellulosic feedstock is subjected to enzymatic hydrolysis with cellulase enzymes.

As used herein, the term "lignocellulosic biomass" refers to any plant biomass comprising cellulose and hemicellulose, bound to lignin. In some embodiments, the biomass may optionally be pretreated to increase the susceptibility of cellulose to hydrolysis by chemical, physical and biological pretreatments (such as steam explosion, pulping, grinding, acid hydrolysis, solvent exposure, and the like, as well as combinations thereof). Various lignocellulosic feedstocks find use, including those that comprise fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size reduction is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction.

As used herein, the term "lignocellulosic feedstock" refers to any type of lignocellulosic biomass that is suitable for use as feedstock in saccharification reactions.

As used herein, the term "pretreated lignocellulosic feedstock," refers to lignocellulosic feedstocks that have been subjected to physical and/or chemical processes to make the fiber more accessible and/or receptive to the actions of cellulolytic enzymes, as described above.

As used herein, the term "recovered" refers to the harvesting, isolating, collecting, or recovering of protein from a cell and/or culture medium. In the context of saccharification, it is used in reference to the harvesting of fermentable sugars produced during the saccharification reaction from the culture medium and/or cells. In the context of fermentation, it is used in reference to harvesting the fermentation product from the culture medium and/or cells. Thus, a process can be said to comprise "recovering" a product of a reaction (such as a soluble sugar recovered from saccharification) if the process includes separating the product from other components of a reaction mixture subsequent to at least some of the product being generated in the reaction.

As used herein, the term "slurry" refers to an aqueous solution in which are dispersed one or more solid components, such as a cellulosic substrate.

As used herein, "increasing" the yield of a product (such as a fermentable sugar) from a reaction occurs when a particular component of interest is present during the reaction (e.g., xylanase or xylosidase) causes more product to be produced, compared with a reaction conducted under the same conditions with the same substrate and other substituents, but in the absence of the component of interest (e.g., without xylanase or xylosidase).

As used herein, a reaction is said to be "substantially free" of a particular enzyme if the amount of that enzyme compared with other enzymes that participate in catalyzing the reaction is less than about 2%, about 1%, or about 0.1% (wt/wt).

As used herein, "fractionating" a liquid (e.g., a culture broth) means applying a separation process (e.g., salt precipitation, column chromatography, size exclusion, and filtration) or a combination of such processes to provide a solution in which a desired protein (such as xylanase, xylosidase, a cellulase enzyme, and/or a combination thereof) comprises a greater percentage of total protein in the solution than in the initial liquid product.

As used herein, the term "enzymatic hydrolysis", refers to a process comprising at least one cellulases and at least one glycosidase enzyme and/or a mixture glycosidases that act on polysaccharides, (e.g., cellulose), to convert all or a portion thereof to fermentable sugars. "Hydrolyzing" cellulose or other polysaccharide occurs when at least some of the glycosidic bonds between two monosaccharides present in the substrate are hydrolyzed, thereby detaching from each other the two monomers that were previously bonded.

It is intended that the enzymatic hydrolysis be carried out with any suitable type of cellulase enzymes capable of hydrolyzing the cellulose to glucose, regardless of their source, including those obtained from fungi, such as *Trichoderma* spp., *Aspergillus* spp., *Hypocrea* spp., *Humicola* spp., *Neurospora* spp., *Orpinomyces* spp., *Gibberella* spp., *Emericella* spp., *Chaetomium* spp., *Chrysosporium* spp., *Fusarium* spp., *Penicillium* spp., *Magnaporthe* spp., *Phanerochaete* spp., *Trametes* spp., *Lentinula edodes*, *Gleophyllum trabeiu*, *Ophiostoma piliferum*, *Corpinus cinereus*, *Geomyces pannorum*, *Cryptococcus laurentii*, *Aureobasidium pullulans*, *Amorphotheca resinae*, *Leucosporidium scotti*, *Cunninghamella elegans*, *Thermomyces lanuginosus*, *Myceliopthora thermophila*, and *Sporotrichum thermophile*, as well as those obtained from bacteria of the genera *Bacillus*, *Thermomyces*, *Clostridium*, *Streptomyces* and *Thermobifida*. Cellulase compositions typically comprise one or more cellobiohydrolase, endoglucanase, and beta-glucosidase enzymes. In some cases, the cellulase compositions additionally contain hemicellulases, esterases, swollenins, cips, etc. Many of these enzymes are readily commercially available.

In some embodiments, the enzymatic hydrolysis is carried out at a pH and temperature that is at or near the optimum for the cellulase enzymes being used. For example, the enzymatic hydrolysis may be carried out at about 30° C. to about 75° C., or any suitable temperature therebetween, for example a temperature of about 30° C., about 35° C., about 40° C., about 45° C., about 50° C., about 55° C., about 60° C., about 65° C., about 70° C., about 75° C., or any temperature therebetween, and a pH of about 3.5 to about 7.5, or any pH therebetween (e.g., about 3.5, about 4.0, about 4.5, about 5.0, about 5.5, about 6.0, about 6.5, about 7.0, about 7.5, or any suitable pH therebetween). In some embodiments, the initial concentration of cellulose, prior to the start of enzymatic hydrolysis, is preferably about 0.1% (w/w) to about 20% (w/w), or any suitable amount therebetween (e.g., about 0.1%, about 0.5%, about 1%, about 2%, about 4%, about 6%, about 8%, about 10%, about 12%, about 14%, about 15%, about 18%, about 20%, or any suitable amount therebetween.) In some embodiments, the combined dosage of all cellulase enzymes is about 0.001 to about 100 mg protein per gram cellulose, or any suitable amount therebetween (e.g., about 0.001, about 0.01, about 0.1, about 1, about 5, about 10, about 15, about 20, about 25, about 30, about 40, about 50, about 60, about 70, about 80, about 90, about 100 mg protein per gram cellulose or any amount therebetween. The enzymatic hydrolysis is carried out for any suitable time period. In some embodiments, the enzymatic hydrolysis is carried out for a time period of about 0.5 hours to about 200 hours, or any time therebetween (e.g., about 2 hours to about 100 hours, or any suitable time therebetween). For example, in some embodiments, it is carried out for about 0.5, about 1, about 2, about 5, about 7, about 10, about 12, about 14, about 15, about 20, about 25, about 30, about 35, about 40, about 45, about 50, about 55, about 60, about 65, about 70, about 75, about 80, about 85, about 90, about 95, about 100, about 120, about 140, about 160, about 180, about 200, or any suitable time therebetween.)

In some embodiments, the enzymatic hydrolysis is batch hydrolysis, continuous hydrolysis, and/or a combination thereof. In some embodiments, the hydrolysis is agitated, unmixed, or a combination thereof. The enzymatic hydrolysis is typically carried out in a hydrolysis reactor. The cellulase enzyme composition is added to the pretreated lignocellulosic substrate prior to, during, or after the addition of the substrate to the hydrolysis reactor. Indeed it is not intended that reaction conditions be limited to those provided herein, as modifications are well-within the knowledge of those skilled in the art. In some embodiments, following cellulose hydrolysis, any insoluble solids present in the resulting lignocellulosic hydrolysate, including but not limited to lignin, are removed using conventional solid-liquid separation techniques prior to any further processing. In some embodiments, these solids are burned to provide energy for the entire process.

As used herein, the term "by-product" refers to an organic molecule that is an undesired product of a particular process (e.g., saccharification).

DETAILED DESCRIPTION OF THE INVENTION

The present invention provides xylanase and xylosidase enzymes suitable for use in saccharification reactions. The present application further provides genetically modified fungal organisms that produce xylanase(s) and/or xylosidase(s), as well as enzyme mixtures exhibiting enhanced hydrolysis of cellulosic material to fermentable sugars, enzyme mixtures produced by the genetically modified fungal organisms, and methods for producing fermentable sugars from cellulose using such enzyme mixtures. In some embodiments, the xylanase and xylosidase is obtained from a *Myceliophthora thermophila* strain.

In some embodiments, the present invention provides methods and compositions suitable for use in the degradation of cellulose. In some additional embodiments, the present invention provides xylanase and xylosidase enzymes suitable for use in saccharification reactions to hydrolyze cellulose components in biomass feedstock. In some additional embodiments, the xylanase and xylosidase enzymes are used in combination with additional enzymes, including but not limited to EG1a, Eg1b, EG2, EG3, EG5, EG6, cellobiohydrolase(s), GH61s, etc., in saccharification reactions.

Fungi, bacteria, and other organisms produce a variety of cellulases and other enzymes that act in concert to catalyze decrystallization and hydrolysis of cellulose to yield fermentable sugars. One such fungus is *M. thermophila*, which is described herein. Cellulases of interest include the xylanase and xylosidase enzymes provided herein. The xylanase and xylosidase sequences provided herein are particularly useful for the production of fermentable sugars from cellulosic biomass. In some embodiments, the present invention provides methods of generating fermentable sugars from cellulosic biomass, by contacting the biomass with a cellulase composition comprising at least one xylanase and/or xylosidase described herein under conditions suitable for the production of fermentable sugars For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2): 157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391: 288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

Xylanase and xylosidase activity and thermostability can be determined by methods described in the Examples, and/or using other suitable assay methods known in the art (e.g., the PAHBAH kit [Megazyme] and/or HPLC). Additional methods of cellobiose quantification include, but are not limited chromatographic methods (e.g., HPLC; See e.g., U.S. Pat. Nos. 6,090,595 and 7,419,809, both of which are incorporated by reference in their entireties).

The present invention provides xylanase and xylosidases suitable for use in saccharification reactions. In some embodiments, the present invention provides methods and compositions suitable for use in the degradation of cellulose. In some additional embodiments, the present invention provides xylanase and xylosidase enzymes suitable for use in saccharification reactions to hydrolyze cellulose components in biomass feedstock. In some additional embodiments, the xylanase and xylosidase(s) are used in combination with additional enzymes, including but not limited to at least one EG (e.g., EG1b, EG1a, EG2, EG3, EG4, EG5, and/or EG6), cellobiohydrolase, GH61, and/or beta-glucosidases, etc., in saccharification reactions.

Fungi, bacteria, and other organisms produce a variety of cellulases and other enzymes that act in concert to catalyze decrystallization and hydrolysis of cellulose to yield fermentable sugars. One such fungus is *M. thermophila*, which is described herein. The xylanase and xylosidase sequences provided herein are particularly useful for the production of fermentable sugars from cellulosic biomass and other feedstocks. In some additional embodiments, the present invention provides methods for generating fermentable sugars from biomass, involving contacting the biomass with a cellulase composition comprising at least one xylanase and/or at least one xylosidase as described herein, under conditions suitable for the production of fermentable sugars.

In some embodiments, the xylanase and xylosidases of the present invention further comprise additional sequences which do not alter the encoded activity of the enzyme. For example, in some embodiments, the xylanase or xylosidases are linked to an epitope tag or to another sequence useful in purification.

In some embodiments, the xylanase and xylosidase polypeptides of the present invention are secreted from the host cell in which they are produced (e.g., a yeast or filamentous fungal host cell) and are produced as a pre-protein including a signal peptide (i.e., an amino acid sequence linked to the amino terminus of a polypeptide and which directs the encoded polypeptide into the cell secretory pathway). In some embodiments, the signal peptide is an endogenous *M. thermophila* xylanase and xylosidase signal peptide. In some other embodiments, signal peptides from other *M. thermophila* secreted proteins are used. In some embodiments, other signal peptides find use, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, and *T. reesei* cellobiohydrolase II. Signal peptide coding regions for bacterial host cells include, but are not limited to the signal peptide coding regions obtained from the genes for *Bacillus* NC1B 11837 maltogenic amylase, *Bacillus stearothermophilus* alpha-amylase, *Bacillus licheniformis* subtilisin, *Bacillus lichenformis* β-lactamase, *Bacillus stearothermophilus* neutral proteases (nprT, nprS, nprM), and *Bacillus subtilis* prsA. In some additional embodiments, other signal peptides find use in the present invention (See e.g., Simonen and Palva, Microbiol. Rev., 57: 109-137 [1993], incorporated herein by reference). Additional useful signal peptides for yeast host cells include those from the genes for *Saccharomyces cerevisiae* alpha-factor, *Saccharomyces cerevisiae* SUC2 invertase (See e.g., Taussig and Carlson, Nucl. Acids Res., 11:1943-54 [1983]; SwissProt Accession No. P00724; and Romanos et al., Yeast 8:423-488 [1992]). In some embodiments, variants of these signal peptides and other signal peptides find use.

In some embodiments, the present invention provides polynucleotides encoding xylanase and/or xylosidase polypeptides, and/or biologically active fragments thereof, as described herein. In some embodiments, the polynucleotide is operably linked to one or more heterologous regulatory or control sequences that control gene expression to create a recombinant polynucleotide capable of expressing the polypeptide. In some embodiments, expression constructs containing a heterologous polynucleotide encoding xylanase and/or xylosidase is introduced into appropriate host cells to express the xylanase and/or xylosidase.

Those of ordinary skill in the art understand that due to the degeneracy of the genetic code, a multitude of nucleotide sequences encoding xylanase and xylosidase polypeptides of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that "U" in an RNA sequence corresponds to "T" in a DNA sequence. The invention contemplates and provides each and every possible variation of nucleic acid sequence encoding a polypeptide of the invention that could be made by selecting combinations based on possible codon choices.

A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. A codon whose frequency increases with the level of gene expression is typically an optimal codon for expression. In particular, a DNA sequence can be optimized for expression in a particular host organism. A variety of methods are well-known in the art for determining the codon frequency (e.g., codon usage, relative synonymous codon usage) and codon preference in specific organisms, including multivariate analysis (e.g., using cluster analysis or correspondence analysis,) and the effective number of codons used in a gene. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTs), or predicted coding regions of genomic sequences, as is well-known in the art. Polynucleotides encoding xylanase and/or xylosidases can be prepared using any suitable methods known in the art. Typically, oligonucleotides are individually synthesized, then joined (e.g., by enzymatic or chemical ligation methods, or polymerase-mediated methods) to form essentially any desired continuous sequence. In some embodiments, polynucleotides of the present invention are prepared by chemical synthesis using, any suitable methods known in the art, including but not limited to automated synthetic methods. For example, in the phosphoramidite method, oligonucleotides are synthesized (e.g., in an automatic DNA synthesizer), purified, annealed, ligated and cloned in appropriate vectors. In some embodiments, double stranded DNA fragments are then obtained either by synthesizing the complementary strand and annealing the strands together under appropriate conditions, or by adding the complementary strand using DNA polymerase with an appropriate primer sequence. There are numerous general and standard texts that provide methods useful in the present invention are well known to those skilled in the art.

The present invention also provides recombinant constructs comprising a sequence encoding at least one xylanase and/or at least one xylosidase, as provided herein. In some embodiments, the present invention provides an expression vector comprising a xylanase and/or xylosidase polynucleotide operably linked to a heterologous promoter. In some embodiments, expression vectors of the present invention are used to transform appropriate host cells to permit the host cells to express the xylanase and/or xylosidase protein. Methods for recombinant expression of proteins in fungi and other organisms are well known in the art, and a number expression vectors are available or can be constructed using routine methods. In some embodiments, nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. In some embodiments, polynucleotides of the present invention are incorporated into any one of a variety of expression vectors suitable for expressing xylanase and/or xylosidase polypeptide(s). Suitable vectors include, but are not limited to chromosomal, nonchromosomal and synthetic DNA sequences (e.g., derivatives of SV40), as well as bacterial plasmids, phage DNA, baculovirus, yeast plasmids, vectors derived from combinations of plasmids and phage DNA, viral DNA such as vaccinia, adenovirus, fowl pox virus, pseudorabies, adenovirus, adeno-associated virus, retroviruses, and many others. Any suitable vector that transduces genetic material into a cell, and, if replication is desired, which is replicable and viable in the relevant host finds use in the present invention. In some embodiments, the construct further comprises regulatory sequences, including but not limited to a promoter, operably linked to the protein encoding sequence. Large numbers of suitable vectors and promoters are known to those of skill in the art. Indeed, in some embodiments, in order to obtain high levels of expression in a particular host it is often useful to express the xylanase and/or xylosidases of the present invention under the control of a heterologous promoter. In some embodiments, a promoter sequence is operably linked to the 5' region of the xylanase and/or xylosidase coding sequence using any suitable method known in the art. Examples of useful promoters for expression of xylanase and/or xylosidases include, but are not limited to promoters from fungi. In some embodiments, a promoter sequence that drives expression of a gene other than a xylanase and/or xylosidase gene in a fungal strain finds use. As a non-limiting example, a fungal promoter from a gene encoding an endoglucanase may be used. In some embodiments, a promoter sequence that drives the expression of a xylanase and/or xylosidase gene in a fungal strain other than the fungal strain from which the xylanase and/or xylosidases were derived finds use. Examples of other suitable promoters useful for directing the transcription of the nucleotide constructs of the present invention in a filamentous fungal host cell include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (See e.g., Nunberg et al., Mol. Cell. Biol., 4:2306-2315 [1984]; Boel et al., EMBO J. 3:1581-85 [1984]; and European Patent Appln. 137280, all of which are incorporated herein by reference), and mutant, truncated, and hybrid promoters thereof. In a yeast host, useful promoters include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Additional useful promoters useful for yeast host cells are known in the art (See e.g., Romanos et al., Yeast 8:423-488 [1992], incorporated herein by reference). In addition, promoters associated with chitinase production in fungi find use in the present invention (See e.g., Blaiseau and Lafay, Gene 120243-248 [1992]; and Limon et al., Curr. Genet, 28:478-83 [1995], both of which are incorporated herein by reference).

In some embodiments, cloned xylanase and/or xylosidases of the present invention also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice finds use in the present invention. Exemplary transcription terminators for filamentous fungal host cells include, but are not limited to those obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease (See also, U.S. Pat. No. 7,399,627, incorporated herein by reference). In some embodiments, exemplary terminators for yeast host cells include those obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are well-known to those skilled in the art (See e.g., Romanos et al., Yeast 8:423-88 [1992]).

In some embodiments, a suitable leader sequence is part of a cloned xylanase and/or xylosidase sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice finds use in the present invention. Exemplary leaders for filamentous fungal host cells include, but are not limited to those obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

In some embodiments, the sequences of the present invention also comprise a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice finds use in the present invention. Exemplary polyadenylation sequences for filamentous fungal host cells include, but are not limited to those obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are known in the art (See e.g., Guo and Sherman, Mol Cell Biol., 15:5983-5990 [1995]).

In some embodiments, the expression vector of the present invention contains one or more selectable markers, which permit easy selection of transformed cells. A "selectable marker" is a gene, the product of which provides for biocide or viral resistance, resistance to antimicrobials or heavy metals, prototrophy to auxotrophs, and the like. Any suitable selectable markers for use in a filamentous fungal host cell find use in the present invention, including, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Additional markers useful in host cells such as *Aspergillus*, include but are not limited to the amdS and pyrG genes of *Aspergillus nidulans* or *Aspergillus oryzae* and the bar gene of *Streptomyces hygroscopicus*. Suitable markers for yeast host cells include, but are not limited to ADE2, HIS3, LEU2, LYS2, MET3, TRP1, and URA3.

In some embodiments, a vector comprising a sequence encoding at least one xylanase and/or xylosidase is transformed into a host cell in order to allow propagation of the vector and expression of the xylanase and/or xylosidase(s). In some embodiments, the xylanase and/or xylosidases are post-translationally modified to remove the signal peptide and in some cases may be cleaved after secretion. In some embodiments, the transformed host cell described above is cultured in a suitable nutrient medium under conditions permitting the expression of the xylanase and/or xylosidase(s). Any suitable medium useful for culturing the host cells finds use in the present invention, including, but not limited to minimal or complex media containing appropriate supplements. In some embodiments, host cells are grown in HTP media. Suitable media are available from various commercial suppliers or may be prepared according to published recipes (e.g., in catalogues of the American Type Culture Collection).

In some embodiments, the host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. In some embodiments, the fungal host cells are yeast cells and filamentous fungal cells. The filamentous fungal host cells of the present invention include all filamentous forms of the subdivision Eumycotina and Oomycota. Filamentous fungi are characterized by a vegetative mycelium with a cell wall composed of chitin, cellulose and other complex polysaccharides. The filamentous fungal host cells of the present invention are morphologically distinct from yeast.

In some embodiments of the present invention, the filamentous fungal host cells are of any suitable genus and species, including, but not limited to Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, and/or Volvariella, and/or teleomorphs, or anamorphs, and synonyms, basionyms, or taxonomic equivalents thereof.

In some embodiments of the present invention, the filamentous fungal host cell is of the Trichoderma species (e.g., T. longibrachiatum, T. viride [e.g., ATCC 32098 and 32086]), Hypocrea jecorina or T. reesei (NRRL 15709, ATTC 13631, 56764, 56765, 56466, 56767 and RL-P37 and derivatives thereof (See e.g., Sheir-Neiss et al., Appl. Microbiol. Biotechnol., 20:46-53 [1984]), T. koningii, and T. harzianum. In addition, the term "Trichoderma" refers to any fungal strain that was previously and/or currently classified as Trichoderma. In some embodiments of the present invention, the filamentous fungal host cell is of the Aspergillus species (e.g., A. awamori, A. fumigatus, A. japonicus, A. nidulans, A. niger, A. aculeatus, A. foetidus, A. oryzae, A. sojae, and A. kawachi, See e.g., Kelly and Hynes, EMBO J., 4:475-479 [1985]; NRRL 3112, ATCC 11490, 22342, 44733, and 14331; Yelton et al., Proc. Natl. Acad. Sci. USA, 81, 1470-1474 [1984]; Tilburn et al., Gene 26:205-221 [1982]; and Johnston, et al., EMBO J., 4:1307-1311 [1985]). In some embodiments of the present invention, the filamentous fungal host cell is a Chrysosporium species (e.g., C. lucknowense, C. keratinophilum, C. tropicum, C. merdarium, C. inops, C. pannicola, and C. zonatum). In some embodiments of the present invention, the filamentous fungal host cell is a Myceliophthora species (e.g., M. thermophila). In some embodiments of the present invention, the filamentous fungal host cell is a Fusarium species (e.g., F. bactridioides, F. cerealis, F. crookwellense, F. culmorum, F. graminearum, F. graminum. F. oxysporum, F. roseum, and F. venenatum). In some embodiments of the present invention, the filamentous fungal host cell is a Neurospora species (e.g., N. crassa; See e.g., Case et al., Proc. Natl. Acad. Sci. USA, 76:5259-5263 [1979]; U.S. Pat. No. 4,486,553; and Kinsey and Rambosek (1984) Mol. Cell. Biol., 4:117-122 [1984], all of which are hereby incorporated by reference). In some embodiments of the present invention, the filamentous fungal host cell is a Humicola species (e.g., H. insolens, H. grisea, and H. lanuginosa). In some embodiments of the present invention, the filamentous fungal host cell is a Mucor species (e.g., M. miehei and M. circinelloides). In some embodiments of the present invention, the filamentous fungal host cell is a Rhizopus species (e.g., R. oryzae and R. niveus.). In some embodiments of the invention, the filamentous fungal host cell is a Penicillium species (e.g., P. purpurogenum, P. chrysogenum, and P. verruculosum). In some embodiments of the invention, the filamentous fungal host cell is a Talaromyces species (e.g., T. emersonii, T. flavus, T. helicus, T. rotundus, and T. stipitatus). In some embodiments of the invention, the filamentous fungal host cell is a Thielavia species (e.g., T. terrestris and T. heterothallica). In some embodiments of the present invention, the filamentous fungal host cell is a Tolypocladium species (e.g., T. inflatum and T. geodes). In some embodiments of the present invention, the filamentous fungal host cell is a Trametes species (e.g., T. villosa and T. versicolor). In some embodiments of the present invention, the filamentous fungal host cell is a Sporotrichum species. In some embodiments of the present invention, the filamentous fungal host cell is a Corynascus species.

In some embodiments of the present invention, the host cell is a yeast cell, including but not limited to cells of Candida, Hansenula, Saccharomyces, Schizosaccharomyces, Pichia, Kluyveromyces, or Yarrowia species. In some embodiments of the present invention, the yeast cell is Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans, or Yarrowia lipolytica.

In some embodiments of the invention, the host cell is an algal cell such as Chlamydomonas (e.g., C. reinhardtii) and Phormidium (P. sp. ATCC29409).

In some other embodiments, the host cell is a prokaryotic cell. Suitable prokaryotic cells include, but are not limited to Gram-positive, Gram-negative and Gram-variable bacterial cells. Any suitable bacterial organism finds use in the present invention, including but not limited to Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechoccus, Thermococcus, Ureaplasma, Xanthomonas, Xylella, Yersinia and Zymomonas. In some embodiments, the host cell is a species of Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces, or Zymomonas. In some embodiments, the bacterial host strain is non-pathogenic to humans. In some embodiments the bacterial host strain is an industrial strain. Numerous bacterial industrial strains are known and suitable in the present invention. In some embodiments of the present invention, the bacterial host cell is an Agrobacterium species (e.g., A. radiobacter, A. rhizogenes, and A. rubi). In some embodiments of the present invention, the bacterial host cell is an Arthrobacter species (e.g., A. aurescens, A. citreus, A. globformis, A. hydrocarboglutamicus, A. mysorens, A. nicotianae, A. paraffineus, A. proto-

*phonniae, A. roseoparaffinus, A. sulfureus,* and *A. ureafaciens*). In some embodiments of the present invention, the bacterial host cell is a *Bacillus* species (e.g., *B. thuringensis, B. anthracis, B. megaterium, B. subtilis, B. lentus, B. circulans, B. pumilus, B. lautus, B. coagulans, B. brevis, B. firmus, B. alkaophius, B. licheniformis, B. clausii, B. stearothermophilus, B. halodurans,* and *B. amyloliquefaciens*). In some embodiments, the host cell is an industrial *Bacillus* strain including but not limited to *B. subtilis, B. pimilus, B. licheniformis, B. megaterium, B. clausii, B. stearothermophilus,* or *B. amyloliquefaciens*. In some embodiments, the *Bacillus* host cells are *B. subtilis, B. licheniformis, B. megaterium, B. stearothermophilus,* and/or *B. amyloliquefaciens*. In some embodiments, the bacterial host cell is a *Clostridium* species (e.g., *C. acetobutylicum, C. tetani* E88, *C. lituseburense, C. saccharobutylicum, C. perfringens,* and *C. beijerinckii*). In some embodiments, the bacterial host cell is a *Corynebacterium* species (e.g., *C. glutamicum* and *C. acetoacidophilum*). In some embodiments the bacterial host cell is a *Escherichia* species (e.g., *E. coli*). In some embodiments, the bacterial host cell is an *Erwinia* species (e.g., *E. uredovora, E. carotovora, E. ananas, E. herbicola, E. punctata,* and *E. terreus*). In some embodiments, the bacterial host cell is a *Pantoea* species (e.g., *P. citrea,* and *P. agglomerans*). In some embodiments the bacterial host cell is a *Pseudomonas* species (e.g., *P. putida, P. aeruginosa, P. mevalonii,* and P. sp. D-01 10). In some embodiments, the bacterial host cell is a *Streptococcus* species (e.g., *S. equisimiles, S. pyogenes,* and *S. uberis*). In some embodiments, the bacterial host cell is a *Streptomyces* species (e.g., *S. ambofaciens, S. achromogenes, S. avermitilis, S. coelicolor, S. aureofaciens, S. aureus, S. fungicidicus, S. griseus,* and *S. lividans*). In some embodiments, the bacterial host cell is a *Zymomonas* species (e.g., *Z. mobilis,* and *Z. lipolytica*).

Many prokaryotic and eukaryotic strains that find use in the present invention are readily available to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some embodiments, host cells are genetically modified to have characteristics that improve protein secretion, protein stability and/or other properties desirable for expression and/or secretion of a protein. For example, knockout of Alp1 function results in a cell that is protease deficient. Knockout of pyr5 function results in a cell with a pyrimidine deficient phenotype. In some embodiments, the host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by genetic engineering techniques and/or classical microbiological techniques (e.g., chemical or UV mutagenesis and subsequent selection). Indeed, in some embodiments, combinations of recombinant modification and classical selection techniques are used to produce the host cells. Using recombinant technology, nucleic acid molecules can be introduced, deleted, inhibited or modified, in a manner that results in increased yields of xylanase and/or xylosidase within the host cell and/or in the culture medium. For example, knockout of Alp1 function results in a cell that is protease deficient, and knockout of pyr5 function results in a cell with a pyrimidine deficient phenotype. In one genetic engineering approach, homologous recombination is used to induce targeted gene modifications by specifically targeting a gene in vivo to suppress expression of the encoded protein. In alternative approaches, siRNA, antisense and/or ribozyme technology find use in inhibiting gene expression.

In some embodiments, host cells (e.g., *Myceliophthora thermophila*) used for expression of xylanase and/or xylosidases have been genetically modified to reduce the amount of endogenous cellobiose dehydrogenase (EC 1.1.3.4) and/or other enzymes activity that is secreted by the cell. A variety of methods are known in the art for reducing expression of protein in cells, including, but not limited to deletion of all or part of the gene encoding the protein and site-specific mutagenesis to disrupt expression or activity of the gene product. (See e.g., Chaveroche et al., Nucl. Acids Res., 28:22 e97 [2000]; Cho et al., MPMI 19: 1:7-15 [2006]; Maruyama and Kitamoto, Biotechnol Lett, 30:1811-1817 [2008]; Takahashi et al., *Mol. Gen. Genom.,* 272: 344-352 [2004]; and You et al., Arch Micriobiol., 191:615-622 [2009], all of which are incorporated by reference herein). Random mutagenesis, followed by screening for desired mutations also finds use (See e.g., Combier et al., FEMS Microbiol Lett 220:141-8 [2003]; and Firon et al., Eukary. Cell 2:247-55 [2003], both of which are incorporated by reference). In some embodiments, the host cell is modified to reduce production of endogenous cellobiose dehydrogenases. In some embodiments, the cell is modified to reduce production of cellobiose dehydrogenase (e.g., CDH1 or CDH2). In some embodiments, the host cell has less than 75%, sometimes less than 50%, sometimes less than 30%, sometimes less than 25%, sometimes less than 20%, sometimes less than 15%, sometimes less than 10%, sometimes less than 5%, and sometimes less than 1% of the cellobiose dehydrogenase (e.g., CDH1 and/or CDH2) activity of the corresponding cell in which the gene is not disrupted. Exemplary *Myceliophthora thermophila* cellobiose dehydrogenases include, but are not limited to CDH1 and CDH2. The genomic sequence for the Cdh1 encoding CDH1 has accession number AF074951.1. In one approach, gene disruption is achieved using genomic flanking markers (See e.g., Rothstein, Meth. Enzymol., 101:202-11 [1983]). In some embodiments, site-directed mutagenesis is used to target a particular domain of a protein, in some cases, to reduce enzymatic activity (e.g., glucose-methanol-choline oxido-reductase N and C domains of a cellobiose dehydrogenase or heme binding domain of a cellobiose dehydrogenase; See e.g., Rotsaert et al., Arch. Biochem. Biophys., 390:206-14 [2001], which is incorporated by reference herein in its entirety).

Introduction of a vector or DNA construct into a host cell can be accomplished using any suitable method known in the art, including but not limited to calcium phosphate transfection, DEAE-Dextran mediated transfection, PEG-mediated transformation, electroporation, or other common techniques known in the art.

In some embodiments, the engineered host cells (i.e., "recombinant host cells") of the present invention are cultured in conventional nutrient media modified as appropriate for activating promoters, selecting transformants, or amplifying the cellobiohydrolase polynucleotide. Culture conditions, such as temperature, pH and the like, are those previously used with the host cell selected for expression, and are well-known to those skilled in the art. As noted, many standard references and texts are available for the culture and production of many cells, including cells of bacterial, plant, animal (especially mammalian) and archebacterial origin.

In some embodiments, cells expressing the xylanase and/or xylosidase polypeptides of the invention are grown under batch or continuous fermentations conditions. Classical "batch fermentation" is a closed system, wherein the compositions of the medium is set at the beginning of the fermentation and is not subject to artificial alternations during the fermentation. A variation of the batch system is a "fed-batch fermentation" which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. "Continuous fermentation" is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments of the present invention, cell-free transcription/translation systems find use in producing xylanase and/or xylosidase. Several systems are commercially available and the methods are well-known to those skilled in the art.

The present invention provides methods of making xylanase and/or xylosidase polypeptides or biologically active fragments thereof. In some embodiments, the method comprises: providing a host cell transformed with a polynucleotide encoding an amino acid sequence that comprises at least about 70% (or at least about 75%, at least about 80%, at least about 85%, at least about 90%, at least about 95%, at least about 96%, at least about 97%, at least about 98%, or at least about 99%) sequence identity to SEQ ID NO:2 and comprising at least one mutation as provided herein; culturing the transformed host cell in a culture medium under conditions in which the host cell expresses the encoded xylanase and/or xylosidase polypeptide; and optionally recovering or isolating the produced xylanase and/or xylosidase polypeptide, and/or recovering or isolating the culture medium containing the produced xylanase and/or xylosidase polypeptide. In some embodiments, the methods further provide optionally lysing the transformed host cells after expressing the encoded xylanase and/or xylosidase polypeptide and optionally recovering and/or isolating the produced xylanase and/or xylosidase polypeptide from the cell lysate. The present invention further provides methods of making a xylanase and/or xylosidase polypeptide comprising cultivating a host cell transformed with a xylanase and/or xylosidase polypeptide under conditions suitable for the production of the xylanase and/or xylosidase polypeptide and recovering the xylanase and/or xylosidase polypeptide. Typically, recovery or isolation of the xylanase and/or xylosidase polypeptide is from the host cell culture medium, the host cell or both, using protein recovery techniques that are well known in the art, including those described herein. In some embodiments, host cells are harvested by centrifugation, disrupted by physical or chemical means, and the resulting crude extract retained for further purification. Microbial cells employed in expression of proteins can be disrupted by any convenient method, including, but not limited to freeze-thaw cycling, sonication, mechanical disruption, and/or use of cell lysing agents, as well as many other suitable methods well known to those skilled in the art.

In some embodiments, the resulting polypeptide is recovered/isolated and optionally purified by any of a number of methods known in the art. For example, in some embodiments, the polypeptide is isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. In some embodiments, protein refolding steps are used, as desired, in completing the configuration of the mature protein. In addition, in some embodiments, high performance liquid chromatography (HPLC) is employed in the final purification steps. For example, in some embodiments, methods for purifying BGL known in the art, find use in the present invention (See e.g., Parry et al., Biochem. J., 353:117 [2001]; and Hong et al., Appl. Microbiol. Biotechnol., 73:1331 [2007], both incorporated herein by reference). Indeed, any suitable purification methods known in the art find use in the present invention.

In some embodiments, immunological methods are used to purify xylanase and/or xylosidase. In one approach, antibody raised against a xylanase and/or xylosidase polypeptide (e.g., against a polypeptide comprising any of SEQ ID NOS: 2, 3, 5, 6, 8, 9, 11, 13, 15, 16, 18, 19, 21, 22, 24, 25, 27, 28, 30, 31, 33, 34, 36, 37, 39, 40, 42, 43, 45, 46, 48, 49, 51, 52, 54, 55, 57, 59, 61, 63, and/or 65, and/or an immunogenic fragment thereof) using conventional methods is immobilized on beads, mixed with cell culture media under conditions in which the xylanase and/or xylosidase is bound, and precipitated. In a related approach, immunochromatography finds use.

In some embodiments, the xylanase and/or xylosidases are produced as a fusion protein including a non-enzyme portion. In some embodiments, the xylanase and/or xylosidase sequence is fused to a purification facilitating domain. As used herein, the term "purification facilitating domain" refers to a domain that mediates purification of the polypeptide to which it is fused. Suitable purification domains include, but are not limited to metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; See e.g., Wilson et al., Cell 37:767 [1984]), maltose binding protein sequences, the FLAG epitope utilized in the FLAGS extension/affinity purification system (e.g., the system available from Immunex Corp, Seattle, Wash.), and the like. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography; See e.g., Porath et al., Prot. Exp. Purif., 3:263-281 [1992]) while the enterokinase cleavage site provides a means for separating the xylanase and/or xylosidase polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

The xylanase and/or xylosidases and biologically active fragments thereof as described herein have multiple industrial applications, including but not limited to, sugar production (e.g., glucose syrups), biofuels production, textile treatment, pulp or paper treatment, bio-based chemical production, and applications in detergents and/or animal feed. A host cell containing at least one xylanase and/or xylosidase of the present invention finds use without recovery and purification of the recombinant xylanase and/or xylosidase(s) (e.g., for use in a large scale biofermentor). Alternatively, recombinant xylanase and/or xylosidases are produced and purified from the host cell.

The xylanase and/or xylosidases provided herein are particularly useful in methods used to break down cellulose to smaller oligosaccharides, disaccharides and monosaccharides. In some embodiments, the xylanase and/or xylosidases are used in saccharification methods. In some embodiments, the xylanase and/or xylosidases are used in combination with other cellulase enzymes in conventional enzymatic saccharification methods to produce fermentable sugars. In some embodiments, the present invention provides methods for producing at least one end-product from a cellulosic substrate, the methods comprising contacting the cellulosic substrate with at least one xylanase and/or xylosidase as described herein (and optionally other cellulases) under conditions in which fermentable sugars are produced. The fermentable sugars are then used in a fermentation reaction comprising a microorganism (e.g., a yeast) to produce at least one end-product. In some embodiments, the methods further comprise pretreating the cellulosic substrate to increase its susceptibility to hydrolysis prior to contacting the cellulosic substrate with at least one xylanase and/or xylosidase (and optionally other cellulases).

In some embodiments, enzyme compositions comprising at least one xylanase and/or xylosidase of the present invention are reacted with a biomass substrate in the range of about 25° C. to about 100° C., about 30° C. to about 90° C., about 30° C. to about 80° C., or about 30° C. to about 70° C. Also the biomass may be reacted with the enzyme compositions at about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. Generally the pH range will be from about pH 3.0 to about 8.5, about pH 3.5 to about 8.5, about pH 4.0 to about 7.5, about pH 4.0 to about 7.0 and about pH 4.0 to about 6.5. In some embodiments, the incubation time varies (e.g., from about 1.0 to about 240 hours, from about 5.0 to about 180 hrs and from about 10.0 to about 150 hrs). In some embodiments, the incubation time is at least about 1 hr, at least about 5 hrs, at least about 10 hrs, at least about 15 hrs, at least about 25 hrs, at least about 50 hr, at least about 100 hrs, at least about 180 hrs, etc. In some embodiments, incubation of the cellulase under these conditions and subsequent contact with the substrate results in the release of substantial amounts of fermentable sugars from the substrate (e.g., glucose when the cellulase is combined with β-glucosidase). For example, in some embodiments, at least about 20%, at least about 30%, at least about 40%, at least about 50%, at least about 60%, at least about 70%, at least about 80%, at least about 90% or more fermentable sugar is available as compared to the release of sugar by a reference enzyme.

In some embodiments, an "end-product of fermentation" is any product produced by a process including a fermentation step using a fermenting organism. Examples of end-products of a fermentation include, but are not limited to, alcohols (e.g., fuel alcohols such as ethanol and butanol), organic acids (e.g., citric acid, acetic acid, acrylic acid, lactic acid, gluconic acid, and succinic acid), glycerol, ketones, diols, amino acids (e.g., glutamic acid), antibiotics (e.g., penicillin and tetracycline), vitamins (e.g., beta-carotene and B12), hormones, and fuel molecules other than alcohols (e.g., hydrocarbons).

In some embodiments, the fermentable sugars produced by the methods of the present invention are used to produce at least one alcohol (e.g., ethanol, butanol, etc.). The xylanase and/or xylosidases of the present invention find use in any method suitable for the generation of alcohols or other biofuels from cellulose. It is not intended that the present invention be limited to the specific methods provided herein. Two methods commonly employed are separate saccharification and fermentation (SHF) methods (See e.g., Wilke et al., Biotechnol. Bioengin., 6:155-75 [1976]) and simultaneous saccharification and fermentation (SSF) methods (See e.g., U.S. Pat. Nos. 3,990,944 and 3,990,945). In some embodiments, the SHF saccharification method comprises the steps of contacting a cellulase with a cellulose containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol. In some embodiments, the method of consolidated bioprocessing (CBP) finds use, in which the cellulase production from the host is simultaneous with saccharification and fermentation either from one host or from a mixed cultivation. In addition, SSF methods find use in the present invention. In some embodiments, SSF methods provide a higher efficiency of alcohol production than that provided by SHF methods (See e.g., Drissen et al., Biocat. Biotrans., 27:27-35 [2009]).

In some embodiments, for cellulosic substances to be effectively used as substrates for the saccharification reaction in the presence of a cellulase of the present invention, it is desirable to pretreat the substrate. Means of pretreating a cellulosic substrate are well-known in the art, including but not limited to chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms), and the present invention is not limited by such methods.

In some embodiments, any suitable alcohol-producing microorganism known in the art (e.g., *Saccharomyces cerevisiae*), finds use in the present invention for the fermentation of fermentable sugars to alcohols and other end-products. The fermentable sugars produced from the use of the xylanase and/or xylosidase(s) provided by the present invention find use in the production of other end-products besides alcohols, including, but not limited to biofuels and/or biofuels compounds, acetone, amino acids (e.g., glycine, lysine, etc.), organic acids (e.g., lactic acids, etc.), glycerol, ascorbic acid, diols (e.g., 1,3-propanediol, butanediol, etc.), vitamins, hormones, antibiotics, other chemicals, and animal feeds. In addition, the xylanase and/or xylosidases provided herein further find use in the pulp and paper industry. Indeed, it is not intended that the present invention be limited to any particular end-products.

In some embodiments, the present invention provides an enzyme mixture that comprises at least one xylanase and/or xylosidase polypeptide as provided herein. The enzyme mixture may be cell-free, or in alternative embodiments, may not be separated from host cells that secrete an enzyme mixture component. A cell-free enzyme mixture typically comprises enzymes that have been separated from cells. Cell-free enzyme mixtures can be prepared by any of a variety of methodologies that are known in the art, such as filtration or centrifugation methodologies. In some embodiments, the enzyme mixtures are partially cell-free, substantially cell-free, or entirely cell-free.

In some embodiments, at least one xylanase and/or xylosidase and any additional enzymes present in the enzyme mixture are secreted from a single genetically modified fungal cell or by different microbes in combined or separate fermentations. Similarly, in additional embodiments, the xylanase and/or xylosidase(s) and any additional enzymes present in the enzyme mixture are produced individually or in sub-groups from different strains of different organisms and the enzymes are combined in vitro to make the enzyme mixture. It is also contemplated that the xylanase and/or xylosidase(s) and any additional enzymes in the enzyme mixture will be produced individually or in sub-groups from different strains of a single organism, and the enzymes combined to make the enzyme mixture. In some embodiments, all of the enzymes are produced from a single host organism, such as a genetically modified fungal cell.

In some embodiments, the enzyme mixture comprises at least one cellulase, selected from cellobiohydrolase (CBH), endoglucanase (EG), glycoside hydrolase 61 (GH61) and/or beta-glucosidase (BGL). In some embodiments, the cellobiohydrolase is *T. reesei* cellobiohydrolase II. In some embodiments, the endoglucanase comprises a catalytic domain derived from the catalytic domain of a *Streptomyces avermitilis* endoglucanase. In some embodiments, at least one cellulase is *Acidothermus cellulolyticus, Thermobifida fusca, Humicola grisea*, and/or a *Chrysosporium* sp. cellulase. Cellulase enzymes of the cellulase mixture work together in decrystallizing and hydrolyzing the cellulose from a biomass substrate to yield fermentable sugars, such as but not limited to glucose (See e.g., Brigham et al. in Wyman ([ed.], *Handbook on Bioethanol*, Taylor and Francis, Washington D.C. [1995], pp 119-141, incorporated herein by reference). Indeed, it is not intended that the present invention be limited to any enzyme compositions comprising any particular cellulase component(s), as various combinations of cellulases find use in the enzyme compositions of the present invention.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some embodiments, at least one xylanase and/or xylosidase polypeptide of the present invention is present in mixtures comprising enzymes other than cellulases that degrade cellulose, hemicellulose, pectin, and/or lignocellulose.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some additional embodiments, the present invention provides at least one xylanase and/or xylosidase and at least one endoxylanase. Endoxylanases (EC 3.2.1.8) catalyze the endohydrolysis of 1,4-β-D-xylosidic linkages in xylans. This enzyme may also be referred to as endo-1,4-β-xylanase or 1,4-β-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some additional embodiments, the present invention provides at least one xylanase and/or xylosidase and at least one alpha-L-arabinofuranosidase. Alpha-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some additional embodiments, the present invention provides at least one xylanase and/or xylosidase and at least one alpha-glucuronidase. Alpha-glucuronidases (EC 3.2.1.139) catalyze the hydrolysis of an alpha-D-glucuronoside to D-glucuronate and an alcohol.

In some additional embodiments, the present invention provides at least one xylanase and/or xylosidase and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some additional embodiments, the present invention provides at least one xylanase and/or xylosidase and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

In some additional embodiments, the present invention provides at least one xylanase and/or xylosidase and at least one coumaroyl esterase. Coumaroyl esterases (EC 3.1.1.73) catalyze a reaction of the form: coumaroyl-saccharide+ $H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

In some additional embodiments, the present invention provides at least one xylanase and/or xylosidase and at least one alpha-galactosidase. Alpha-galactosidases (EC 3.2.1.22) catalyze the hydrolysis of terminal, non-reducing α-D-galactose residues in α-D-galactosides, including galactose oligosaccharides, galactomannans, galactans and arabinogalactans. This enzyme may also be referred to as melibiase.

In some additional embodiments, the present invention provides at least one xylanase and/or xylosidase and at least one beta-galactosidase. Beta-galactosidases (EC 3.2.1.23) catalyze the hydrolysis of terminal non-reducing β-D-galactose residues in beta-D-galactosides. In some embodiments, the polypeptide is also capable of hydrolyzing alpha-L-arabinosides. This enzyme may also be referred to as exo-(1→4)-β-D-galactanase or lactase.

In some additional embodiments, the present invention provides at least one xylanase and/or xylosidase and at least one beta-mannanase. Beta-mannanases (EC 3.2.1.78) catalyze the random hydrolysis of 1,4-beta-D-mannosidic linkages in mannans, galactomannans and glucomannans. This enzyme may also be referred to as mannan endo-1,4-beta-mannosidase or endo-1,4-mannanase.

In some additional embodiments, the present invention provides at least one xylanase and/or xylosidase and at least one beta-mannosidase. Beta-mannosidases (EC 3.2.1.25) catalyze the hydrolysis of terminal, non-reducing beta-D-mannose residues in beta-D-mannosides. This enzyme may also be referred to as mannanase or mannase.

In some additional embodiments, the present invention provides at least one xylanase and/or xylosidase and at least one glucoamylase. Glucoamylases (EC 3.2.1.3) catalyzes the release of D-glucose from non-reducing ends of oligo- and polysaccharide molecules. Glucoamylase is also generally considered a type of amylase known as amylo-glucosidase.

In some additional embodiments, the present invention provides at least one xylanase and/or xylosidase and at least one amylase. Amylases (EC 3.2.1.1) are starch cleaving enzymes that degrade starch and related compounds by hydrolyzing the alpha-1,4 and/or alpha-1,6 glucosidic linkages in an endo- or an exo-acting fashion. Amylases include alpha-amylases (EC 3.2.1.1); beta-amylases (3.2.1.2), amylo-amylases (EC 3.2.1.3), alpha-glucosidases (EC 3.2.1.20), pullulanases (EC 3.2.1.41), and isoamylases (EC 3.2.1.68). In some embodiments, the amylase is an alpha-amylase.

In some embodiments one or more enzymes that degrade pectin are included in enzyme mixtures that comprise at least one xylanase and/or xylosidase of the present invention. A pectinase catalyzes the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some additional embodiments, the present invention provides at least one xylanase and/or xylosidase and at least one endo-polygalacturonase. Endo-polygalacturonases (EC 3.2.1.15) catalyze the random hydrolysis of 1,4-alpha-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-alpha-1,4-galacturonide glycanohydrolase, endogalacturonase; endo-D-galacturonase or poly(1,4-alpha-D-galacturonide) glycanohydrolase.

In some additional embodiments, the present invention provides at least one xylanase and/or xylosidase and at least one pectin methyl esterase. Pectin methyl esterases (EC 3.1.1.11) catalyze the reaction: pectin+n $H_2O$=n methanol+pectate. The enzyme may also been known as pectin esterase, pectin demethoxylase, pectin methoxylase, pectin methylesterase, pectase, pectinoesterase or pectin pectylhydrolase.

In some additional embodiments, the present invention provides at least one xylanase and/or xylosidase and at least one endo-galactanase. Endo-galactanases (EC 3.2.1.89) catalyze the endohydrolysis of 1,4-beta-D-galactosidic linkages in arabinogalactans. The enzyme may also be known as arabinogalactan endo-1,4-beta-galactosidase, endo-1,4-beta-galactanase, galactanase, arabinogalactanase or arabinogalactan 4-beta-D-galactanohydrolase.

In some additional embodiments, the present invention provides at least one xylanase and/or xylosidase and at least one pectin acetyl esterase. Pectin acetyl esterases catalyze the deacetylation of the acetyl groups at the hydroxyl groups of GalUA residues of pectin.

In some additional embodiments, the present invention provides at least one xylanase and/or xylosidase and at least one endo-pectin lyase. Endo-pectin lyases (EC 4.2.2.10) catalyze the eliminative cleavage of (1→4)-alpha-D-galacturonan methyl ester to give oligosaccharides with 4-deoxy-6-β-methyl-alpha-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-alpha-D-galacturonan lyase.

In some additional embodiments, the present invention provides at least one xylanase and/or xylosidase and at least one pectate lyase. Pectate lyases (EC 4.2.2.2) catalyze the eliminative cleavage of (1→4)-alpha-D-galacturonan to give oligosaccharides with 4-deoxy-alpha-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, alpha-1,4-D-endopolygalacturonic acid lyase, PGA lyase, PPase-N, endo-alpha-1,4-polygalacturonic acid lyase, polygalacturonic acid lyase, pectin trans-eliminase, polygalacturonic acid trans-eliminase or (1→4)-alpha-D-galacturonan lyase.

In some additional embodiments, the present invention provides at least one xylanase and/or xylosidase and at least one alpha-rhamnosidase. Alpha-rhamnosidases (EC 3.2.1.40) catalyze the hydrolysis of terminal non-reducing alpha-L-rhamnose residues in alpha-L-rhamnosides or alternatively in rhamnogalacturonan. This enzyme may also be known as alpha-L-rhamnosidase T, alpha-L-rhamnosidase N or alpha-L-rhamnoside rhamnohydrolase.

In some additional embodiments, the present invention provides at least one xylanase and/or xylosidase and at least one exo-galacturonase. Exo-galacturonases (EC 3.2.1.82) hydrolyze pectic acid from the non-reducing end, releasing digalacturonate. The enzyme may also be known as exo-poly-α-galacturonosidase, exopolygalacturonosidase or exopolygalacturanosidase.

In some additional embodiments, the present invention provides at least one xylanase and/or xylosidase and at least one exo-galacturan 1,4-alpha galacturonidase. Exo-galacturonases (EC 3.2.1.67) catalyze a reaction of the following type: (1,4-alpha-D-galacturoniden+H2O=(1,4-alpha-D-galacturonide)n-i+D-galacturonate. The enzyme may also be known as poly[1→4)alpha-D-galacturonide]galacturonohydrolase, exopolygalacturonase, poly(galacturonate)hydrolase, exo-D-galacturonase, exo-D-galacturonanase, exopoly-D-galacturonase or poly(1,4-alpha-D-galacturonide) galacturonohydrolase.

In some additional embodiments, the present invention provides at least one xylanase and/or xylosidase and at least one exopolygalacturonate lyase. Exopolygalacturonate lyases (EC 4.2.2.9) catalyze eliminative cleavage of 4-(4-deoxy-alpha-D-galact-4-enuronosyl)-D-galacturonate from the reducing end of pectate (i.e., de-esterified pectin). This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-alpha-D-galacturonan reducing-end-disaccharide-lyase.

In some additional embodiments, the present invention provides at least one xylanase and/or xylosidase and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some additional embodiments, the present invention provides at least one xylanase and/or xylosidase and at least one rhamnogalacturonan lyase. Rhamnogalacturonan lyases cleave alpha-L-Rhap-(1→4)-alpha-D-GalpA linkages in an endo-fashion in rhamnogalacturonan by beta-elimination.

In some additional embodiments, the present invention provides at least one xylanase and/or xylosidase and at least one rhamnogalacturonan acetyl esterase. Rhamnogalacturonan acetyl esterases catalyze the deacetylation of the backbone of alternating rhamnose and galacturonic acid residues in rhamnogalacturonan.

In some additional embodiments, the present invention provides at least one xylanase and/or xylosidase and at least one rhamnogalacturonan galacturonohydrolase. Rhamnogalacturonan galacturonohydrolases hydrolyze galacturonic acid from the non-reducing end of strictly alternating rhamnogalacturonan structures in an exo-fashion. This enzyme may also be known as xylogalacturonan hydrolase.

In some additional embodiments, the present invention provides at least one xylanase and/or xylosidase and at least one endo-arabinanase. Endo-arabinanases (EC 3.2.1.99) catalyze endohydrolysis of 1,5-alpha-arabinofuranosidic linkages in 1,5-arabinans. The enzyme may also be known as endo-arabinase, arabinan endo-1,5-alpha-L-arabinosidase, endo-1,5-alpha-L-arabinanase, endo-alpha-1,5-arabanase; endo-arabanase or 1,5-alpha-L-arabinan 1,5-alpha-L-arabinanohydrolase.

In some additional embodiments, the present invention provides at least one xylanase and/or xylosidase and at least one enzyme that participates in lignin degradation in an enzyme mixture. Enzymatic lignin depolymerization can be accomplished by lignin peroxidases, manganese peroxidases, laccases and cellobiose dehydrogenases (CDH), often working in synergy. These extracellular enzymes are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC).

In some additional embodiments, the present invention provides at least one xylanase and/or xylosidase and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some additional embodiments, the present invention provides at least one xylanase and/or xylosidase and at least one Mn-dependent peroxidase. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g., Glenn et al., Arch. Biochem. Biophys., 251:688-696 [1986]). Subsequently, phenolic substrates are oxidized by the $Mn^{3+}$ generated.

In some additional embodiments, the present invention provides at least one xylanase and/or xylosidase and at least one lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalyzed oxidation of lignin in vivo (See e.g., Harvey, et al., FEBS Lett., 195:242-246 [1986]).

In some additional embodiments, the present invention provides at least one xylanase and/or xylosidase and at least one protease, amylase, glucoamylase, and/or a lipase that participates in cellulose degradation.

As used herein, the term "protease" includes enzymes that hydrolyze peptide bonds (peptidases), as well as enzymes that hydrolyze bonds between peptides and other moieties, such as sugars (glycopeptidases). In some additional embodiments, the present invention provides at least one xylanase and/or xylosidase and at least one protease. Many proteases are characterized under EC 3.4, and are suitable for use in the present invention. Some suitable proteases include, but are not limited to cysteine proteases including pepsin, papain and serine proteases including chymotrypsins, carboxypeptidases and metal loendopeptidases.

As used herein, the term "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin. In some additional embodiments, the present invention provides at least one xylanase and/or xylosidase and at least one lipase.

In some additional embodiments, the present invention provides at least one xylanase and/or xylosidase and at least one expansin or expansin-like protein, such as a swollenin (See e.g., Salheimo et al., Eur. J. Biochem., 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without comprising hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some additional embodiments, the present invention provides at least one xylanase and/or xylosidase and at least one polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both of such domains.

In some additional embodiments, the present invention provides at least one xylanase and/or xylosidase and at least one cellulose induced protein or modulating protein, for example as encoded by cip1 or cip2 gene or similar genes from *Trichoderma reesei* (See e.g., Foreman et al., J. Biol. Chem., 278:31988-31997 [2003]).

In some additional embodiments, the present invention provides at least one xylanase and/or xylosidase and at least one member of each of the classes of the polypeptides described above, several members of one polypeptide class, or any combination of these polypeptide classes to provide enzyme mixtures suitable for various uses.

In some embodiments, the enzyme mixture comprises other types of cellulases, selected from but not limited to cellobiohydrolase, endoglucanase, beta-glucosidase, and glycoside hydrolase 61 protein (GH61) cellulases. These enzymes may be wild-type or recombinant enzymes. In some embodiments, the cellobiohydrolase is a type 1 cellobiohydrolase (e.g., a *T. reesei* cellobiohydrolase I). In some embodiments, the endoglucanase comprises a catalytic domain derived from the catalytic domain of a *Streptomyces avermitilis* endoglucanase (See e.g., US Pat. Appln. Pub. No. 2010/0267089, incorporated herein by reference). In some embodiments, the at least one cellulase is derived from *Acidothermus cellulolyticus, Thermobifida fusca, Humicola grisea, Myceliophthora thermophila, Chaetomium thermophilum, Acremonium* sp., *Thielavia* sp, *Trichoderma reesei, Aspergillus* sp., or a *Chrysosporium* sp. Cellulase enzymes in the cellulase mixtures work together resulting in decrystallization and hydrolysis of the cellulose from a biomass substrate to yield fermentable sugars, such as but not limited to glucose.

Some cellulase mixtures for efficient enzymatic hydrolysis of cellulose are known (See e.g., Viikari et al., Adv. Biochem. Eng. Biotechnol., 108:121-45 [2007]; and US Pat. Appln. Pubin. Nos. US 2009/0061484, US 2008/0057541, and US 2009/0209009, each of which is incorporated herein by reference in their entireties). In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, are combined with cellulosic feedstock or a product of cellulose hydrolysis.

In some embodiments, the enzyme mixture comprises commercially available purified cellulases. Commercial cellulases are known and available (e.g., C2730 cellulase from *Trichoderma reesei* ATCC No. 25921 available from Sigma-Aldrich, Inc.).

In some embodiments, the enzyme mixture comprises at least one xylanase and/or xylosidase as provided herein and at least one or more cellobiohydrolase type 1a such as a CBH1a, CBH2b, endoglucanase (EG) such as a type 2 endoglucanase (EG2) or type 1 endoglucane (EG 1), β-glucosidase (Bgl), and/or a glycoside hydrolase 61 protein (GH61). In some embodiments, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 35%, at least about 40%, at least about 45%, or at least about 50% of the enzyme mixture comprises at least one xylanase and/or xylosidase. In some embodiments, the enzyme mixture further comprises at least one cellobiohydrolase type 1 (e.g., CBH1a), cellobiohydrolase type 2 (e.g., CBH2b), and at least one xylanase and/or xylosidase, wherein the enzymes together comprise at least about 25%, at least about 30%, at least about 35%, at least about 40%, at least about 45%, at least about 50%, at least about 55%, at least about 60%, at least about 65%, at least about 70%, at least about 75%, or at least about 80% of the enzyme mixture. In some embodiments, the enzyme mixture further comprises at least one β-glucosidase (Bgl), at least one xylanase and/or xylosidase, CBH1a, and CBH2b, wherein the four/five enzymes together comprise at least about 30%, at least about 35%, at least about 40%, at least about 45%, at least about 50%, at least about 55%, at least about 60%, at least about 65%, at least about 70%, at least about 75%, at least about 80%, or at least about 85% of the enzyme mixture.

In some embodiments, the enzyme mixture further comprises at least one additional endoglucanase (e.g., EG2 and/or EG1), xylanase and/or xylosidase, CBH2b, CBH1a, and/or Bgl, wherein the five enzymes together comprise at least about 35%, at least about 40%, at least about 45%, at least about 50%, at least about 55%, at least about 60%, at least about 65%, at least about 70%, at least about 75%, at least about 80%, at least about 85%, or at least about 90% of the enzyme mixture.

In some embodiments, the enzyme mixture comprises at least one or a combination of xylanase and/or xylosidase, CBH2b, CBH1a, Bgl, EG2, EG1, and/or glycoside hydrolase 61 protein (GH61), in any suitable proportion for the desired reaction. In some embodiments, the enzyme mixture composition comprises isolated cellulases in the following proportions by weight (wherein the total weight of the cellulases is 100%): about 20% to about 5% of xylanase and/or xylosidase, about 20% to about 10% of Bgl, about 30% to about 15% of CBH1a, about 50% to about 0% of GH61, and about 10% to about 25% of CBH2b. In some embodiments, the enzyme mixture composition comprises isolated cellulases in the following proportions by weight: about 20% to about 10% of xylanase and/or xylosidase, about 25% to about 15% of Bgl, about 20% to about 30% of CBH1a, about 10% to about 15% of GH61, and about 25% to about 30% of CBH2b. In some embodiments, the enzyme mixture composition comprises isolated cellulases in the following proportions by weight: about 10% to about 15% of xylanase and/or xylosidase, about 20% to about 25% of Bgl, about 30% to about 20% of CBH1a, about 15% to about 5% of GH61, and about 25% to about 35% of CBH2b. In some embodiments, the enzyme mixture composition comprises isolated cellulases in the following proportions by weight: about 15% to about 5% of xylanase and/or xylosidase, about 15% to about 10% of Bgl, about 45% to about 30% of CBH1a, about 25% to about 5% of GH61, and about 40% to about 10% of CBH2b. In some embodiments, the enzyme mixture composition comprises isolated cellulases in the following proportions by weight: about 10% of xylanase and/or xylosidase, about 15% of Bgl, about 40% of CBH1a, about 25% of GH61, and about 10% of CBH2b. In some embodiments, the enzyme mixture comprises isolated cellulases in the following proportions by weight: about 12% xylanase and/or xylosidase, about 33% GH61, about 10% Bgl, about 22% CBH1a, and about 23% CBH2b/EG2. In some other embodiments, the enzyme mixture comprises cellulases in the following proportions by weight: about 9% xylanase and/or xylosidase, about 9% EG2, about 28% GH61, about 10% about BGL1, about 30% CBH1a, and about 14% CBH2b. In some further embodiments, the enzyme mixture comprises cellulases in the following proportions: about 2% to about 100% xylanase and/or xylosidase, about 0% to about 35% Bgl, about 0% to about 75% CBH1 (i.e., CBH1a and/or b), about 0% to about 75% CBH2 (i.e., CBH2a and/or CBH2b), about 0% to about 50% EG (i.e., EG2 and/or EG1, etc.), and/or about 0% to about 50% GH61 (i.e., GH61a, etc.). In some additional embodiments, the enzyme compositions comprise further enzymes.

In some embodiments, additional enzymes, such as other cellulases, esterases, amylases, proteases, glucoamylases, etc., are included in the enzyme mixtures. Indeed, it is not intended that the present invention be limited to any particular enzyme composition and/or any particular additional enzymes, as any suitable enzyme and/or composition find use in the present invention. It is also not intended that the present invention be limited to any particular combinations nor proportions of cellulases in the enzyme mixture, as any suitable combinations of cellulases and/or proportions of cellulases find use in various embodiments of the invention. In addition to the use of a single xylanase and/or xylosidase, any combination of xylanase and/or xylosidases provided herein find use in these embodiments.

In some embodiments, the enzyme component comprises more than one CBH2b, CBH1a, EG, Bgl, and/or GH61 enzyme (e.g., 2, 3 or 4 different variants of one or more of these enzymes) in addition to at least one xylanase and/or xylosidase, in any suitable combination. In some embodiments, an enzyme mixture composition of the invention further comprises at least one additional protein and/or enzyme. In some embodiments, enzyme mixture compositions of the present invention further comprise at least one additional enzyme other than Bgl, CBH1a, GH61, and/or CBH2b. In some embodiments, the enzyme mixture compositions of the invention further comprise at least one additional cellulase, other than the xylanase and/or xylosidase, EG2, EG1, Bgl, CBH1a, GH61, and/or CBH2b recited herein. In some embodiments, the xylanase and/or xylosidase polypeptide of the invention is also present in mixtures with non-cellulase enzymes that degrade cellulose, hemicellulose, pectin, and/or lignocellulose.

In some embodiments, xylanase and/or xylosidase polypeptide of the present invention is used in combination with other optional ingredients such as at least one buffer, surfactant, and/or scouring agent. In some embodiments, at least one buffer is used with the xylanase and/or xylosidase polypeptide of the present invention (optionally combined with other enzymes) to maintain a desired pH within the solution in which the xylanase and/or xylosidase is employed. The exact concentration of buffer employed depends on several factors which the skilled artisan can determine. Suitable buffers are well known in the art. In some embodiments, at least one surfactant is used in with the xylanase and/or xylosidase(s) of the present invention. Suitable surfactants include any surfactant compatible with the xylanase and/or xylosidase(s) and, optionally, with any other enzymes being used in the mixture. Exemplary surfactants include anionic, non-ionic, and ampholytic surfactants. Indeed, it indeed that any suitable surfactant will find use in the present invention. Suitable anionic surfactants include, but are not limited to, linear or branched alkylbenzenesulfonates; alkyl or alkenyl ether sulfates comprising linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines comprising from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants also find use in the present invention, as is known in the art.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar); uM and μM (micromolar); nM (nanomolar); mol (moles); gm and g (gram); mg (milligrams); ug and ng (micrograms); L and l (liter); ml and mL (milliliter); ul, uL, μL, and μl (microliter); cm (centimeters); mm (millimeters); um and nm (micrometers); sec. and """ (i.e., quote symbol) (seconds); min(s) and "'" (i.e., an apostrophe) (minute(s)); h(s) and hr(s) (hour(s)); U (units); MW (molecular weight); rpm (rotations per minute); rt (room temperature); ° C. (degrees Centigrade); DNA (deoxyribonucleic acid); RNA (ribonucleic acid); HPLC (high pressure liquid chromatography); MES (2-N-morpholino ethanesulfonic acid); Calbiochem (Calbiochem, available from EMD Millipore Corp., Billerica, Mass.); Finnzymes (Finnzymes, part of Thermo Fisher Scientific, Lafayette, Colo.); NEB (New England Biolabs, Ipswich, Mass.); Megazyme (Megazyme International Ireland, Ltd., Wicklow, Ireland); Sigma-Aldrich (Sigma-Aldrich, St. Louis, Mo.); Infors (Infors AG, Bottminger/Basel, Switzerland); Difco (Difco Laboratories, BD Diagnostic Systems, Detroit, Mich.); KapaBiosystems (KapaBiosystems, Inc., Woburn, Mass.); Stratagene (Stratagene, now an Agilent Technologies company); Agilent (Agilent Technologies, Inc., Santa Clara, Calif.); Molecular Devices (Molecular Devices, Sunnyvale, Calif.); Symbio (Symbio, Inc., Menlo Park, Calif.); USBio (US Biological, Swampscott, Mass.); Qiagen (Qiagen Inc., Germantown, Md.); and Bio-Rad (Bio-Rad Laboratories, Hercules, Calif.).

Various culture media find use in the present invention. Indeed, any suitable media known in the art for growing filamentous fungi such as *M. thermophila* find use (See e.g., Berka et al., Nat. Biotechnol., 29:922-927 [2011]).

Strain CF-417 is a derivative of C1 strain (UV18#100f Δalp1 Δpyr5 Δku70::pyr5 Δcdh1 Δcdh2) further modified with an insertion of variant bgl1. Strain CF-418 is a derivative of CF-417, further modified by insertion of wild-type *M. thermophila* GH61a enzyme. Strain CF-419 a derivative of CF-417, further modified by deletion of an endogenous protease.

Wild-type xylanase Xyl5 cDNA (SEQ ID NO:1) and amino acid (SEQ ID NO:2) sequences are provided below. SEQ ID NO:3 provides the sequence of xylanase Xyl5, without the signal sequence. Wild-type beta-xylosidase BXyl7 cDNA (SEQ ID NO:4) and amino acid (SEQ ID NO:5) sequences are provided below. SEQ ID NO:6 provides the sequence of beta-xylosidase BXyl7, without the signal sequence. cDNA (SEQ ID NO:7) and polypeptide (SEQ ID NO:8) of a wild-type beta-xylosidase "BXyl8 WT1" are provided below. SEQ ID NO:9 provides the sequence of beta-xylosidase BXyl8 WT1, without the signal sequence. SEQ ID NOS:10 and 11 provide the cDNA sand polypeptide sequences of another wild-type beta-xylosidase "BXyl8 WT2." SEQ ID NOS:12 and 13 provide polynucleotide and polypeptide sequences (respectively) of a cloned beta-xylosidase ("Bxyl8-233"). All of the sequences below are *M. thermophila* sequences.

Beta-xylanase Xy15:

(SEQ ID NO: 1)
ATGGTTACCCTCACTCGCCTGGCGGTCGCCGCGGCGGCCATGATCTCCAGCACTGGCCTGGC

TGCCCCGACGCCCGAAGCTGGCCCCGACCTTCCCGACTTTGAGCTCGGGGTCAACAACCTCG

CCCGCCGCGCGCTGGACTACAACCAGAACTACAGGACCAGCGGCAACGTCAACTACTCGCC

CACCGACAACGGCTACTCGGTCAGCTTCTCCAACGCGGGAGATTTTGTCGTCGGGAAGGGCT

GGAGGACGGGAGCCACCAGAAACATCACCTTCTCGGGATCGACACAGCATACCTCGGGCAC

CGTGCTCGTCTCCGTCTACGGCTGGACCCGGAACCCGCTGATCGAGTACTACGTGCAGGAGT

ACACGTCCAACGGGGCCGGCTCCGCTCAGGGCGAGAAGCTGGGCACGGTCGAGAGCGACGG

GGGCACGTACGAGATCTGGCGGCACCAGCAGGTCAACCAGCCGTCGATCGAGGGCACCTCG

ACCTTCTGGCAGTACATCTCGAACCGCGTGTCCGGCCAGCGGCCCAACGGCGGCACCGTCAC

CCTCGCCAACCACTTCGCCGCCTGGCAGAAGCTCGGCCTGAACCTGGGCCAGCACGACTACC

AGGTCCTGGCCACCGAGGGCTGGGGCAACGCCGGCGGCAGCTCCCAGTACACCGTCAGCGGC (SEQ ID NO: 2)
MVTLTRLAVAAAAMISSTGLAAPTPEAGPDLPDFELGVNNLARRALDYNQNYRTSGNVNYSPT

DNGYSVSFSNAGDFVVGKGWRTGATRNITFSGSTQHTSGTVLVSVYGWTRNPLIEYYVQEYTSN

GAGSAQGEKLGTVESDGGTYEIWRHQQVNQPSIEGTSTFWQYISNRVSGQRPNGGTVTLANHFA

AWQKLGLNLGQHDYQVLATEGWGNAGGSSQYTVSG (SEQ ID NO: 3)
APTPEAGPDLPDFELGVNNLARRALDYNQNYRTSGNVNYSPTDNGYSVSFSNAGDFVVGKGWR

TGATRNITFSGSTQHTSGTVLVSVYGWTRNPLIEYYVQEYTSNGAGSAQGEKLGTVESDGGTYEI

WRHQQVNQPSIEGTSTFWQYISNRVSGQRPNGGTVTLANHFAAWQKLGLNLGQHDYQVLATE

GWGNAGGSSQYTVSG

Beta-xylosidase BXy17:

(SEQ ID NO: 4)
ATGTTCTTCGCTTCTCTGCTGCTCGGTCTCCTGGCGGGCGTGTCCGCTTCACCGGGACACGGG

CGGAATTCCACCTTCTACAACCCCATCTTCCCCGGCTTCTACCCCGATCCGAGCTGCATCTAC

GTGCCCGAGCGTGACCACACCTTCTTCTGTGCCTCGTCGAGCTTCAACGCCTTCCCGGGCATC

CCGATTCATGCCAGCAAGGACCTGCAGAACTGGAAGTTGATCGGCCATGTGCTGAATCGCA

AGGAACAGCTTCCCCGGCTCGCTGAGACCAACCGGTCGACCAGCGGCATCTGGGCACCCAC

CCTCCGGTTCCATGACGACACCTTCTGGTTGGTCACCACACTAGTGGACGACGACCGGCCGC

AGGAGGACGCTTCCAGATGGGACAATATTATCTTCAAGGCAAAGAATCCGTATGATCCGAG

GTCCTGGTCCAAGGCCGTCCACTTCAACTTCACTGGCTACGACACGGAGCCTTTCTGGGACG

AAGATGGAAAGGTGTACATCACCGGCGCCCATGCTTGGCATGTTGGCCCATACATCCAGCAG

GCCGAAGTCGATCTCGACACGGGGGCCGTCGGCGAGTGGCGCATCATCTGGAACGGAACGG

GCGGCATGGCTCCTGAAGGGCCGCACATCTACCGCAAAGATGGGTGGTACTACTTGCTGGCT

GCTGAAGGGGGGACCGGCATCGACCATATGGTGACCATGGCCCGGTCGAGAAAAATCTCCA

GTCCTTACGAGTCCAACCCAAACAACCCCGTGTTGACCAACGCCAACACGACCAGTTACTTT

CAAACCGTCGGGCATTCAGACCTGTTCCATGACAGACATGGGAACTGGTGGGCAGTCGCCCT

CTCCACCCGCTCCGGTCCAGAATATCTTCACTACCCCATGGGCCGCGAGACCGTCATGACAG

CCGTGAGCTGGCCGAAGGACGAGTGGCCAACCTTCACCCCCATATCTGGCAAGATGAGCGG

CTGGCCGATGCCTCCTTCGCAGAAGGACATTCGCGGAGTCGGCCCCTACGTCAACTCCCCCG

ACCCGGAACACCTGACCTTCCCCCGCTCGGCGCCCCTGCCGGCCCACCTCACCTACTGGCGA

TACCCGAACCCGTCCTCCTACACGCCGTCCCCGCCCGGGCACCCCAACACCCTCCGCCTGAC

-continued

```
CCCGTCCCGCCTGAACCTGACCGCCCTCAACGGCAACTACGCGGGGGCCGACCAGACCTTCG

TCTCGCGCCGGCAGCAGCACACCCTCTTCACCTACAGCGTCACGCTCGACTACGCGCCGCGG

ACCGCCGGGGAGGAGGCCGGCGTGACCGCCTTCCTGACGCAGAACCACCACCTCGACCTGG

GCGTCGTCCTGCTCCCTCGCGGCTCCGCCACCGCGCCCTCGCTGCCGGGCCTGAGTAGTAGT

ACAACTACTACTAGTAGTAGTAGTAGTCGTCCGGACGAGGAGGAGGAGCGCGAGGCGGGCG

AAGAGGAAGAAGAGGGCGGACAAGACTTGATGATCCCGCATGTGCGGTTCAGGGGCGAGTC

GTACGTGCCCGTCCCGGCGCCCGTCGTGTACCCGATACCCCGGGCCTGGAGAGGCGGGAAG

CTTGTGTTAGAGATCCGGGCTTGTAATTCGACTCACTTCTCGTTCCGTGTCGGGCCGGACGGG

AGACGGTCTGAGCGGACGGTGGTCATGGAGGCTTCGAACGAGGCCGTTAGCTGGGGCTTTA

CTGGAACGCTGCTGGGCATCTATGCGACCAGTAATGGTGGCAACGGAACCACGCCGGCGTA

TTTTTCGGATTGGAGGTACACACCATTGGAGCAGTTTAGGGAT
```

(SEQ ID NO: 5)
```
MFFASLLLGLLAGVSASPGHGRNSTFYNPIFPGFYPDPSCIYVPERDHTFFCASSSFNAFPGIPIHAS

KDLQNWKLIGHVLNRKEQLPRLAETNRSTSGIWAPTLRFHDDTFWLVTTLVDDDRPQEDASRW

DNIIFKAKNPYDPRSWSKAVHFNFTGYDTEPFWDEDGKVYITGAHAWHVGPYIQQAEVDLDTG

AVGEWRIIWNGTGGMAPEGPHIYRKDGWYYLLAAEGGTGIDHMVTMARSRKISSPYESNPNNP

VLTNANTTSYFQTVGIISDLFHDRHGNWWAVALSTRSGPEYLHYPMGRETVMTAVSWPKDEWP

TFTPISGKMSGWPMPPSQKDIRGVGPYVNSPDPEHLTFPRSAPLPAHLTYWRYPNPSSYTPSPPGH

PNTLRLTPSRLNLTALNGNYAGADQTFVSRRQQHTLFTYSVTLDYAPRTAGEEAGVTAFLTQNH

HLDLGVVLLPRGSATAPSLPGLSSSTTTTSSSSSRPDEEEEREAGEEEEEGGQDLMIPHVRFRGESY

VPVPAPVVYPIPRAWRGGKLVLEIRACNSTHFSFRVGPDGRRSERTVVMEASNEAVSWGFTGTL

LGIYATSNGGNGTTPAYFSDWRYTPLEQFRD
```

(SEQ ID NO: 6)
```
SPGHGRNSTFYNPIFPGFYPDPSCIYVPERDHTFFCASSSFNAFPGIPIHASKDLQNWKLIGHVLNR

KEQLPRLAETNRSTSGIWAPTLRFHDDTFWLVTTLVDDDRPQEDASRWDNIIFKAKNPYDPRSW

SKAVHFNFTGYDTEPFWDEDGKVYITGAHAWHVGPYIQQAEVDLDTGAVGEWRIIWNGTGGM

APEGPHIYRKDGWYYLLAAEGGTGIDHMVTMARSRKISSPYESNPNNPVLTNANTTSYFQTVGH

SDLFHDRHGNWWAVALSTRSGPEYLHYPMGRETVMTAVSWPKDEWPTFTPISGKMSGWPMPP

SQKDIRGVGPYVNSPDPEHLTFPRSAPLPAHLTYWRYPNPSSYTPSPPGHPNTLRLTPSRLNLTAL

NGNYAGADQTFVSRRQQHTLFTYSVTLDYAPRTAGEEAGVTAFLTQNHELDLGVVLLPRGSAT

APSLPGLSSSTTTTSSSSSRPDEEEEREAGEEEEEGGQDLMIPHVRFRGESYVPVPAPVVYPIPRAW

RGGKLVLEIRACNSTHFSFRVGPDGRRSERTVVMEASNEAVSWGFTGTLLGIYATSNGGNGTTP

AYFSDWRYTPLEQFRD
```

Beta-xylosidase BXy18 WT1:

(SEQ ID NO: 7)
```
ATGAAGGCCTCTGTATCATGCCTCGTCGGCATGAGCGCCGTGGCCTACGGCCTCGATGGCCC

TTTCCAGACCTACCCCGACTGCACCAAGCCCCCCCTGTCCGATATTAAGGTGTGCGACCGGA

CACTGCCCGAGGCGGAGCGGGCGGCAGCCCTCGTGGCAGCCCTGACCGACGAGGAGAAGCT

GCAAAACCTGGTCAGCAAGGCGCCGGGGGCGCCGCGGATCGGCCTGCCCGCGTACAACTGG

TGGAGCGAGGCGCTGCACGGGGTGGCCCACGCGCCCGGGACGCAGTTCCGCGACGGGCCGG

GGGACTTCAACTCGTCCACGTCGTTCCCGATGCCGCTGCTGATGGCCGCCGCCTTCGACGAC

GAGCTGATCGAGGCCGTCGGCGACGTCATCGGCACCGAGGCCCGCGCCTTTGGCAACGCCG
```

-continued

```
GCTGGTCCGGCCTCGACTACTGGACCCCCAACGTCAACCCCTTCCGGGACCCCCGCTGGGC
CGCGGCTCCGAGACGCCGGGCGAGGACGTCGTGCGCCTCAAGCGCTACGCCGCCTCCATGA
TCCGCGGGCTCGAGGGTCGTTCCTCCTCCTCCTCCTCCTGCTCCTTCGGATCCGGAGGGAGC
CGCCGCGCGTCATCTCGACCTGCAAGCACTACGCCGGCAACGACTTTGAGGACTGGAACGG
CACGACGCGGCACGACTTCGACGCCGTCATCTCGGCGCAGGACCTGGCCGAGTACTACCTGG
CGCCGTTCCAGCAGTGCGCGCGCGACTCGCGCGTCGGCTCCGTCATGTGCGCCTACAACGCC
GTCAACGGGGTGCCGTCGTGCGCCAACTCGTACCTCATGAACACGATCCTGCGCGGGCACTG
GAACTGGACCGAGCACGACAACTACGTCACCAGCGACTGCGAGGCCGTCCTCGACGTCTCG
GCCCACCACCACTACGCCGACACCAACGCCGAGGGCACCGGCCTCTGCTTCGAGGCCGGCA
TGGACACGAGCTGCGAGTACGAGGGCTCCTCCGACATCCCGGGCGCCTCCGCCGGCGGCTTC
CTGACCTGGCCCGCCGTCGACCGCGCCCTGACGCGGCTGTACCGGAGCCTGGTGCGGGTCGG
CTACTTTGACGGCCCCGAGTCGCCGCACGCCTCGCTGGGCTGGGCCGACGTCAACCGGCCCG
AGGCGCAGGAGCTGGCCCTGCGCGCTGCCGTCGAGGGCATCGTGCTGCTCAAGAACGACAA
CGACACGCTGCCGCTGCCGCTGCCGGACGATGTCGTTGTCACCGCTGATGGTGGCCGCCGCC
GCGTCGCCATGATCGGCTTCTGGGCCGACGCCCCGGACAAGCTGTTTGGCGGGTACAGCGGC
GCGCCCCCTTCGCGCGCTCGCCCGCGAGCGCCGCCCGGCAGCTGGGCTGGAACGTCACGGT
CGCCGGAGGGCCCGTCCTGGAGGGAGACTCGGACGAGGAGGAGGACACGTGGACGGCGCC
GGCCGTCGAGGCGGCCGCCGACGCCGACTACATCGTCTACTTTGGCGGCCTGGACACGTCGG
CGGCGGGCGAGACCAAGGACCGGATGACGATCGGGTGGCCGGCGGCGCAGCTGGCGCTCAT
CTCGGAGCTGGCGCGGCTCGGCAAGCCCGTCGTGGTGGTGCAGATGGGCGACCAGCTCGAC
GACACGCCCCTCTTCGAGCTGGACGGGGTGGGCGCCGTCCTGTGGGCCAACTGGCCGGGCC
AGGACGGCGGCACGGCCGTGGTCCGGCTGCTCAGCGGCGCCGAGAGCCCGGCCGGCCGCCT
GCCCGTGACCCAGTACCCGGCCAACTACACCGACGCGGTGCCCCTGACCGACATGACCCTGC
GCCCGTCGGCGACCAACCCGGGCCGGACCTACCGCTGGTACCCGACTCCCGTCCGGCCCTTC
GGCTTCGGCCTCCACTATACCACCTTCCGGGCCGAGTTCGGCCCCCACCCCTTCTTCCCGGGG
GCGGGCAAGGGCGATGGCGACGGCGAGGACAAGGGCGAGAGCAAGAGCGAGATCAGGACG
CAGCAGCAGCAACAGCAGCAGCAGCAGCGCAGGGCGGCGGCGGCGGCCACCACGCCG
ATCCGGGACCTGCTCCGCGACTGCGACAAGACGTACCCGGACACGTGCCCGCTGCCGCCGCT
GACGGTGCGCGTGACCAACGAGGGCGAGCGCGCGTCCGACTACGTGGTGCTGGCCTTCGTG
TCGGGCGAGTACGGGCCGGCGCCGTACCCGATCAAGACGCTGGTCTCGTACGCGCGGGCGC
GCGGGCTAAAGGGGAAGGGCGGGACGGGCGCCGGCGACGGCGACGTCGCCACCACTACCG
TCTCGCTCGACTGGACCGTCGGCAACCTGGCCCGCCACGACGAGCGCGGCAACACAATCCTG
TACCCGGGAACTTACACCCTCACTCTCGACGAGCCGGCCCAGGCGAGCGTGCAGTTCGCCCT
CGAGGGCGAGCCCGTCGTGCTCGACGAGTGGCCTGCGCCGCCGAGTGCCAACTCCACCGCC
AGGGGGAGGCACAGG
```

(SEQ ID NO: 8)
```
MKASVSCLVGMSAVAYGLDGPFQTYPDCTKPPLSDIKVCDRTLPEAERAAALVAALTDEEKLQ
NLVSKAPGAPRIGLPAYNWWSEALHGVAHAPGTQFRDGPGDENSSTSFPMPLLMAAAFDDELIE
AVGDVIGTEARAFGNAGWSGLDYWTPNVNPFRDPRWGRGSETPGEDVVRLKRYAASMIRGLE
GRSSSSSSCSFGSGGEPPRVISTCKHYAGNDFEDWNGTTRHDFDAVISAQDLAEYYLAPFQQCAR
DSRVGSVMCAYNAVNGVPSCANSYLMNTILRGHWNWTEHDNYVTSDCEAVLDVSAHHHYAD
```

-continued

TNAEGTGLCFEAGMDTSCEYEGSSDIPGASAGGELTWPAVDRALTRLYRSLVRVGYEDGPESPH
ASLGWADVNRPEAQELALRAAVEGIVLLKNDNDTLPLPLPDDVVVTADGGRRRVAMIGFWAD
APDKLFGGYSGAPPFARSPASAARQLGWNVTVAGGPVLEGDSDEEEDTWTAPAVEAAADADYI
VYFGGLDTSAAGETKDRMTIGWPAAQLALISELARLGKPVVVVQ1VIGDQLDDTPLFELDGVGAV
LWANWPGQDGGTAVVRLLSGAESPAGRLPVTQYPANYTDAVPLTDMTLRPSATNPGRTYRWY
PTPVRPFGEGLHYTTFRAEFGPHPFFPGAGKGDGDGEDKGESKSEIRTQQQQQQQQQQRRAAAA
ATTPIRDLLRDCDKTYPDTCPLPPLTVRVTNEGERASDYVVLAFVSGEYGPAPYPIKTLVSYARA
RGLKGKGGTGAGDGDVATTTVSLDWTVGNLARHDERGNTILYPGTYTLTLDEPAQASVQFALE
GEPVVLDEWPAPPSANSTARGRHR (SEQ ID NO: 9)
LDGPFQTYPDCTKPPLSDIKVCDRTLPEAERAAALVAALTDEEKLQNLVSKAPGAPRIGLPAYNW
WSEALHGVAHAPGTQFRDGPGDFNSSTSFPMPLLMAAAFDDELIEAVGDVIGTEARAFGNAGW
SGLDYWTPNVNPFRDPRWGRGSETPGEDVVRLKRYAASMIRGLEGRSSSSSSCSFGSGGEPPRVI
STCKHYAGNDFEDWNGTTRHDFDAVISAQDLAEYYLAPFQQCARDSRVGSVMCAYNAVNGVP
SCANSYLMNTILRGHWNWTEHDNYVTSDCEAVLDVSAHHHYADTNAEGTGLCFEAGMDTSCE
YEGSSDIPGASAGGFLTWPAVDRALTRLYRSLVRVGYEDGPESPHASLGWADVNRPEAQELALR
AAVEGIVLLKNDNDTLPLPLPDDVVVTADGGRRRVAMIGFWADAPDKLFGGYSGAPPFARSPAS
AARQLGWNVTVAGGPVLEGDSDEEEDTWTAPAVEAAADADYIVYFGGLDTSAAGETKDRMTI
GWPAAQLALISELARLGKPVVVVQMGDQLDDTPLFELDGVGAVLWANWPGQDGGTAVVRLLS
GAESPAGRLPVTQYPANYTDAVPLTDMTLRPSATNPGRTYRWYPTPVRPFGEGLHYTTFRAEFG
PHPFFPGAGKGDGDGEDKGESKSEIRTQQQQQQQQQQRRAAAAATTPIRDLLRDCDKTYPDTCP
LPPLTVRVTNEGERASDYVVLAFVSGEYGPAPYPIKTLVSYARARGLKGKGGTGAGDGDVATTT
VSLDWTVGNLARHDERGNTILYPGTYTLTLDEPAQASVQFALEGEPVVLDEWPAPPSANSTARG
RHR

Beta-xylosidase BXy18-WT2:

(SEQ ID NO: 10)
ATGAAGGCCTCTGTATCATGCCTCGTCGGCATGAGCGCCGTGGCCTACGGCCTCGATGGCCC
TTTCCAGACCTACCCCGACTGCACCAAGCCCCCCCTGTCCGATATTAAGGTGTGCGACCGGA
CACTGCCCGAGGCGGAGCGGGCGGCAGCCCTCGTGGCAGCCCTGACCGACGAGGAGAAGCT
GCAAAACCTGGTCAGCAAGGCGCCGGGGGCGCCGCGGATCGGCCTGCCCGCGTACAACTGG
TGGAGCGAGGCGCTGCACGGGGTGGCCCACGCGCCCGGGACGCAGTTCCGCGACGGGCCGG
GGGACTTCAACTCGTCCACGTCGTTCCCGATGCCGCTGCTGATGGCCGCCGCCTTCGACGAC
GAGCTGATCGAGGCCGTCGGCGACGTCATCGGCACCGAGGCCCGCGCCTTTGGCAACGCCG
GCTGGTCCGGCCTCGACTACTGGACCCCCAACGTCAACCCCTTCCGGGACCCCCGCTGGGGC
CGCGGCTCCGAGACGCCGGGCGAGGACGTCGTGCGCCTCAAGCGCTACGCCGCCTCCATGA
TCCGCGGGCTCGAGGGTCGTTCCTCCTCCTCCTCCTGCTCCTTCGGATCCGGAGGGGAGC
CGCCGCGCGTCATCTCGACCTGCAAGCACTACGCCGGCAACGACTTTGAGGACTGGAACGG
CACGACGCGGCACGACTTCGACGCCGTCATCTCGGCGCAGGACCTGGCCGAGTACTACCTGG
CGCCGTTCCAGCAGTGCGCGCGCGACTCGCGCGTCGGCTCCGTCATGTGCGCCTACAACGCC
GTCAACGGGGTGCCGTCGTGCGCCAACTCGTACCTCATGAACACGATCCTGCGCGGGCACTG
GAACTGGACCGAGCACGACAACTACGTCACCAGCGACTGCGAGGCCGTCCTCGACGTCTCG
GCCCACCACCACTACGCCGACACCAACGCCGAGGGCACCGGCCTCTGCTTCGAGGCCGGCA

-continued

```
TGGACACGAGCTGCGAGTACGAGGGCTCCTCCGACATCCCGGGCGCCTCCGCCGGCGGCTTC

CTGACCTGGCCCGCCGTCGACCGCGCCCTGACGCGGCTGTACCGGAGCCTGGTGCGGGTCGG

CTACTTTGACGGCCCCGAGTCGCCGCACGCCTCGCTGGGCTGGGCCGACGTCAACCGGCCCG

AGGCGCAGGAGCTGGCCCTGCGCGCTGCCGTCGAGGGCATCGTGCTGCTCAAGAACGACAA

CGACACGCTGCCGCTGCCGCTGCCGGACGATGTCGTTGTCACCGCTGATGGTGGCCGCCGCC

GCGTCGCCATGATCGGCTTCTGGGCCGACGCCCCGGACAAGCTGTTTGGCGGGTACAGCGGC

GCGCCCCCTTCGCGCGCTCGCCCGCGAGCGCCGCCCGGCAGCTGGGCTGGAACGTCACGGT

CGCCGGAGGGCCCGTCCTGGAGGGAGACTCGGACGAGGAGGAGGACACGTGGACGGCGCC

GGCCGTCGAGGCGGCCGCCGACGCCGACTACATCGTCTACTTTGGCGGCCTGGACACGTCGG

CGGCGGGCGAGACCAAGGACCGGATGACGATCGGGTGGCCGGCGGCGCAGCTGGCGCTCAT

CTCGGAGCTGGCGCGGCTCGGCAAGCCCGTCGTGGTGGTGCAGATGGGCGACCAGCTCGAC

GACACGCCCCTCTTCGAGCTGGACGGGGTGGGCGCCGTCCTGTGGGCCAACTGGCCGGGCC

AGGACGGCGGCACGGCCGTGGTCCGGCTGCTCAGCGGCGCCGAGAGCCCGGCCGGCCGCCT

GCCCGTGACCCAGTACCCGGCCAACTACACCGACGCGGTGCCCCTGACCGACATGACCCTGC

GCCCGTCGGCGACCAACCCGGGCCGGACCTACCGCTGGTACCCGACTCCCGTCCGGCCCTTC

GGCTTCGGCCTCCACTATACCACCTTCCGGGCCGAGTTCGGCCCCCACCCCTTCTTCCCGGGG

GCGGGCAAGGGCGATGGCGACGGCGAGGACAAGGGCGAGAGCAAGAGCGAGATCAGGACG

CAGCAGCAGCAACAGCAGCAGCAGCAGCGCAGGGCGGCGGCGGCGCCACCACGCCG

ATCCGGGACCTGCTCCGCGACTGCGACAAGACGTACCCGGACACGTGCCCGCTGCCGCCGCT

GACGGTGCGCGTGACCAACGAGGGCGAGCGCGCGTCCGACTACGTGGTGCTGGCCTTCGTG

TCGGGCGAGTACGGGCCGGCGCCGTACCCGATCAAGACGCTGGTCTCGTACGCGCGGGCGC

GCGGGCTAAAGGGGAAGGGCGGCGACGGCGACGGCGACGGCGACGGCGCCACCACTACCG

TCTCGCTCGACTGGACCGTCGGCAACCTGGCCCGCCACGACGAGCGCGGCAACACAATCCTG

TACCCGGGAACTTACACCCTCACTCTCGACGAGCCGGCCCAGGCGAGCGTGCAGTTCGCCCT

CGAGGGCGAGCCCGTCGTGCTCGACGAGTGGCCTGCGCCGCCGAGTGCCAACTCCACCGCC

AGGGGGAGGCACAGG
```

(SEQ ID NO: 11)
```
MKASVSCLVGMSAVAYGLDGPFQTYPDCTKPPLSDIKVCDRTLPEAERAAALVAALTDEEKLQ

NLVSKAPGAPRIGLPAYN WWSEALHGVAHAPGTQFRDGPGDFNSSTSFPMPLLMAAAFDDELIE

AVGDVIGTEARAFGNAGWSGLDYWTPNVNPFRDPRWGRGSETPGEDVVRLKRYAASMIRGLE

GRSSSSSSCSEGSGGEPPRVISTCKHYAGNDFEDWNGTTRHDFDAVISAQDLAEYYLAPFQQCAR

DSRVGSVMCAYNAVNGVPSCANSYLMNTILRGHWNWTEHDNYVTSDCEAVLDVSAHHHYAD

TNAEGTGLCFEAGMDTSCEYEGSSDIPGASAGGELTWPAVDRALTRLYRSLVRVGYEDGPESPH

ASLGWADVNRPEAQELALRAAVEGIVLLKNDNDTLPLPLPDDVVVTADGGRRRVAMIGFWAD

APDKLEGGYSGAPPFARSPASAARQLGWNVTVAGGPVLEGDSDEEEDTWTAPAVEAAADADYI

VYFGGLDTSAAGETKDRMTIGWPAAQLALISELARLGKPVVVVQMGDQLDDTPLFELDGVGAV

LWANWPGQDGGTAVVRLLSGAESPAGRLPVTQYPANYTDAVPLTDMTLRPSATNPGRTYRWY

PTPVRPFGFGLHYTTFRAEFGPHPFFPGAGKGDGDEDKGESKSEIRTQQQQQQQQQQRRAAAA

ATTPIRDLLRDCDKTYPDTCPLPPLTVRVTNEGERASDYVVLAFVSGEYGPAPYPIKTLVSYARA

RGLKGKGGDGDGDGATTTVSLDWTVGNLARHDERGNTILYPGTYTLTLDEPAQASVQFALE

GEPVVLDEWPAPPSANSTARGRHR
```

-continued

Beta-xylosidase BXyl8-233:

(SEQ ID NO: 12)

ATGAAGGCCTCTGTATCATGCCTCGTCGGCATGAGCGCCGTGGCCTACGGCCTCGATGGCCC

TTTCCAGACCTACCCCGACTGCACCAAGCCCCCCTGTCCGATATTAAGGTGTGCGACCGGA

CACTGCCCGAGGCGGAGCGGGCGGCAGCCCTCGTGGCAGCCCTGACCGACGAGGAGAAGCT

GCAAAACCTGGTCAGCAAGGCGCCGGGGGCGCCGCGGATCGGCCTGCCCGCGTACAACTGG

TGGAGCGAGGCGCTGCACGGGGTGGCCCACGCGCCCGGGACGCAATTCCGCGACGGGCCGG

GGGACTTCAACTCGTCCACGTCGTTCCCGATGCCGCTGCTGATGGCCGCCGCCTTCGACGAC

GAGCTGATCGAGGCCGTCGGCGACGTCATCGGCACCGAGGCCCGCGCCTTTGGCAACGCCG

GCTGGTCCGGCCTCGACTACTGGACCCCCAACGTCAACCCCTTCCGGGACCCCCGCTGGGC

CGCGGCTCCGAGACGCCGGGCGAGGACGTCGTGCGCCTCAAGCGCTACGCCGCCTCCATGA

TCCGCGGGCTCGAGGGTCGTTCCTCCTCCTCCTCCTCCTGCTCCTTCGGATCCGGAGGGGAGC

CGCCGCGCGTCATCTCGACCTGCAAGCACTACGCCGGCTACGACTTTGAGGACTGGAACGGC

ACGACGCGGCACGACTTCGACGCCGTCATCTCGGCGCAGGACCTGGCCGAGTACTACCTGGC

GCCGTTCCAGCAGTGCGCGCGCGACTCGCGCGTCGGCTCCGTCATGTGCGCCTACAACGCCG

TCAACGGGGTGCCGTCGTGCGCCAACTCGTACCTCATGAACACGATCCTGCGCGGGCACTGG

AACTGGACCGAGCACGACAACTACGTCACCAGCGACTGCGAGGCCGTCCTCGACGTCTCGG

CCCACCACCACTACGCCGACACCAACGCCGAGGGCACCGCCTCTGCTTCGAGGCCGGCAT

GGACACGAGCTGCGAGTACGAGGGCTCCTCCGACATCCCGGGCGCCTCCGCCGGCGGCTTCC

TGACCTGGCCCGCCGTCGACCGCGCCCTGACGCGGCTGTACCGGAGCCTGGTGCGGGTCGGC

TACTTTGACGGCCCCGAGTCGCCGCACGCCTCGCTGGGCTGGGCCGACGTCAACCGGCCCGA

GGCGCAGGAGCTGGCCCTGCGCGCTGCCGTCGAGGGCATCGTGCTGCTCAAGAACGACAAC

GACACGCTGCCGCTGCCGCTGCCGGACGATGTCGTTGTCACCGCTGATGGTGGCCGCCGCCG

CGTCGCCATGATCGGCTTCTGGGCCGACGCCCCGGACAAGCTGTTTGGCGGGTACAGCGGCG

CGCCCCCCTTCGCGCGCTCGCCCGCGAGCGCCGCCCGGCAGCTGGGCTGGAACGTCACGGTC

GCCGGAGGGCCCGTCCTGGAGGGAGACTCGGACGAGGAGGAGGACACGTGGACGGCGCCG

GCCGTCGAGGCGGCCGCCGACGCCGACTACATCGTCTACTTTGGCGGCCTGGACACGTCGGC

GGCGGGCGAGACCAAGGACCGGATGACGATCGGGTGGCCGGCGGCGCAGCTGGCGCTCATC

TCGGAGCTGGCGCGGCTCGGCAAGCCCGTCGTGGTGGTGCAGATGGGCGACCAGCTCGACG

ACACGCCCCTCTTCGAGCTGGACGGGGTGGGCGCCGTCCTGTGGGCCAACTGGCCGGGCCA

GGACGGCGGCACGGCCGTGGTCCGGCTGCTCAGCGGCGCCGAGAGCCCGGCCGGCCGCCTG

CCCGTGACCCAGTACCCGGCCAACTACACCGACGCGGTGCCCCTGACCGACATGACCCTGCG

CCCGTCGGCGACCAACCCGGGCCGGACCTACCGCTGGTACCCGACTCCCGTCCGGCCCTTCG

GCTTCGGCCTCCACTATACCACCTTCCGGGCCGAGTTCGGCCCCCACCCCTTCTTCCCGGGGG

CGGGCAAGGGCGATGGCGACGGCGAGGACAAGGGCGAGAGCAAGAGCGAGATCAGGACGC

AGCAGCAGCAACAGCAGCAGCAGCAGCGCAGGGCGGCGGCGGCGGCCACCACGCCGA

TCCGGGACCTGCTCCGCGACTGCGACAAGACGTACCCGGACACGTGCCCGCTGCCGCCGCTG

ACGGTGCGCGTGACCAACGAGGGCGAGCGCGCGTCCGACTACGTGGTGCTGGCCTTCGTGTC

GGGCGAGTACGGGCCGGCGCCGTACCCGATCAAGACGCTGGTCTCGTACGCGCGGGCGCGC

GGGCTAAAGGGGAAGGGCGGCGACGGCGACGGCGACGGCGACGGCGCCACCACTACCGTC

TCGCTCGACTGGACCGTCGGCAACCTGGCCCGCCACGACGAGCGCGGCAACACAATCCTGT

ACCCGGGAACTTACACCCTCACTCTCGACGAGCCGGCCCAGGCGAGCGTGCAGTTCGCCCTC

-continued

GAGGGCGAGCCCGTCGTGCTCGACGAGTGGCCTGCGCCGCCGAGTGCCAACTCCACCGCCA

GGGGGAGGCACAGG (SEQ ID NO: 13)
MKASVSCLVGMSAVAYGLDGPFQTYPDCTKPPLSDIKVCDRTLPEAERAAALVAALTDEEKLQ

NLVSKAPGAPRIGLPAYNWWSEALHGVAHAPGTQFRDGPGDFNSSTSFPMPLLMAAAFDDELIE

AVGDVIGTEARAFGNAGWSGLDYWTPNVNPFRDPRWGRGSETPGEDVVRLKRYAASMIRGLE

GRSSSSSSCSFGSGGEPPRVISTCKHYAGYDFEDWNGTTRHDFDAVISAQDLAEYYLAPFQQCAR

DSRVGSVMCAYNAVNGVPSCANSYLMNTILRGHWNWTEHDNYVTSDCEAVLDVSAHHHYAD

TNAEGTGLCFEAGMDTSCEYEGSSDIPGASAGGFLTWPAVDRALTRLYRSLVRVGYFDGPESPH

ASLGWADVNRPEAQELALRAAVEGIVLLKNDNDTLPLPLPDDVVVTADGGRRRVAMIGFWAD

APDKLFGGYSGAPPFARSPASAARQLGWNVTVAGGPVLEGDSDEEEDTWTAPAVEAAADADYI

VYFGGLDTSAAGETKDRMTIGWPAAQLALISELARLGKPVVVVQMGDQLDDTPLFELDGVGAV

LWANWPGQDGGTAVVRLLSGAESPAGRLPVTQYPANYTDAVPLTDMTLRPSATNPGRTYRWY

PTPVRPFGEGLHYTTFRAEFGPHPFFPGAGKGDGDGEDKGESKSEIRTQQQQQQQQQQRRAAAA

ATTPIRDLLRDCDKTYPDTCPLPPLTVRVTNEGERASDYVVLAFVSGEYGPAPYPIKTLVSYARA

RGLKGKGGDGDGDGDGATTTVSLDWTVGNLARHDERGNTILYPGTYTLTLDEPAQASVQFALE

GEPVVLDEWPAPPSANSTARGRHR

The following sequences comprise additional xylanase (Xyl), beta-xylosidase (Bxyl), and alpha-xylosidase (Axyl) sequences of interest. The first sequence provided in each set below comprises the cDNA sequence, the second sequence is the polypeptide sequence with the predicted signal sequence included, and the third sequence is the polypeptide sequence without the signal sequence.

Xyl1974:

(SEQ ID NO: 14)
ATGGTTGCTCTCTCTTCTCTCCTCGTCGCTGCCTCTGCGGCGGCCGTGGCCGTGGCTGCGCCG

AGCGAGGCCCTCCAGAAGCGCCAGACGCTCACGAGCAGCCAGACGGGCTTCCACGACGGCT

TTTACTACTCCTTCTGGACCGACGGTGCCGGCAACGTCCGGTACACGAACGAGGCCGGCGGC

CGGTACAGTGTCACCTGGTCCGGCAACAACGGCAACTGGGTTGGCGGCAAGGGCTGGAACC

CGGGGGCTGCTCGCAACATCAGCTTCACGGGGCAGTATAACCCCAACGGCAACTCGTACCTG

GCCGTGTACGGGTGGACGCGCAACCCGCTGATCGAGTACTACATCGTCGAGAACTTCGGCAC

GTACGACCCGTCGACGGGGGCGCAGCGGCTCGGCAGCATCACGGTGGACGGGTCGACGTAC

AACATCCTCAAGACGACGCGGGTCAACCAGCCGTCCATCGAGGGCACCAGCACCTTTGACC

AGTTCTGGTCCGTCCGGACCAACAAGCGCAGCAGCGGCTCCGTCAACGTCAAGGCTCACTTC

GACGCTTGGGCCCAGGCCGGCCTCCGCCTGGGCACCCACGACTACCAGATCATGGCCACCG

AGGGCTACTTCTCGAGCGGCTCCGCCACCATCACCGTCGGCGAGGGCACCAGCAGCGGCGG

CGGCGGCGACAATGGCGGCGGCAACAACGGCGGCGGCGGCAACACCGGCACCTGCAGCGC

CCTGTACGGCCAGTGCGGTGGCCAGGGGTGGACGGGCCCGACTTGCTGCTCCCAGGGAACC

TGCCGCGTCTCCAACCAGTGGTACTCGCAGTGCTTGTAA (SEQ ID NO: 15)
MVALSSLLVAASAAAVAVAAPSEALQKRQTLTSSQTGFHDGFYYSFWTDGAGNVRYTNEAGG

RYSVTWSGNNGNWVGGKGWNPGAARNISFTGQYNPNGNSYLAVYGWTRNPLIEYYIVENFGT

YDPSTGAQRLGSITVDGSTYNILKTTRVNQPSIEGTSTFDQFWSVRTNKRSSGSVNVKAHFDAWA

-continued

QAGLRLGTHDYQIMATEGYFSSGSATITVGEGTSSGGGGDNGGGNNGGGGNTGTCSALYGQCG
GQGWTGPTCCSQGTCRVSNQWYSQCL (SEQ ID NO: 16)
APSEALQKRQTLTSSQTGFHDGFYYSFWTDGAGNVRYTNEAGGRYSVTWSGNNGNWVGGKG
WNPGAARNISFTGQYNPNGNSYLAVYGWTRNPLIEYYIVENFGTYDPSTGAQRLGSITVDGSTY
NILKTTRVNQPSIEGTSTFDQFWSVRTNKRSSGSVNVKAHFDAWAQAGLRLGTHDYQIMATEGY
FSSGSATITVGEGTSSGGGGDNGGGNNGGGGNTGTCSALYGQCGGQGWTGPTCCSQGTCRVSN
QWYSQCL

Xy140741:

(SEQ ID NO: 17)
ATGAAGGCCAATCTCCTGGTCCTCGCGCCGCTGGCCGTCTCGGCAGCGCCCGCGCTCGAGCA
CCGCCAGGCAACTGAGAGCATCGACGCGCTCATTAAGGCCAAGGGCAAGCTCTACTTTGGC
ACCTGTACCGACCAGGGCCGGCTGACGTCGGGCAAGAACGCGGACATCATCAGGGCCAACT
TCGGCCAGGTGACGCCCGAGAACAGCATGAAGTGGCAGAGCATCGAGCCATCGCGGGGTCA
GTTCACCTGGGGCCAGGCTGACTACCTCGTCGACTGGGCCACTCAGAACAACAAGACCATCC
GCGGCCACACGCTCGTCTGGCACTCGCAGCTCGCCGGCTACGTTCAGCAGATCGGCGACCGG
AACACCTTGACCCAGACCATCCAGGACCACATTGCCGCCGTCATGGGCCGCTACAAGGGCA
AGATCTACGCCTGGGATGTCATCAACGAGATGTTCAACGAGGATGGCTCGCTTCGCAGCAGC
GTCTTCTCCAACGTCCTCGGAGAGGACTTTGTTGGGATCGCCTTCAAGGCGGCGCGCGAGGC
CGACCCCGACACCAAGTTGTACATCAACGACTACAACCTCGACAGCCCCAACTACGCCAAG
CTGACCAACGGCATGGTCGCTCACGTCAAGAAGTGGCTCGCGGCCGGCATCCCCATCGACG
GCATCGGCACCCAGGGTCACCTGCAGTCTGGCCAGGGTTCCGGTCTTGCGCAGGCCATCAAG
GCTCTCGCCCAGGCTGGCGTCGAGGAGGTTGCCGTCACCGAGCTCGATATCCAGAACCAGA
ACACCAACGACTACACTGCCGTTGTCCAGGGCTGCTTGGACGAGCCCAAGTGCGTCGGTATC
ACCGTCTGGGGTGTCCGCGATCCCGACTCGTGGCGTCCCCAGGGCAACCCCTTGCTCTTCGA
CAGCAACTTCAACCCCAAGGCGAACTACAATGCCATCGTCCAGCTCCTCAAGCAGTAG (SEQ ID NO: 18)
MKANLLVLAPLAVSAAPALEHRQATESIDALIKAKGKLYFGTCTDQGRLTSGKNADIIRANFGQ
VTPENSMKWQSIEPSRGQFTWGQADYLVDWATQNNKTIRGHTLVWHSQLAGYVQQIGDRNTL
TQTIQDHIAAVMGRYKGKIYAWDVINEMFNEDGSLRSSVFSNVLGEDFVGIAFKAAREADPDTK
LYINDYNLDSPNYAKLTNGMVAHVKKWLAAGIPIDGIGTQGHLQSGQGSGLAQAIKALAQAGV
EEVAVTELDIQNQNTNDYTAVVQGCLDEPKCVGITVWGVRDPDSWRPQGNPLLFDSNFNPKAN
YNAIVQLLKQ (SEQ ID NO: 19)
APALEHRQATESIDALIKAKGKLYFGTCTDQGRLTSGKNADIIRANFGQVTPENSMKWQSIEPSR
GQFTWGQADYLVDWATQNNKTIRGHTLVWHSQLAGYVQQIGDRNTLTQTIQDHIAAVMGRYK
GKIYAWDVINEMFNEDGSLRSSVFSNVLGEDFVGIAFKAAREADPDTKLYINDYNLDSPNYAKL
TNGMVAHVKKWLAAGIPIDGIGTQGHLQSGQGSGLAQAIKALAQAGVEEVAVTELDIQNQNTN
DYTAVVQGCLDEPKCVGITVWGVRDPDSWRPQGNPLLFDSNFNPKANYNAIVQLLKQ

Xy134208:

(SEQ ID NO: 20)
ATGGTCAAGCTCTCTCTCATCGCAGCGAGCCTTGTGGCACCTAGCGTGCTTGCGGGTCCTCTC
ATCGGCCCCAAGACGCAAACCGAGAGCCAGCTGAACCCGCGTCAAGGCGGCTACAACTACT
TCCAGAATTGGTCCGAGGGAGGCAGCAATATCCGCTGCAACAACGGCCCTGGGGGTTCCTA

-continued

```
CACGGCCGACTGGAACAGCAGGGGCGGCTTCGTCTGTGGCAAGGGCTGGAGCTATGGAGGC

AATCGCGCCATCACGTACACCGGCGAATACAACGCCAGCGGCCCCGGCTACCTCGCCGTCTA

CGGGTGGACCCGCAACCCGCTGATTGAATACTACATCATCGAGGCCCATGCCGACCTCGCCC

CCAACGAGCCGTGGACATCCAAGGGTAATTTCAGCTTCGAGGAGGGCGAGTACGAGGTCTT

CACCAGCACCCGCGTCAACAAGCCGTCCATCGAGGGCACCAGGACTTTTCAGCAGTACTGGT

CGCTGCGCAAGGAGCAGCGGGTCGGCGGCACCGTCACCACCCAGAGGCACTTTGAAGAGTG

GGCCAAGCTGGGCATGAAGCTGGGCAATCATGACTATGTCATCCTGGCGACCGAAGGATAC

ACTGCCAACGGAGGATCCGGTAGCAGCGGGCACTCGAGCATTACTCTGCAGTAG
```

(SEQ ID NO: 21)
MVKLSLIAASLVAPSVLAGPLIGPKTQTESQLNPRQGGYNYFQNWSEGGSNIRCNNGPGGSYTA
DWNSRGGFVCGKGWSYGGNRAITYTGEYNASGPGYLAVYGWTRNPLIEYYIIEAHADLAPNEP
WTSKGNFSFEEGEYEVFTSTRVNKPSIEGTRTFQQYWSLRKEQRVGGTVTTQRHFEEWAKLGM
KLGNHDYVILATEGYTANGGSGSSGHSSITLQ (SEQ ID NO: 22)
GPLIGPKTQTESQLNPRQGGYNYFQNWSEGGSNIRCNNGPGGSYTADWNSRGGFVCGKGWSYG
GNRAITYTGEYNASGPGYLAVYGWTRNPLIEYYHEAHADLAPNEPWTSKGNFSFEEGEYEVFTS
TRVNKPSIEGTRTFQQYWSLRKEQRVGGTVTTQRHFEEWAKLGMKLGNHDYVILATEGYTANG
GSGSSGHSSITLQ

Xy17143:

(SEQ ID NO: 23)
```
ATGGTCTCGTTCACTCTCCTCCTCACGGTCATCGCCGCTGCGGTGACGACGGCCAGCCCTCTC

GAGGTGGTCAAGCGCGGCATCCAGCCGGGCACGGGCACCCACGAGGGGTACTTCTACTCGT

TCTGGACCGACGGCCGTGGCTCGGTCGACTTCAACCCCGGGCCCCGCGGCTCGTACAGCGTC

ACCTGGAACAACGTCAACAACTGGGTTGGCGGCAAGGGCTGGAACCCGGGCCCGCCGCGCA

AGATTGCGTACAACGGCACCTGGAACAACTACAACGTGAACAGCTACCTCGCCCTGTACGG

CTGGACTCGCAACCCGCTGGTCGAGTATTACATCGTGGAGGCATACGGCACGTACAACCCCT

CGTCGGGCACGGCGCGGCTGGGCACCATCGAGGACGACGGCGGCGTGTACGACATCTACAA

GACGACGCGGTACAACCAGCCGTCCATCGAGGGGACCTCCACCTTCGACCAGTACTGGTCCG

TCCGCCGCCAGAAGCGCGTCGGCGGCACTATCGACACGGGCAAGCACTTTGACGAGTGGAA

GCGCCAGGGCAACCTCCAGCTCGGCACCTGGAACTACATGATCATGGCCACCGAGGGCTAC

CAGAGCTCTGGTTCGGCCACTATCGAGGTCCGGGAGGCCTAA
```

(SEQ ID NO: 24)
MVSFTLLLTVIAAAVTTASPLEVVKRGIQPGTGTHEGYFYSFWTDGRGSVDENPGPRGSYSVTW
NNVNNWVGGKGWNPGPPRKIAYNGTWNNYNVNSYLALYGWTRNPLVEYYIVEAYGTYNPSS
GTARLGTIEDDGGVYDIYKTTRYNQPSIEGTSTFDQYWSVRRQKRVGGTIDTGKHEDEWKRQGN
LQLGTWNYMIMATEGYQSSGSATIEVREA (SEQ ID NO: 25)
SPLEVVKRGIQPGTGTHEGYFYSFWTDGRGSVDFNPGPRGSYSVTWNNVNNWVGGKGWNPGP
PRKIAYNGTWNNYNVNSYLALYGWTRNPLVEYYIVEAYGTYNPSSGTARLGTIEDDGGVYDIY
KTTRYNQPSIEGTSTEDQYWSVRRQKRVGGTIDTGKHEDEWKRQGNLQLGTWNYMIMATEGY
QSSGSATIEVREA

Xyl42827:
(SEQ ID NO: 26)
ATGGTCTCGCTCAAGTCCCTCCTCCTCGCCGCGGCGGCGACGTTGACGGCGGTGACGGCGCG

CCCGTTCGACTTTGACGACGGCAACTCGACCGAGGCGCTGGCCAAGCGCCAGGTCACGCCC

AACGCGCAGGGCTACCACTCGGGCTACTTCTACTCGTGGTGGTCCGACGGCGGCGGCCAGGC

CACCTTCACCCTGCTCGAGGGCAGCCACTACCAGGTCAACTGGAGGAACACGGGCAACTTTG

TCGGTGGCAAGGGCTGGAACCCGGGTACCGGCCGGACCATCAACTACGGCGGCTCGTTCAA

CCCGAGCGGCAACGGCTACCTGGCCGTCTACGGCTGGACGCACAACCCGCTGATCGAGTACT

ACGTGGTCGAGTCGTACGGGACCTACAACCCGGGCAGCCAGGCCCAGTACAAGGGCAGCTT

CCAGAGCGACGGCGGCACCTACAACATCTACGTCTCGACCCGCTACAACGCGCCCTCGATCG

AGGGCACCCGCACCTTCCAGCAGTACTGGTCCATCCGCACCTCCAAGCGCGTCGGCGGCTCC

GTCACCATGCAGAACCACTTCAACGCCTGGGCCCAGCACGGCATGCCCCTCGGCTCCCACGA

CTACCAGATCGTCGCCACCGAGGGCTACCAGAGCAGCGGCTCCTCCGACATCTACGTCCAGA

CTCACTAG (SEQ ID NO: 27)
MVSLKSLLLAAAATLTAVTARPFDFDDGNSTEALAKRQVTPNAQGYHSGYFYSWWSDGGGQA

TFTLLEGSHYQVNWRNTGNFVGGKGWNPGTGRTINYGGSFNPSGNGYLAVYGWTHNPLIEYYV

VESYGTYNPGSQAQYKGSFQSDGGTYNIYVSTRYNAPSIEGTRTFQQYWSIRTSKRVGGSVTMQ

NHFNAWAQHGMPLGSHDYQIVATEGYQSSGSSDIYVQTH (SEQ ID NO: 28)
RPFDFDDGNSTEALAKRQVTPNAQGYHSGYFYSWWSDGGGQATFTLLEGSHYQVNWRNTGNF

VGGKGWNPGTGRTINYGGSFNPSGNGYLAVYGWTHNPLIEYYVVESYGTYNPGSQAQYKGSFQ

SDGGTYNIYVSTRYNAPSIEGTRTFQQYWSIRTSKRVGGSVTMQNHFNAWAQHGMPLGSHDYQI

VATEGYQSSGSSDIYVQTH

BXy11883:
(SEQ ID NO: 29)
ATGGCCTTCCTTTCCTCCTTTGCCCTTGCCGCCCTCGGGGCACTCGTCGTCCCGGCGAGGGGC

GGCGTGACGTACCCGGACTGCGCAAACGGACCGCTCAAGTCAAATACGGTGTGCGATACGT

CGGCGTCCCCGGGAGCCCGAGCCGCTGCTCTTGTGAGTGTAATGAACAACAACGAAAAACT

TGCAAATCTTGTCAACAATTCGCCCGGCGTCTCGCGGCTCGGCCTGAGTGCGTACCAGTGGT

GGAACGAAGCCCTCCACGGAGTAGCCCATAACCGCGGCATTACCTGGGGCGGCGAGTTCAG

CGCGGCAACCCAGTTCCCGCAGGCTATCACGACTTCCGCCACTTTCGATGACGCTTTGATCG

AGCAAATCGGCACCATTATCAGCACCGAGGCCCGTGCCTTTGCCAACAATGGGCGCGCTCAT

CTCGACTTCTGGACGCCCAACGTCAACCCGTTTCGAGACCCGCGATGGGGTCGCGGACACGA

GACGCCGGGAGAGGATGCATTCAAGAATAAGAAGTGGGCCGAGGCCTTCGTCAAGGGCATG

CAAGGACCCGGACCGACGCACCGAGTCATCGCCACATGTAAGCACTACGCCGCCTACGACC

TCGAGAACTCCGGGAGCACGACCCGATTCAACTTCGATGCGAAGGTGTCAACTCAAGATCTC

GCCGAGTACTATCTCCCTCCGTTCCAACAGTGCGCCCGGACTCTAAGGTGGGCTCCATCAT

GTGCAGCTACAATGCGGTCAATGAAATCCCGGCCTGCGCGAATCCTTACCTGATGGATACCA

TCCTGCGGAAACATTGGAATTGGACCGACGAGCACCAGTATATTGTGAGCGACTGCGATGCC

GTGTACTATCTCGGCAATGCGAACGGCGGCCACCGATACAAGCCGAGCTATGCGGCGGCGA

TCGGAGCATCTCTCGAGGCTGGTTGCGATAACATGTGCTGGGCGACCGGCGGCACCGCCCCG

GATCCCGCCTCAGCCTTCAATTCCGGCCAGTTCAGCCAGACGACACTGGACACGGCTATTTT

-continued

```
GCGCCAGATGCAGGGCCTCGTCCTAGCGGGATACTTTGACGGTCCGGGCGGTATGTACCGCA

ACCTGAGCGTGGCGGACGTGAACACGCAGACCGCCCAGGACACTGCACTCAAGGCGGCGGA

AGGAGGCATCGTGCTCCTCAAGAACGATGGGATCCTTCCGCTGTCGGTTAACGGTTCCAATT

TCCAGGTCGCTATGATCGGGTTCTGGGCGAACGCAGCCGACAAGATGCTCGGGGGTTACAG

CGGGAGCCCGCCGTTCAACCATGATCCCGTGACCGCTGCAAGATCGATGGGCATCACGGTCA

ACTACGTCAACGGGCCATTGACGCAACCCAACGGGGATACGTCGGCAGCACTCAATGCGGC

CCAAAAGTCCAACGCGGTGGTATTCTTTGGTGGAATCGACAATACGGTGGAGAAGGAGAGT

CAGGACAGAACGTCCATCGAGTGGCCCTCAGGGCAACTGGCTCTGATTCGGAGGCTAGCCG

AAACCGGCAAACCAGTCATCGTCGTCAGGCTCGGGACGCACGTCGACGACACCCCGCTCCTC

AGCATTCCGAATGTGAGAGCCATTTTGTGGGCAGGATACCCGGGTCAAGACGGCGGGACTG

CTGTGGTGAAAATCATTACCGGCCTTGCTAGTCCGGCGGGAGGCTGCCCGCCACTGTGTAT

CCGTCTTCGTACACCAGCCAAGCGCCCTTTACAAACATGGCCCTGAGGCCTTCTTCGTCCTAT

CCCGGGCGAACATACCGCTGGTACAGTAACGCCGTCTTTCCATTTGGCCACGGCCTACATTA

TACCAATTTCAGTGTCTCGGTGCGGGACTTTCCGGCCAGCTTCGCGATTGCCGATCTCCTGGC

TTCCTGCGGGATTCCGTGGCGTATCTTGATCTTTGCCCCTTCCCGTCCGTGTCGCTCAATGT

GACCAATACAGGCACCCGCGTGTCCGATTACGTTGCGCTTGGGTTCTTGTCGGGAGATTTTG

GTCCCAGCCCACATCCCATCAAGACATTGGCGACGTATAAGCGCGTGTTTAACATCGAACCT

GGGGAAACACAGGTGGCCGAGCTAGACTGGAAGCTGGAGAGCCTGGTCCGGGTAGATGAG

AAGGGCAACAGGGTACTCTACCCCGGAACATATACGCTTCTTGTGGATCAGCCAACCTTGGC

AAATATCACCTTTATTTTGACAGGAGAAGAGGCAGTGTTGGATAGTTGGCCGCAGCCGTGA
```

(SEQ ID NO: 30)
MAFLSSFALAALGALVVPARGGVTYPDCANGPLKSNTVCDTSASPGARAAALVSVMNNNEKLA
NLVNNSPGVSRLGLSAYQWWNEALHGVAHNRGITWGGEFSAATQFPQAITTSATFDDALIEQIG
TIISTEARAFANNGRAHLDFWTPNVNPFRDPRWGRGHETPGEDAFKNKKWAEAFVKGMQGPGP
THRVIATCKHYAAYDLENSGSTTRFNFDAKVSTQDLAEYYLPPFQQCARDSKVGSIMCSYNAVN
EIPACANPYLMDTILRKHWNWTDEHQYIVSDCDAVYYLGNANGGHRYKPSYAAAIGASLEAGC
DNMCWATGGTAPDPASAFNSGQFSQTTLDTAILRQMQGLVLAGYFDGPGGMYRNLSVADVNT
QTAQDTALKAAEGGIVLLKNDGILPLSVNGSNFQVAMIGFWANAADKMLGGYSGSPPFNHDPV
TAARSMGITVNYVNGPLTQPNGDTSAALNAAQKSNAVVFFGGIDNTVEKESQDRTSIEWPSGQL
ALIRRLAETGKPVIVVRLGTHVDDTPLLSIPNVRAILWAGYPGQDGGTAVVKIITGLASPAGRLPA
TVYPSSYTSQAPFTNMALRPSSSYPGRTYRWYSNAVFPPFGHGLHYTNFSVSVRDFPASFAIADLL
ASCGDSVAYLDLCPFPSVSLNVTNTGTRVSDYVALGFLSGDFGPSPHPIKTLATYKRVFNIEPGET
QVAELDWKLESLVRVDEKGNRVLYPGTYTLLVDQPTLANITFILTGEEAVLDSWPQP (SEQ ID NO: 31)
GVTYPDCANGPLKSNTVCDTSASPGARAAALVSVMNNNEKLANLVNNSPGVSRLGLSAYQWW
NEALHGVAHNRGITWGGEFSAATQFPQAITTSATFDDALIEQIGTHSTEARAFANNGRAHLDFWT
PNVNPFRDPRWGRGHETPGEDAFKNKKWAEAFVKGMQGPGPTHRVIATCKHYAAYDLENSGS
TTRFNFDAKVSTQDLAEYYLPPFQQCARDSKVGSIMCSYNAVNEIPACANPYLMDTILRKHWN
WTDEHQYIVSDCDAVYYLGNANGGHRYKPSYAAAIGASLEAGCDNMCWATGGTAPDPASAFN
SGQFSQTTLDTAILRQMQGLVLAGYFDGPGGMYRNLSVADVNTQTAQDTALKAAEGGIVLLKN
DGILPLSVNGSNFQVAMIGFWANAADKMLGGYSGSPPFNHDPVTAARSMGITVNYVNGPLTQP
NGDTSAALNAAQKSNAVVFFGGIDNTVEKESQDRTSIEWPSGQLALIRRLAETGKPVIVVRLGTH

VDDTPLLSIPNVRAILWAGYPGQDGGTAVVKIITGLASPAGRLPATVYPSSYTSQAPFTNMALRPS

SSYPGRTYRWYSNAVFPFGHGLHYTNFSVSVRDFPASFAIADLLASCGDSVAYLDLCPFPSVSLN

VTNTGTRVSDYVALGFLSGDFGPSPHPIKTLATYKRVFNIEPGETQVAELDWKLESLVRVDEKGN

RVLYPGTYTLLVDQPTLANITFILTGEEAVLDSWPQP

Xy125453:

(SEQ ID NO: 32)
ATGCGTACTCTTACGTTCGTGCTGGCAGCCGCCCCGGTGGCTGTGCTTGCCCAATCTCCTCTG

TGGGGCCAGTGCGGCGGTCAAGGCTGGACAGGTCCCACGACCTGCGTTTCTGGCGCAGTATG

CCAATTCGTCAATGACTGGTACTCCCAATGCGTGCCCGGATCGAGCAACCCTCCTACGGGCA

CCACCAGCAGCACCACTGGAAGCACCCCGGCTCCTACTGGCGGCGGCGGCAGCGGAACCGG

CCTCCACGACAAATTCAAGGCCAAGGGCAAGCTCTACTTCGGAACCGAGATCGATCACTACC

ATCTCAACAACAATGCCTTGACCAACATTGTCAAGAAAGACTTTGGTCAAGTCACTCACGAG

AACAGCTTGAAGTGGGATGCTACTGAGCCGAGCCGCAATCAATTCAACTTTGCCAACGCCGA

CGCGGTTGTCAACTTTGCCCAGGCCAACGGCAAGCTCATCCGCGGCCACACCCTCCTCTGGC

ACTCTCAGCTGCCGCAGTGGGTGCAGAACATCAACGACCGCAACACCTTGACCCAGGTCATC

GAGAACCACGTCACCACCCTTGTCACTCGCTACAAGGGCAAGATCCTCCACTGGGACGTCGT

TAACGAGATCTTTGCCGAGGACGGCTCGCTCCGCGACAGCGTCTTCAGCCGCGTCCTCGGCG

AGGACTTTGTCGGCATCGCCTTCCGCGCCGCCCGCGCCGCCGATCCCAACGCCAAGCTCTAC

ATCAACGACTACAACCTCGACATTGCCAACTACGCCAAGGTGACCCGGGGCATGGTCGAGA

AGGTCAACAAGTGGATCGCCCAGGGCATCCCGATCGACGGCATCGGCACCCAGTGCCACCT

GGCCGGGCCCGGCGGGTGGAACACGGCCGCCGGCGTCCCCGACGCCCTCAAGGCCCTCGCC

GCGGCCAACGTCAAGGAGATCGCCATCACCGAGCTCGACATCGCCGGCGCCTCCGCCAACG

ACTACCTCACCGTCATGAACGCCTGCCTCCAGGTCTCCAAGTGCGTCGGCATCACCGTCTGG

GGCGTCTCTGACAAGGACAGCTGGAGGTCGAGCAGCAACCCGCTCCTCTTCGACAGCAACT

ACCAGCCAAAGGCGGCATACAATGCTCTGATTAATGCCTTGTAA (SEQ ID NO: 33)
MRTLTFVLAAAPVAVLAQSPLWGQCGGQGWTGPTTCVSGAVCQFVNDWYSQCVPGSSNPPTG

TTSSTTGSTPAPTGGGGSGTGLHDKFKAKGKLYFGTEIDHYHLNNNALTNIVKKDFGQVTHENS

LKWDATEPSRNQFNFANADAVVNFAQANGKLIRGHTLLWHSQLPQWVQNINDRNTLTQVIENH

VTTLVTRYKGKILHWDVVNEIFAEDGSLRDSVFSRVLGEDFVGIAFRAARAADPNAKLYINDYN

LDIANYAKVTRGMVEKVNKWIAQGIPIDGIGTQCHLAGPGGWNTAAGVPDALKALAAANVKEI

AITELDIAGASANDYLTVMNACLQVSKCVGITVWGVSDKDSWRSSSNPLLFDSNYQPKAAYNA

LINAL (SEQ ID NO: 34)
QSPLWGQCGGQGWTGPTTCVSGAVCQFVNDWYSQCVPGSSNPPTGTTSSTTGSTPAPTGGGGS

GTGLHDKFKAKGKLYFGTEIDHYHLNNNALTNIVKKDFGQVTHENSLKWDATEPSRNQFNFAN

ADAVVNFAQANGKLIRGHTLLWHSQLPQWVQNINDRNTLTQVIENHVTTLVTRYKGKILHWDV

VNEIFAEDGSLRDSVFSRVLGEDFVGIAFRAARAADPNAKLYINDYNLDIANYAKVTRGMVEKV

NKWIAQGIPIDGIGTQCHLAGPGGWNTAAGVPDALKALAAANVKEIAITELDIAGASANDYLTV

MNACLQVSKCVGITVWGVSDKDSWRSSSNPLLFDSNYQPKAAYNALINAL

-continued

Xy1805:

(SEQ ID NO: 35)
ATGCATCTCTCCTCGTCTCTCCTCCTCCTCGCCGCCTTGCCCCTGGGCATCGCCGGCAAGGGC

AAGGGCCACGGCCACGGCCCCCATACCGGGCTCCACACCCTCGCCAAGCAGGCCGGCCTCA

AGTACTTCGGCTCTGCCACCGACTCTCCCGGCCAGCGTGAGCGCGCCGGCTACGAGGACAAG

TACGCCCAGTACGACCAGATCATGTGGAAGTCGGGCGAGTTCGGCCTGACGACCCCGACCA

ACGGCCAAAAGTGGCTGTTTACTGAGCCCGAGCGTGGCGTGTTCAACTTCACCGAGGGTGAC

ATCGTGACGAACCTGGCCCGGAAGCACGGTTTCATGCAGCGGTGCCACGCGCTCGTCTGGCA

CAGCCAGCTCGCCCCTTGGGTCGAGTCGACCGAGTGGACGCCCGAGGAGCTGCGCCAGGTC

ATTGTCAACCACATCACCCACGTGGCCGGCTACTACAAGGGCAAGTGCTATGCCTGGGACGT

CGTCAACGAGGCCCTGAACGAGGACGGCACCTACCGCGAGTCCGTCTTCTACAAGGTGCTCG

GCGAGGACTACATCAAGCTGGCCTTCGAGACGGCCGCCAAGGTCGACCCCCACGCCAAGCT

CTACTACAACGACTACAACCTCGAGTCCCCCAGCGCCAAGACCGAGGGCGCCAAGCGCATC

GTCAAGATGCTCAAGGACGCCGGCATCCGCATCGACGGCGTCGGCCTGCAGGCCCACCTCGT

CGCCGAGAGCCACCCGACCCTCGACGAGCACATCGATGCCATCAAGGGCTTCACCGAGCTC

GGCGTCGAGGTCGCCCTGACCGAGCTCGACATCCGCCTCTCCATCCCGGCCAACGCCACCAA

CCTCGCCCAGCAGAGGGAGGCGTACAAGAACGTCGTCGGCGCTTGCGTCCAGGTTCGCGGC

TGCATTGGCGTGGAGATCTGGGACTTCTATGACCCCTTCAGCTGGGTCCCTGCCACCTTCCCC

GGCCAGGGCGCCCCCCTGCTCTGGTTCGAGGACTTTTCCAAGCACCCCGCCTACGACGGCGT

CGTCGAGGCCCTGACCAACAGGACCACGGGCGGGTGCAAGGGCAAGGGCAAGGGCAAGGG

CAAGGTTTGGAAGGCCTAA (SEQ ID NO: 36)
MHLSSSLLLLAALPLGIAGKGKGHGHGPHTGLHTLAKQAGLKYFGSATDSPGQRERAGYEDKY

AQYDQIMWKSGEFGLTTPTNGQKWLFTEPERGVENFTEGDIVTNLARKHGFMQRCHALVWHSQ

LAPWVESTEWTPEELRQVIVNHITHVAGYYKGKCYAWDVVNEALNEDGTYRESVFYKVLGED

YIKLAFETAAKVDPHAKLYYNDYNLESPSAKTEGAKRIVKMLKDAGIRIDGVGLQAHLVAESHP

TLDEHIDAIKGFTELGVEVALTELDIRLSIPANATNLAQQREAYKNVVGACVQVRGCIGVEIWDF

YDPFSWVPATFPGQGAPLLWFEDFSKHPAYDGVVEALTNRTTGGCKGKGKGKGKVWKA (SEQ ID NO: 37)
KGKGHGHGPHTGLHTLAKQAGLKYFGSATDSPGQRERAGYEDKYAQYDQIMWKSGEFGLTTP

TNGQKWLFTEPERGVFNFTEGDIVTNLARKHGFMQRCHALVWHSQLAPWVESTEWTPEELRQV

IVNHITHVAGYYKGKCYAWDVVNEALNEDGTYRESVFYKVLGEDYIKLAFETAAKVDPHAKLY

YNDYNLESPSAKTEGAKRIVKMLKDAGIRIDGVGLQAHLVAESHPTLDEHIDAIKGFTELGVEVA

LTELDIRLSIPANATNLAQQREAYKNVVGACVQVRGCIGVEIWDFYDPFSWVPATFPGQGAPLL

WFEDFSKHPAYDGVVEALTNRTTGGCKGKGKGKGKVWKA

Xy136882:

(SEQ ID NO: 38)
ATGCACTCCAAAGCTTTCTTGGCAGCGCTTCTTGCGCCTGCCGTCTCAGGGCAACTGAACGA

CCTCGCCGTCAGGGCTGGACTCAAGTACTTTGGTACTGCTCTTAGCGAGAGCGTCATCAACA

GTGATACTCGGTATGCTGCCATCCTCAGCGACAAGAGCATGTTCGGCCAGCTCGTCCCCGAG

AATGGCATGAAGTGGGATGCTACTGAGCCGTCCCGTGGCCAGTTCAACTACGCCTCGGGCGA

CATCACGGCCAACACGGCCAAGAAGAATGGCCAGGGCATGCGTTGCCACACCATGGTCTGG

TACAGCCAGCTCCCGAGCTGGGTCTCCTCGGGCTCGTGGACCAGGGACTCGCTCACCTCGGT

-continued

```
CATCGAGACGCACATGAACAACGTCATGGGCCACTACAAGGGCCAATGCTACGCCTGGGAT

GTCATCAACGAGGCCATCAATGACGACGGCAACTCCTGGCGCGACAACGTCTTTCTCCGGAC

CTTTGGGACCGACTACTTCGCCCTGTCCTTCAACCTAGCCAAGAAGGCCGATCCCGATACCA

AGCTGTACTACAACGACTACAACCTCGAGTACAACCAGGCCAAGACGGACCGCGCTGTTGA

GCTCGTCAAGATGGTCCAGGCCGCCGGCGCGCCCATCGACGGTGTCGGCTTCCAGGGCCACC

TCATTGTCGGCTCGACCCCGACGCGCTCGCAGCTGGCCACCGCCCTCCAGCGCTTCACCGCG

CTCGGCCTCGAGGTCGCCTACACCGAGCTCGACATCCGCCACTCGAGCCTGCCGGCCTCTTC

GTCGGCGCTCGCGACCCAGGGCAACGACTTCGCCAACGTGGTCGGCTCTTGCCTCGACACCG

CCGGCTGCGTCGGCGTCACCGTCTGGGGCTTCACCGATGCGCACTCGTGGATCCCGAACACG

TTCCCCGGCCAGGGCGACGCCCTGATCTACGACAGCAACTACAACAAGAAGCCCGCGTGGA

CCTCGATCTCGTCCGTCCTGGCCGCCAAGGCCACCGGCGCCCCGCCCGCCTCGTCCTCCACC

ACCCTCGTCACCATCACCACCCCTCCGCCGGCATCCACCACCGCCTCCTCCTCCTCCAGTGCC

ACGCCCACGAGCGTCCCGACGCAGACGAGGTGGGGACAGTGCGGCGGCATCGGATGGACGG

GGCCGACCCAGTGCGAGAGCCCATGGACCTGCCAGAAGCTGAACGACTGGTACTGGCAGTG

CCTGTAA
```

(SEQ ID NO: 39)
MHSKAFLAALLAPAVSGQLNDLAVRAGLKYFGTALSESVINSDTRYAAILSDKSMFGQLVPENG
MKWDATEPSRGQFNYASGDITANTAKKNGQGMRCHTMVWYSQLPSWVSSGSWTRDSLTSVIE
THMNNVMGHYKGQCYAWDVINEAINDDGNSWRDNVFLRTEGTDYFALSFNLAKKADPDTKLY
YNDYNLEYNQAKTDRAVELVKMVQAAGAPIDGVGFQGHLIVGSTPTRSQLATALQRFTALGLE
VAYTELDIRHSSLPASSSALATQGNDFANVVGSCLDTAGCVGVTVWGFTDAHSWIPNTFPGQGD
ALIYDSNYNKKPAWTSISSVLAAKATGAPPASSSTTLVTITTPPPASTTASSSSSATPTSVPTQTRW
GQCGGIGWTGPTQCESPWTCQKLNDWYWQCL (SEQ ID NO: 40)
QLNDLAVRAGLKYFGTALSESVINSDTRYAAILSDKSMFGQLVPENGMKWDATEPSRGQFNYAS
GDITANTAKKNGQGMRCHTMVWYSQLPSWVSSGSWTRDSLTSVIETHMNNVMGHYKGQCYA
WDVINEAINDDGNSWRDNVFLRTFGTDYFALSFNLAKKADPDTKLYYNDYNLEYNQAKTDRA
VELVKMVQAAGAPIDGVGFQGHLIVGSTPTRSQLATALQRFTALGLEVAYTELDIRHSSLPASSS
ALATQGNDFANVVGSCLDTAGCVGVTVWGFTDAHSWIPNTFPGQGDALIYDSNYNKKPAWTSI
SSVLAAKATGAPPASSSTTLVTITTPPPASTTASSSSSATPTSVPTQTRWGQCGGIGWTGPTQCESP
WTCQKLNDWYWQCL

Xyl5123:

(SEQ ID NO: 41)
```
ATGGTCTCCTTCAAGGCCCTCGTTCTCGGCGCCGTTGGCGCCCTCTCCTTCCCTTTCAACGTC

ACCGAGCTGTCCGAGGCGCACGCCCGGGGCGAGAATGTGACCGAGCTCTTGATGTCTCGCG

CCGGCACGCCGAGCCAGACCGGCTGGCACGGGGGCTACTACTTCTCCTTCTGGACCGACAAC

GGCGGCACCGTCAACTACTGGAACGGCGACAATGGCAGATACGGTGTCCAGTGGCAGAACT

GCGGCAACTTTGTCGGCGGTAAGGGATGGAACCCCGGCGCGGCGCGGACCATCAACTTCAG

CGGCTCCTTCAACCCGTCGGGCAACGGGTACCTGGCCGTGTACGGGTGGACGCAGAACCCG

CTGATCGAGTACTACATCGTCGAGTCGTTCGGCACGTACGACCCGTCGTCGCAGGCCCAGGT

CCTCGGCACCTTCTACCAGGACGGCAGCAACTACAAGATCGCCAAGACGACCCGCTACAAC

CAGCCCTCCATCGAGGGCACCAGCACCTTCGACCAGTTCTGGTCCGTCCGCGAGAACCACCG

CACCAGCGGCAGCGTCAACGTCGGCGCCCACTTCGCCCGCTGGCAGCAGGCCGGCCTCCGCC
```

-continued

```
TCGGCACCCACAACTACCAAATCATGGCCACCGAGGGCTACCAGAGCAGCGGCTCCTCCGA
TATCACCGTCTGGTAA
```

(SEQ ID NO: 42)
```
MVSFKALVLGAVGALSFPFNVTELSEAHARGENVTELLMSRAGTPSQTGWHGGYYFSFWTDNG
GTVNYWNGDNGRYGVQWQNCGNFVGGKGWNPGAARTINFSGSFNPSGNGYLAVYGWTQNPL
IEYYIVESFGTYDPSSQAQVLGTFYQDGSNYKIAKTTRYNQPSIEGTSTFDQFWSVRENHRTSGSV
NVGAHFARWQQAGLRLGTHNYQIMATEGYQSSGSSDITVW
```

(SEQ ID NO: 43)
```
FPFNVTELSEAHARGENVTELLMSRAGTPSQTGWHGGYYFSFWTDNGGTVNYWNGDNGRYGV
QWQNCGNFVGGKGWNPGAARTINFSGSFNPSGNGYLAVYGWTQNPLIEYYIVESFGTYDPSSQA
QVLGTFYQDGSNYKIAKTTRYNQPSIEGTSTFDQFWSVRENHRTSGSVNVGAHFARWQQAGLR
LGTHNYQIMATEGYQSSGSSDITVW
```

Xyl2202:
(SEQ ID NO: 44)
```
ATGGTTTCTGTCAAGGCAGTCCTCCTCCTCGGCGCCGCCGGCACCACCCTGGCCTTCCCGTTC
AACGCTACCCAGTTCAGCGAGCTCGTTGCCCGGGCCGGCACCCCGAGCGGCACCGGCACGC
ACGACGGCTTCTACTACTCCTTCTGGACCGACGGCGGCGGCAACGTCAACTACGAGAACGGT
CCTGGCGGCTCCTACACCGTCCAGTGGCAGAACTGCGGCAACTTTGTCGGCGGCAAGGGCTG
GAACCCCGGCCAGGCCCGCACCATCACCTACTCGGGCACCGTCGACTTCCAGGGCGGCAAC
GGCTACCTGGCCATCTACGGCTGGACGCAGAACCCGCTGATCGAGTACTACATCGTCGAGTC
GTTCGGCTCGTACGACCCCTCGTCGCAGGCCCAGACTTTCGGCACCGTCGAGGTGGACGGCG
GCACCTACACGCTGGCCAAGACGACGCGCGTCAACCAGCCCTCGATCGAGGGCACCAGCAC
CTTCGACCAGTTCTGGTCCGTCCGCCAGCAGCACCGCACCTCCGGCTCCGTCGACGTCGGCG
CCCACTTCGACGCCTGGGCCAAGGCCGGCCTCCAGCTCGGCACCCACAACTACAGATCGTCG
CCACCGAGGGCTACCAGAGCAGCGGCTCCTCTTCCATCACCGTCCAGGCCTAAGAGGGCCCT
CAGGCCTTTGCTCTACTGCCCTCTCCTCTCCTCTGCGCTTTCCGTAAGGGAGATCTAA
```

(SEQ ID NO: 45)
```
MVSVKAVLLLGAAGTTLAFPFNATQFSELVARAGTPSGTGTHDGFYYSFWTDGGGNVNYENGP
GGSYTVQWQNCGNFVGGKGWNPGQARTITYSGTVDFQGGNGYLAIYGWTQNPLIEYYIVESFG
SYDPSSQAQTFGTVEVDGGTYTLAKTTRVNQPSIEGTSTFDQFWSVRQQHRTSGSVDVGAHFDA
WAKAGLQLGTHNYRSSPPRATRAAAPLPSPSRPKRALRPLLYCPLLSSALSVREI
```

(SEQ ID NO: 46)
```
FPFNATQFSELVARAGTPSGTGTHDGFYYSFWTDGGGNVNYENGPGGSYTVQWQNCGNFVGG
KGWNPGQARTITYSGTVDFQGGNGYLAIYGWTQNPLIEYYIVESFGSYDPSSQAQTFGTVEVDG
GTYTLAKTTRVNQPSIEGTSTFDQFWSVRQQHRTSGSVDVGAHFDAWAKAGLQLGTHNYRSSP
PRATRAAAPLPSPSRPKRALRPLLYCPLLSSALSVREI
```

BXyl117994:
(SEQ ID NO: 47)
```
ATGATAATGATGAGACTCAAGTCGGGACTGGCCGGGGCGCTGGCCTGGGGAACGACGGCGG
CGGCGGCGGCGGTGGCGAGAGTGGGAGCCGGCGCGGCCGCGAACTCGACCTACTACAA
CCCGATCCTCCCCGGGTGGCACTCGGACCCGTCGTCGTGCAGGTGGAGGGGATCTTCTACT
GCGTGACGTCGACCTTCATCTCGTTCCCCGGCCTGCCCATCTACGCGTCCCGGGACCTGATCA
ACTGGAAGCACGTCAGCCACGTGTGGAACCGCGAGTCCCAGCTGCCCGGGTACAGCTGGGC
GACGGAGGGCCAGCAGGAGGGCATGTACGCGGCGACGATCCGGCACCGCGAGGGCGTCTTC
```

-continued

```
TATGTCATCTGCGAGTACCTGGGCGTCGGCGGCAGGGACGCCGGCGTGCTCTTCCGGGCGAC
GGACCCGTTCGACGACGCGGCCTGGAGCGACGCCCTGACCTTCGCCGCGCCCAAGATCGAC
CCGGACCTGTTCTGGGACGACGACGGGACGGCCTACGTGGCGACGCAGGGCGTGCAGGTGC
AGCGCATGGACCTCGACACGGGCGCCATCGGCCCGCCCGTGCCGCTGTGGAACGGGACGGG
CGGGGTGTGGCCCGAGGGCCCGCACATCTACCGCCGCGCCGACCACTTCTACCTCATGATCG
CCGAGGGCGGCACGGCCGAGGACCACGCCATCACCATCGCCCGCAGCGACCGGCTGACGGG
GCCCTACGTCTCCTGCCCGCACAACCCGATCCTGACCAACCGCGGCACGGACGAGTACTTCC
AGACGGTCGGCCACGGCGACCTCTTCCAGGACGCCGCCGGCAACTGGTGGGGCGTCGCCCT
GGCCACGCGCTCCGGCCCGGAGTACCGCGTCTACCCGATGGGGCGCGAGACCGTGCTGTTCC
CCGTCACCTGGCGCGAGGGCGACTGGCCGGTCCTGCAGCCCGTGCGCGGCGCCATGTCGGG
CTGGCCGCTGCCGCCGCCGACGCGCGACCTGCCCGGCGACGGGCCCTTCAACGCGGACCCG
GACGTGAAGGCGATGCCGCGGAACCTGGTGCACTGGCGGGTCCCGCGCGAGGGCGCCTTCG
CGACCACGGCGCGCGGGCTCCGCGTCGCGCTGGGGCGCAACCGGCTCGACGGCTGGCCCGG
GGGCGCCGAGCCGGCCGCCAGGGCCGTCTCCTTCGTGGGGCGCCGCCAGACCGACAGCCTC
TTCACCTTCAGCGAGGCCGGCGTGACCGCGTTCCTGACCCAGCTCGCCAACCTGCAGCTCGG
CCTGGTCCTCCCTGGACGGCGGGCCAGCTGCGGCTCCGCTTCATCGCGTCGGGCCACGTCAC
GCGATACCGCGGTGCCGGAGGACTGCACCGATGTCGGCAGCTGTGACGGCGGTGACGACGG
CGGTGACGGCGGGTACCGGTTCGCGGCCATGCTGGCGTCCGACCCGGACCCGGACCGGACC
CGGATCGAGGTCGGCACCGCGCCGGCCGAGCTGCTCAGCGGCGGCTCCGGCTCCTTCGTCGG
CACCCTGCTCGGCGTCTACGCCACCTGCAACGGGGCCGGGGAGGGCATCGACTGCCCCGCC
GGCACGCCCGACGCTTACTTCACCCGGTGGAGGTACACGGGCGAGGGCCAGTTCTACACCG
AGACCGATCTCGTCCCGCCCGACGAGGGCCAGGGCAAGGGTAAAGGTAAAGGGAACGGTA
AAGGCAAGGGCAACGGCAACGGCAACGGCAAAGCCGCCAAGAGAAGCAGGTTTCCAAGGT
GGACGCCGGGTCTAAATGGCGTCGTTATCCCGCCCCTGTGGATCATGGAGGACGACCCGGA
GACCCGCTGGCCGGCCCAGAAGCGGGCTGGGGCGGGCGGGCAGAGCTACGTCTTCCGCCAC
GGCAACCTGCACACAGTTCGGGATGAGAATGATGCCTTCAAGGGCGCCTCTCTCTGCGTACC
TTACCATACCTACCTTGCCAAGGTGATCCAGGCACTTACTCTCAACTTTGCGCATCTTTTCGG
GGCGTGGAGACTGACGGTGTAG
```

(SEQ ID NO: 48)
MIMMRLKSGLAGALAWGTTAAAAAAVARVGAGAAANSTYYNPILPGWHSDPSCVQVEGIFYC
VTSTFISFPGLPIYASRDLINWKHVSHVWNRESQLPGYSWATEGQQEGMYAATIRHREGVFYVIC
EYLGVGGRDAGVLFRATDPFDDAAWSDALTFAAPKIDPDLFWDDDGTAYVATQGVQVQRMDL
DTGAIGPPVPLWNGTGGVWPEGPHIYRRADHFYLMIAEGGTAEDHAITIARSDRLTGPYVSCPHN
PILTNRGTDEYFQTVGHGDLFQDAAGNWWGVALATRSGPEYRVYPMGRETVLFPVTWREGDW
PVLQPVRGAMSGWPLPPPTRDLPGDGPFNADPDVKAMPRNLVHWRVPREGAFATTARGLRVAL
GRNRLDGWPGGAEPAARAVSFVGRRQTDSLFTFSEAGVTAFLTQLANLQLGLVLPGRRASCGSA
SSRRATSRDTAVPEDCTDVGSCDGGDDGGDGGYRFAAMLASDPDPDRTRIEVGTAPAELLSGGS
GSFVGTLLGVYATCNGAGEGIDCPAGTPDAYFTRWRYTGEGQFYTETDLVPPDEGQGKGKGKG
NGKGKGNGNGNGKAAKRSRFPRWTPGLNGVVIPPLWIMEDDPETRWPAQKRAGAGGQSYVFR
HGNLHTVRDENDAFKGASLCVPYHTYLAKVIQALTLNFAHLFGAWRLTV

-continued

```
                                                              (SEQ ID NO: 49)
WGTTAAAAAAVARVGAGAAANSTYYNPILPGWHSDPSCVQVEGIFYCVTSTFISFPGLPIYASRD

LINWKHVSHVWNRESQLPGYSWATEGQQEGMYAATIRHREGVFYVICEYLGVGGRDAGVLFR

ATDPFDDAAWSDALTFAAPKIDPDLFWDDDGTAYVATQGVQVQRMDLDTGAIGPPVPLWNGT

GGVWPEGPHIYRRADHFYLMIAEGGTAEDHAITIARSDRLTGPYVSCPHNPILTNRGTDEYFQTV

GHGDLFQDAAGNWWGVALATRSGPEYRVYPMGRETVLFPVTWREGDWPVLQPVRGAMSGWP

LPPPTRDLPGDGPFNADPDVKAMPRNLVHWRVPREGAFATTARGLRVALGRNRLDGWPGGAEP

AARAVSFVGRRQTDSLFTFSEAGVTAFLTQLANLQLGLVLPGRRASCGSASSRRATSRDTAVPED

CTDVGSCDGGDDGGDGGYRFAAMLASDPDPDRTRIEVGTAPAELLSGGSGSFVGTLLGVYATC

NGAGEGIDCPAGTPDAYFTRWRYTGEGQFYTETDLVPPDEGQGKGKGKGNGKGKGNGNGNGK

AAKRSRFPRWTPGLNGVVIPPLWIMEDDPETRWPAQKRAGAGGQSYVFRHGNLHTVRDENDAF

KGASLCVPYHTYLAKVIQALTLNFAHLFGAWRLTV

BXy145310:
                                                              (SEQ ID NO: 50)
ATGGGGCGCCTAAACGATCTCATAGCCCTCCTTGCACTGTTGAGCGGCAGTGCCACATCCGC

TGCCGTAAGAAACACGGCTTCTCAGGCTCGCGCGGCGGAATTCAACAACCCGGTGCTCTGGG

AGGACTATCCGGACCTGGACGTGTTCCGGGTCGGGTCGACCTTCTACTACTCCTCCTCCACGT

TCGCCTACTCCCCGGGGGCTCCGGTGCTCAAGTCGTACGACCTGGTGAACTGGACCCCCGTC

ACCCACTCGGTCCCGACGCTCAACTTTGGGGACCGCTACAACCTCACGGGCGGCACGCCGGC

CGGCTACGTCAAGGGCATCTGGGCGTCGACGCTGCGGTACCGGCCCTCCAACGACAAGTTCT

ACTGGTACGGCTGCGTCGAGTTCGGCAAGACGTACATCTGGACCAGCTCCGGCACGCGCGC

GGGCGACAGGGACGGCGAGGTGGACCCCGCCGACTGGGTCTGGGAGCCGCACCCGCCCATC

GACCGGTGCTACTACGACAGCGGCCTGTTGATCGACGACGACGACAAGATGTACATCGCGT

ACGGCAACCCCAAGATCGAGGTCGCCGAGCTGTCCGACGACGGGCTCACCGAGGTCTCCTC

CCGGGTCGTCTACACCCCGCCGGCCGGCACCACCATCGAGGGCTCGCGCATGTACAAGGTCG

GCGACGCCTACTACATCCTGGTGACGCGGCCGGCCGACGCCGAGTGGGTGCTCCGGTCGAC

GTCCGGGCCCTTTCGGCCCGGCGGCATGGTCGACACCCCGGACGGCCGCAGCTGGTACTACG

TCGCCTTCATGGACGCGTACCCGGGGGGCCGCATCCCCGTGGTCGCGCCGCTGCGCTGGACG

GACGACGGGTGGCCCGAGGTGGTGACGGACGCGCAGGGCGGCTGGGGCGCCAGCTACCCGG

TCCCCGTGGAGACGGGCAAGACGGTGCCGGACGACGGCTGGGAGCTGGACGAGTTCAGGGG

CGGCCGGCTGAGCCACCACTGGGAGTGGAACCACAACCCGGACCCGGCCCGCTTCGCGCTC

GCGGGCGGGACGAGGGCGGGCTGGTGCTGCAGGCGGCGACGGTGACGGAGGACCTGTTCG

CGGCCAGGAACACGCTCACGCGGAGGATCAGGGGCCCCAAGTCGAGCGGCACGTTCCGGCT

GGACGTCAGCAGGATGCGCGACGGCGACCGGGCCGGGCCGTGCTGTTCCGGGACACGGCG

GCGTATATCGGCGTGTGGAAGCAAGGGGACGAGGCCACCATCGTCGTAGTCGACGGCCTTG

AGCTGGCTCTGAGCTCCTGGACGACCGTCTCGACCGGGAGGGTGGCCGAGACGGGCCCGAC

CCTGAGCAGCACGCAGGATGTCTGGCTCCGGATCGAGGCCGACATCACGCCCGCGTTCGGG

ACCAACACGGCAAGGACCACGACTTTCTCGTACAGTGTGGACGGCGGGAAGACCTTTGTCC

GTCTTGGCCCGGCCTTCTCGATGAGCAATACTTGGCAATACTTTACGGGCTACAGGTTCGGA

GTCTTCAACTTTGCCACCAAGGAGCTTGGGGGCGAAGTCAAGGTCAAGAGCTTCCAGATGCA

GCCTCTGTGA
```

(SEQ ID NO: 51)
MGRLNDLIALLALLSGSATSAAVRNTASQARAAEFNNPVLWEDYPDLDVFRVGSTFYYSSSTFA

YSPGAPVLKSYDLVNWTPVTHSVPTLNFGDRYNLTGGTPAGYVKGIWASTLRYRPSNDKFYWY

GCVEFGKTYIWTSSGTRAGDRDGEVDPADWVWEPHPPIDRCYYDSGLLIDDDDKMYIAYGNPKI

EVAELSDDGLTEVSSRVVYTPPAGTTIEGSRMYKVGDAYYILVTRPADAEWVLRSTSGPFRPGG

MVDTPDGRSWYYVAFMDAYPGGRIPVVAPLRWTDDGWPEVVTDAQGGWGASYPVPVETGKT

VPDDGWELDEFRGGRLSHHWEWNHNPDPARFALAGGDEGGLVLQAATVTEDLFAARNTLTRRI

RGPKSSGTFRLDVSRMRDGDRAGAVLFRDTAAYIGVWKQGDEATIVVVDGLELALSSWTTVST

GRVAETGPTLSSTQDVWLRIEADITPAFGTNTARTTTFSYSVDGGKTFVRLGPAFSMSNTWQYFT

GYRFGVFNFATKELGGEVKVKSFQMQPL (SEQ ID NO: 52)
VRNTASQARAAEFNNPVLWEDYPDLDVFRVGSTFYYSSSTFAYSPGAPVLKSYDLVNWTPVTHS

VPTLNFGDRYNLTGGTPAGYVKGIWASTLRYRPSNDKFYWYGCVEFGKTYIWTSSGTRAGDRD

GEVDPADWVWEPHPPIDRCYYDSGLLIDDDDKMYIAYGNPKIEVAELSDDGLTEVSSRVVYTPP

AGTTIEGSRMYKVGDAYYILVTRPADAEWVLRSTSGPFRPGGMVDTPDGRSWYYVAFMDAYP

GGRIPVVAPLRWTDDGWPEVVTDAQGGWGASYPVPVETGKTVPDDGWELDEFRGGRLSHHWE

WNHNPDPARFALAGGDEGGLVLQAATVTEDLFAARNTLTRRIRGPKSSGTFRLDVSRMRDGDR

AGAVLFRDTAAYIGVWKQGDEATIVVVDGLELALSSWTTVSTGRVAETGPTLSSTQDVWLRIEA

DITPAFGTNTARTTTESYSVDGGKTEVRLGPAFSMSNTWQYFTGYRFGVENFATKELGGEVKVK

SFQMQPL

BXy120937:

(SEQ ID NO: 53)
ATGACGATGCTCAAGTCGGCCCTCCCCGCGGCGCTGGCCCTCCTCCTAACGGCGGCCAACGG

CCACCCTTCCAGGACCCCGGCGGCGGCGGCGGGGGGATGGGCACCGCTGGCGAATGGG

ACATTCCGGAACCCGATCCTGTACGAGGACTTCCCGGACAACGACGTGTCGGTCGGGCCGG

ACGGGGCCTTCTACCTGTCGGCGTCCAACTTCCACTTCAGCCCCGGGGCGCCCATCCTGCGG

TCTTACGACCTGGTCGACTGGGAGTTTGTGGGCCACTCGATCCCGCGCCTCGACTTCGGCGC

CGGCTACGACCTGCCGCCGACGGGCGAGCGGGCGTACCGCGCGGGCACGTGGGCGTCGACG

CTGCGGTACCGCGAGAGCACGGGGCTCTGGTACTGGATCGGGTGCACCAACTTCTGGCGCAC

CTGGGTCTTCACCGCCCCGGCGCCCGAGGGGCCCTGGACCCGGGCGGGCGACTTCGGCGAC

GGCGTGTGCTTCTACGACAACGGCCTGCTGGTCGACGACGACGACACCATGTACGTCGTCTA

CACCCACGACGGCGGCAAGCGGGTCCACGTGACCCAGCTGAGCGCGGACGGGCTGAGCGCC

GTCCGCACCGAGACCGTCCTGGTGCCGGAGCAGGCCGGCGTCGACGCCCTCGAGGGCAACC

GCATGTACAAGATCGACGGCCGCTACTACATCCTCAACGACCACCCGGGCACCACCGCCTAC

GTCTGGAAGTCCGACTCGCCCTGGGGTCCCTACGAGGGCAAGGCGCTGGCCGACAACGTCG

CCAGCCCCCTGCCCGGCGGCGGCGCCCCGCACCAGGGCAGCCTGGTGCCCACGCCCTCGGG

CGCCTGGTACTTTATGTCCTTCACCTGGGCCTACCCGTCCGCCGCCTGCCCGTGCTGGCCCC

GATCGAGTTCCAGCCGGACGGGTTCCCGACCCTCGGCGCCTGGTACTTTATGTCCTTCACCTG

GGCCTACCCGTCCGGCCGCCTGCCCGTGCTGGCCCCGATCGAGTTCCAGCCGGACGGGTTCC

CGACCCTCGTCACCGCCAAGGACAACAACAACAACAACAACAACGCCTGGGGCGCCAG

CTACCCGCTGCCGCCGCTACCGCGCCGGCCGCTGGGCTACCCGTGGTCGCGGGCGCGGTACG

ACTTCAGCGCGCTCGCCGAACTGCCGCCCGCGTTCGAGTGGAACCACAACCCGGACGCGAG

-continued
```
CAACTACACGCTGGGAGGGAACGGCGCTGCCGGCCTGATCCTGCGGGCCGCCACCGTCGCG

CCCGACGACGACCTGTACTCGGCGCGCAACACGCTGACGCACCGCGCCCACGGGCCCTTCCC

CTCGGCCACGCTGGTCCTCGACGTCGCGGACATGGCCGACGGCGACCGCGCCGGGCTGGCC

GCCTTCCGCGACCGCAGTGCCTACATCGGCATCCACTGCTCCTCCTCCTCTGATGAGAAGAA

GAAGAAGACGTACGAGGTGGTGGCGCGATTCAACATGACGCTGGACGAGTGGGGCAGCGGC

GAGACGCTCGATCTGGGCGAGGTGGTGGAGCGGGTCGAGCTGGCCTCGGGCGTGACGCGCG

TGTGGCTGCGGGCGAGCATGGACGCGCGGCCCGACGGCGAGCGGACGGCCCGGTTCGGGTA

CAGCGTCGACGGGGGCGAGACCTTTGCCGGCCTGGGGCCCGCCTACCAACTCTACGCCGGGT

GGCCCTTCTTTGTCGGCTACCGCTTCGCCGTCTTCAACTACGCCACCAAGGCCCTCGGCGGG

AGCGTCACCGTCCTGAGCCTCGAGACCGACTCGGGCGAGGGTGAGCGCGATGCCGAGCAAG

CGTGA
```

```
                                                        (SEQ ID NO: 54)
MTMLKSALPAALALLLTAANGHPSRTPAAAAAGGWAPLANGTFRNPILYEDFPDNDVSVGPDG

AFYLSASNFHFSPGAPILRSYDLVDWEFVGHSIPRLDFGAGYDLPPTGERAYRAGTWASTLRYRE

STGLWYWIGCTNFWRTWVFTAPAPEGPWTRAGDFGDGVCFYDNGLLVDDDDTMYVVYTHDG

GKRVHVTQLSADGLSAVRTETVLVPEQAGVDALEGNRMYKIDGRYYILNDHPGTTAYVWKSDS

PWGPYEGKALADNVASPLPGGGAPHQGSLVPTPSGAWYFMSFTWAYPSGRLPVLAPIEFQPDGF

PTLGAWYFMSFTWAYPSGRLPVLAPIEFQPDGFPTLVTAKDNNNNNNNNAWGASYPLPPLPRRP

LGYPWSRARYDFSALAELPPAFEWNHNPDASNYTLGGNGAAGLILRAATVAPDDDLYSARNTL

THRAHGPFPSATLVLDVADMADGDRAGLAAFRDRSAYIGIHCSSSSDEKKKKTYEVVARFNMTL

DEWGSGETLDLGEVVERVELASGVTRVWLRASMDARPDGERTARFGYSVDGGETFAGLGPAY

QLYAGWPFFVGYRFAVFNYATKALGGSVTVLSLETDSGEGERDAEQA
```

```
                                                        (SEQ ID NO: 55)
HPSRTPAAAAAGGWAPLANGTFRNPILYEDFPDNDVSVGPDGAFYLSASNFHFSPGAPILRSYDL

VDWEFVGHSIPRLDFGAGYDLPPTGERAYRAGTWASTLRYRESTGLWYWIGCTNFWRTWVFTA

PAPEGPWTRAGDFGDGVCFYDNGLLVDDDDTMYVVYTHDGGKRVHVTQLSADGLSAVRTETV

LVPEQAGVDALEGNRMYKIDGRYYILNDHPGTTAYVWKSDSPWGPYEGKALADNVASPLPGG

GAPHQGSLVPTPSGAWYFMSFTWAYPSGRLPVLAPIEFQPDGFPTLGAWYFMSFTWAYPSGRLP

VLAPIEFQPDGFPTLVTAKDNNNNNNNNAWGASYPLPPLPRRPLGYPWSRARYDFSALAELPPA

FEWNHNPDASNYTLGGNGAAGLILRAATVAPDDDLYSARNTLTHRAHGPFPSATLVLDVADMA

DGDRAGLAAFRDRSAYIGIHCSSSSDEKKKKTYEVVARFNMTLDEWGSGETLDLGEVVERVELA

SGVTRVWLRASMDARPDGERTARFGYSVDGGETFAGLGPAYQLYAGWPFFVGYRFAVFNYAT

KALGGSVTVLSLETDSGEGERDAEQA
```

The following sequences comprise additional xylanase (Xyl), beta-xylosidase (BXyl), and alpha-xylosidase (AXyl) sequences of interest. The first sequence provided in each set below comprises the cDNA sequence, the second sequence is the polypeptide sequence with no signal sequence predicted.

```
Xy18836:
                                                        (SEQ ID NO: 56)
ATGCTGAACCTATCCCACACCGAGCACACTCTCTTTCGCCCTCTCCCCCTTTCCCTCCCTCAT

CACCACCACCACCACCACTTCATTGTCGGCCGCCGCCCGCCCGAGGCGCTGCGCGGCGCCAT

CACGCGCCACATCCGCGCCGTCGCCGGCTACTACCGCGGCCGCTGCTACGCCTGGGACGTGG

TCAACGAGGCGCTCGACGAGGACGGCACCTACCGCAAGAGCCTCTTCTACAACGTCCTCGGC
```

-continued

GACGAGTACATCCGCATCGTCAAGACCTTCGAGAAGCTGATCCGCGAGAAGCCAAAGCCGG

GCTTCAAGCGCAAGAGGAAAACCGTAGCAGCAAACTAA (SEQ ID NO: 57)
MLNLSHTEHTLFRPLPLSLPHHHHHHHFIVGRRPPEALRGAITRHIRAVAGYYRGRCYAWDVVN

EALDEDGTYRKSLFYNVLGDEYIRIVKTFEKLIREKPKPGFKRKRKTVAAN

AXy1267:
(SEQ ID NO: 58)
ATGGAGGAGGAAGCGACTCCAAGACCCCAATCGAGTATCGTGCAGATGCAGAGGCACATGC

TCAACTCGCGCTGGCATGCCAGGCGTTTGGCCAACAAACCCCACGGCGTCTTCCCAAGCTTG

GATGGACATCTAAGGACCTACACCAAGGATATCCGACCAGCCCCGACCTGGCGGGTCGGAC

AATGGCTCGTGGCCGAGGGCGTACAAGTCCAATACGCCGAGGAAGTATACCGAATCACTCC

CACGGCCTCGGGCAAGGGAATCAGCCTCTTGTGCCCGACGCGCAAGATCTTGAACCGTGGG

AACACTCTGAACCTGGCAACGCTCAGCATCGACATCGAGCCGGCTTTTGATGGCGTCCTCTC

TGTCGAGACCACCCACTGGCAAGGCGCCGTCCGTCGCGGACCCGACTTCGACCTCTTCCCCG

CCGGCCGGCCCGAGGTGGACGCCAAGGTGACCAAGACGGAGAGCGGCACCACCCTGTCGTC

CGGGACGCTCTCGGCGACAGTCAGCGGCAAGCCGCACGAGTTCGAGATCGCCTTCCATCCG

ACCGGGGGCAAGAAGCCCCTGACCACCCTGCTCAACCGGTCAGTCGGCCTGGCCTACACGC

CCGCCCCGAGCACGCCCATGCAGCTGGCCGACATGCGCAACTTCCGCCACTACATCTTCACC

CAGACCACCCTCGCCGTCGGCGAGTCCATCCACGGGCTCGGCGAGCGCTTCGGGCCCTTCAA

CAAGGTCGGCCAGAGGGTCGAGCTGTGGAACGCGGACGGGGGCACCTCGTCCGACCAGGCG

TACAAGAACGTGGGCTTCTGGATGAGCTCGCGCGGCTACGGTGTCTTCGTCGACACTCCCGG

GCGCGTCGAGCTCGAGATCGGGAGCGAGCGGTGCTGCCGGCTCCAGACGAGCGTCGAGGGG

CAGCGGCTCCGCTGGTTCATCATCTACGGGCCCTCCCCGCGCGACATCCTGCGCCGGTACTC

GGTCCTCACCGGAGCCCCCGGCAGCGTGCCCAGCTGGTCCTTCGGCCTGTGGCTCAGCACGT

CCTTCACCACCTCGTACGACGAGGAGACGGTCAACAGCTTCCTGGCCGGCATGAGGGCGCG

CGACATACCCGTCGAGGTCTTCCACTTCGACTGCTTCTGGCTCAAGGCGTTCCAGTGGTGCG

ACTTCGAGTTCGACCGCGACATGTTCCCGGACCCGAGGGGCCAGATCGGGCGCCTCAAGGC

CGGCGGCCTCGTCAAGAAGGTCTGCGTCTGGACGAACCCGTACCTGGGCCAGGCGTCCCCCG

TCTTCGCCGAGGCCGCGGCCAGGGGCTACCTGCTCCGGCGCAGGAACGGCGACGTCTTCCAG

TGGGACCTGTGGCAGACGGGCATGGGCATCGTCGACTTCACCAACCCGGACGCCCGCGCCT

GGTTCGCCGCCTGTCTCGACCGCCTCTTCGACACGGGCGTCGACTGCATCAAGACCGACTTT

GGCGAGCGCATCCCCTCCGAGGATGTGCAGTGGTTCGACCCTTCGGTCGACCCGGAGCGGAT

GCACAACTACTACGCCTTCATCTACAACAAGCTCGTCTACGAGGCCCTGCAGAGGCGTTACG

GCGCCAACGAGGCCGTCCTGTTCGCCCGCGCCGCCACCGCCGGCTGCCAGCGGTTCCCCCTC

ACCTGGGGCGGCGACTGCGAGTCGACCCCCGAGGCCATGGCCGAGTCGCTACGCGGTGGTT

TGTCCCTCGGCCTGTCCGGGTTCGCCTTCTGGAGCGTCGACATTGGCGGCTTCGAGGGGTCG

CCGCCTCCCTGGATCTACAAGCGCTGGGTCGCCTTCGGCCTCCTCTGCTCCCACTCGCGCCTG

CACGGCTCCAACTCGTACCGGGTCCCCTGGACGGTCGACGGCGACGACCAGTCCGAGGAGG

GATGCTCCGCCACGCTGCGCAAGTGGACCCATCTCAAGGCTCGCCTGATGCCCTACCTCTTC

TCCCAGGCGCAGGAGAGCGTCCGGGGCGGGCTCCCGCTCAGCCTGAGGGCCATGTGCATCG

AGTTCCCCGACGACCCGACCGCCTGGACCCTCGATCGCCAGTTCATGCTCGGCGACGGCCTC

CTCGTCGCCCCCGTCTTCGAGGAGGACGGCACCGTCGAGTTCTACCTGCCCAGGGGCAAGTG

-continued

```
GACCAACTTCTTCACCGGCGAGGTCAAGGAGGGCCCCGGCTGGTTCGCCGAGACCCACGGG

TTCGGCACCCTGCCGCTCTACGTCCGGCCCAACACGCTCCTGGTTCTGGGCAAGGAAGGAGA

GACGAGGACCGTGTACGACTACACGAGCGACGTCGAGGTGAGGGCGTATTTTGCCAGTGAC

AGCGCCAGCGCCGTGCTGGTCGACGCCGAGGGCAAGACTGTAGGTACCCTGCGTGTCAAGG

ACGGGGAGATTATCGGAAAGGAACTGCTATCTGGCAACTCGGTCATCAATGTCGTGAGCTCC

TGA
```

(SEQ ID NO: 59)
```
MEEEATPRPQSSIVQMQRHMLNSRWHARRLANKPHGVFPSLDGHLRTYTKDIRPAPTWRVGQW

LVAEGVQVQYABEVYRITPTASGKGISLLCPTRKILNRGNTLNLATLSIDIEPAFDGVLSVETTHW

QGAVRRGPDFDLFPAGRPEVDAKVTKTESGTTLSSGTLSATVSGKPHEFEIAFHPTGGKKPLTTLL

NRSVGLAYTPAPSTPMQLADMRNFRHY1FTQTTLAVGESIFIGLGERFGPFNKVGQRVELWNADG

GTSSDQAYKNVGFWMSSRGYGVFVDTPGRVELEIGSERCCRLQTSVEGQRLRWFIIYGPSPRDIL

RRYSVLTGAPGSVPSWSFGLWLSTSFTTSYDEETVNSFLAGMRARDIPVEVFHFDCFWLKAFQW

CDFEFDRDMFPDPRGQIGRLKAGGLVKKVCVWTNPYLGQASPVFAEAAARGYLLRRRNGDVFQ

WDLWQTGMGIVDFTNPDARAWFAACLDRLFDTGVDCIKTDFGERIPSEDVQWFDPSVDPERMH

NYYAFIYNKLVYEALQRRYGANEAVLFARAATAGCQRFPLTWGGDCESTPEAMAESLRGGLSL

GLSGFAFWSVDIGGFEGSPPPWIYKRWVAFGLLCSHSRLHGSNSYRVPWTVDGDDQSEEGCSAT

LRKWTHLKARLMPYLFSQAQESVRGGLPLSLRAMCIEFPDDPTAWTLDRQFMLGDGLLVAPVF

EEDGTVEFYLPRGKWTNFFTGEVKEGPGWFAETHGFGTLPLYVRPNTLLVLGKEGETRTVYDYT

SDVEVRAYFASDSASAVLVDAEGKTVGTLRVKDGEIIGKELLSGNSVINVVSS
```

AXy16158:

(SEQ ID NO: 60)
```
ATGGCCAGCAGCCGGTACCGGTACACGTTCCCGAGGAATCCGAAGGCCAATCCGAAGGCCG

TCGTGACAGGCGGCAAGGGATCCTCTTACTATCGCTTCACCCTCCTCACCGAACGGTTGATC

CGTTACGAGTGGTCCGAGGACGGAGGCTTCGAGGATCGCGCGTCCACGTTCGCGGTATTCAG

ATACTTTGATGCCCCGCAGTACCGCGTTGTCGAGACAAACGACAGTCTCGAGATCATCACGG

ACTACTTTCACCTCACCTATGACAAGAAGAAGTTCTCATCGGAAGGACTTTCCGTCAGAGTC

GGCTCCGACCTCTGGAATTACGACGGCAAGAGTTATGGAGACCTGGGCGGCACCGCCCGGA

CCCTAGACGGCGCCTATGGCCGCGTGGACCTGGAACCGGGTGTGCTCTCGCGCAAAGCTTAT

GCGGTTCTCGACGACAGCAAGTCTATGCTCTTTGACGACGACGGGTGGATTGCCATTCGCGA

GCCGGGCCGCATTGACGGTTACGTGTTTGCCTACAGCGGCGAGCACAAGGCCGCCATCAGG

GACTTCTACCGCCTCTCCGGGCGTCAGCCGGTGCTCCCCCGCTGGGTGCTGGGGAACTGGTG

GTCCAGGTACCACGCATACTCGGCCGACGAATACATCGAGCTTATGGACCACTTCAAACGCG

AAGGAATCCCGCTCACGACGAGCATCGTGGATATGGACTGGCACCGGGTTGACGACGTCCC

GCCCAAGTACGGCTCAGGATGGACGGGCTACAGCTGGAACCGCAAGCTGTTCCCGGACCCC

GAGGGGTTCCTGCAGGAGCTGCGTAATCGGAACCTGAAAGTGGCCCTCAACGACCACCCGG

CGGACGGCATCCGGGCGTATGAGGATCTGTACCCGGCGGTGGCCAAGGCCCTGAATCACGA

CACGTCGCGAGAGGAACCGATCAAGTTTGACTGCACCGATCGCAAGTTCATGGACGCCTACT

TCGACGTTCTGAAGCTCAGCCTTGAGAAGCAGGGCGTCATGTTCTGGTGGATCGACTGGCAG

CAAGGCACCGGCAGCAAGCTCCCCAGCGTAGACCCGCTGTGGGTGCTCAATCACTACCACTA

CCTCACCAGTAAGCGCAACGCGAAAGACATCCAACGTCCCATCACATTCTCCCGCTACGCCG

GCGCCGGTGCCCATCGGTACCCGATCGGCTTCTCGGGCGACACGCAGACGACTTGGGAAGG
```

-continued

```
TCTCGAGTTCCAGCCCGAGTTTACCGCAACGGCATCCAACATCGGCTATGGCTGGTGGAGCC

ACGACATCGGCGGGCATTGGGGCGGCGTCCGCTCCAACCAGCTGACGGTCCGCTGGGTCCA

GCTGGGCTGCTTCTCCCCGATCCTGCGGCTGCACTCGAACAAGAGCCCGTGGAACTCGAGAG

AGCCGTGGAACTACGAGGACGAGGCGCACAGGATCATGAAGGACTTCCTCATCCTGCGCCA

CCGCCTCATCCCCTTCCTCTACACCATGAACATCCGGGCCAGCTACGAGAGCGAGCCGCTCA

TCCAGCCCATGTACTGGAATCACCCGAAGGACGAAGAGGCCTACACGGTGCCGACGCAGTA

CTACTTCGGGCCGGACCTCCTCGTGGCCCCCATCACGTCTCCCAACAGCACCGTCACCCTGA

TGGGCCGCGTGCGCGCCTGGCTGCCGCCGGGCCGGTACGTCGACCTGTTCTACCCGCACCTG

GTCTACGACGGCGGCCGGTACATGCACCTGCACCGCGACCTGTCGCAGATCCCCGTGCTCGC

GCGGGAGGGCACCATCGTGCCGCTGGACACGACGCCCAGGACGGGCCACGGCGCCGCGCGG

CCGACCGAGATCACCCTCCTCCTCGTCGTCGGCCGGGACGCGCACTTTGAGCTGGTCGAGGA

GCCGGAGCAGCAGGACCACCATCGCCACGGCGGCGGCGACGACGGCGATGACCAACCCCCG

CTCAGCGCGTTCGCCCGGACCCCCATCTCGTGGTCGCAGGCGGACGGCGTGCTCACCATCGG

GCCGGAGTGGAACGGCGCCGGGGCCCGCCGCTGGCGGCAGTGGAACGTCAAGCTGGTCGGG

CACACCAACACGGACGTGCAGGCGCAGGTGCCCGGGTTCCGGGTCACGCGCGACGTCGAGG

GCGGGTGCACGACGGTGGCGCTCGGCAACGTGCACCGGTGGCAGCAGCCGCACCAGCGGGA

CGGCGGCGGGTTCGAGATCTCGCTGGGGCGCGACCTGCAGCTGGACGTGGTGGACGTGCGC

GCGCGCGCCTTCGAGGTCCTGCACCGGGCCGAGATGGGGTACGAGGCCAAGGACCCCGTCT

GGGACGTCTTCACGTCCGGCGACGCGGTGCAGACGCGGGTGCAGCGGCTGGCGGCGCTCGA

CGTCGACGCCGCGCTCAAGAACGCCCTCATGGAGGTCTGGGCGGCCGACGGGCGGGCCGAG

GGCAGCGCGGCGGGCTACGAGACCTGGGTGGACGTGAAGGCGTGCGCGGGAGACGCGGTC

GAGGAGGCGCTCAAGGAGTACGTTATCGTGTGA
```

(SEQ ID NO: 61)

MASSRYRYTFPRNPKANPKAVVTGGKGSSYYRFTLLTERLIRYEWSEDGGFEDRASTFAVFRYF

DAPQYRVVETNDSLEIITDYFHLTYDKKKFSSEGLSVRVGSDLWNYDGKSYGDLGGTARTLDGA

YGRVDLEPGVLSRKAYAVLDDSKSMLFDDDGWIAIREPGRIDGYVFAYSGEHKAAIRDFYRLSG

RQPVLPRWVLGNWWSRYHAYSADEYIELMDHFKREGIPLTTSIVDMDWHRVDDVPPKYGSGW

TGYSWNRKLFPDPEGFLQELRNRNLKVALNDHPADGIRAYEDLYPAVAKALNHDTSREEPIKFD

CTDRKFMDAYFDVLKLSLEKQGVMFWWIDWQQGTGSKLPSVDPLWVLNHYHYLTSKRNAKDI

QRPITFSRYAGAGAHRYPIGFSGDTQTTWEGLEFQPEFTATASNIGYGWWSHDIGGHWGGVRSN

QLTVRWVQLGCFSPILRLHSNKSPWNSREPWNYEDEAHRIMKDFLILRHRLIPFLYTMNIRASYE

SEPLIQPMYWNHPKDEEAYTVPTQYYFGPDLLVAPITSPNSTVTLMGRVRAWLPPGRYVDLFYP

HLVYDGGRYMHLHRDLSQIPVLAREGTIVPLDTTPRTGHGAARPTEITLLLVVGRDAHFELVEEP

EQQDHHRHGGGDDGDDQPPLSAFARTPISWSQADGVLTIGPEWNGAGARRWRQWNVKLVGHT

NTDVQAQVPGFRVTRDVEGGCTTVALGNVHRWQQPHQRDGGGFEISLGRDLQLDVVDVRARA

FEVLHRAEMGYEAKDPVWDVFTSGDAVQTRVQRLAALDVDAALKNALMEVWAADGRAEGSA

AGYETWVDVKACAGDAVEEALKEYVIV

BXy1323:

(SEQ ID NO: 62)
```
ATGCCGCAGGTTCGAAACCCCATCCTCCCCGGCTTCAACCCCGACCCTTCCATCCTCCGGGTT

GGGGATGACTACTACATCGCCACTTCAACCTTTGAGTGGTACCCGGGTGTTCAGATCCACCA

CTCCATGGACCTCGCAAACTGGGAACTTGTCACCCGTCCCCTAAACCGCAAGAGCCAACTGG
```

-continued
```
ATATGCGAGGAGATCCGGACAGCTGCGGCATCTGGGCTCCCTGCCTGACGCATGACGGCGA

CAGGTTCTGGCTGGTATACACGGACGTCAAACGCAAGGACGGCTCGTTCAAGGACGCACAC

AACTACATCGTCAGTGCGCCCGCCATCGAGGGTCCCTGGTCGGACCCCTTCTATGTCAACTC

GTCCGGGTTCGACCCCTCGCTCTTCCATGACGACGACGGCCGGAAGTGGTTCGTCAACATGA

TGTGGGACCACCGCAGCCGCCCGCGAACCTTTGCCGGCATCGCGCTGCAAGAGTTCGACCCC

AAGGCCGGGAAGCTGGTTGGGCCGCGCAAGAACATTTACCAAGGCACCGACCTGGGCCTCG

TCGAGGGCCCGCACTTGTACAAGCGCAACGGGTGGTACTATCTCCTGACAGCAGAGGGCGG

GACTGGCTATGAGCATGCCTGCACCCTCGCCCGGTCTCGGAACATCTGGGGCCCGTACGAAG

ATCACCCGCAGAAGTACATCTTGACGTCTAAGGACCACCCGCACGCAGCCCTGCAGCGAGC

CGGCCACGGCGACATCGTCGACACCCCCGACGGGCGTACCTACGTCGTTCACCTGACCGGCC

GGCCCATCACGCAGTTCCGCCGCTGTGTCTTGGGGCGCGAGACGGCCATCCAGGAGGCCTAC

TGGGGCGACGACGACTGGCTCTACGTCAAGAACGGCCCTGTGCCCAGCCTGTTCGTGGACCT

CCCGGCCGCCCGCAACGACGACGACTACTGGGCCGAGAAGAGGTACACGTTCGAGGCGGGC

CTGCACAAGGACTTCCAGTGGCTGCGCACGCCCGAGACGGACCGCATCTTCAGGACGGACA

ACGGGAAGTTGACGCTCATCGGCCGCGAGTCCATCGGCTCCTGGTTCGAGCAGGCCCTGGTC

GCCCGGCGCCAGACGCACTTCTCGTACGACGCCGAGACCGTCATCGACTTCAAGCCTGCCGA

CGAGCGCCAGTTCGCCGGCCTGACGGCCTATTACTGCCGCTACAACTTCTTCTACCTGACCGT

CACGGCCCACTCGGACGGCCGGCGGGAGCTGCTCATCATGGCCTCCGAGGCCTCCTGGCCCC

TCGGCGCCCTCCGGTCCCCTTATCCGGGACCCGTCCAGATCCCCAACGAGGGCAAGGTCCGG

CTCGCGCTCAAGATCAGGGGCAAGGAGCTGCAGTTCTACTACGCTCTCGAGGGCGAAGAGC

TAAAACAGATTGGGCCCGTATTCGACGCTAGCATCGTTTCTGACGAGTGCGGCGGCCACCAG

AAGCACGGCAGCTTCACGGGCGCCTTCGTCGGCGTGGCTGCTTCCGACATCAACGGTACTGC

TGCCGAGGCGACCTTTGACTACTTTGTGTACAAGCCCGTGCACCATGAGAGTGACCGGTACG

AGATTTAA
```
                                                        (SEQ ID NO: 63)
```
MPQVRNPILPGFNPDPSILRVGDDYYIATSTFEWYPGVQIHHSMDLANWELVTRPLNRKSQLDM

RGDPDSCGIWAPCLTHDGDRFWLVYTDVKRKDGSFKDAHNYIVSAPAIEGPWSDPFYVNSSGFD

PSLFHDDDGRKWFVNMMWDHRSRPRTFAGIALQEFDPKAGKLVGPRKNIYQGTDLGLVEGPHL

YKRNGWYYLLTAEGGTGYEHACTLARSRNIWGPYEDHPQKYILTSKDHPHAALQRAGHGDIVD

TPDGRTYVVHLTGRPITQFRRCVLGRETAIQEAYWGDDDWLYVKNGPVPSLFVDLPAARNDDD

YWAEKRYTFEAGLHKDFQWLRTPETDRIFRTDNGKLTLIGRESIGSWFEQALVARRQTHFSYDA

ETVIDFKPADERQFAGLTAYYCRYNFFYLTVTAHSDGRRELLIMASEASWPLGALRSPYPGPVQI

PNEGKVRLALKIRGKELQFYYALEGEELKQIGPVFDASIVSDECGGHQKHGSFTGAFVGVAASDI

NGTAAEATFDYFVYKPVHHESDRYEI
```
BXy16880:
                                                        (SEQ ID NO: 64)
```
ATGGCGCCCCTCATCACCAACATCTTCACGGCCGACCCGTCGGCCCACGTCTTCGAGGGCAA

GCTCTTCATATACCCGTCGCACGATCGCGAGACGGACATCAAGTTCAACGACGACGGCGACC

AGTACGACATGGTCGACTACCACGTATTCAGCACCGAGTCGCTGGACCCGGCCGCCCCCGTG

ACCGACCACGGCGTCGTGCTCCGGGCCGAAGACGTCCCCTGGGTGTCCAAGCAGCTCTGGGC

CCCCGACGCCGCCTACAAGGACGGCAGGTACTACCTCTACTTCCCCGCCGCGACAAGCAGG

GCGTCTTCCGCATCGGCGTCGCCGTCGGCGACCGCCCCGAGGGCCCCTTCACCCCCGACCCG
```

-continued
```
GAGCCCATCCGGGACAGCTACAGCATCGACCCGGCCGTCTTCGTCGACGACGACGGCCGGG

CCTACATGTACTTTGGCGGGCTCTGGGGCGGCCAGCTGCAGTGCTACCAGAAGGGCAACGG

CATCTTCGACCCCGAGTGGCTGGGGCCCAGGGAGCCCTCGGGCGAGGGCGTCCGGGCGCTG

GGGCCGCGCGTCGCCCGGCTGGCGGACGACATGCGCCAGTTCGCCAGCGAGGTGAAGGAGA

TTTCGATCCTGGCGCCCGAGACGGGCGAGCCGATCGCGGCCGACGACCACGACCGCCGCTTC

TTCGAGGCCGCCTGGATGCACAAGTACGACGGCAAGTACTACTTCAGCTACTCCACCGGCGA

CACCCACTACCTCGTCTACGCCGTCGGCGACAGCCCCTACGGGCCCTTCACCTACGCCGGCC

GCATCCTCGAGCCCGTCCTCGGCTGGACCACGCACCACTCCATCGTCGAGTTCCACGGCCGC

TGGTGGCTCTTCCACCACGACTGCGAGCTCAGCGGCGGAGTCGACCACCTGCGCTCCGTCAA

GGTCAAGGAGATCTTCTACGACAAGGACGGCAAGATTGTCACTGAAAAGCCCGAATAG
```
(SEQ ID NO: 65)

MAPLITNIFTADPSAHVFEGKLFIYPSHDRETDIKFNDDGDQYDMVDYHVFSTESLDPAAPVTDH

GVVLRAEDVPWVSKQLWAPDAAYKDGRYYLYFPARDKQGVFRIGVAVGDRPEGPFTPDPEPIR

DSYSIDPAVFVDDDGRAYMYFGGLWGGQLQCYQKGNGIFDPEWLGPREPSGEGVRALGPRVAR

LADDMRQFASEVKEISILAPETGEPIAADDHDRRFFEAAWMHKYDGKYYFSYSTGDTHYLVYA

VGDSPYGPFTYAGRILEPVLGWTTHHSIVEFHGRWWLFHHDCELSGGVDHLRSVKVKEIFYDKD

GKIVTEKPE

Example 1

Cloning Xyl5, BXyl7, and BXyl8 into Transformation Vectors

In this Example, cloning Xyl5 (SEQ ID NO:1), BXyl7 (SEQ ID NO:4), and BXyl8 (SEQ ID NO:7) into a pC1DX10PrR vector, are described. Genomic DNA was isolated from the M. thermophila C1 strain using standard procedures. Briefly, hyphal inoculum was seeded into a growth medium and allowed to grow for 72 hours at 35° C. The mycelial mat was collected by centrifugation, washed, and 50 uL DNA extraction buffer (200 mM Tris, pH 8.0; 250 mM NaCl; 125 mM EDTA; 0.5% SDS) was added. The mycelia were ground with a conical grinder, re-extracted with 250 uL extraction buffer, and the suspension was centrifuged. The supernatant was transferred to a new tube containing 300 μL isopropanol. DNA was collected by centrifugation, washed twice with 70% ethanol, dried, and resuspended in 100 μL of water.

The indicated genes were amplified using primers indicated below from isolated M. thermophila genomic DNA, based on SEQ ID NOS:1, 4 and 7. PCR reactions were performed by using Phusion Hot Start II High Fidelity DNA Polymerase (Finnzymes F-540L). PCR conditions were used following manufacturer's instructions with GC buffer, plus 2% DMSO final concentration. For Xyl5 and BXyl7, PCR cycles were: 98° C. 30", 35 cycles of 98° C. 10", 69° C. 20", 72° C. 30" and final extension at 72° C. 5'. The primers used are provided below.

TABLE 1.1

Primers Used for Xyl5 (SEQ ID NO: 1) and BXyl7 (SEQ ID NO: 4)

| | |
|---|---|
| Pcbhxyl5_F | 5'-TGATCCTCTTCCGTCATGGTTACCCTCA CTCGCCTGGCG-3' (SEQ ID NO: 66) |

TABLE 1.1-continued

Primers Used for Xyl5 (SEQ ID NO: 1) and BXyl7 (SEQ ID NO: 4)

| | |
|---|---|
| Tcbhxyl5_R | 5'-TCGTTTACTTACTTATCAGCCGCTGAC GGTGTACTGGGA-3' (SEQ ID NO: 67) |
| Pcbhb-xyl7_F | 5'-TGATCCTCTTCCGTCATGTTCTTCGCT TCTCTGCTGC-3' (SEQ ID NO: 68) |
| Tebhb-xyl7_R | 5'-TCGTTTACTTACTTATCAATCCCTAAA CTGCTCCAATGG-3' (SEQ ID NO: 69) |

For BXyl8 (SEQ ID NO:7), PCR cycling conditions were: 98° C. 30", 35 cycles of 98° C. 10", 61° C. 30", 72° C. 1'15" and final extension at 72° C. 5'.

TABLE 1.2

Primers Used for BXyl8 (SEQ ID NO: 7)

| | |
|---|---|
| IF 10-b-xyl8-Forward | 5'-TGTGCTGATCCTCTTCCGTCATGAAGGCCTCTG TATCATGCCT-3' (SEQ ID NO: 70) |
| IF 10-b-xyl8-Reverse | 5'-GAGGTTCGTTTACTTACTTATTACCTGTGCCTC CCCCTGGC-3' (SEQ ID NO: 71) |

PCR fragments were spin column purified (QIAquick PCR Purification Kit), and eluted in 50 μl elution buffer. The purified PCR products were cloned into pC1DX10PhR vector (previously digested with PacI/PmlI and gel purified), 3' to the Pcbh promoter to create expression vectors that expressed the desired protein transcripts under the control of the Pcbh promoter. The In-Fusion HD Cloning Kit (Clontech cat. no. 639645) was used for cloning according to the manufacturer instructions. In this process, 100 ng of PCR product and 50 ng of PmlI-PacI restriction enzyme digested vector were used in the cloning reaction. FIG. 1 provides the maps of the vectors used for the xylanase and each xylosidase. Two microliters of the In-Fusion cloning reaction were used to transform 50 microliters of E. coli DH10B-T1 phage resistant electrocompetent cells (Invitrogen, cat. no. 12033-015) following the manufacturer's instructions. Cells were plated onto LB medium containing 100 mg/L of carbenicillin for positive selection of clones. Colonies were picked and screened for clones containing correct DNA sequences by sequencing of whole-cell colony PCR products. Colony PCR reactions were performed using Kapa2G Robust Hot Start DNA Polymerase (KapaBiosystems, cat. no. KK5515) with the indicated primers. PCR conditions were used following manufacturer's instructions with Buffer GC and 2% DMSO final concentration. PCR cycling conditions were: 95° C. 3:30", 35 cycles of 95° C. 20", 60° C. 15", 72° C. 1'15". PCR products were treated with EXOSAP-IT (Affymetrix, cat. no. 78250) following the manufacturer's instructions, and then submitted for DNA sequencing. Plasmid was prepared from *E. coli* clones with correct DNA sequence (QIAprep spin Miniprep kit) for transformation into a *M. thermophila* strain.

Example 2

Transformation and Expression of *M. thermophila* Genes

In this Example, experiments to transform xylanase and beta-xylosidase genes into *M. thermophila* CF-417 cells are described. CF-417 cells were inoculated in 100 ml minimal medium containing 2% glucose in a 500 ml Erlenmeyer flat bottom flask using $10^8$ spores/ml. The culture was incubated for 24 hours at 35° C., at 250 rpm. To harvest the mycelia, the culture was filtered over a sterile Miracloth filter (Calbiochem) and washed with 100 mL 1700 mM NaCl/CaCl$_2$ solution (0.6 M NaCl, 0.27 M CaCl$_2$*H$_2$O). The washed mycelia were transferred into a 50 mL tube and weighed. Caylase (20 mg/gram mycelia) was dissolved in 1700 mM NaCl/CaCl$_2$ and UV-sterilized for 90 sec. Then, 3 mL of sterile Caylase solution was added into the tube containing washed mycelia and mixed. Then, 15 mL of 1700 mM NaCl/CaCl$_2$ solution was added into the tube and mixed. The mycelium/Caylase suspension was incubated at 30° C., 70 rpm for 3 hours. Protoplasts were harvested by filtering through a sterile Miracloth filter into a sterile 50 mL tube. Then, 25 mL cold STC (1.2 M sorbitol, 50 mM CaCl$_2$*H$_2$O, 35 mM NaCl, 10 mM Tris-HCl) were added to the flow through and spun down at 2720 rpm (1500×g) for 10 min at 4° C. The pellet was resuspended in 50 mL STC and centrifuged again. After the washing steps, the pellet was resuspended in 1 mL STC.
Transformation Into the bottom of a 15 mL sterile tube, 2 μg DNA plasmid containing the desired transformants, and 1 ug DNA of plasmid containing KU70 ligase for increased transformation efficiency were pipetted, and 1 μL aurintricarboxylic acid and 100 μL protoplasts were added. The content was mixed and the protoplasts with the DNA were incubated at room temperature for 25 min. Then, 1.7 mL PEG4000 solution (60% PEG4000 (polyethylene glycol, average molecular weight 4000 daltons), 50 mM CaCl$_2$.H$_2$O, 35 mM NaCl, 10 mM Tris-HCl) were added and mixed thoroughly. The solution was kept at room temperature for 20 min. The tube was filled with STC, mixed and centrifuged at 2500 rpm (1250 xg) for 10 min at 4° C. The STC was poured off and the pellet was resuspended in the remaining STC and plated on minimal media agar plates containing sucrose, as well as 20 mg/L phleomycin for selection. The plates were incubated for 7 days at 35° C. to allow for growth and sporulation of colonies.
Colony Picking and Fermentation Colonies of transformants were picked using sterile toothpicks into 400 uL minimal media in a 96-well CORNING® COSTAR® deep well culture plate. The plates were incubated for 96 hours at 35° C., at 250 rpm. Then, 40 uL of culture was transferred into CORNING® COSTAR® deep well culture plates containing 360 uL of minimal media supplemented with biotin. Plates were incubated for 96 hours at 35° C., at 250 rpm. Supernatants were harvested for assay by centrifugation of the plates at 1500×g for 10 min. To confirm protein expression, supernatants of the transformants were analyzed by SDS-PAGE analysis. The SDS-PAGE results showed a 24 kDa protein for Xyl5 (SEQ ID NO:2); a 67 kDa protein for BXyl7 (SEQ ID NO:4); and three proteins of 24, 34 and 49 kDa for BXyl8 [SEQ ID NO:8]). It is noted that BXyl8 (SEQ ID NO:8) is proteolyzed during production in *M. thermophile*. These fragments are active and appear as three bands on SDS-PAGE with these molecular weights. On gel-filtration columns and native gels, there is one peak/band for BXyl8 (SEQ ID NO:8).

Example 3

BXyl8 Cloning and Expression in *S. cerevisiae*

In this Example, cloning of BXyl8 (SEQ ID NO:8) into pYTsec72tc vector is described. Cloning of BXyl8 for expression in yeast required the removal of a 130 bp intron. PCR primers were designed such that each exon PCR product contained a 20 bp overlap with the adjacent exon and 40 bp overlaps with corresponding vector sequences for recombination cloning in yeast. PCR products were amplified using pC1DX10PhR-v4chr1-b-xyl8m26 plasmid as template and primers b-xyl8-ADHtc_Fwd and b-xyl8-exon1_Rev for a 260 bp product and b-xyl8exon2_Fwd and b-xyl8_ter_Rev for a 2395 bp product. PCR reactions were performed by using Phusion Hot Start II High Fidelity DNA Polymerase (Finnzymes F-540L). PCR conditions were used following the manufacturer's instructions with 5% DMSO final concentration. PCR cycling conditions were: 98° C. 30", 30 cycles of 98° C. 10", 60° C. 20", 72° C. 2' and final extension at 72° C. for 5'.

TABLE 3.1

Primers Used

| | |
|---|---|
| b-xyl8-<br>ADHtc_Fwd | TACAATCAACTATCAACTATTAACTATATCGTAATA<br>CACAATGAAGGCCTCTGTATCATG<br>(SEQ ID NO: 72) |
| b-xyl8-<br>exon1_Rev | GCGGCGCCCCCGGCGCCTTGCTGACCAGGTTTTGCA<br>GCTT (SEQ ID NO: 73) |
| b-<br>xyl8_exon2_Fwd | AAGCTGCAAAACCTGGTCAGCAAGGCGCCGGGGGCG<br>CCGC (SEQ ID NO: 74) |
| b-xyl8_ter_Rev | TCAGAACCTCCTTCAGAGAGGTTCGTTTACTTACTT<br>ATTACCTGTGCCTCCCCCTGGCGG<br>(SEQ ID NO: 75) |

Figure 2:
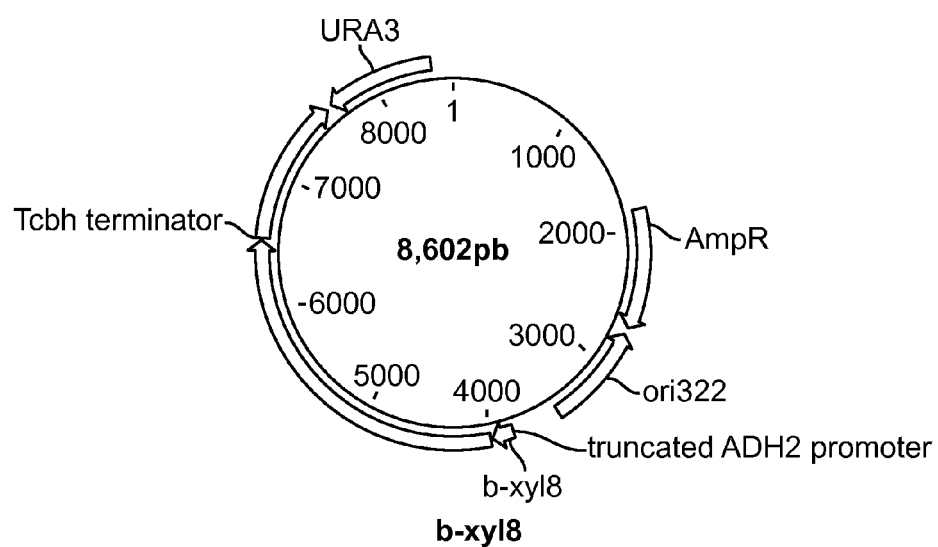
FIG. 2 provides the map of the construct used to transform *S. cerevisiae* with BXyl8 (SEQ ID NO:7, 19, or 12).

PCR fragments were spin column purified (QIAquick PCR Purification Kit), and eluted in 50 μl elution buffer. The purified PCR products were cloned into pYTsec72tc vector (See, FIG. 2) by co-transformation of the two PCR products and vector DNA that was previously linearized with PmlI restriction endonuclease downstream from the ADH2 promoter to allow for expression of the BXyl8 (SEQ ID NO:7) gene under this promoter.

Yeast transformation was done using standard methods. The transformation was plated on minimal media lacking uracil for positive selection of clones. Colonies were picked and screened for the correct BXyl8 DNA (SEQ ID NO:7) sequence by sequencing of plasmid DNA extracted from these colonies.

Protein Expression

Colonies of transformants were picked using sterile inoculating loops into 5 mL of minimal medium lacking uracil for selection and supplemented with 6% glucose. Cultures were incubated at 30° C., 250 RPM for 24 hours. Cultures were then used to inoculate 250 mL of minimal medium lacking uracil and supplemented with 2% glucose. Cultures were incubated at 30° C., 250 RPM for 48 hours. Cells and supernatant were harvested by centrifugation at 3000 RPM for 5 minutes and assayed for activity using the PNP-X assay described in Example 4.

Example 4

Xylanase and Xylosidase Activity

Figure 3:
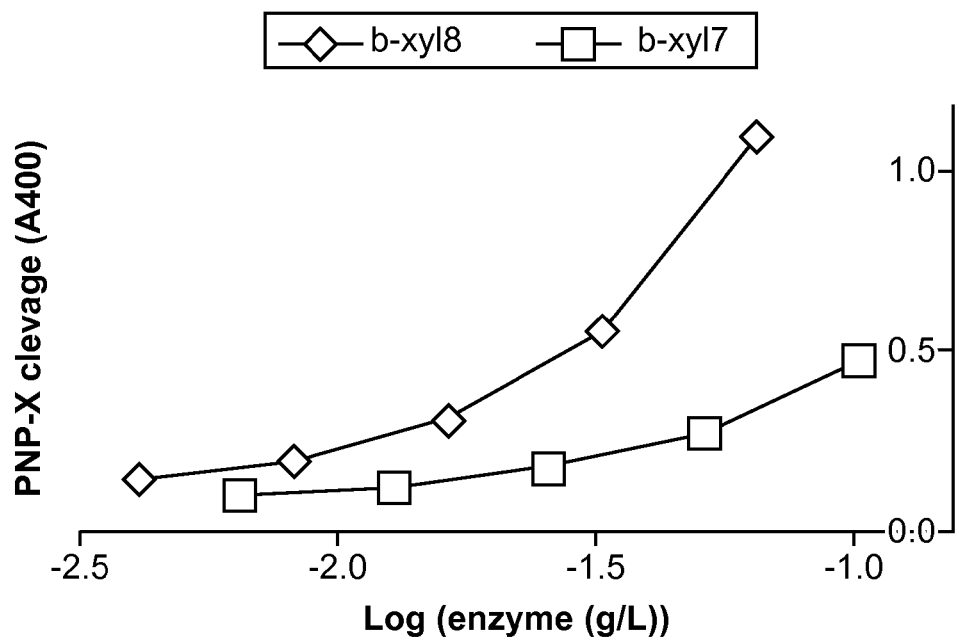
FIG. 3 provides a graph showing that increasing the concentration of BXyl7 (SEQ ID NO:5) or BXyl8 (SEQ ID NO:8) results in increased cleavage of PNP-X.

In order to demonstrate activity for the xylanase and xylosidases they were tested against birchwood xylan (Sigma Aldrich) and p-nitrophenyl-beta-xylanopyranoside (PNP-X) (Sigma Aldrich) respectively. Broths from cultures overexpressing the beta-xylosidases (BXyl7 [SEQ ID NO:5] and BXyl8 [SEQ ID NO:8]) were diluted to 0.1025 or 0.065 g/L total protein in 150 mM sodium acetate pH 6.0. These solutions were further serially diluted in 150 mM sodium acetate pH 6.0 four times, two-fold each dilution. Then, 20 uL of the diluted supernatants were added to 80 uL of 6.25 mM PNP-X in 150 mM sodium acetate pH 6.0 in a Nunc 96-well flat bottom plate. The samples were incubated at 37° C. for 30 minutes, quenched with 150 uL of 1 M sodium carbonate and absorbance was measured at 400 nm on a SpectraMax M2 spectrophotometer. The results are shown in FIG. 3. In this Figure, the values are reported as the average and standard deviation of three replicate experiments.

Figure 4:
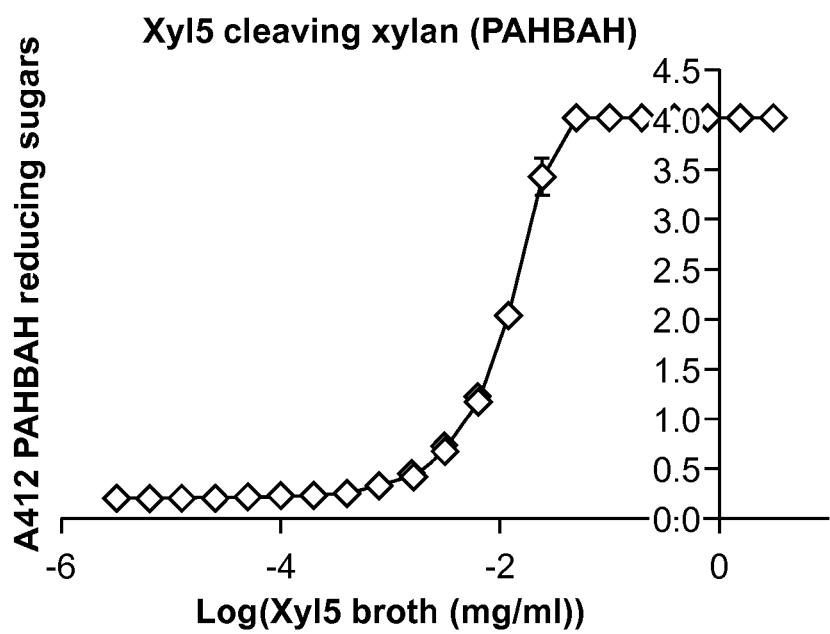
FIG. 4 provides a graph showing that increasing the concentration of Xyl5 (SEQ ID NO:2) leads to greater cleavage of birchwood xylan.

Activity of xylanase Xyl5 (SEQ ID NO:2) was measured versus birchwood xylan. In this assay, 35 mg of birchwood xylan was placed into a CORNING®COSTAR® deep well culture plate. Broth from a culture overexpressing Xyl5 (SEQ ID NO:2) was serially diluted in 75 mM sodium acetate pH 6.0 from 79 g/L to 3E-06 g/L. Then, 480 uL of 75 mM sodium acetate pH 6.0, and 20 uL of enzyme dilutions were added to the 96-well plate, and it was incubated at 45° C., 950 rpm for 2.5 h in a Multitron II incubator shaker (Infors HT [Infors]). The reactions were centrifuged (2800×g, 6 min), and 20 uL of the reaction supernatant were added to 80 uL of active PAHBAH reagent in a hard-shell 96-well skirted PCR plate (Biorad). (PAHBAH reagent A: 10 g p-hydroxy benzoic acid hydrazide, 10 ml of 12 N HCl, in 200 ml water. PAHBAH reagent B: 24.9 g sodium citrate, 2.2 g calcium chloride, 40.0 g sodium hydroxide in 2 L water. Active PAHBAH reagent: 10 ml reagent B+1 ml reagent A). The PAHBAH reaction was heated to 60° C. for 10 minutes in a DNA engine Tetrad 2 Thermal Cycler (Biorad). Then, 80 uL of the reaction was transferred to a Nunc 96 well-flat bottom plate and the absorbance was measured at 412 nm on a SpectraMax M2 spectrophotometer. The results are shown in FIG. 4. In this Figure, the values are reported as the average and standard deviation of three replicate experiments.

Example 5

Improved Wheat Straw Saccharification

Figure 5:
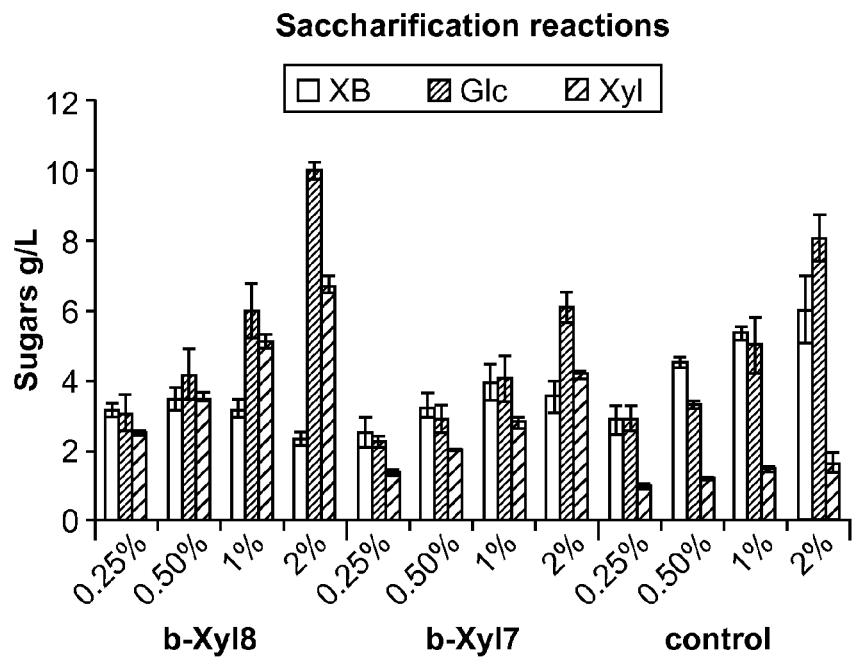
FIG. 5 provides a graph showing that BXyl7 (SEQ ID NO:5) and BXyl8 (SEQ ID NO:8) increase conversion of xylobiose to xylose in a saccharification reaction.

To assess the roles of the xylosidases in saccharification reactions, broths containing the overproduced enzymes were added to pre-treated wheat straw. First, 20 uL of diluted enzyme broths containing the xylosidases (corresponding to 0.25, 0.5, 1 or 2% enzyme with regard to glucan) were added to a mixture of 26 mg pressed and sieved pre-treated wheat straw, 21 uL of pre-treated wheat straw filtrate, 8 uL of 1 mM copper sulfate, 24 ul of 1 M sodium acetate pH 6.0, and 65 uL of water. Reactions were centrifuged 3200×g for 4 min, and agitated at 950 rpm, 45° C. for 48 h. The reactions were diluted with 300 uL of water, shaken for 30 min at rt, and centrifuged 2800×g for 10 min. The supernatant was transferred to a Multiscreen Solivinert filter plate (Millipore) and centrifuged at 1250×g for 5 min into a CORNING® COSTAR® round bottom 96-well culture plate. Filtrates were heated to 95° C. for 10 min, cooled to rt and analyzed on an Agilent HPLC 1200. Numerous strains with improved levels of glucose, xylose and xylobiose utilization were identified, as shown in FIG. 5. Both enzymes increased the proportion of xylose to xylobiose compared to the results provided by a strain containing an empty vector control.

Figure 6:
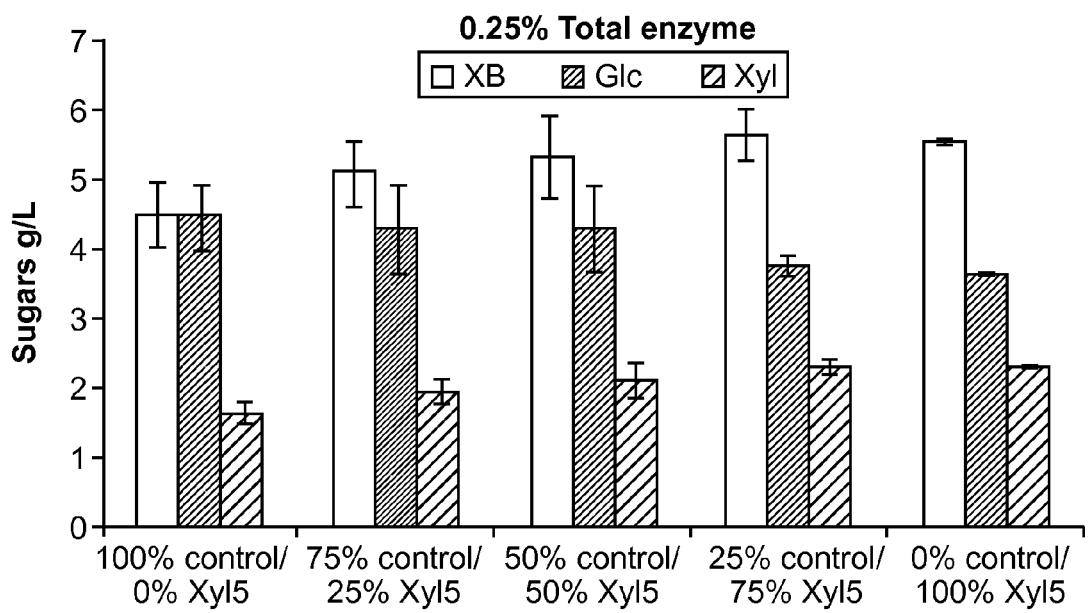
FIG. 6 provides a graph showing that broth containing Xyl5 (SEQ ID NO:2) increases the level of xylobiose and xylose production in saccharification reactions, as compared to control broth.

To assess the role of Xyl5 (SEQ ID NO:2) in a saccharification reaction, broth containing the overproduced enzyme was cross titrated with CF-418 broth and added to pre-treated wheat straw. CF-418 and Xyl5 (SEQ ID NO:2)-containing broths were mixed at various ratios, and 20 uL of diluted enzymes (0.25% enzyme with regard to glucan) were added to a mixture of 28 mg pressed and sieved pre-treated wheat straw, 24 uL of pre-treated wheat straw filtrate, 9 uL of 1 mM copper sulfate, 27 ul of 1 M sodium acetate pH 6.0, and 77 uL of water. Reactions were centrifuged 3200×g for 4 min, and agitated at 950 rpm, 45° C. for 48 h. The reactions were diluted with 300 uL of water, shaken for 30 min at rt, and centrifuged 2800×g for 10 min. The supernatant was transferred to a Multiscreen Solivinert filter plate (Millipore) and centrifuged 1250×g for 5 min into a CORNING® COSTAR® round bottom 96-well culture plate. Filtrates were heated to 95° C. for 10 min, cooled to rt and analyzed on an Agilent HPLC 1200. Numerous strains with improved levels of glucose, xylose and xylobiose were identified, as shown in FIG. 6. As indicated in this Figure, increasing proportions of Xyl5 (SEQ ID NO:2) increase the levels of xylose and xylobiose.

Example 6

Temperature and pH Stability

Figure 7:
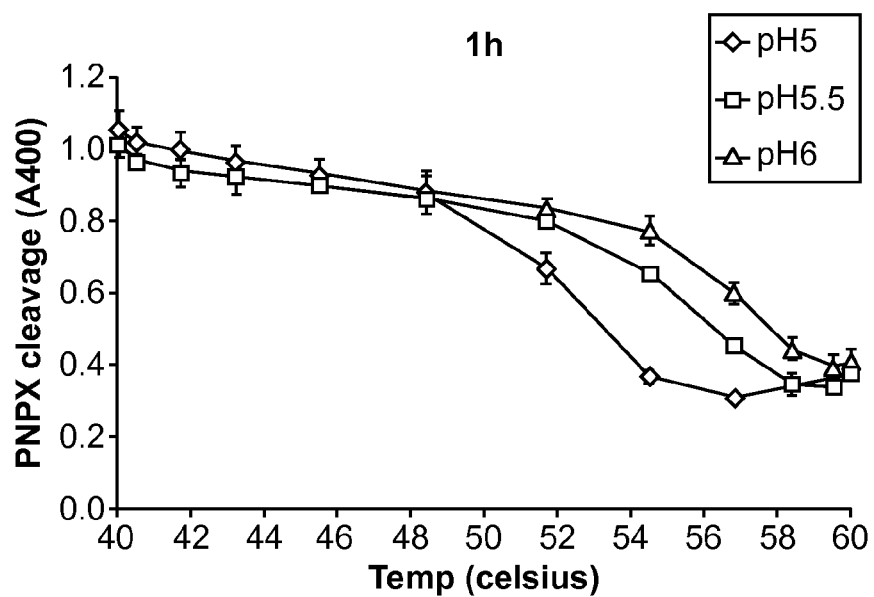
FIG. 7 provides a graph showing the temperature/pH activity profiles of BXyl8 (SEQ ID NO:8) after 1 hour incubation at 40-60° C., at pH 5, 5.5, and 6.
Figure 8:
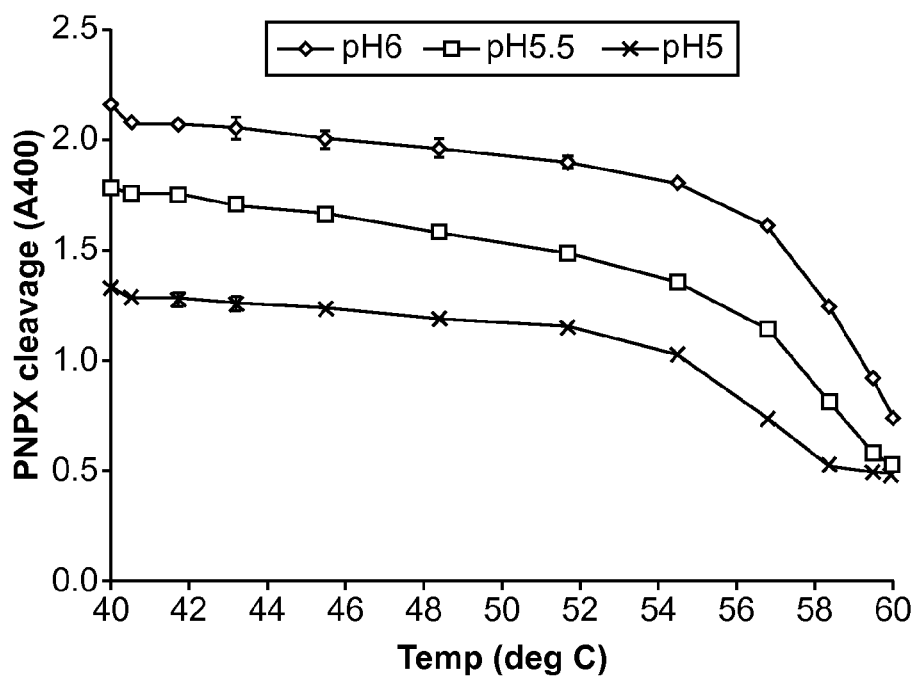
FIG. 8 provides a graph showing the temperature/pH activity profiles of BXyl7 (SEQ ID NO:5) after 1 hour incubation at 40-60° C., at pH 5, 5.5, and 6.

To assess the stability of xylosidases BXyl8 (SEQ ID NO:8) and BXyl7 (SEQ ID NO:5), broths containing the overproduced enzymes were diluted 1:100 or 1:140 respectively in 100 mM sodium acetate pH 5.0, 5.5, or 6.0. The diluted enzymes were heated across a gradient of temperatures from 40-60° C. for 1h in a DNA engine Tetrad 2 Thermal Cycler (Biorad). Then, 20 uL of the heated enzymes were added to 80 uL of 6.25 mM PNP-X in 100 mM sodium acetate pH 6.0 (BXyl8 [SEQ ID NO:8]) or 100 mM sodium acetate pH 5, 5.5 or 6 (BXyl7 [SEQ ID NO:5]). The samples were incubated at 37° C. for 30 minutes, quenched with 150 uL of 1 M sodium carbonate and absorbance was measured at 400 nm. The results are shown in FIGS. 7 and 8. In these Figures, the values are reported as the average and standard deviation of two replicate experiments.

Figure 9:
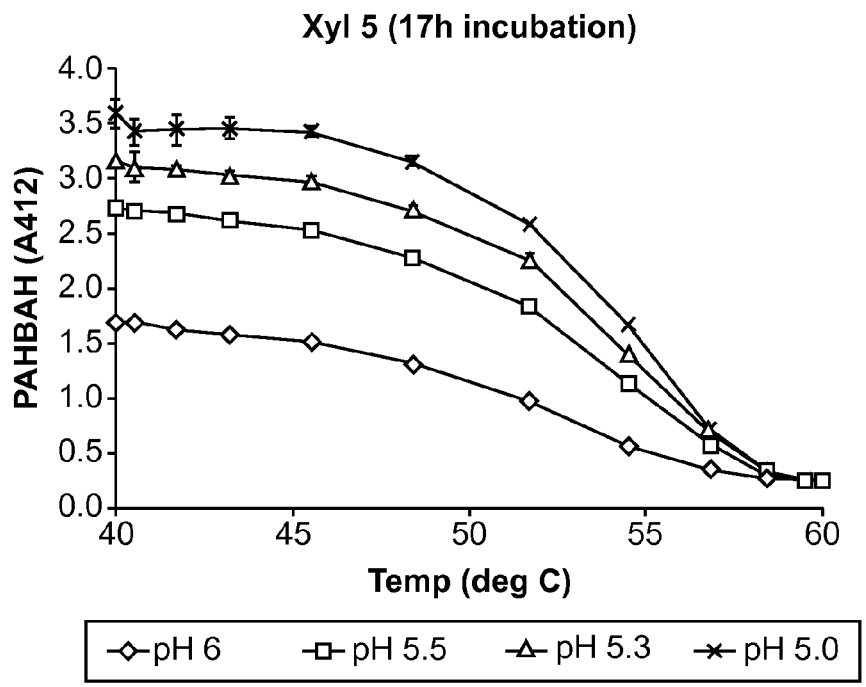
FIG. 9 provides a graph showing the temperature/pH activity profiles of BXyl8 (SEQ ID NO:7) after 17 hours incubation at 40-60° C., at pH 6, 5.5, 5.3, and 5.0.

To test the pH and thermal stability of Xyl5 (SEQ ID NO:2), broth overexpressing the enzyme was diluted to 1.3 mg/ml with water. Then, 25 uL of diluted broth were mixed with 75 uL of 200 mM sodium acetate pH 5, 5.3, 5.5 or 6, and heated to 40-60° C. for 17 h. Residual activity of the enzymes was determined in 100 mM sodium acetate at their respective pHs, via the method described in Example 4. FIG. 9 provides the results.

Example 7

Transformation of CF-419 with Multiple Genes

CF-419 cells were inoculated into 100 mL growth medium in a 500 mL Erlenmeyer flask using $10^6$ spores/mL. The culture was incubated for 48 hours at 35° C., 250 rpm. To harvest the mycelia, the culture was filtered over a sterile Miracloth filter (Calbiochem) and washed with 100 mL 1700 mM NaCl/$CaCl_2$ solution (0.6 M NaCl, 0.27 M $CaCl_2$*$H_2O$). The washed mycelia were transferred into a 50 mL tube and weighed. Caylase (20 mg/gram mycelia) was dissolved in 1700 mM NaCl/$CaCl_2$ and UV-sterilized for 90 sec. Then, 3 mL of sterile Caylase solution were added into the tube containing washed mycelia and mixed. Then, 15 mL of 1700 mM NaCl/$CaCl_2$ solution were added into the tube and mixed. The mycelium/Caylase suspension was incubated at 30° C., 70 rpm for 3 hours. Protoplasts were harvested by filtering through a sterile Miracloth filter into a sterile 50 mL tube. Then, 25 mL cold STC (1.2 M sorbitol, 50 mM $CaCl_2$*$H_2O$, 35 mM NaCl, 10 mM Tris-HCl) were added to the flow through and spun down at 2720 rpm (1500×g) for 10 min at 4° C. The pellet was resuspended in 50 mL STC and centrifuged again. After the washing steps the pellet was resuspended in 1 mL STC.

Transformation was carried out in CF-417, with KU70 cotransformation, in order to increase the number of transformed colonies. Into the bottom of a 15 mL sterile tube, 2 µg DNA of each plasmids containing Xyl5 (SEQ ID NO:1), BXyl8 (SEQ ID NO:7), and GH61a were pipetted and 1 µL aurintricarboxylic acid and 100 µL protoplasts were added. The contents were mixed and the protoplasts with the DNA were incubated at room temperature for 25 min. Then, 1.7 mL PEG4000 solution (60% PEG4000 (polyethylene glycol, average molecular weight 4000 daltons), 50 mM $CaCl_2$.$H_2O$, 35 mM NaCl, 10 mM Tris-HCl) were added and mixed thoroughly. The solution was kept at room temperature for 20 min. The tube was filled with STC, mixed and centrifuged at 2500 rpm (1250×g) for 10 min at 4° C. The STC was poured off and the pellet was resuspended in the remaining STC and plated on M4 minimal media petri plates with 20 mg/L phleomycin for selection. The plates were incubated for 7 days at 35° C. to allow for growth and sporulation of colonies.

Colonies were picked into 96-well CORNING® COSTAR® sterile square deep well culture plates containing 400 uL minimal medium. Plates were incubated for 96 hours at 35° C., 250 rpm, 85% relative humidity. First, 200 uL of seed culture were transferred into 24-well deep well plates containing 1.8 mL rich media. These plates were then incubated for 168 hours at 35° C., 250 rpm, 85% relative humidity.

Figure 10:
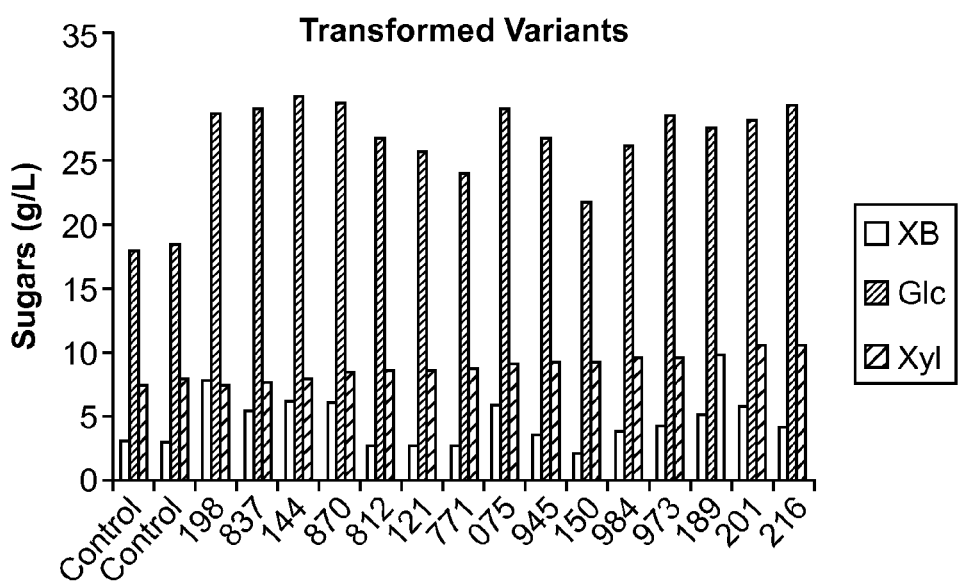
FIG. 10 provides a graph showing the activity of xylanase and beta-xylosidases produced by transformed *M. thermophila* strains in saccharification reactions, as measured by HPLC and as compared to untransformed controls.

To assay activity, cell cultures were spun 3200×g for 10 min. The supernatant was removed from the cell pellet, diluted 2× with water, mixed for 20 minutes, and centrifuged at 3200×g for 10 min. To assess the activity of the enzymes in a saccharification reaction, 10 uL of the diluted enzymes were added to a mixture of 28 mg pressed and sieved pre-treated wheat straw, 23 uL of pre-treated wheat straw filtrate, 9 uL of 1 mM copper sulfate, 54 ul of 1 M MES pH 6.0, and 55 uL of water. Reactions were centrifuged 3200×g for 4 min, and agitated at 950 rpm, 45° C. for 48 h. The reactions were diluted with 300 uL of water, shaken for 30 min at rt, and centrifuged 2800×g for 10 min. The supernatant was transferred to a Multiscreen Solivinert filter plate (Millipore) and centrifuged 1250×g for 5 min into a CORNING® COSTAR® round bottom 96-well culture plate. Filtrates were heated to 95° C. for 10 min, cooled to rt and analyzed on an Agilent HPLC 1200. Numerous strains were identified that exhibited improved levels of glucose (glc), xylose (xyl), and xylobiose (XB), as shown in FIG. 10.

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of the present invention.

---

We claim:

1. A recombinant microorganism transformed by a vector comprising a polynucleotide sequence encoding the xylosidase of SEQ ID NO:8.

2. The recombinant microorganism comprising at least one polynucleotide comprising at least one nucleic acid sequence encoding the xylosidase of claim 1, wherein said polynucleotide comprises SEQ ID NO:7.

3. An enzyme composition comprising the xylosidase of SEQ ID NO:8 and at least one additional enzyme, selected from the group consisting of cellulases, hemicellulases, xylanases, amylases, glucoamylases, proteases, esterases, and lipases, wherein said at least one additional enzyme is obtained from a microorganism other than *Myceliophthora thermophile*.

4. The enzyme composition of claim 3, wherein one or more cellulase is selected from the group consisting of endoglucanases (EG), β-glucosidases (BGL), Type 1 cellobiohydrolases (CBH1), Type 2 cellobiohydrolases (CBH2), and/or GH61 enzymes.

5. A recombinant nucleic acid construct comprising at least one polynucleotide sequence, wherein the polynucleotide is the cDNA SEQ ID NO:7.

6. The nucleic acid construct of claim 5, wherein the polynucleotide sequence is operably linked to a promoter.

7. The nucleic acid construct of claim 6, wherein said nucleic acid sequence is operably linked to at least one additional regulatory sequence.

8. A recombinant host cell transformed with the nucleic acid construct of claim 5.

9. The recombinant host cell of claim 8, wherein at least one xylanase and/or xylosidase is produced by said cell.

10. The recombinant host cell of claim 8, wherein said host cell further produces at least one enzyme selected from the group consisting of endoglucanases (EG), β-glucosidases (BGL), Type 1 cellobiohydrolases (CBH1), Type 2 cellobiohydrolases (CBH2), and GH61 enzymes.

11. The recombinant host cell of claim 5, wherein said cell produces at least two recombinant cellulases.

12. The recombinant cell of claim 5, wherein said cell is a prokaryotic or eukaryotic cell.

13. The recombinant cell of claim 12, wherein said cell is a yeast cell or filamentous fungal cell.

14. The recombinant host cell of claim 13, wherein the cell is a *Myceliophthora*, a *Thielavia*, a *Trichoderma*, a *Aspergillus* or a *Saccharomyces* cell.

* * * * *

UNITED STATES PATENT AND TRADEMARK OFFICE
CERTIFICATE OF CORRECTION

PATENT NO. : 8,956,844 B2  
APPLICATION NO. : 13/914475  
DATED : February 17, 2015  
INVENTOR(S) : Agard et al.

Page 1 of 1

It is certified that error appears in the above-identified patent and that said Letters Patent is hereby corrected as shown below:

In the Claims

Column 253

In Claim 2, lines 5-7, please delete "comprising at least one polynucleotide comprising at least one nucleic acid sequence encoding the xylosidase".

In Claim 3, line 15, please replace "thermophile" with "thermophila".

Column 254

In Claim 9, line 9, please delete "xylanase and/or".

In Claim 11, line 15, please replace "claim 5" with "claim 8".

In Claim 12, line 17, please replace "claim 5" with "claim 8".

Signed and Sealed this
Fourteenth Day of July, 2015

Michelle K. Lee
*Director of the United States Patent and Trademark Office*

SEQUENCE LISTING

```
<160> NUMBER OF SEQ ID NOS: 75

<210> SEQ ID NO 1
<211> LENGTH: 678
<212> TYPE: DNA
<213> ORGANISM: Myceliophthora thermophila

<400> SEQUENCE: 1
atggttaccc tcactcgcct ggcggtcgcc gcggcggcca tgatctccag cactggcctg      60
gctgccccga cgcccgaagc tggccccgac cttcccgact ttgagctcgg ggtcaacaac     120
ctcgcccgcc gcgcgctgga ctacaaccag aactacagga ccagcggcaa cgtcaactac    180
```

```
tcgcccaccg acaacggcta ctcggtcagc ttctccaacg cgggagattt tgtcgtcggg      240
aagggctgga ggacgggagc caccagaaac atcaccttct cgggatcgac acagcatacc      300
tcgggcaccg tgctcgtctc cgtctacggc tggacccgga acccgctgat cgagtactac      360
gtgcaggagt acacgtccaa cggggccggc tccgctcagg gcgagaagct gggcacggtc      420
gagagcgacg ggggcacgta cgagatctgg cggcaccagc aggtcaacca gccgtcgatc      480
gagggcaccc tcgaccttct gcagtacatc tcgaaccgcg tgtccggcca gcggcccaac      540
ggcggcaccg tcaccctcgc caaccacttc gccgcctggc agaagctcgg cctgaacctg      600
ggccagcacg actaccaggt cctggccacc gagggctggg gcaacgccgg cggcagctcc      660
cagtacaccg tcagcggc                                                    678
```

<210> SEQ ID NO 2
<211> LENGTH: 226
<212> TYPE: PRT
<213> ORGANISM: Myceliophthora thermophila

<400> SEQUENCE: 2

```
Met Val Thr Leu Thr Arg Leu Ala Val Ala Ala Ala Met Ile Ser
1               5                   10                  15

Ser Thr Gly Leu Ala Ala Pro Thr Pro Glu Ala Gly Pro Asp Leu Pro
            20                  25                  30

Asp Phe Glu Leu Gly Val Asn Asn Leu Ala Arg Arg Ala Leu Asp Tyr
        35                  40                  45

Asn Gln Asn Tyr Arg Thr Ser Gly Asn Val Asn Tyr Ser Pro Thr Asp
    50                  55                  60

Asn Gly Tyr Ser Val Ser Phe Ser Asn Ala Gly Asp Phe Val Val Gly
65                  70                  75                  80

Lys Gly Trp Arg Thr Gly Ala Thr Arg Asn Ile Thr Phe Ser Gly Ser
                85                  90                  95

Thr Gln His Thr Ser Gly Thr Val Leu Val Ser Val Tyr Gly Trp Thr
            100                 105                 110

Arg Asn Pro Leu Ile Glu Tyr Tyr Val Gln Glu Tyr Thr Ser Asn Gly
        115                 120                 125

Ala Gly Ser Ala Gln Gly Glu Lys Leu Gly Thr Val Glu Ser Asp Gly
    130                 135                 140

Gly Thr Tyr Glu Ile Trp Arg His Gln Gln Val Asn Gln Pro Ser Ile
145                 150                 155                 160

Glu Gly Thr Ser Thr Phe Trp Gln Tyr Ile Ser Asn Arg Val Ser Gly
                165                 170                 175

Gln Arg Pro Asn Gly Gly Thr Val Thr Leu Ala Asn His Phe Ala Ala
            180                 185                 190

Trp Gln Lys Leu Gly Leu Asn Leu Gly Gln His Asp Tyr Gln Val Leu
        195                 200                 205

Ala Thr Glu Gly Trp Gly Asn Ala Gly Gly Ser Ser Gln Tyr Thr Val
    210                 215                 220

Ser Gly
225
```

<210> SEQ ID NO 3
<211> LENGTH: 205
<212> TYPE: PRT
<213> ORGANISM: Myceliophthora thermophila

<400> SEQUENCE: 3

Ala Pro Thr Pro Glu Ala Gly Pro Asp Leu Pro Asp Phe Glu Leu Gly
1               5                   10                  15

Val Asn Asn Leu Ala Arg Arg Ala Leu Asp Tyr Asn Gln Asn Tyr Arg
            20                  25                  30

Thr Ser Gly Asn Val Asn Tyr Ser Pro Thr Asp Asn Gly Tyr Ser Val
        35                  40                  45

Ser Phe Ser Asn Ala Gly Asp Phe Val Val Gly Lys Gly Trp Arg Thr
    50                  55                  60

Gly Ala Thr Arg Asn Ile Thr Phe Ser Gly Ser Thr Gln His Thr Ser
65                  70                  75                  80

Gly Thr Val Leu Val Ser Val Tyr Gly Trp Thr Arg Asn Pro Leu Ile
                85                  90                  95

Glu Tyr Tyr Val Gln Glu Tyr Thr Ser Asn Gly Ala Gly Ser Ala Gln
            100                 105                 110

Gly Glu Lys Leu Gly Thr Val Glu Ser Asp Gly Gly Thr Tyr Glu Ile
        115                 120                 125

Trp Arg His Gln Gln Val Asn Gln Pro Ser Ile Glu Gly Thr Ser Thr
    130                 135                 140

Phe Trp Gln Tyr Ile Ser Asn Arg Val Ser Gly Gln Arg Pro Asn Gly
145                 150                 155                 160

Gly Thr Val Thr Leu Ala Asn His Phe Ala Ala Trp Gln Lys Leu Gly
                165                 170                 175

Leu Asn Leu Gly Gln His Asp Tyr Gln Val Leu Ala Thr Glu Gly Trp
            180                 185                 190

Gly Asn Ala Gly Gly Ser Ser Gln Tyr Thr Val Ser Gly
        195                 200                 205

<210> SEQ ID NO 4
<211> LENGTH: 1833
<212> TYPE: DNA
<213> ORGANISM: Myceliophthora thermophila

<400> SEQUENCE: 4
atgttcttcg cttctctgct gctcggtctc ctggcgggcg tgtccgcttc accgggacac      60
gggcggaatt ccaccttcta caaccccatc ttccccggct tctaccccga tccgagctgc     120
atctacgtgc ccgagcgtga ccacaccttc ttctgtgcct cgtcgagctt caacgccttc     180
ccgggcatcc cgattcatgc cagcaaggac ctgcagaact ggaagttgat cggccatgtg     240
ctgaatcgca aggaacagct tccccggctc gctgagacca accggtcgac cagcggcatc     300
tgggcaccca ccctccggtt ccatgacgac accttctggt tggtcaccac actagtggac     360
gacgaccggc cgcaggagga cgcttccaga tgggacaata ttatcttcaa ggcaaagaat     420
ccgtatgatc cgaggtcctg gtccaaggcc gtccacttca acttcactgg ctacgacacg     480
gagcctttct gggacgaaga tggaaaggtg tacatcaccg cgcccatgc ttggcatgtt      540
ggcccataca tccagcaggc cgaagtcgat ctcgacacgg gggccgtcgg cgagtggcgc     600
atcatctgga acggaacggg cggcatggct cctgaagggc gcacatctac cgcaaagat     660
gggtggtact acttgctggc tgctgaaggg gggaccggca tcgaccatat ggtgaccatg     720
gcccggtcga gaaaaatctc cagtccttac gagtccaacc caaacaaccc cgtgttgacc     780
aacgccaaca cgaccagtta ctttcaaacc gtcgggcatt cagacctgtt ccatgacaga     840
catgggaact ggtgggcagt cgccctctcc acccgctccg gtccagaata tcttcactac     900
cccatgggcc gcgagaccgt catgacagcc gtgagctggc gaaggacga gtggccaacc     960

-continued

```
ttcaccccca tatctggcaa gatgagcggc tggccgatgc ctccttcgca gaaggacatt    1020
cgcggagtcg gccctacgt caactccccc gacccggaac acctgacctt ccccgctcg     1080 gcgccctgc cggccacct cacctactgg cgatacccga accgtcctc ctacacgccg      1140 tccccgcccg ggcaccccaa caccctccgc ctgaccccgt cccgcctgaa cctgaccgcc    1200
ctcaacggca actacgcggg ggccgaccag accttcgtct cgcgccggca gcagcacacc    1260
ctcttcacct acagcgtcac gctcgactac gcgccgcgga ccgccgggga ggaggccggc    1320
gtgaccgcct tcctgacgca gaaccaccac ctcgacctgg gcgtcgtcct gctccctcgc    1380
ggctccgcca ccgcgccctc gctgccgggc ctgagtagta gtacaactac tactagtagt    1440
agtagtagtc gtccggacga ggaggaggag cgcgaggcgg cgaagagga agaagagggc     1500 ggacaagact tgatgatccc gcatgtgcgg ttcaggggcg agtcgtacgt gcccgtcccg    1560
gcgcccgtcg tgtacccgat accccgggcc tggagaggcg ggaagcttgt gttagagatc    1620
cgggcttgta attcgactca cttctcgttc cgtgtcgggc cggacgggag acggtctgag    1680
cggacggtgg tcatggaggc ttcgaacgag gccgttagct ggggctttac tggaacgctg    1740
ctgggcatct atgcgaccag taatggtggc aacggaacca cgccggcgta ttttttcggat   1800 tggaggtaca caccattgga gcagtttagg gat                                1833
```

<210> SEQ ID NO 5
<211> LENGTH: 611
<212> TYPE: PRT
<213> ORGANISM: Myceliophthora thermophila

<400> SEQUENCE: 5

```
Met Phe Phe Ala Ser Leu Leu Gly Leu Leu Ala Gly Val Ser Ala
1               5                   10                  15

Ser Pro Gly His Gly Arg Asn Ser Thr Phe Tyr Asn Pro Ile Phe Pro
            20                  25                  30

Gly Phe Tyr Pro Asp Pro Ser Cys Ile Tyr Val Pro Glu Arg Asp His
        35                  40                  45

Thr Phe Phe Cys Ala Ser Ser Ser Phe Asn Ala Phe Pro Gly Ile Pro
    50                  55                  60

Ile His Ala Ser Lys Asp Leu Gln Asn Trp Lys Leu Ile Gly His Val
65                  70                  75                  80

Leu Asn Arg Lys Glu Gln Leu Pro Arg Leu Ala Glu Thr Asn Arg Ser
                85                  90                  95

Thr Ser Gly Ile Trp Ala Pro Thr Leu Arg Phe His Asp Asp Thr Phe
            100                 105                 110

Trp Leu Val Thr Thr Leu Val Asp Asp Asp Arg Pro Gln Glu Asp Ala
        115                 120                 125

Ser Arg Trp Asp Asn Ile Ile Phe Lys Ala Lys Asn Pro Tyr Asp Pro
    130                 135                 140

Arg Ser Trp Ser Lys Ala Val His Phe Asn Phe Thr Gly Tyr Asp Thr
145                 150                 155                 160

Glu Pro Phe Trp Asp Glu Asp Gly Lys Val Tyr Ile Thr Gly Ala His
                165                 170                 175

Ala Trp His Val Gly Pro Tyr Ile Gln Gln Ala Glu Val Asp Leu Asp
            180                 185                 190

Thr Gly Ala Val Gly Glu Trp Arg Ile Ile Trp Asn Gly Thr Gly Gly
        195                 200                 205

Met Ala Pro Glu Gly Pro His Ile Tyr Arg Lys Asp Gly Trp Tyr Tyr
    210                 215                 220
```

Leu Leu Ala Ala Glu Gly Gly Thr Gly Ile Asp His Met Val Thr Met
225                 230                 235                 240

Ala Arg Ser Arg Lys Ile Ser Ser Pro Tyr Glu Ser Asn Pro Asn Asn
            245                 250                 255

Pro Val Leu Thr Asn Ala Asn Thr Thr Ser Tyr Phe Gln Thr Val Gly
        260                 265                 270

His Ser Asp Leu Phe His Asp Arg His Gly Asn Trp Trp Ala Val Ala
    275                 280                 285

Leu Ser Thr Arg Ser Gly Pro Glu Tyr Leu His Tyr Pro Met Gly Arg
290                 295                 300

Glu Thr Val Met Thr Ala Val Ser Trp Pro Lys Asp Glu Trp Pro Thr
305                 310                 315                 320

Phe Thr Pro Ile Ser Gly Lys Met Ser Gly Trp Pro Met Pro Pro Ser
            325                 330                 335

Gln Lys Asp Ile Arg Gly Val Gly Pro Tyr Val Asn Ser Pro Asp Pro
        340                 345                 350

Glu His Leu Thr Phe Pro Arg Ser Ala Pro Leu Pro Ala His Leu Thr
    355                 360                 365

Tyr Trp Arg Tyr Pro Asn Pro Ser Ser Tyr Thr Pro Ser Pro Pro Gly
370                 375                 380

His Pro Asn Thr Leu Arg Leu Thr Pro Ser Arg Leu Asn Leu Thr Ala
385                 390                 395                 400

Leu Asn Gly Asn Tyr Ala Gly Ala Asp Gln Thr Phe Val Ser Arg Arg
            405                 410                 415

Gln Gln His Thr Leu Phe Thr Tyr Ser Val Thr Leu Asp Tyr Ala Pro
        420                 425                 430

Arg Thr Ala Gly Glu Glu Ala Gly Val Thr Ala Phe Leu Thr Gln Asn
    435                 440                 445

His His Leu Asp Leu Gly Val Val Leu Leu Pro Arg Gly Ser Ala Thr
450                 455                 460

Ala Pro Ser Leu Pro Gly Leu Ser Ser Ser Thr Thr Thr Thr Ser Ser
465                 470                 475                 480

Ser Ser Ser Arg Pro Asp Glu Glu Glu Arg Glu Ala Gly Glu Glu
            485                 490                 495

Glu Glu Glu Gly Gly Gln Asp Leu Met Ile Pro His Val Arg Phe Arg
        500                 505                 510

Gly Glu Ser Tyr Val Pro Val Pro Ala Pro Val Val Tyr Pro Ile Pro
    515                 520                 525

Arg Ala Trp Arg Gly Gly Lys Leu Val Leu Glu Ile Arg Ala Cys Asn
530                 535                 540

Ser Thr His Phe Ser Phe Arg Val Gly Pro Asp Gly Arg Arg Ser Glu
545                 550                 555                 560

Arg Thr Val Val Met Glu Ala Ser Asn Glu Ala Val Ser Trp Gly Phe
            565                 570                 575

Thr Gly Thr Leu Leu Gly Ile Tyr Ala Thr Ser Asn Gly Gly Asn Gly
        580                 585                 590

Thr Thr Pro Ala Tyr Phe Ser Asp Trp Arg Tyr Thr Pro Leu Glu Gln
    595                 600                 605

Phe Arg Asp
610

<210> SEQ ID NO 6
<211> LENGTH: 595

```
<212> TYPE: PRT
<213> ORGANISM: Myceliophthora thermophila

<400> SEQUENCE: 6
```

| | | | | | | | | | | | | | | | |
|---|---|---|---|---|---|---|---|---|---|---|---|---|---|---|---|
| Ser | Pro | Gly | His | Gly | Arg | Asn | Ser | Thr | Phe | Tyr | Asn | Pro | Ile | Phe | Pro |
| 1 | | | | 5 | | | | | 10 | | | | | 15 | |
| Gly | Phe | Tyr | Pro | Asp | Pro | Ser | Cys | Ile | Tyr | Val | Pro | Glu | Arg | Asp | His |
| | | | 20 | | | | | 25 | | | | | 30 | | |
| Thr | Phe | Phe | Cys | Ala | Ser | Ser | Phe | Asn | Ala | Phe | Pro | Gly | Ile | Pro | |
| | | 35 | | | | | 40 | | | | | 45 | | | |
| Ile | His | Ala | Ser | Lys | Asp | Leu | Gln | Asn | Trp | Lys | Leu | Ile | Gly | His | Val |
| | 50 | | | | | 55 | | | | | 60 | | | | |
| Leu | Asn | Arg | Lys | Glu | Gln | Leu | Pro | Arg | Leu | Ala | Glu | Thr | Asn | Arg | Ser |
| 65 | | | | | 70 | | | | | 75 | | | | | 80 |
| Thr | Ser | Gly | Ile | Trp | Ala | Pro | Thr | Leu | Arg | Phe | His | Asp | Asp | Thr | Phe |
| | | | | 85 | | | | | 90 | | | | | 95 | |
| Trp | Leu | Val | Thr | Thr | Leu | Val | Asp | Asp | Arg | Pro | Gln | Glu | Asp | Ala | |
| | | | 100 | | | | | 105 | | | | | 110 | | |
| Ser | Arg | Trp | Asp | Asn | Ile | Ile | Phe | Lys | Ala | Lys | Asn | Pro | Tyr | Asp | Pro |
| | | 115 | | | | | 120 | | | | | 125 | | | |
| Arg | Ser | Trp | Ser | Lys | Ala | Val | His | Phe | Asn | Phe | Thr | Gly | Tyr | Asp | Thr |
| | 130 | | | | | 135 | | | | | 140 | | | | |
| Glu | Pro | Phe | Trp | Asp | Glu | Asp | Gly | Lys | Val | Tyr | Ile | Thr | Gly | Ala | His |
| 145 | | | | | 150 | | | | | 155 | | | | | 160 |
| Ala | Trp | His | Val | Gly | Pro | Tyr | Ile | Gln | Gln | Ala | Glu | Val | Asp | Leu | Asp |
| | | | | 165 | | | | | 170 | | | | | 175 | |
| Thr | Gly | Ala | Val | Gly | Glu | Trp | Arg | Ile | Ile | Trp | Asn | Gly | Thr | Gly | Gly |
| | | | 180 | | | | | 185 | | | | | 190 | | |
| Met | Ala | Pro | Glu | Gly | Pro | His | Ile | Tyr | Arg | Lys | Asp | Gly | Trp | Tyr | Tyr |
| | | 195 | | | | | 200 | | | | | 205 | | | |
| Leu | Leu | Ala | Ala | Glu | Gly | Gly | Thr | Gly | Ile | Asp | His | Met | Val | Thr | Met |
| | 210 | | | | | 215 | | | | | 220 | | | | |
| Ala | Arg | Ser | Arg | Lys | Ile | Ser | Ser | Pro | Tyr | Glu | Ser | Asn | Pro | Asn | Asn |
| 225 | | | | | 230 | | | | | 235 | | | | | 240 |
| Pro | Val | Leu | Thr | Asn | Ala | Asn | Thr | Thr | Ser | Tyr | Phe | Gln | Thr | Val | Gly |
| | | | | 245 | | | | | 250 | | | | | 255 | |
| His | Ser | Asp | Leu | Phe | His | Asp | Arg | His | Gly | Asn | Trp | Trp | Ala | Val | Ala |
| | | | 260 | | | | | 265 | | | | | 270 | | |
| Leu | Ser | Thr | Arg | Ser | Gly | Pro | Glu | Tyr | Leu | His | Tyr | Pro | Met | Gly | Arg |
| | | 275 | | | | | 280 | | | | | 285 | | | |
| Glu | Thr | Val | Met | Thr | Ala | Val | Ser | Trp | Pro | Lys | Asp | Glu | Trp | Pro | Thr |
| | 290 | | | | | 295 | | | | | 300 | | | | |
| Phe | Thr | Pro | Ile | Ser | Gly | Lys | Met | Ser | Gly | Pro | Met | Pro | Pro | Ser | |
| 305 | | | | | 310 | | | | | 315 | | | | | 320 |
| Gln | Lys | Asp | Ile | Arg | Gly | Val | Gly | Pro | Tyr | Val | Asn | Ser | Pro | Asp | Pro |
| | | | | 325 | | | | | 330 | | | | | 335 | |
| Glu | His | Leu | Thr | Phe | Pro | Arg | Ser | Ala | Pro | Leu | Pro | Ala | His | Leu | Thr |
| | | | 340 | | | | | 345 | | | | | 350 | | |
| Tyr | Trp | Arg | Tyr | Pro | Asn | Pro | Ser | Ser | Tyr | Thr | Pro | Ser | Pro | Pro | Gly |
| | | 355 | | | | | 360 | | | | | 365 | | | |
| His | Pro | Asn | Thr | Leu | Arg | Leu | Thr | Pro | Ser | Arg | Leu | Asn | Leu | Thr | Ala |
| | 370 | | | | | 375 | | | | | 380 | | | | |
| Leu | Asn | Gly | Asn | Tyr | Ala | Gly | Ala | Asp | Gln | Thr | Phe | Val | Ser | Arg | Arg |
| 385 | | | | | 390 | | | | | 395 | | | | | 400 |

```
Gln Gln His Thr Leu Phe Thr Tyr Ser Val Thr Leu Asp Tyr Ala Pro
            405                 410                 415

Arg Thr Ala Gly Glu Glu Ala Gly Val Thr Ala Phe Leu Thr Gln Asn
        420                 425                 430

His His Leu Asp Leu Gly Val Val Leu Leu Pro Arg Gly Ser Ala Thr
    435                 440                 445

Ala Pro Ser Leu Pro Gly Leu Ser Ser Thr Thr Thr Ser Ser
450                 455                 460

Ser Ser Ser Arg Pro Asp Glu Glu Glu Arg Glu Ala Gly Glu Glu
465                 470                 475                 480

Glu Glu Glu Gly Gly Gln Asp Leu Met Ile Pro His Val Arg Phe Arg
                485                 490                 495

Gly Glu Ser Tyr Val Pro Val Pro Ala Pro Val Val Tyr Pro Ile Pro
            500                 505                 510

Arg Ala Trp Arg Gly Gly Lys Leu Val Leu Glu Ile Arg Ala Cys Asn
        515                 520                 525

Ser Thr His Phe Ser Phe Arg Val Gly Pro Asp Gly Arg Arg Ser Glu
530                 535                 540

Arg Thr Val Val Met Glu Ala Ser Asn Glu Ala Val Ser Trp Gly Phe
545                 550                 555                 560

Thr Gly Thr Leu Leu Gly Ile Tyr Ala Thr Ser Asn Gly Gly Asn Gly
                565                 570                 575

Thr Thr Pro Ala Tyr Phe Ser Asp Trp Arg Tyr Thr Pro Leu Glu Gln
            580                 585                 590

Phe Arg Asp
        595

<210> SEQ ID NO 7
<211> LENGTH: 2535
<212> TYPE: DNA
<213> ORGANISM: Myceliophthora thermophila

<400> SEQUENCE: 7
atgaaggcct ctgtatcatg cctcgtcggc atgagcgccg tggcctacgg cctcgatggc      60 ccttttccaga cctaccccga ctgcaccaag cccccctgt ccgatattaa ggtgtgcgac     120
cggacactgc ccgaggcgga gcgggcggca gccctcgtgg cagccctgac cgacgaggag    180
aagctgcaaa acctggtcag caaggcgccg ggggcgccgc ggatcggcct gcccgcgtac    240
aactggtgga gcgaggcgct gcacggggtg gcccacgcgc ccgggacgca gttccgcgac    300
gggccggggg acttcaactc gtccacgtcg ttcccgatgc cgctgctgat ggccgccgcc    360
ttcgacgacg agctgatcga ggccgtcggc gacgtcatcg gcaccgaggc ccgcgccttt    420
ggcaacgccg gctggtccgg cctcgactac tggaccccca acgtcaaccc cttccgggac    480
ccccgctggg gccgcggctc cgagacgccg ggcgaggacg tcgtgcgcct caagcgctac    540
gccgcctcca tgatccgcgg gctcgagggt cgttcctcct cctcctcctc ctgctccttc    600
ggatccggag gggagccgcc gcgcgtcatc tcgacctgca agcactacgc cggcaacgac    660
tttgaggact ggaacggcac gacgcggcac gacttcgacg ccgtcatctc ggcgcaggac    720
ctggccgagt actacctggc gccgttccag cagtgcgcgc gcgactcgcg cgtcggctcc    780
gtcatgtgcg cctacaacgc cgtcaacggg gtgccgtcgt cgccaactc gtacctcatg    840 aacacgatcc tgcgcgggca ctggaactgg accgagcacg acaactacgt caccagcgac    900
tgcgaggccg tcctcgacgt ctcggcccac caccactacg ccgacaccaa cgccgagggc    960
```

-continued

```
accggcctct gcttcgaggc cggcatggac acgagctgcg agtacgaggg ctcctccgac    1020
atcccgggcg cctccgccgg cggcttcctg acctggcccg ccgtcgaccg cgccctgacg    1080
cggctgtacc ggagcctggt gcgggtcggc tactttgacg ccccgagtc gccgcacgcc     1140 tcgctgggct gggccgacgt caaccggccc gaggcgcagg agctggccct gcgcgctgcc    1200
gtcgagggca tcgtgctgct caagaacgac aacgacacgc tgccgctgcc gctgccggac    1260
gatgtcgttg tcaccgctga tggtggccgc cgccgcgtcg ccatgatcgg cttctgggcc    1320
gacgccccgg acaagctgtt tggcgggtac agcggcgcgc cccccttcgc gcgctcgccc    1380
gcgagcgccg cccggcagct gggctggaac gtcacggtcg ccgagggcc cgtcctggag    1440 ggagactcgg acgaggagga ggacacgtgg acggcgccgg ccgtcgaggc ggccgccgac    1500
gccgactaca tcgtctactt tggcggcctg gacacgtcgg cggcgggcga gaccaaggac    1560
cggatgacga tcgggtggcc ggcggcgcag ctggcgctca tctcggagct ggcgcggctc    1620
ggcaagcccg tcgtggtggt gcagatgggc gaccagctcg acgacacgcc cctcttcgag    1680
ctggacgggg tgggcgccgt cctgtgggcc aactggccgg ccaggacgg cggcacggcc    1740 gtggtccggc tgctcagcgg cgccgagagc ccggccggcc gctgcccgt gacccagtac    1800 ccggccaact acaccgacgc ggtgcccctg accgacatga ccctgcgccc gtcggcgacc    1860
aacccgggcc ggacctaccg ctggtacccg actcccgtcc ggcccttcgg cttcggcctc    1920
cactatacca ccttccgggc cgagttcggc ccccacccct tcttcccggg ggcgggcaag    1980
ggcgatggcg acggcgagga caagggcgag agcaagagcg agatcaggac gcagcagcag    2040
caacagcagc agcagcagca gcgcagggcg gcggcggcgg ccaccacgcc gatccgggac    2100
ctgctccgcg actgcgacaa gacgtacccg gacacgtgcc cgctgccgcc gctgacggtg    2160
cgcgtgacca acgagggcga gcgcgcgtcc gactacgtgg tgctggcctt cgtgtcgggc    2220
gagtacgggc cggcgccgta cccgatcaag acgctggtct cgtacgcgcg ggcgcgcggg    2280
ctaaagggga agggcgggac gggcgccggc gacggcgacg tcgccaccac taccgtctcg    2340
ctcgactgga ccgtcggcaa cctgccccgc cacgacgagc gcggcaacac aatcctgtac    2400
ccgggaactt acaccctcac tctcgacgag ccggcccagg cgagcgtgca gttcgccctc    2460
gagggcgagc ccgtcgtgct cgacgagtgg cctgcgccgc cgagtgccaa ctccaccgcc    2520
agggggaggc acagg                                                    2535
```

<210> SEQ ID NO 8
<211> LENGTH: 845
<212> TYPE: PRT
<213> ORGANISM: Myceliophthora thermophila

<400> SEQUENCE: 8

```
Met Lys Ala Ser Val Ser Cys Leu Val Gly Met Ser Ala Val Ala Tyr
1               5                   10                  15

Gly Leu Asp Gly Pro Phe Gln Thr Tyr Pro Asp Cys Thr Lys Pro Pro
            20                  25                  30

Leu Ser Asp Ile Lys Val Cys Asp Arg Thr Leu Pro Glu Ala Glu Arg
        35                  40                  45

Ala Ala Ala Leu Val Ala Ala Leu Thr Asp Glu Glu Lys Leu Gln Asn
    50                  55                  60

Leu Val Ser Lys Ala Pro Gly Ala Pro Arg Ile Gly Leu Pro Ala Tyr
65                  70                  75                  80

Asn Trp Trp Ser Glu Ala Leu His Gly Val Ala His Ala Pro Gly Thr
```

```
                        85                  90                  95
Gln Phe Arg Asp Gly Pro Gly Asp Phe Asn Ser Ser Thr Ser Phe Pro
                100                 105                 110

Met Pro Leu Leu Met Ala Ala Ala Phe Asp Asp Glu Leu Ile Glu Ala
                115                 120                 125

Val Gly Asp Val Ile Gly Thr Glu Ala Arg Ala Phe Gly Asn Ala Gly
            130                 135                 140

Trp Ser Gly Leu Asp Tyr Trp Thr Pro Asn Val Asn Pro Phe Arg Asp
145                 150                 155                 160

Pro Arg Trp Gly Arg Gly Ser Glu Thr Pro Gly Glu Asp Val Val Arg
                165                 170                 175

Leu Lys Arg Tyr Ala Ala Ser Met Ile Arg Gly Leu Glu Gly Arg Ser
                180                 185                 190

Ser Ser Ser Ser Ser Cys Ser Phe Gly Ser Gly Gly Glu Pro Pro Arg
            195                 200                 205

Val Ile Ser Thr Cys Lys His Tyr Ala Gly Asn Asp Phe Glu Asp Trp
            210                 215                 220

Asn Gly Thr Thr Arg His Asp Phe Asp Ala Val Ile Ser Ala Gln Asp
225                 230                 235                 240

Leu Ala Glu Tyr Tyr Leu Ala Pro Phe Gln Gln Cys Ala Arg Asp Ser
                245                 250                 255

Arg Val Gly Ser Val Met Cys Ala Tyr Asn Ala Val Asn Gly Val Pro
                260                 265                 270

Ser Cys Ala Asn Ser Tyr Leu Met Asn Thr Ile Leu Arg Gly His Trp
            275                 280                 285

Asn Trp Thr Glu His Asp Asn Tyr Val Thr Ser Asp Cys Glu Ala Val
290                 295                 300

Leu Asp Val Ser Ala His His His Tyr Ala Asp Thr Asn Ala Glu Gly
305                 310                 315                 320

Thr Gly Leu Cys Phe Glu Ala Gly Met Asp Thr Ser Cys Glu Tyr Glu
                325                 330                 335

Gly Ser Ser Asp Ile Pro Gly Ala Ser Ala Gly Gly Phe Leu Thr Trp
            340                 345                 350

Pro Ala Val Asp Arg Ala Leu Thr Arg Leu Tyr Arg Ser Leu Val Arg
            355                 360                 365

Val Gly Tyr Phe Asp Gly Pro Glu Ser Pro His Ala Ser Leu Gly Trp
            370                 375                 380

Ala Asp Val Asn Arg Pro Glu Ala Gln Glu Leu Ala Leu Arg Ala Ala
385                 390                 395                 400

Val Glu Gly Ile Val Leu Leu Lys Asn Asp Asn Asp Thr Leu Pro Leu
                405                 410                 415

Pro Leu Pro Asp Asp Val Val Thr Ala Asp Gly Arg Arg
            420                 425                 430

Val Ala Met Ile Gly Phe Trp Ala Asp Ala Pro Asp Lys Leu Phe Gly
            435                 440                 445

Gly Tyr Ser Gly Ala Pro Pro Phe Ala Arg Ser Pro Ala Ser Ala Ala
            450                 455                 460

Arg Gln Leu Gly Trp Asn Val Thr Val Ala Gly Gly Pro Val Leu Glu
465                 470                 475                 480

Gly Asp Ser Asp Glu Glu Glu Asp Thr Trp Thr Ala Pro Ala Val Glu
                485                 490                 495

Ala Ala Ala Asp Ala Asp Tyr Ile Val Tyr Phe Gly Gly Leu Asp Thr
                500                 505                 510
```

```
Ser Ala Ala Gly Glu Thr Lys Asp Arg Met Thr Ile Gly Trp Pro Ala
        515                 520                 525

Ala Gln Leu Ala Leu Ile Ser Glu Leu Ala Arg Leu Gly Lys Pro Val
    530                 535                 540

Val Val Val Gln Met Gly Asp Gln Leu Asp Thr Pro Leu Phe Glu
545                 550                 555                 560

Leu Asp Gly Val Gly Ala Val Leu Trp Ala Asn Trp Pro Gly Gln Asp
                565                 570                 575

Gly Gly Thr Ala Val Val Arg Leu Leu Ser Gly Ala Glu Ser Pro Ala
                580                 585                 590

Gly Arg Leu Pro Val Thr Gln Tyr Pro Ala Asn Tyr Thr Asp Ala Val
        595                 600                 605

Pro Leu Thr Asp Met Thr Leu Arg Pro Ser Ala Thr Asn Pro Gly Arg
        610                 615                 620

Thr Tyr Arg Trp Tyr Pro Thr Pro Val Arg Pro Phe Gly Phe Gly Leu
625                 630                 635                 640

His Tyr Thr Thr Phe Arg Ala Glu Phe Gly Pro His Pro Phe Phe Pro
                645                 650                 655

Gly Ala Gly Lys Gly Asp Gly Asp Gly Glu Asp Lys Gly Glu Ser Lys
                660                 665                 670

Ser Glu Ile Arg Thr Gln Gln Gln Gln Gln Gln Gln Gln Gln Gln Arg
        675                 680                 685

Arg Ala Ala Ala Ala Thr Thr Pro Ile Arg Asp Leu Leu Arg Asp
    690                 695                 700

Cys Asp Lys Thr Tyr Pro Asp Thr Cys Pro Leu Pro Pro Leu Thr Val
705                 710                 715                 720

Arg Val Thr Asn Glu Gly Glu Arg Ala Ser Asp Tyr Val Val Leu Ala
                725                 730                 735

Phe Val Ser Gly Glu Tyr Gly Pro Ala Pro Tyr Pro Ile Lys Thr Leu
                740                 745                 750

Val Ser Tyr Ala Arg Ala Arg Gly Leu Lys Gly Lys Gly Gly Thr Gly
        755                 760                 765

Ala Gly Asp Gly Asp Val Ala Thr Thr Thr Val Ser Leu Asp Trp Thr
    770                 775                 780

Val Gly Asn Leu Ala Arg His Asp Glu Arg Gly Asn Thr Ile Leu Tyr
785                 790                 795                 800

Pro Gly Thr Tyr Thr Leu Thr Leu Asp Glu Pro Ala Gln Ala Ser Val
                805                 810                 815

Gln Phe Ala Leu Glu Gly Glu Pro Val Val Leu Asp Glu Trp Pro Ala
                820                 825                 830

Pro Pro Ser Ala Asn Ser Thr Ala Arg Gly Arg His Arg
        835                 840                 845

<210> SEQ ID NO 9
<211> LENGTH: 828
<212> TYPE: PRT
<213> ORGANISM: Myceliophthora thermophila

<400> SEQUENCE: 9

Leu Asp Gly Pro Phe Gln Thr Tyr Pro Asp Cys Thr Lys Pro Pro Leu
1               5                   10                  15

Ser Asp Ile Lys Val Cys Asp Arg Thr Leu Pro Glu Ala Glu Arg Ala
            20                  25                  30

Ala Ala Leu Val Ala Ala Leu Thr Asp Glu Glu Lys Leu Gln Asn Leu
```

```
                35                  40                  45
Val Ser Lys Ala Pro Gly Ala Pro Arg Ile Gly Leu Pro Ala Tyr Asn
 50                  55                  60

Trp Trp Ser Glu Ala Leu His Gly Val Ala His Ala Pro Gly Thr Gln
 65                  70                  75                  80

Phe Arg Asp Gly Pro Gly Asp Phe Asn Ser Thr Ser Phe Pro Met
                 85                  90                  95

Pro Leu Leu Met Ala Ala Ala Phe Asp Asp Glu Leu Ile Glu Ala Val
                100                 105                 110

Gly Asp Val Ile Gly Thr Glu Ala Arg Ala Phe Gly Asn Ala Gly Trp
            115                 120                 125

Ser Gly Leu Asp Tyr Trp Thr Pro Asn Val Asn Pro Phe Arg Asp Pro
        130                 135                 140

Arg Trp Gly Arg Gly Ser Glu Thr Pro Gly Glu Asp Val Val Arg Leu
145                 150                 155                 160

Lys Arg Tyr Ala Ala Ser Met Ile Arg Gly Leu Glu Gly Arg Ser Ser
                165                 170                 175

Ser Ser Ser Ser Cys Ser Phe Gly Ser Gly Gly Glu Pro Pro Arg Val
            180                 185                 190

Ile Ser Thr Cys Lys His Tyr Ala Gly Asn Asp Phe Glu Asp Trp Asn
        195                 200                 205

Gly Thr Thr Arg His Asp Phe Asp Ala Val Ile Ser Ala Gln Asp Leu
    210                 215                 220

Ala Glu Tyr Tyr Leu Ala Pro Phe Gln Gln Cys Ala Arg Asp Ser Arg
225                 230                 235                 240

Val Gly Ser Val Met Cys Ala Tyr Asn Ala Val Asn Gly Val Pro Ser
                245                 250                 255

Cys Ala Asn Ser Tyr Leu Met Asn Thr Ile Leu Arg Gly His Trp Asn
            260                 265                 270

Trp Thr Glu His Asp Asn Tyr Val Thr Ser Asp Cys Glu Ala Val Leu
        275                 280                 285

Asp Val Ser Ala His His His Tyr Ala Asp Thr Asn Ala Glu Gly Thr
    290                 295                 300

Gly Leu Cys Phe Glu Ala Gly Met Asp Thr Ser Cys Glu Tyr Glu Gly
305                 310                 315                 320

Ser Ser Asp Ile Pro Gly Ala Ser Ala Gly Gly Phe Leu Thr Trp Pro
                325                 330                 335

Ala Val Asp Arg Ala Leu Thr Arg Leu Tyr Arg Ser Leu Val Arg Val
            340                 345                 350

Gly Tyr Phe Asp Gly Pro Glu Ser Pro His Ala Ser Leu Gly Trp Ala
        355                 360                 365

Asp Val Asn Arg Pro Glu Ala Gln Glu Leu Ala Leu Arg Ala Ala Val
    370                 375                 380

Glu Gly Ile Val Leu Leu Lys Asn Asp Asn Asp Thr Leu Pro Leu Pro
385                 390                 395                 400

Leu Pro Asp Asp Val Val Thr Ala Asp Gly Gly Arg Arg Arg Val
                405                 410                 415

Ala Met Ile Gly Phe Trp Ala Asp Ala Pro Asp Lys Leu Phe Gly Gly
            420                 425                 430

Tyr Ser Gly Ala Pro Pro Phe Ala Arg Ser Pro Ala Ser Ala Ala Arg
        435                 440                 445

Gln Leu Gly Trp Asn Val Thr Val Ala Gly Gly Pro Val Leu Glu Gly
    450                 455                 460
```

Asp Ser Asp Glu Glu Glu Asp Thr Trp Thr Ala Pro Ala Val Glu Ala
465                 470                 475                 480

Ala Ala Asp Ala Asp Tyr Ile Val Tyr Phe Gly Gly Leu Asp Thr Ser
            485                 490                 495

Ala Ala Gly Glu Thr Lys Asp Arg Met Thr Ile Gly Trp Pro Ala Ala
        500                 505                 510

Gln Leu Ala Leu Ile Ser Glu Leu Ala Arg Leu Gly Lys Pro Val Val
    515                 520                 525

Val Val Gln Met Gly Asp Gln Leu Asp Asp Thr Pro Leu Phe Glu Leu
530                 535                 540

Asp Gly Val Gly Ala Val Leu Trp Ala Asn Trp Pro Gly Gln Asp Gly
545                 550                 555                 560

Gly Thr Ala Val Val Arg Leu Leu Ser Gly Ala Glu Ser Pro Ala Gly
            565                 570                 575

Arg Leu Pro Val Thr Gln Tyr Pro Ala Asn Tyr Thr Asp Ala Val Pro
        580                 585                 590

Leu Thr Asp Met Thr Leu Arg Pro Ser Ala Thr Asn Pro Gly Arg Thr
    595                 600                 605

Tyr Arg Trp Tyr Pro Thr Pro Val Arg Pro Phe Gly Phe Gly Leu His
610                 615                 620

Tyr Thr Thr Phe Arg Ala Glu Phe Gly Pro His Pro Phe Phe Pro Gly
625                 630                 635                 640

Ala Gly Lys Gly Asp Gly Asp Gly Glu Asp Lys Gly Glu Ser Lys Ser
            645                 650                 655

Glu Ile Arg Thr Gln Gln Gln Gln Gln Gln Gln Gln Gln Gln Arg Arg
        660                 665                 670

Ala Ala Ala Ala Ala Thr Thr Pro Ile Arg Asp Leu Leu Arg Asp Cys
    675                 680                 685

Asp Lys Thr Tyr Pro Asp Thr Cys Pro Leu Pro Pro Leu Thr Val Arg
690                 695                 700

Val Thr Asn Glu Gly Glu Arg Ala Ser Asp Tyr Val Val Leu Ala Phe
705                 710                 715                 720

Val Ser Gly Glu Tyr Gly Pro Ala Pro Tyr Pro Ile Lys Thr Leu Val
            725                 730                 735

Ser Tyr Ala Arg Ala Arg Gly Leu Lys Gly Lys Gly Thr Gly Ala
        740                 745                 750

Gly Asp Gly Asp Val Ala Thr Thr Thr Val Ser Leu Asp Trp Thr Val
    755                 760                 765

Gly Asn Leu Ala Arg His Asp Glu Arg Gly Asn Thr Ile Leu Tyr Pro
770                 775                 780

Gly Thr Tyr Thr Leu Thr Leu Asp Glu Pro Ala Gln Ala Ser Val Gln
785                 790                 795                 800

Phe Ala Leu Glu Gly Glu Pro Val Val Leu Asp Glu Trp Pro Ala Pro
            805                 810                 815

Pro Ser Ala Asn Ser Thr Ala Arg Gly Arg His Arg
        820                 825

<210> SEQ ID NO 10
<211> LENGTH: 2535
<212> TYPE: DNA
<213> ORGANISM: Myceliophthora thermophila

<400> SEQUENCE: 10
atgaaggcct ctgtatcatg cctcgtcggc atgagcgccg tggcctacgg cctcgatggc    60

```
cctttccaga cctaccccga ctgcaccaag ccccccctgt ccgatattaa ggtgtgcgac    120
cggacactgc ccgaggcgga gcgggcggca gccctcgtgg cagccctgac cgacgaggag    180
aagctgcaaa acctggtcag caaggcgccg ggggcgccgc ggatcggcct gcccgcgtac    240
aactggtgga gcgaggcgct gcacggggtg cccacgcgc ccgggacgca gttccgcgac    300
gggccggggg acttcaactc gtccacgtcg ttcccgatgc cgctgctgat ggccgccgcc    360
ttcgacgacg agctgatcga ggccgtcggc gacgtcatcg gcaccgaggc ccgcgccttt    420
ggcaacgccg gctggtccgg cctcgactac tggacccca acgtcaaccc cttccgggac    480
ccccgctggg gccgcggctc cgagacgccg ggcgaggacg tcgtgcgcct caagcgctac    540
gccgcctcca tgatccgcgg gctcgagggt cgttcctcct cctcctcctc ctgctccttc    600
ggatccggag gggagccgcc gcgcgtcatc tcgacctgca agcactacgc cggcaacgac    660
tttgaggact ggaacggcac gacgcggcac gacttcgacg ccgtcatctc ggcgcaggac    720
ctggccgagt actacctggc gccgttccag cagtgcgcgc gcgactcgcg cgtcggctcc    780
gtcatgtgcg cctacaacgc cgtcaacggg gtgccgtcgt gcgccaactc gtacctcatg    840
aacacgatcc tgcgcgggca ctggaactgg accgagcacg acaactacgt caccagcgac    900
tgcgaggccg tcctcgacgt ctcggcccac caccactacg ccgacaccaa cgccgagggc    960
accggcctct gcttcgaggc cggcatggac acgagctgcg agtacagggg ctcctccgac    1020
atcccgggcg cctccgccgg cggcttcctg acctggcccg ccgtcgaccg cgccctgacg    1080
cggctgtacc ggagcctggt gcgggtcggc tactttgacg gccccgagtc gccgcacgcc    1140
tcgctgggct gggccgacgt caaccggccc gaggcgcagg agctggccct gcgcgctgcc    1200
gtcgagggca tcgtgctgct caagaacgac aacgacacgc tgccgctgcc gctgccggac    1260
gatgtcgttg tcaccgctga tggtggccgc cgccgcgtcg ccatgatcgg cttctgggcc    1320
gacgccccgg acaagctgtt tggcgggtac agcggcgcgc ccccttcgc gcgctcgccc    1380 gcgagcgccg cccggcagct gggctggaac gtcacggtcg ccggagggcc cgtcctggag    1440
ggagactcgg acgaggagga ggacacgtgg acggcgccgg ccgtcgaggc ggccgccgac    1500
gccgactaca tcgtctactt tggcggcctg gacacgtcgg cggcgggcga gaccaaggac    1560
cggatgacga tcgggtggcc ggcggcgcag ctggcgctca tctcggagct ggcgcggctc    1620
ggcaagcccg tcgtggtggt gcagatgggc gaccagctcg acgacacgcc cctcttcgag    1680
ctggacgggg tgggcgccgt cctgtgggcc aactggccgg ccaggacgg cggcacggcc    1740 gtggtccggc tgctcagcgg cgccgagagc ccggccggcc gctgcccgt gacccagtac    1800 ccggccaact acaccgacgc ggtgcccctg accgacatga ccctgcgccc gtcggcgacc    1860 aacccggggcc ggacctaccg ctggtacccg actcccgtcc ggcccttcgg cttcggcctc    1920
cactatacca ccttccgggc cgagttcggc ccccaccct tcttcccggg ggcgggcaag    1980
ggcgatggcg acggcgagga caagggcgag agcaagagcg agatcaggac gcagcagcag    2040
caacagcagc agcagcagca gcgcagggcg gcggcggcgg ccaccacgcc gatccgggac    2100
ctgctccgcg actgcgacaa gacgtacccg gacacgtgcc cgctgccgcc gctgacggtg    2160
cgcgtgacca cgagggcga gcgcgcgtcc gactacgtgg tgctggcctt cgtgtcgggc    2220
gagtacgggc cggcgccgta cccgatcaag acgctggtct cgtacgcgcg ggcgcgcggg    2280 ctaaaggggga agggcggcga cggcgacggc gacggcgacg gcgccaccac taccgtctcg    2340
ctcgactgga ccgtcggcaa cctggcccgc cacgacgagc gcggcaacac aatcctgtac    2400
```

```
ccgggaactt acaccctcac tctcgacgag ccggcccagg cgagcgtgca gttcgccctc    2460
gagggcgagc ccgtcgtgct cgacgagtgg cctgcgccgc cgagtgccaa ctccaccgcc    2520 aggggaggc acagg                                                      2535
```

<210> SEQ ID NO 11
<211> LENGTH: 845
<212> TYPE: PRT
<213> ORGANISM: Myceliophthora thermophila

<400> SEQUENCE: 11

```
Met Lys Ala Ser Val Ser Cys Leu Val Gly Met Ser Ala Val Ala Tyr
  1               5                  10                  15

Gly Leu Asp Gly Pro Phe Gln Thr Tyr Pro Asp Cys Thr Lys Pro Pro
             20                  25                  30

Leu Ser Asp Ile Lys Val Cys Asp Arg Thr Leu Pro Glu Ala Glu Arg
         35                  40                  45

Ala Ala Ala Leu Val Ala Ala Leu Thr Asp Glu Glu Lys Leu Gln Asn
     50                  55                  60

Leu Val Ser Lys Ala Pro Gly Ala Pro Arg Ile Gly Leu Pro Ala Tyr
 65                  70                  75                  80

Asn Trp Trp Ser Glu Ala Leu His Gly Val Ala His Ala Pro Gly Thr
                 85                  90                  95

Gln Phe Arg Asp Gly Pro Gly Asp Phe Asn Ser Ser Thr Ser Phe Pro
            100                 105                 110

Met Pro Leu Leu Met Ala Ala Phe Asp Asp Glu Leu Ile Glu Ala
        115                 120                 125

Val Gly Asp Val Ile Gly Thr Glu Ala Arg Ala Phe Gly Asn Ala Gly
    130                 135                 140

Trp Ser Gly Leu Asp Tyr Trp Thr Pro Asn Val Asn Pro Phe Arg Asp
145                 150                 155                 160

Pro Arg Trp Gly Arg Gly Ser Glu Thr Pro Gly Glu Asp Val Val Arg
                165                 170                 175

Leu Lys Arg Tyr Ala Ala Ser Met Ile Arg Gly Leu Glu Gly Arg Ser
            180                 185                 190

Ser Ser Ser Ser Ser Cys Ser Phe Gly Ser Gly Gly Glu Pro Pro Arg
        195                 200                 205

Val Ile Ser Thr Cys Lys His Tyr Ala Gly Asn Asp Phe Glu Asp Trp
    210                 215                 220

Asn Gly Thr Thr Arg His Asp Phe Asp Ala Val Ile Ser Ala Gln Asp
225                 230                 235                 240

Leu Ala Glu Tyr Tyr Leu Ala Pro Phe Gln Gln Cys Ala Arg Asp Ser
                245                 250                 255

Arg Val Gly Ser Val Met Cys Ala Tyr Asn Ala Val Asn Gly Val Pro
            260                 265                 270

Ser Cys Ala Asn Ser Tyr Leu Met Asn Thr Ile Leu Arg Gly His Trp
        275                 280                 285

Asn Trp Thr Glu His Asp Asn Tyr Val Thr Ser Asp Cys Glu Ala Val
    290                 295                 300

Leu Asp Val Ser Ala His His His Tyr Ala Asp Thr Asn Ala Glu Gly
305                 310                 315                 320

Thr Gly Leu Cys Phe Glu Ala Gly Met Asp Thr Ser Cys Glu Tyr Glu
                325                 330                 335

Gly Ser Ser Asp Ile Pro Gly Ala Ser Ala Gly Gly Phe Leu Thr Trp
            340                 345                 350
```

```
Pro Ala Val Asp Arg Ala Leu Thr Arg Leu Tyr Arg Ser Leu Val Arg
        355                 360                 365

Val Gly Tyr Phe Asp Gly Pro Glu Ser Pro His Ala Ser Leu Gly Trp
    370                 375                 380

Ala Asp Val Asn Arg Pro Glu Ala Gln Glu Leu Ala Leu Arg Ala Ala
385                 390                 395                 400

Val Glu Gly Ile Val Leu Leu Lys Asn Asp Asn Asp Thr Leu Pro Leu
            405                 410                 415

Pro Leu Pro Asp Asp Val Val Thr Ala Asp Gly Arg Arg Arg
        420                 425                 430

Val Ala Met Ile Gly Phe Trp Ala Asp Ala Pro Asp Lys Leu Phe Gly
        435                 440                 445

Gly Tyr Ser Gly Ala Pro Pro Phe Ala Arg Ser Pro Ala Ser Ala Ala
    450                 455                 460

Arg Gln Leu Gly Trp Asn Val Thr Val Ala Gly Gly Pro Val Leu Glu
465                 470                 475                 480

Gly Asp Ser Asp Glu Glu Asp Thr Trp Thr Ala Pro Ala Val Glu
                485                 490                 495

Ala Ala Asp Ala Asp Tyr Ile Val Tyr Phe Gly Gly Leu Asp Thr
            500                 505                 510

Ser Ala Ala Gly Glu Thr Lys Asp Arg Met Thr Ile Gly Trp Pro Ala
        515                 520                 525

Ala Gln Leu Ala Leu Ile Ser Glu Leu Ala Arg Leu Gly Lys Pro Val
        530                 535                 540

Val Val Val Gln Met Gly Asp Gln Leu Asp Asp Thr Pro Leu Phe Glu
545                 550                 555                 560

Leu Asp Gly Val Gly Ala Val Leu Trp Ala Asn Trp Pro Gly Gln Asp
                565                 570                 575

Gly Gly Thr Ala Val Val Arg Leu Leu Ser Gly Ala Glu Ser Pro Ala
            580                 585                 590

Gly Arg Leu Pro Val Thr Gln Tyr Pro Ala Asn Tyr Thr Asp Ala Val
        595                 600                 605

Pro Leu Thr Asp Met Thr Leu Arg Pro Ser Ala Thr Asn Pro Gly Arg
        610                 615                 620

Thr Tyr Arg Trp Tyr Pro Thr Pro Val Arg Pro Phe Gly Phe Gly Leu
625                 630                 635                 640

His Tyr Thr Thr Phe Arg Ala Glu Phe Gly Pro His Pro Phe Phe Pro
                645                 650                 655

Gly Ala Gly Lys Gly Asp Gly Asp Glu Asp Lys Gly Glu Ser Lys
                660                 665                 670

Ser Glu Ile Arg Thr Gln Gln Gln Gln Gln Gln Gln Gln Gln Arg
        675                 680                 685

Arg Ala Ala Ala Ala Thr Thr Pro Ile Arg Asp Leu Leu Arg Asp
690                 695                 700

Cys Asp Lys Thr Tyr Pro Asp Thr Cys Pro Leu Pro Pro Leu Thr Val
705                 710                 715                 720

Arg Val Thr Asn Glu Gly Glu Arg Ala Ser Asp Tyr Val Val Leu Ala
            725                 730                 735

Phe Val Ser Gly Glu Tyr Gly Pro Ala Pro Tyr Pro Ile Lys Thr Leu
                740                 745                 750

Val Ser Tyr Ala Arg Ala Arg Gly Leu Lys Gly Lys Gly Gly Asp Gly
        755                 760                 765
```

Asp Gly Asp Gly Asp Gly Ala Thr Thr Thr Val Ser Leu Asp Trp Thr
            770                 775                 780

Val Gly Asn Leu Ala Arg His Asp Glu Arg Gly Asn Thr Ile Leu Tyr
785                 790                 795                 800

Pro Gly Thr Tyr Thr Leu Thr Leu Asp Glu Pro Ala Gln Ala Ser Val
                805                 810                 815

Gln Phe Ala Leu Glu Gly Glu Pro Val Val Leu Asp Glu Trp Pro Ala
                820                 825                 830

Pro Pro Ser Ala Asn Ser Thr Ala Arg Gly Arg His Arg
            835                 840                 845

<210> SEQ ID NO 12
<211> LENGTH: 2535
<212> TYPE: DNA
<213> ORGANISM: Artificial sequence
<220> FEATURE:
<223> OTHER INFORMATION: Synthetic polynucleotide

<400> SEQUENCE: 12
atgaaggcct ctgtatcatg cctcgtcggc atgagcgccg tggcctacgg cctcgatggc      60
cctttccaga cctaccccga ctgcaccaag ccccccctgt ccgatattaa ggtgtgcgac     120
cggacactgc ccgaggcgga gcgggcggca gccctcgtgg cagccctgac cgacgaggag     180
aagctgcaaa acctggtcag caaggcgccg ggggcgccgc ggatcggcct gcccgcgtac     240
aactggtgga gcgaggcgct gcacggggtg gcccacgcgc ccgggacgca attccgcgac     300
gggccggggg acttcaactc gtccacgtcg ttcccgatgc cgctgctgat ggccgccgcc     360
ttcgacgacg agctgatcga ggccgtcggc gacgtcatcg gcaccgaggc ccgcgccttt     420
ggcaacgccg gctggtccgg cctcgactac tggacccca acgtcaaccc cttccgggac     480
ccccgctggg gccgcggctc cgagacgccg gcgaggacg tcgtgcgcct caagcgctac     540
gccgcctcca tgatccgcgg gctcgagggt cgttcctcct cctcctcctc ctgctccttc     600
ggatccggag gggagccgcc gcgcgtcatc tcgacctgca agcactacgc cggctacgac     660
tttgaggact ggaacggcac gacgcggcac gacttcgacg ccgtcatctc ggcgcaggac     720
ctggccgagt actacctggc gccgttccag cagtgcgcgc gcgactcgcg cgtcggctcc     780
gtcatgtgcg cctacaacgc cgtcaacggg gtgccgtcgt gcgccaactc gtacctcatg     840
aacacgatcc tgcgcgggca ctggaactgg accgagcacg acaactacgt caccagcgac     900
tgcgaggccg tcctcgacgt ctcggcccac caccactacg ccgacaccaa cgccgagggc     960
accggcctct gcttcgaggc cggcatggac acgagctgcg agtacgaggg ctcctccgac    1020
atcccgggcg cctccgccgg cggcttcctg acctggcccg ccgtcgaccg cgccctgacg    1080
cggctgtacc ggagcctggt gcgggtcggc tactttgacg cccccgagtc gccgcacgcc    1140
tcgctgggct gggccgacgt caaccggccc gaggcgcagg agctggccct gcgcgctgcc    1200
gtcgagggca tcgtgctgct caagaacgac aacgacacgc tgccgctgcc gctgccggac    1260
gatgtcgttg tcaccgctga tggtggccgc cgccgcgtcg ccatgatcgg cttctgggcc    1320
gacgccccgg acaagctgtt tggcgggtac agcggcgcgc ccccctcgc gcgctcgccc    1380 gcgagcgccg cccggcagct gggctggaac gtcacggtcg ccggagggcc cgtcctggag    1440
ggagactcgg acgaggagga ggacacgtgg acggcgccgg ccgtcgaggc ggccgccgac    1500
gccgactaca tcgtctactt tggcggcctg gacacgtcgg cggcgggcga gaccaaggac    1560
cggatgacga tcgggtggcc ggcggcgcag ctggcgctca tctcggagct ggcgcggctc    1620

| | | |
|---|---|---|
| ggcaagcccg tcgtggtggt gcagatgggc gaccagctcg acgacacgcc cctcttcgag | 1680 | |
| ctggacgggg tgggcgccgt cctgtgggcc aactggccgg ccaggacgg cggcacggcc | 1740 | |
| gtggtccggc tgctcagcgg cgccgagagc ccggccggcc gcctgccgt gacccagtac | 1800 | |
| ccggccaact acaccgacgc ggtgcccctg accgacatga ccctgcgccc gtcggcgacc | 1860 | |
| aacccgggcc ggacctaccg ctggtacccg actcccgtcc ggcccttcgg cttcggcctc | 1920 | |
| cactatacca ccttccgggc cgagttcggc ccccacccct tcttcccggg ggcgggcaag | 1980 | |
| ggcgatggcg acggcgagga caagggcgag agcaagagcg agatcaggac gcagcagcag | 2040 | |
| caacagcagc agcagcagca gcgcagggcg cggcggcgg ccaccacgcc gatccgggac | 2100 | |
| ctgctccgcg actgcgacaa gacgtacccg gacacgtgcc cgctgccgcc gctgacggtg | 2160 | |
| cgcgtgacca acgagggcga gcgcgcgtcc gactacgtgg tgctggcctt cgtgtcgggc | 2220 | |
| gagtacgggc cggcgccgta cccgatcaag acgctggtct cgtacgcgcg ggcgcgcggg | 2280 | |
| ctaaagggga agggcggcga cggcgacggc gacggcgacg gcgccaccac taccgtctcg | 2340 | |
| ctcgactgga ccgtcggcaa cctggcccgc acgacgagc gcggcaacac aatcctgtac | 2400 | |
| ccgggaactt acaccctcac tctcgacgag ccggcccagg cgagcgtgca gttcgccctc | 2460 | |
| gagggcgagc ccgtcgtgct cgacgagtgg cctgcgccgc cgagtgccaa ctccaccgcc | 2520 | |
| agggggaggc acagg | 2535 | |

<210> SEQ ID NO 13
<211> LENGTH: 845
<212> TYPE: PRT
<213> ORGANISM: Artificial sequence
<220> FEATURE:
<223> OTHER INFORMATION: Synthetic polypeptide

<400> SEQUENCE: 13

Met Lys Ala Ser Val Ser Cys Leu Val Gly Met Ser Ala Val Ala Tyr
1               5                   10                  15

Gly Leu Asp Gly Pro Phe Gln Thr Tyr Pro Asp Cys Thr Lys Pro Pro
            20                  25                  30

Leu Ser Asp Ile Lys Val Cys Asp Arg Thr Leu Pro Glu Ala Glu Arg
        35                  40                  45

Ala Ala Ala Leu Val Ala Ala Leu Thr Asp Glu Glu Lys Leu Gln Asn
    50                  55                  60

Leu Val Ser Lys Ala Pro Gly Ala Pro Arg Ile Gly Leu Pro Ala Tyr
65                  70                  75                  80

Asn Trp Trp Ser Glu Ala Leu His Gly Val Ala His Ala Pro Gly Thr
                85                  90                  95

Gln Phe Arg Asp Gly Pro Gly Asp Phe Asn Ser Ser Thr Ser Phe Pro
            100                 105                 110

Met Pro Leu Leu Met Ala Ala Ala Phe Asp Asp Glu Leu Ile Glu Ala
        115                 120                 125

Val Gly Asp Val Ile Gly Thr Glu Ala Arg Ala Phe Gly Asn Ala Gly
    130                 135                 140

Trp Ser Gly Leu Asp Tyr Trp Thr Pro Asn Val Asn Pro Phe Arg Asp
145                 150                 155                 160

Pro Arg Trp Gly Arg Gly Ser Glu Thr Pro Gly Glu Asp Val Val Arg
                165                 170                 175

Leu Lys Arg Tyr Ala Ala Ser Met Ile Arg Gly Leu Glu Gly Arg Ser
            180                 185                 190

Ser Ser Ser Ser Ser Cys Ser Phe Gly Ser Gly Gly Glu Pro Pro Arg

-continued

```
            195                 200                 205
Val Ile Ser Thr Cys Lys His Tyr Ala Gly Tyr Asp Phe Glu Asp Trp
210                 215                 220
Asn Gly Thr Thr Arg His Asp Phe Asp Ala Val Ile Ser Ala Gln Asp
225                 230                 235                 240
Leu Ala Glu Tyr Tyr Leu Ala Pro Phe Gln Gln Cys Ala Arg Asp Ser
                245                 250                 255
Arg Val Gly Ser Val Met Cys Ala Tyr Asn Ala Val Asn Gly Val Pro
                260                 265                 270
Ser Cys Ala Asn Ser Tyr Leu Met Asn Thr Ile Leu Arg Gly His Trp
            275                 280                 285
Asn Trp Thr Glu His Asp Asn Tyr Val Thr Ser Asp Cys Glu Ala Val
        290                 295                 300
Leu Asp Val Ser Ala His His Tyr Ala Asp Thr Asn Ala Glu Gly
305                 310                 315                 320
Thr Gly Leu Cys Phe Glu Ala Gly Met Asp Thr Ser Cys Glu Tyr Glu
                325                 330                 335
Gly Ser Ser Asp Ile Pro Gly Ala Ser Ala Gly Gly Phe Leu Thr Trp
                340                 345                 350
Pro Ala Val Asp Arg Ala Leu Thr Arg Leu Tyr Arg Ser Leu Val Arg
            355                 360                 365
Val Gly Tyr Phe Asp Gly Pro Glu Ser Pro His Ala Ser Leu Gly Trp
        370                 375                 380
Ala Asp Val Asn Arg Pro Glu Ala Gln Glu Leu Ala Leu Arg Ala Ala
385                 390                 395                 400
Val Glu Gly Ile Val Leu Leu Lys Asn Asp Asn Asp Thr Leu Pro Leu
                405                 410                 415
Pro Leu Pro Asp Asp Val Val Thr Ala Asp Gly Arg Arg Arg
                420                 425                 430
Val Ala Met Ile Gly Phe Trp Ala Asp Ala Pro Asp Lys Leu Phe Gly
            435                 440                 445
Gly Tyr Ser Gly Ala Pro Pro Phe Ala Arg Ser Pro Ala Ser Ala Ala
        450                 455                 460
Arg Gln Leu Gly Trp Asn Val Thr Val Ala Gly Pro Val Leu Glu
465                 470                 475                 480
Gly Asp Ser Asp Glu Glu Glu Asp Thr Trp Thr Ala Pro Ala Val Glu
                485                 490                 495
Ala Ala Ala Asp Ala Asp Tyr Ile Val Tyr Phe Gly Gly Leu Asp Thr
                500                 505                 510
Ser Ala Ala Gly Glu Thr Lys Asp Arg Met Thr Ile Gly Trp Pro Ala
            515                 520                 525
Ala Gln Leu Ala Leu Ile Ser Glu Leu Ala Arg Leu Gly Lys Pro Val
        530                 535                 540
Val Val Gln Met Gly Asp Gln Leu Asp Asp Thr Pro Leu Phe Glu
545                 550                 555                 560
Leu Asp Gly Val Gly Ala Val Leu Trp Ala Asn Trp Pro Gly Gln Asp
                565                 570                 575
Gly Gly Thr Ala Val Val Arg Leu Leu Ser Gly Ala Glu Ser Pro Ala
                580                 585                 590
Gly Arg Leu Pro Val Thr Gln Tyr Pro Ala Asn Tyr Thr Asp Ala Val
            595                 600                 605
Pro Leu Thr Asp Met Thr Leu Arg Pro Ser Ala Thr Asn Pro Gly Arg
        610                 615                 620
```

```
Thr Tyr Arg Trp Tyr Pro Thr Pro Val Arg Pro Phe Gly Phe Gly Leu
625                 630                 635                 640

His Tyr Thr Thr Phe Arg Ala Glu Phe Gly Pro His Pro Phe Phe Pro
            645                 650                 655

Gly Ala Gly Lys Gly Asp Gly Asp Gly Glu Asp Lys Gly Glu Ser Lys
        660                 665                 670

Ser Glu Ile Arg Thr Gln Gln Gln Gln Gln Gln Gln Gln Gln Gln Arg
        675                 680                 685

Arg Ala Ala Ala Ala Thr Thr Pro Ile Arg Asp Leu Leu Arg Asp
690                 695                 700

Cys Asp Lys Thr Tyr Pro Asp Thr Cys Pro Leu Pro Pro Leu Thr Val
705                 710                 715                 720

Arg Val Thr Asn Glu Gly Glu Arg Ala Ser Asp Tyr Val Val Leu Ala
                725                 730                 735

Phe Val Ser Gly Glu Tyr Gly Pro Ala Pro Tyr Pro Ile Lys Thr Leu
            740                 745                 750

Val Ser Tyr Ala Arg Ala Arg Gly Leu Lys Gly Lys Gly Gly Asp Gly
        755                 760                 765

Asp Gly Asp Gly Asp Gly Ala Thr Thr Thr Val Ser Leu Asp Trp Thr
770                 775                 780

Val Gly Asn Leu Ala Arg His Asp Glu Arg Gly Asn Thr Ile Leu Tyr
785                 790                 795                 800

Pro Gly Thr Tyr Thr Leu Thr Leu Asp Glu Pro Ala Gln Ala Ser Val
                805                 810                 815

Gln Phe Ala Leu Glu Gly Glu Pro Val Val Leu Asp Glu Trp Pro Ala
            820                 825                 830

Pro Pro Ser Ala Asn Ser Thr Ala Arg Gly Arg His Arg
        835                 840                 845

<210> SEQ ID NO 14
<211> LENGTH: 837
<212> TYPE: DNA
<213> ORGANISM: Myceliophthora thermophila

<400> SEQUENCE: 14
atggttgctc tctcttctct cctcgtcgct gcctctgcgg cggccgtggc cgtggctgcg      60
ccgagcgagg ccctccagaa gcgccagacg ctcacgagca gccagacggg cttccacgac     120
ggcttttact actccttctg gaccgacggt gccggcaacg tccggtacac gaacgaggcc     180
ggcggccggt acagtgtcac ctggtccggc aacaacggca actgggttgg cggcaagggc     240
tggaacccgg ggctgctcg caacatcagc ttcacggggc agtataaccc caacggcaac     300
tcgtacctgg ccgtgtacgg gtggacgcgc aacccgctga tcgagtacta catcgtcgag     360
aacttcggca cgtacgaccc gtcgacgggg gcgcagcggc tcggcagcat cacggtggac     420
gggtcgacgt acaacatcct caagacgacg cgggtcaacc agccgtccat cgagggcacc     480
agcaccttg accagttctg gtccgtccgg accaacaagc gcagcagcgg ctccgtcaac     540
gtcaaggctc acttcgacgc ttgggcccag gccggcctcc gcctgggcac ccacgactac     600
cagatcatgg ccaccgaggg ctacttctcg agcggctccg ccaccatcac cgtcggcgag     660
ggcaccagca gcggcggcgg cggcgacaat ggcggcggca caacggcgg cggcggcaac     720
accggcacct gcagcgccct gtacggccag tgcgtggcc aggggtggac gggcccgact     780
tgctgctccc agggaacctg ccgcgtctcc aaccagtggt actcgcagtg cttgtaa       837
```

<210> SEQ ID NO 15
<211> LENGTH: 278
<212> TYPE: PRT
<213> ORGANISM: Myceliophthora thermophila

<400> SEQUENCE: 15

| Met | Val | Ala | Leu | Ser | Leu | Leu | Val | Ala | Ser | Ala | Ala | Val |
|---|---|---|---|---|---|---|---|---|---|---|---|---|
| 1 | | | | 5 | | | | 10 | | | | 15 |

Ala Val Ala Ala Pro Ser Glu Ala Leu Gln Lys Arg Gln Thr Leu Thr
                20                  25                  30

Ser Ser Gln Thr Gly Phe His Asp Gly Phe Tyr Tyr Ser Phe Trp Thr
            35                  40                  45

Asp Gly Ala Gly Asn Val Arg Tyr Thr Asn Glu Ala Gly Gly Arg Tyr
        50                  55                  60

Ser Val Thr Trp Ser Gly Asn Asn Gly Asn Trp Val Gly Gly Lys Gly
65                  70                  75                  80

Trp Asn Pro Gly Ala Ala Arg Asn Ile Ser Phe Thr Gly Gln Tyr Asn
                85                  90                  95

Pro Asn Gly Asn Ser Tyr Leu Ala Val Tyr Gly Trp Thr Arg Asn Pro
            100                 105                 110

Leu Ile Glu Tyr Tyr Ile Val Glu Asn Phe Gly Thr Tyr Asp Pro Ser
        115                 120                 125

Thr Gly Ala Gln Arg Leu Gly Ser Ile Thr Val Asp Gly Ser Thr Tyr
    130                 135                 140

Asn Ile Leu Lys Thr Thr Arg Val Asn Gln Pro Ser Ile Glu Gly Thr
145                 150                 155                 160

Ser Thr Phe Asp Gln Phe Trp Ser Val Arg Thr Asn Lys Arg Ser Ser
                165                 170                 175

Gly Ser Val Asn Val Lys Ala His Phe Asp Ala Trp Ala Gln Ala Gly
            180                 185                 190

Leu Arg Leu Gly Thr His Asp Tyr Gln Ile Met Ala Thr Glu Gly Tyr
        195                 200                 205

Phe Ser Ser Gly Ser Ala Thr Ile Thr Val Gly Glu Gly Thr Ser Ser
    210                 215                 220

Gly Gly Gly Gly Asp Asn Gly Gly Asn Asn Gly Gly Gly Asn
225                 230                 235                 240

Thr Gly Thr Cys Ser Ala Leu Tyr Gly Gln Cys Gly Gly Gln Gly Trp
                245                 250                 255

Thr Gly Pro Thr Cys Cys Ser Gln Gly Thr Cys Arg Val Ser Asn Gln
            260                 265                 270

Trp Tyr Ser Gln Cys Leu
        275

<210> SEQ ID NO 16
<211> LENGTH: 259
<212> TYPE: PRT
<213> ORGANISM: Myceliophthora thermophila

<400> SEQUENCE: 16

Ala Pro Ser Glu Ala Leu Gln Lys Arg Gln Thr Leu Thr Ser Ser Gln
1               5                   10                  15

Thr Gly Phe His Asp Gly Phe Tyr Tyr Ser Phe Trp Thr Asp Gly Ala
            20                  25                  30

Gly Asn Val Arg Tyr Thr Asn Glu Ala Gly Gly Arg Tyr Ser Val Thr
        35                  40                  45

Trp Ser Gly Asn Asn Gly Asn Trp Val Gly Gly Lys Gly Trp Asn Pro
 50                  55                  60

Gly Ala Ala Arg Asn Ile Ser Phe Thr Gly Gln Tyr Asn Pro Asn Gly
 65                  70                  75                  80

Asn Ser Tyr Leu Ala Val Tyr Gly Trp Thr Arg Asn Pro Leu Ile Glu
                 85                  90                  95

Tyr Tyr Ile Val Glu Asn Phe Gly Thr Tyr Asp Pro Ser Thr Gly Ala
            100                 105                 110

Gln Arg Leu Gly Ser Ile Thr Val Asp Gly Ser Thr Tyr Asn Ile Leu
        115                 120                 125

Lys Thr Thr Arg Val Asn Gln Pro Ser Ile Glu Gly Thr Ser Thr Phe
130                 135                 140

Asp Gln Phe Trp Ser Val Arg Thr Asn Lys Arg Ser Ser Gly Ser Val
145                 150                 155                 160

Asn Val Lys Ala His Phe Asp Ala Trp Ala Gln Ala Gly Leu Arg Leu
                165                 170                 175

Gly Thr His Asp Tyr Gln Ile Met Ala Thr Glu Gly Tyr Phe Ser Ser
            180                 185                 190

Gly Ser Ala Thr Ile Thr Val Gly Glu Gly Thr Ser Ser Gly Gly Gly
        195                 200                 205

Gly Asp Asn Gly Gly Asn Asn Gly Gly Gly Asn Thr Gly Thr
210                 215                 220

Cys Ser Ala Leu Tyr Gly Gln Cys Gly Gly Gln Gly Trp Thr Gly Pro
225                 230                 235                 240

Thr Cys Cys Ser Gln Gly Thr Cys Arg Val Ser Asn Gln Trp Tyr Ser
                245                 250                 255

Gln Cys Leu

<210> SEQ ID NO 17
<211> LENGTH: 981
<212> TYPE: DNA
<213> ORGANISM: Myceliophthora thermophila

<400> SEQUENCE: 17
atgaaggcca atctcctggt cctcgcgccg ctggccgtct cggcagcgcc cgcgctcgag      60
caccgccagg caactgagag catcgacgcg ctcattaagg ccaagggcaa gctctacttt     120
ggcacctgta ccgaccaggg ccggctgacg tcgggcaaga acgcggacat catcagggcc     180
aacttcggcc aggtgacgcc cgagaacagc atgaagtggc agagcatcga gccatcgcgg     240
ggtcagttca cctggggcca ggctgactac ctcgtcgact gggccactca gaacaacaag     300
accatccgcg ccacacgct cgtctggcac tcgcagctcg ccggctacgt tcagcagatc     360
ggcgaccgga cacccttgac ccagaccatc caggaccaca ttgccgccgt catgggccgc     420
tacaagggca agatctacgc ctgggatgtc atcaacgaga tgttcaacga ggatggctcg     480
cttcgcagca gcgtcttctc caacgtcctc ggagaggact tgttgggat cgccttcaag     540 gcggcgcgcg aggccgaccc cgacaccaag ttgtacatca cgactacaa cctcgacagc     600 cccaactacg ccaagctgac caacggcatg gtcgctcacg tcaagaagtg gctcgcggcc     660
ggcatcccca tcgacggcat cggcacccag ggtcacctgc agtctggcca gggttccggt     720
cttgcgcagg ccatcaaggc tctcgcccag gctggcgtcg aggaggttgc cgtcaccgag     780
ctcgatatcc agaaccagaa caccaacgac tacactgccg ttgtccaggg ctgcttggac     840
gagcccaagt gcgtcggtat caccgtctgg ggtgtccgcg atcccgactc gtggcgtccc     900

```
caggcaacc ccttgctctt cgacagcaac ttcaacccca aggcgaacta caatgccatc    960
gtccagctcc tcaagcagta g                                             981
```

<210> SEQ ID NO 18
<211> LENGTH: 326
<212> TYPE: PRT
<213> ORGANISM: Myceliophthora thermophila

<400> SEQUENCE: 18

```
Met Lys Ala Asn Leu Leu Val Leu Ala Pro Leu Ala Val Ser Ala Ala
1               5                   10                  15

Pro Ala Leu Glu His Arg Gln Ala Thr Glu Ser Ile Asp Ala Leu Ile
            20                  25                  30

Lys Ala Lys Gly Lys Leu Tyr Phe Gly Thr Cys Thr Asp Gln Gly Arg
        35                  40                  45

Leu Thr Ser Gly Lys Asn Ala Asp Ile Ile Arg Ala Asn Phe Gly Gln
    50                  55                  60

Val Thr Pro Glu Asn Ser Met Lys Trp Gln Ser Ile Glu Pro Ser Arg
65                  70                  75                  80

Gly Gln Phe Thr Trp Gly Gln Ala Asp Tyr Leu Val Asp Trp Ala Thr
                85                  90                  95

Gln Asn Asn Lys Thr Ile Arg Gly His Thr Leu Val Trp His Ser Gln
            100                 105                 110

Leu Ala Gly Tyr Val Gln Gln Ile Gly Asp Arg Asn Thr Leu Thr Gln
        115                 120                 125

Thr Ile Gln Asp His Ile Ala Ala Val Met Gly Arg Tyr Lys Gly Lys
    130                 135                 140

Ile Tyr Ala Trp Asp Val Ile Asn Glu Met Phe Asn Glu Asp Gly Ser
145                 150                 155                 160

Leu Arg Ser Ser Val Phe Ser Asn Val Leu Gly Glu Asp Phe Val Gly
                165                 170                 175

Ile Ala Phe Lys Ala Ala Arg Glu Ala Asp Pro Asp Thr Lys Leu Tyr
            180                 185                 190

Ile Asn Asp Tyr Asn Leu Asp Ser Pro Asn Tyr Ala Lys Leu Thr Asn
        195                 200                 205

Gly Met Val Ala His Val Lys Lys Trp Leu Ala Gly Ile Pro Ile
    210                 215                 220

Asp Gly Ile Gly Thr Gln Gly His Leu Gln Ser Gly Gln Gly Ser Gly
225                 230                 235                 240

Leu Ala Gln Ala Ile Lys Ala Leu Ala Gln Ala Gly Val Glu Glu Val
                245                 250                 255

Ala Val Thr Glu Leu Asp Ile Gln Asn Gln Asn Thr Asn Asp Tyr Thr
            260                 265                 270

Ala Val Val Gln Gly Cys Leu Asp Glu Pro Lys Cys Val Gly Ile Thr
        275                 280                 285

Val Trp Gly Val Arg Asp Pro Asp Ser Trp Arg Pro Gln Gly Asn Pro
    290                 295                 300

Leu Leu Phe Asp Ser Asn Phe Asn Pro Lys Ala Asn Tyr Asn Ala Ile
305                 310                 315                 320

Val Gln Leu Leu Lys Gln
                325
```

<210> SEQ ID NO 19
<211> LENGTH: 311
<212> TYPE: PRT

<213> ORGANISM: Myceliophthora thermophila

<400> SEQUENCE: 19

```
Ala Pro Ala Leu Glu His Arg Gln Ala Thr Glu Ser Ile Asp Ala Leu
1               5                   10                  15
Ile Lys Ala Lys Gly Lys Leu Tyr Phe Gly Thr Cys Thr Asp Gln Gly
            20                  25                  30
Arg Leu Thr Ser Gly Lys Asn Ala Asp Ile Ile Arg Ala Asn Phe Gly
        35                  40                  45
Gln Val Thr Pro Glu Asn Ser Met Lys Trp Gln Ser Ile Glu Pro Ser
    50                  55                  60
Arg Gly Gln Phe Thr Trp Gly Gln Ala Asp Tyr Leu Val Asp Trp Ala
65                  70                  75                  80
Thr Gln Asn Asn Lys Thr Ile Arg Gly His Thr Leu Val Trp His Ser
                85                  90                  95
Gln Leu Ala Gly Tyr Val Gln Gln Ile Gly Asp Arg Asn Thr Leu Thr
            100                 105                 110
Gln Thr Ile Gln Asp His Ile Ala Ala Val Met Gly Arg Tyr Lys Gly
        115                 120                 125
Lys Ile Tyr Ala Trp Asp Val Ile Asn Glu Met Phe Asn Glu Asp Gly
130                 135                 140
Ser Leu Arg Ser Ser Val Phe Ser Asn Val Leu Gly Glu Asp Phe Val
145                 150                 155                 160
Gly Ile Ala Phe Lys Ala Ala Arg Glu Ala Asp Pro Asp Thr Lys Leu
                165                 170                 175
Tyr Ile Asn Asp Tyr Asn Leu Asp Ser Pro Asn Tyr Ala Lys Leu Thr
            180                 185                 190
Asn Gly Met Val Ala His Val Lys Lys Trp Leu Ala Ala Gly Ile Pro
        195                 200                 205
Ile Asp Gly Ile Gly Thr Gln Gly His Leu Gln Ser Gly Gln Gly Ser
    210                 215                 220
Gly Leu Ala Gln Ala Ile Lys Ala Leu Ala Gln Ala Gly Val Glu Glu
225                 230                 235                 240
Val Ala Val Thr Glu Leu Asp Ile Gln Asn Gln Asn Thr Asn Asp Tyr
                245                 250                 255
Thr Ala Val Val Gln Gly Cys Leu Asp Glu Pro Lys Cys Val Gly Ile
            260                 265                 270
Thr Val Trp Gly Val Arg Asp Pro Asp Ser Trp Arg Pro Gln Gly Asn
        275                 280                 285
Pro Leu Leu Phe Asp Ser Asn Phe Asn Pro Lys Ala Asn Tyr Asn Ala
    290                 295                 300
Ile Val Gln Leu Leu Lys Gln
305                 310
```

<210> SEQ ID NO 20
<211> LENGTH: 669
<212> TYPE: DNA
<213> ORGANISM: Artificial sequence
<220> FEATURE:
<223> OTHER INFORMATION: Synthetic polynucleotide

<400> SEQUENCE: 20

```
atggtcaagc tctctctcat cgcagcgagc cttgtggcac ctagcgtgct tgcgggtcct      60
ctcatcggcc ccaagacgca aaccgagagc cagctgaacc cgcgtcaagg cggctacaac     120
tacttccaga attggtccga gggaggcagc aatatccgct gcaacaacgg ccctgggggt     180
```

-continued

```
tcctacacgg ccgactggaa cagcagggc ggcttcgtct gtggcaaggg ctggagctat      240
ggaggcaatc gcgccatcac gtacaccggc gaatacaacg ccagcggccc cggctacctc      300
gccgtctacg ggtggacccg caacccgctg attgaatact acatcatcga ggcccatgcc      360
gacctcgccc ccaacgagcc gtggacatcc aagggtaatt tcagcttcga ggagggcgag      420
tacgaggtct tcaccagcac ccgcgtcaac aagccgtcca tcgagggcac caggactttt      480
cagcagtact ggtcgctgcg caaggagcag cgggtcggcg caccgtcac cacccagagg       540 cactttgaag agtgggccaa gctgggcatg aagctgggca atcatgacta tgtcatcctg      600
gcgaccgaag gatacactgc caacggagga tccggtagca gcgggcactc gagcattact      660
ctgcagtag                                                              669
```

<210> SEQ ID NO 21
<211> LENGTH: 222
<212> TYPE: PRT
<213> ORGANISM: Artificial sequence
<220> FEATURE:
<223> OTHER INFORMATION: Synthetic polypeptide

<400> SEQUENCE: 21

```
Met Val Lys Leu Ser Leu Ile Ala Ala Ser Leu Val Ala Pro Ser Val
1               5                   10                  15

Leu Ala Gly Pro Leu Ile Gly Pro Lys Thr Gln Thr Glu Ser Gln Leu
            20                  25                  30

Asn Pro Arg Gln Gly Gly Tyr Asn Tyr Phe Gln Asn Trp Ser Glu Gly
        35                  40                  45

Gly Ser Asn Ile Arg Cys Asn Asn Gly Pro Gly Gly Ser Tyr Thr Ala
    50                  55                  60

Asp Trp Asn Ser Arg Gly Gly Phe Val Cys Gly Lys Gly Trp Ser Tyr
65                  70                  75                  80

Gly Gly Asn Arg Ala Ile Thr Tyr Thr Gly Glu Tyr Asn Ala Ser Gly
                85                  90                  95

Pro Gly Tyr Leu Ala Val Tyr Gly Trp Thr Arg Asn Pro Leu Ile Glu
            100                 105                 110

Tyr Tyr Ile Ile Glu Ala His Ala Asp Leu Ala Pro Asn Glu Pro Trp
        115                 120                 125

Thr Ser Lys Gly Asn Phe Ser Phe Glu Glu Gly Glu Tyr Glu Val Phe
    130                 135                 140

Thr Ser Thr Arg Val Asn Lys Pro Ser Ile Glu Gly Thr Arg Thr Phe
145                 150                 155                 160

Gln Gln Tyr Trp Ser Leu Arg Lys Glu Gln Arg Val Gly Gly Thr Val
                165                 170                 175

Thr Thr Gln Arg His Phe Glu Glu Trp Ala Lys Leu Gly Met Lys Leu
            180                 185                 190

Gly Asn His Asp Tyr Val Ile Leu Ala Thr Glu Gly Tyr Thr Ala Asn
        195                 200                 205

Gly Gly Ser Gly Ser Ser Gly His Ser Ser Ile Thr Leu Gln
    210                 215                 220
```

<210> SEQ ID NO 22
<211> LENGTH: 204
<212> TYPE: PRT
<213> ORGANISM: Artificial sequence
<220> FEATURE:
<223> OTHER INFORMATION: Synthetic polypeptide

<400> SEQUENCE: 22

Gly Pro Leu Ile Gly Pro Lys Thr Gln Thr Glu Ser Gln Leu Asn Pro
1               5                   10                  15

Arg Gln Gly Gly Tyr Asn Tyr Phe Gln Asn Trp Ser Glu Gly Gly Ser
            20                  25                  30

Asn Ile Arg Cys Asn Asn Gly Pro Gly Gly Ser Tyr Thr Ala Asp Trp
        35                  40                  45

Asn Ser Arg Gly Gly Phe Val Cys Gly Lys Trp Ser Tyr Gly Gly
    50                  55                  60

Asn Arg Ala Ile Thr Tyr Thr Gly Glu Tyr Asn Ala Ser Gly Pro Gly
65                  70                  75                  80

Tyr Leu Ala Val Tyr Gly Trp Thr Arg Asn Pro Leu Ile Glu Tyr Tyr
                85                  90                  95

Ile Ile Glu Ala His Ala Asp Leu Ala Pro Asn Glu Pro Trp Thr Ser
            100                 105                 110

Lys Gly Asn Phe Ser Phe Glu Glu Gly Glu Tyr Glu Val Phe Thr Ser
        115                 120                 125

Thr Arg Val Asn Lys Pro Ser Ile Glu Gly Thr Arg Thr Phe Gln Gln
130                 135                 140

Tyr Trp Ser Leu Arg Lys Glu Gln Arg Val Gly Gly Thr Val Thr Thr
145                 150                 155                 160

Gln Arg His Phe Glu Glu Trp Ala Lys Leu Gly Met Lys Leu Gly Asn
                165                 170                 175

His Asp Tyr Val Ile Leu Ala Thr Glu Gly Tyr Thr Ala Asn Gly Gly
            180                 185                 190

Ser Gly Ser Ser Gly His Ser Ser Ile Thr Leu Gln
        195                 200

<210> SEQ ID NO 23
<211> LENGTH: 657
<212> TYPE: DNA
<213> ORGANISM: Artificial sequence
<220> FEATURE:
<223> OTHER INFORMATION: Synthetic polynucleotide

<400> SEQUENCE: 23
atggtctcgt tcactctcct cctcacggtc atcgccgctg cggtgacgac ggccagccct      60
ctcgaggtgg tcaagcgcgg catccagccg ggcacgggca cccacgaggg gtacttctac     120
tcgttctgga ccgacggccg tggctcggtc gacttcaacc ccgggccccg cggctcgtac     180
agcgtcacct ggaacaacgt caacaactgg gttggcggca agggctggaa cccgggcccg     240
ccgcgcaaga ttgcgtacaa cggcacctgg aacaactaca acgtgaacag ctacctcgcc     300
ctgtacggct ggactcgcaa cccgctggtc gagtattaca tcgtggaggc atacggcacg     360
tacaacccct cgtcgggcac ggcgcggctg ggcaccatcg aggacgacgg cggcgtgtac     420
gacatctaca gacgacgcg gtacaaccag ccgtccatcg aggggacctc caccttcgac     480
cagtactggt ccgtccgccg ccagaagcgc gtcggcggca ctatcgacac gggcaagcac     540
tttgacgagt ggaagcgcca gggcaacctc agctcggca cctggaacta catgatcatg     600
gccaccgagg gctaccagag ctctggttcg gccactatcg aggtccggga ggcctaa       657

<210> SEQ ID NO 24
<211> LENGTH: 218
<212> TYPE: PRT
<213> ORGANISM: Artificial sequence
<220> FEATURE:

<223> OTHER INFORMATION: Synthetic polypeptide

<400> SEQUENCE: 24

```
Met Val Ser Phe Thr Leu Leu Leu Thr Val Ile Ala Ala Ala Val Thr
1               5                   10                  15

Thr Ala Ser Pro Leu Glu Val Val Lys Arg Gly Ile Gln Pro Gly Thr
            20                  25                  30

Gly Thr His Glu Gly Tyr Phe Tyr Ser Phe Trp Thr Asp Gly Arg Gly
        35                  40                  45

Ser Val Asp Phe Asn Pro Gly Pro Arg Gly Ser Tyr Ser Val Thr Trp
    50                  55                  60

Asn Asn Val Asn Asn Trp Val Gly Gly Lys Gly Trp Asn Pro Gly Pro
65                  70                  75                  80

Pro Arg Lys Ile Ala Tyr Asn Gly Thr Trp Asn Asn Tyr Asn Val Asn
                85                  90                  95

Ser Tyr Leu Ala Leu Tyr Gly Trp Thr Arg Asn Pro Leu Val Glu Tyr
            100                 105                 110

Tyr Ile Val Glu Ala Tyr Gly Thr Tyr Asn Pro Ser Ser Gly Thr Ala
        115                 120                 125

Arg Leu Gly Thr Ile Glu Asp Asp Gly Gly Val Tyr Asp Ile Tyr Lys
    130                 135                 140

Thr Thr Arg Tyr Asn Gln Pro Ser Ile Glu Gly Thr Ser Thr Phe Asp
145                 150                 155                 160

Gln Tyr Trp Ser Val Arg Arg Gln Lys Arg Val Gly Thr Ile Asp
                165                 170                 175

Thr Gly Lys His Phe Asp Glu Trp Lys Arg Gln Gly Asn Leu Gln Leu
            180                 185                 190

Gly Thr Trp Asn Tyr Met Ile Met Ala Thr Gly Tyr Gln Ser Ser
        195                 200                 205

Gly Ser Ala Thr Ile Glu Val Arg Glu Ala
    210                 215
```

<210> SEQ ID NO 25
<211> LENGTH: 200
<212> TYPE: PRT
<213> ORGANISM: Artificial sequence
<220> FEATURE:
<223> OTHER INFORMATION: Synthetic polypeptide

<400> SEQUENCE: 25

```
Ser Pro Leu Glu Val Val Lys Arg Gly Ile Gln Pro Gly Thr Gly Thr
1               5                   10                  15

His Glu Gly Tyr Phe Tyr Ser Phe Trp Thr Asp Gly Arg Gly Ser Val
            20                  25                  30

Asp Phe Asn Pro Gly Pro Arg Gly Ser Tyr Ser Val Thr Trp Asn Asn
        35                  40                  45

Val Asn Asn Trp Val Gly Gly Lys Gly Trp Asn Pro Gly Pro Pro Arg
    50                  55                  60

Lys Ile Ala Tyr Asn Gly Thr Trp Asn Asn Tyr Asn Val Asn Ser Tyr
65                  70                  75                  80

Leu Ala Leu Tyr Gly Trp Thr Arg Asn Pro Leu Val Glu Tyr Tyr Ile
                85                  90                  95

Val Glu Ala Tyr Gly Thr Tyr Asn Pro Ser Ser Gly Thr Ala Arg Leu
            100                 105                 110

Gly Thr Ile Glu Asp Asp Gly Gly Val Tyr Asp Ile Tyr Lys Thr Thr
        115                 120                 125
```

```
Arg Tyr Asn Gln Pro Ser Ile Glu Gly Thr Ser Thr Phe Asp Gln Tyr
        130                 135                 140

Trp Ser Val Arg Arg Gln Lys Arg Val Gly Gly Thr Ile Asp Thr Gly
145                 150                 155                 160

Lys His Phe Asp Glu Trp Lys Arg Gln Gly Asn Leu Gln Leu Gly Thr
                165                 170                 175

Trp Asn Tyr Met Ile Met Ala Thr Glu Gly Tyr Gln Ser Ser Gly Ser
            180                 185                 190

Ala Thr Ile Glu Val Arg Glu Ala
            195                 200

<210> SEQ ID NO 26
<211> LENGTH: 687
<212> TYPE: DNA
<213> ORGANISM: Myceliophthora thermophila

<400> SEQUENCE: 26
atggtctcgc tcaagtccct cctcctcgcc gcggcggcga cgttgacggc ggtgacggcg    60
cgcccgttcg actttgacga cggcaactcg accgaggcgc tggccaagcg ccaggtcacg   120
cccaacgcgc agggctacca ctcgggctac ttctactcgt ggtggtccga cggcggcggc   180
caggccacct tcaccctgct cgagggcagc cactaccagg tcaactggag gaacacgggc   240
aactttgtcg gtggcaaggg ctggaacccg ggtaccggcc ggaccatcaa ctacggcggc   300
tcgttcaacc cgagcggcaa cggctacctg gccgtctacg gctggacgca caacccgctg   360
atcgagtact acgtggtcga gtcgtacggg acctacaacc cgggcagcca ggcccagtac   420
aagggcagct tccagagcga cggcggcacc tacaacatct acgtctcgac ccgctacaac   480
gcgccctcga tcgagggcac ccgcaccttc agcagtact ggtccatccg cacctccaag   540
cgcgtcggcg gctccgtcac catgcagaac cacttcaacg cctgggccca gcacggcatg   600
cccctcggct cccacgacta ccagatcgtc gccaccgagg gctaccagag cagcggctcc   660
tccgacatct acgtccagac tcactag                                       687

<210> SEQ ID NO 27
<211> LENGTH: 228
<212> TYPE: PRT
<213> ORGANISM: Myceliophthora thermophila

<400> SEQUENCE: 27

Met Val Ser Leu Lys Ser Leu Leu Leu Ala Ala Ala Thr Leu Thr
1               5                   10                  15

Ala Val Thr Ala Arg Pro Phe Asp Phe Asp Asp Gly Asn Ser Thr Glu
                20                  25                  30

Ala Leu Ala Lys Arg Gln Val Thr Pro Asn Ala Gln Gly Tyr His Ser
            35                  40                  45

Gly Tyr Phe Tyr Ser Trp Trp Ser Asp Gly Gly Gln Ala Thr Phe
        50                  55                  60

Thr Leu Leu Glu Gly Ser His Tyr Gln Val Asn Trp Arg Asn Thr Gly
65                  70                  75                  80

Asn Phe Val Gly Gly Lys Gly Trp Asn Pro Gly Thr Gly Arg Thr Ile
                85                  90                  95

Asn Tyr Gly Gly Ser Phe Asn Pro Ser Gly Asn Gly Tyr Leu Ala Val
            100                 105                 110

Tyr Gly Trp Thr His Asn Pro Leu Ile Glu Tyr Tyr Val Val Glu Ser
        115                 120                 125
```

```
Tyr Gly Thr Tyr Asn Pro Gly Ser Gln Ala Gln Tyr Lys Gly Ser Phe
            130                 135                 140

Gln Ser Asp Gly Gly Thr Tyr Asn Ile Tyr Val Ser Thr Arg Tyr Asn
145                 150                 155                 160

Ala Pro Ser Ile Glu Gly Thr Arg Thr Phe Gln Gln Tyr Trp Ser Ile
                165                 170                 175

Arg Thr Ser Lys Arg Val Gly Gly Ser Val Thr Met Gln Asn His Phe
            180                 185                 190

Asn Ala Trp Ala Gln His Gly Met Pro Leu Gly Ser His Asp Tyr Gln
        195                 200                 205

Ile Val Ala Thr Glu Gly Tyr Gln Ser Ser Gly Ser Ser Asp Ile Tyr
    210                 215                 220

Val Gln Thr His
225
```

<210> SEQ ID NO 28
<211> LENGTH: 208
<212> TYPE: PRT
<213> ORGANISM: Myceliophthora thermophila

<400> SEQUENCE: 28

```
Arg Pro Phe Asp Phe Asp Asp Gly Asn Ser Thr Glu Ala Leu Ala Lys
1               5                   10                  15

Arg Gln Val Thr Pro Asn Ala Gln Gly Tyr His Ser Gly Tyr Phe Tyr
                20                  25                  30

Ser Trp Trp Ser Asp Gly Gly Gln Ala Thr Phe Thr Leu Leu Glu
            35                  40                  45

Gly Ser His Tyr Gln Val Asn Trp Arg Asn Thr Gly Asn Phe Val Gly
50                  55                  60

Gly Lys Gly Trp Asn Pro Gly Thr Gly Arg Thr Ile Asn Tyr Gly Gly
65                  70                  75                  80

Ser Phe Asn Pro Ser Gly Asn Gly Tyr Leu Ala Val Tyr Gly Trp Thr
                85                  90                  95

His Asn Pro Leu Ile Glu Tyr Tyr Val Val Glu Ser Tyr Gly Thr Tyr
            100                 105                 110

Asn Pro Gly Ser Gln Ala Gln Tyr Lys Gly Ser Phe Gln Ser Asp Gly
        115                 120                 125

Gly Thr Tyr Asn Ile Tyr Val Ser Thr Arg Tyr Asn Ala Pro Ser Ile
130                 135                 140

Glu Gly Thr Arg Thr Phe Gln Gln Tyr Trp Ser Ile Arg Thr Ser Lys
145                 150                 155                 160

Arg Val Gly Gly Ser Val Thr Met Gln Asn His Phe Asn Ala Trp Ala
                165                 170                 175

Gln His Gly Met Pro Leu Gly Ser His Asp Tyr Gln Ile Val Ala Thr
            180                 185                 190

Glu Gly Tyr Gln Ser Ser Gly Ser Ser Asp Ile Tyr Val Gln Thr His
        195                 200                 205
```

<210> SEQ ID NO 29
<211> LENGTH: 2283
<212> TYPE: DNA
<213> ORGANISM: Myceliophthora thermophila

<400> SEQUENCE: 29
atggccttcc tttcctcctt tgcccttgcc gccctcgggg cactcgtcgt cccggcgagg    60

```
ggcggcgtga cgtacccgga ctgcgcaaac ggaccgctca agtcaaatac ggtgtgcgat    120
acgtcggcgt ccccgggagc ccgagccgct gctcttgtga gtgtaatgaa caacaacgaa    180
aaacttgcaa atcttgtcaa caattcgccc ggcgtctcgc ggctcggcct gagtgcgtac    240
cagtggtgga acgaagccct ccacggagta gcccataacc gcggcattac ctggggcggc    300
gagttcagcg cggcaaccca gttcccgcag gctatcacga cttccgccac tttcgatgac    360
gctttgatcg agcaaatcgg caccattatc agcaccgagg cccgtgcctt tgccaacaat    420
gggcgcgctc atctcgactt ctggacgccc aacgtcaacc cgtttcgaga cccgcgatgg    480
ggtcgcggac acgagacgcc gggagaggat gcattcaaga ataagaagtg ggccgaggcc    540
ttcgtcaagg gcatgcaagg acccggaccg acgcaccgag tcatcgccac atgtaagcac    600
tacgccgcct acgacctcga gaactccggg agcacgaccc gattcaactt cgatgcgaag    660
gtgtcaactc aagatctcgc cgagtactat ctccctccgt tccaacagtg cgcccgggac    720
tctaaggtgg gctccatcat gtgcagctac aatgcggtca atgaaatccc ggcctgcgcg    780
aatccttacc tgatggatac catcctgcgg aaacattgga attggaccga cgagcaccag    840
tatattgtga gcgactgcga tgccgtgtac tatctcggca atgcgaacgg cggccaccga    900
tacaagccga gctatgcggc ggcgatcgga gcatctctcg aggctggttg cgataacatg    960
tgctgggcga ccggcggcac cgcccccgat cccgcctcag ccttcaattc cggccagttc   1020
agccagacga cactgacacg gctattttg cgccagatgc agggcctcgt cctagcggga   1080
tactttgacg gtccgggcgg tatgtaccgc aacctgagcg tggcggacgt gaacacgcag   1140
accgcccagg acactgcact caaggcggcg aaggaggca tcgtgctcct caagaacgat   1200
gggatccttc cgctgtcggt taacggttcc aatttccagg tcgctatgat cgggttctgg   1260
gcgaacgcag ccgacaagat gctcgggggt tacagcggga gcccgccgtt caaccatgat   1320
cccgtgaccg ctgcaagatc gatgggcatc acggtcaact acgtcaacgg gccattgacg   1380
caacccaacg gggatacgtc ggcagcactc aatgcgccc aaaagtccaa cgcggtggta   1440
ttctttggtg gaatcgacaa tacggtggag aaggagagtc aggacagaac gtccatcgag   1500
tggccctcag gcaactggc tctgattcgg aggctagccg aaaccggcaa accagtcatc   1560
gtcgtcaggc tcgggacgca cgtcgacgac accccgctcc tcagcattcc gaatgtgaga   1620
gccatttttgt gggcaggata cccgggtcaa gacggcggga ctgctgtggt gaaaatcatt   1680
accggccttg ctagtccggc ggggaggctg cccgccactg tgtatccgtc ttcgtacacc   1740
agccaagcgc cctttacaaa catggccctg aggccttctt cgtcctatcc cgggcgaaca   1800
taccgctggt acagtaacgc cgtctttcca tttggccacg gcctacatta taccaatttc   1860
agtgtctcgg tgcgggactt tccggccagc ttcgcgattg ccgatctcct ggcttcctgc   1920
ggggattccg tggcgtatct tgatctttgc cccttcccgt ccgtgtcgct caatgtgacc   1980
aatacaggca cccgcgtgtc cgattacgtt gcgcttgggt tcttgtcggg agattttggt   2040
cccagcccac atcccatcaa gacattggcg acgtataagc gcgtgtttaa catcgaacct   2100
ggggaaacac aggtggccga gctagactgg aagctggaga gcctggtccg ggtagatgag   2160
aagggcaaca gggtactcta ccccggaaca tatacgcttc ttgtggatca gccaaccttg   2220
gcaaatatca cctttatttt gacaggagaa gaggcagtgt tggatagttg gccgcagccg   2280
tga                                                                2283
```

<210> SEQ ID NO 30
<211> LENGTH: 760

```
<212> TYPE: PRT
<213> ORGANISM: Myceliophthora thermophila

<400> SEQUENCE: 30

Met Ala Phe Leu Ser Ser Phe Ala Leu Ala Ala Leu Gly Ala Leu Val
1               5                   10                  15

Val Pro Ala Arg Gly Gly Val Thr Tyr Pro Asp Cys Ala Asn Gly Pro
            20                  25                  30

Leu Lys Ser Asn Thr Val Cys Asp Thr Ser Ala Ser Pro Gly Ala Arg
        35                  40                  45

Ala Ala Ala Leu Val Ser Val Met Asn Asn Glu Lys Leu Ala Asn
    50                  55                  60

Leu Val Asn Asn Ser Pro Gly Val Ser Arg Leu Gly Leu Ser Ala Tyr
65                  70                  75                  80

Gln Trp Trp Asn Glu Ala Leu His Gly Val Ala His Asn Arg Gly Ile
                85                  90                  95

Thr Trp Gly Gly Glu Phe Ser Ala Ala Thr Gln Phe Pro Gln Ala Ile
            100                 105                 110

Thr Thr Ser Ala Thr Phe Asp Asp Ala Leu Ile Glu Gln Ile Gly Thr
        115                 120                 125

Ile Ile Ser Thr Glu Ala Arg Ala Phe Ala Asn Asn Gly Arg Ala His
    130                 135                 140

Leu Asp Phe Trp Thr Pro Asn Val Asn Pro Phe Arg Asp Pro Arg Trp
145                 150                 155                 160

Gly Arg Gly His Glu Thr Pro Gly Glu Asp Ala Phe Lys Asn Lys Lys
                165                 170                 175

Trp Ala Glu Ala Phe Val Lys Gly Met Gln Gly Pro Gly Pro Thr His
            180                 185                 190

Arg Val Ile Ala Thr Cys Lys His Tyr Ala Ala Tyr Asp Leu Glu Asn
        195                 200                 205

Ser Gly Ser Thr Thr Arg Phe Asn Phe Asp Ala Lys Val Ser Thr Gln
    210                 215                 220

Asp Leu Ala Glu Tyr Tyr Leu Pro Pro Phe Gln Gln Cys Ala Arg Asp
225                 230                 235                 240

Ser Lys Val Gly Ser Ile Met Cys Ser Tyr Asn Ala Val Asn Glu Ile
                245                 250                 255

Pro Ala Cys Ala Asn Pro Tyr Leu Met Asp Thr Ile Leu Arg Lys His
            260                 265                 270

Trp Asn Trp Thr Asp Glu His Gln Tyr Ile Val Ser Asp Cys Asp Ala
        275                 280                 285

Val Tyr Tyr Leu Gly Asn Ala Asn Gly Gly His Arg Tyr Lys Pro Ser
    290                 295                 300

Tyr Ala Ala Ala Ile Gly Ala Ser Leu Glu Ala Gly Cys Asp Asn Met
305                 310                 315                 320

Cys Trp Ala Thr Gly Gly Thr Ala Pro Asp Pro Ala Ser Ala Phe Asn
                325                 330                 335

Ser Gly Gln Phe Ser Gln Thr Thr Leu Asp Thr Ala Ile Leu Arg Gln
            340                 345                 350

Met Gln Gly Leu Val Leu Ala Gly Tyr Phe Asp Gly Pro Gly Gly Met
        355                 360                 365

Tyr Arg Asn Leu Ser Val Ala Asp Val Asn Thr Gln Thr Ala Gln Asp
    370                 375                 380

Thr Ala Leu Lys Ala Ala Glu Gly Gly Ile Val Leu Leu Lys Asn Asp
385                 390                 395                 400
```

```
Gly Ile Leu Pro Leu Ser Val Asn Gly Ser Asn Phe Gln Val Ala Met
            405                 410                 415

Ile Gly Phe Trp Ala Asn Ala Ala Asp Lys Met Leu Gly Gly Tyr Ser
        420                 425                 430

Gly Ser Pro Pro Phe Asn His Asp Pro Val Thr Ala Ala Arg Ser Met
            435                 440                 445

Gly Ile Thr Val Asn Tyr Val Asn Gly Pro Leu Thr Gln Pro Asn Gly
        450                 455                 460

Asp Thr Ser Ala Ala Leu Asn Ala Ala Gln Lys Ser Asn Ala Val Val
465                 470                 475                 480

Phe Phe Gly Gly Ile Asp Asn Thr Val Glu Lys Glu Ser Gln Asp Arg
                485                 490                 495

Thr Ser Ile Glu Trp Pro Ser Gly Gln Leu Ala Leu Ile Arg Arg Leu
            500                 505                 510

Ala Glu Thr Gly Lys Pro Val Ile Val Val Arg Leu Gly Thr His Val
        515                 520                 525

Asp Asp Thr Pro Leu Leu Ser Ile Pro Asn Val Arg Ala Ile Leu Trp
530                 535                 540

Ala Gly Tyr Pro Gly Gln Asp Gly Gly Thr Ala Val Val Lys Ile Ile
545                 550                 555                 560

Thr Gly Leu Ala Ser Pro Ala Gly Arg Leu Pro Ala Thr Val Tyr Pro
            565                 570                 575

Ser Ser Tyr Thr Ser Gln Ala Pro Phe Thr Asn Met Ala Leu Arg Pro
            580                 585                 590

Ser Ser Ser Tyr Pro Gly Arg Thr Tyr Arg Trp Tyr Ser Asn Ala Val
            595                 600                 605

Phe Pro Phe Gly His Gly Leu His Tyr Thr Asn Phe Ser Val Ser Val
        610                 615                 620

Arg Asp Phe Pro Ala Ser Phe Ala Ile Ala Asp Leu Leu Ala Ser Cys
625                 630                 635                 640

Gly Asp Ser Val Ala Tyr Leu Asp Leu Cys Pro Phe Pro Ser Val Ser
                645                 650                 655

Leu Asn Val Thr Asn Thr Gly Thr Arg Val Ser Asp Tyr Val Ala Leu
            660                 665                 670

Gly Phe Leu Ser Gly Asp Phe Gly Pro Ser Pro His Pro Ile Lys Thr
        675                 680                 685

Leu Ala Thr Tyr Lys Arg Val Phe Asn Ile Glu Pro Gly Glu Thr Gln
    690                 695                 700

Val Ala Glu Leu Asp Trp Lys Leu Glu Ser Leu Val Arg Val Asp Glu
705                 710                 715                 720

Lys Gly Asn Arg Val Leu Tyr Pro Gly Thr Tyr Thr Leu Leu Val Asp
                725                 730                 735

Gln Pro Thr Leu Ala Asn Ile Thr Phe Ile Leu Thr Gly Glu Glu Ala
            740                 745                 750

Val Leu Asp Ser Trp Pro Gln Pro
            755                 760

<210> SEQ ID NO 31
<211> LENGTH: 739
<212> TYPE: PRT
<213> ORGANISM: Myceliophthora thermophila

<400> SEQUENCE: 31

Gly Val Thr Tyr Pro Asp Cys Ala Asn Gly Pro Leu Lys Ser Asn Thr
```

-continued

```
1               5                   10                  15
Val Cys Asp Thr Ser Ala Ser Pro Gly Ala Arg Ala Ala Ala Leu Val
                20                  25                  30

Ser Val Met Asn Asn Asn Glu Lys Leu Ala Asn Leu Val Asn Asn Ser
                35                  40                  45

Pro Gly Val Ser Arg Leu Gly Leu Ser Ala Tyr Gln Trp Trp Asn Glu
                50                  55                  60

Ala Leu His Gly Val Ala His Asn Arg Gly Ile Thr Trp Gly Gly Glu
65                  70                  75                  80

Phe Ser Ala Ala Thr Gln Phe Pro Gln Ala Ile Thr Thr Ser Ala Thr
                85                  90                  95

Phe Asp Asp Ala Leu Ile Glu Gln Ile Gly Thr Ile Ile Ser Thr Glu
                100                 105                 110

Ala Arg Ala Phe Ala Asn Asn Gly Arg Ala His Leu Asp Phe Trp Thr
                115                 120                 125

Pro Asn Val Asn Pro Phe Arg Asp Pro Arg Trp Gly Arg Gly His Glu
                130                 135                 140

Thr Pro Gly Glu Asp Ala Phe Lys Asn Lys Trp Ala Glu Ala Phe
145                 150                 155                 160

Val Lys Gly Met Gln Gly Pro Gly Pro Thr His Arg Val Ile Ala Thr
                165                 170                 175

Cys Lys His Tyr Ala Ala Tyr Asp Leu Glu Asn Ser Gly Ser Thr Thr
                180                 185                 190

Arg Phe Asn Phe Asp Ala Lys Val Ser Thr Gln Asp Leu Ala Glu Tyr
                195                 200                 205

Tyr Leu Pro Pro Phe Gln Gln Cys Ala Arg Asp Ser Lys Val Gly Ser
                210                 215                 220

Ile Met Cys Ser Tyr Asn Ala Val Asn Glu Ile Pro Ala Cys Ala Asn
225                 230                 235                 240

Pro Tyr Leu Met Asp Thr Ile Leu Arg Lys His Trp Asn Trp Thr Asp
                245                 250                 255

Glu His Gln Tyr Ile Val Ser Asp Cys Asp Ala Val Tyr Tyr Leu Gly
                260                 265                 270

Asn Ala Asn Gly Gly His Arg Tyr Lys Pro Ser Tyr Ala Ala Ala Ile
                275                 280                 285

Gly Ala Ser Leu Glu Ala Gly Cys Asp Asn Met Cys Trp Ala Thr Gly
                290                 295                 300

Gly Thr Ala Pro Asp Pro Ala Ser Ala Phe Asn Ser Gly Gln Phe Ser
305                 310                 315                 320

Gln Thr Thr Leu Asp Thr Ala Ile Leu Arg Gln Met Gln Gly Leu Val
                325                 330                 335

Leu Ala Gly Tyr Phe Asp Gly Pro Gly Met Tyr Arg Asn Leu Ser
                340                 345                 350

Val Ala Asp Val Asn Thr Gln Thr Ala Gln Asp Thr Ala Leu Lys Ala
                355                 360                 365

Ala Glu Gly Gly Ile Val Leu Leu Lys Asn Asp Gly Ile Leu Pro Leu
                370                 375                 380

Ser Val Asn Gly Ser Asn Phe Gln Val Ala Met Ile Gly Phe Trp Ala
385                 390                 395                 400

Asn Ala Ala Asp Lys Met Leu Gly Gly Tyr Ser Gly Ser Pro Pro Phe
                405                 410                 415

Asn His Asp Pro Val Thr Ala Ala Arg Ser Met Gly Ile Thr Val Asn
                420                 425                 430
```

Tyr Val Asn Gly Pro Leu Thr Gln Pro Asn Gly Asp Thr Ser Ala Ala
                435                 440                 445

Leu Asn Ala Ala Gln Lys Ser Asn Ala Val Val Phe Phe Gly Gly Ile
    450                 455                 460

Asp Asn Thr Val Glu Lys Glu Ser Gln Asp Arg Thr Ser Ile Glu Trp
465                 470                 475                 480

Pro Ser Gly Gln Leu Ala Leu Ile Arg Arg Leu Ala Glu Thr Gly Lys
                485                 490                 495

Pro Val Ile Val Val Arg Leu Gly Thr His Val Asp Asp Thr Pro Leu
                500                 505                 510

Leu Ser Ile Pro Asn Val Arg Ala Ile Leu Trp Ala Gly Tyr Pro Gly
            515                 520                 525

Gln Asp Gly Gly Thr Ala Val Val Lys Ile Ile Thr Gly Leu Ala Ser
    530                 535                 540

Pro Ala Gly Arg Leu Pro Ala Thr Val Tyr Pro Ser Ser Tyr Thr Ser
545                 550                 555                 560

Gln Ala Pro Phe Thr Asn Met Ala Leu Arg Pro Ser Ser Tyr Pro
                565                 570                 575

Gly Arg Thr Tyr Arg Trp Tyr Ser Asn Ala Val Phe Pro Phe Gly His
                580                 585                 590

Gly Leu His Tyr Thr Asn Phe Ser Val Ser Val Arg Asp Phe Pro Ala
            595                 600                 605

Ser Phe Ala Ile Ala Asp Leu Leu Ala Ser Cys Gly Asp Ser Val Ala
        610                 615                 620

Tyr Leu Asp Leu Cys Pro Phe Pro Ser Val Ser Leu Asn Val Thr Asn
625                 630                 635                 640

Thr Gly Thr Arg Val Ser Asp Tyr Val Ala Leu Gly Phe Leu Ser Gly
                645                 650                 655

Asp Phe Gly Pro Ser Pro His Pro Ile Lys Thr Leu Ala Thr Tyr Lys
                660                 665                 670

Arg Val Phe Asn Ile Glu Pro Gly Glu Thr Gln Val Ala Glu Leu Asp
            675                 680                 685

Trp Lys Leu Glu Ser Leu Val Arg Val Asp Glu Lys Gly Asn Arg Val
        690                 695                 700

Leu Tyr Pro Gly Thr Tyr Thr Leu Leu Val Asp Gln Pro Thr Leu Ala
705                 710                 715                 720

Asn Ile Thr Phe Ile Leu Thr Gly Glu Glu Ala Val Leu Asp Ser Trp
                725                 730                 735

Pro Gln Pro

<210> SEQ ID NO 32
<211> LENGTH: 1155
<212> TYPE: DNA
<213> ORGANISM: Artificial sequence
<220> FEATURE:
<223> OTHER INFORMATION: Synthetic polynucleotide

<400> SEQUENCE: 32
atgcgtactc ttacgttcgt gctggcagcc gccccggtgg ctgtgcttgc ccaatctcct      60
ctgtggggcc agtgcggcgg tcaaggctgg acaggtccca cgacctgcgt ttctggcgca     120
gtatgccaat cgtcaatga ctggtactcc caatgcgtgc ccggatcgag caaccctcct     180
acgggcacca ccagcagcac cactggaagc accccggctc ctactggcgg cggcggcagc     240
ggaaccggcc tccacgacaa attcaaggcc aagggcaagc tctacttcgg aaccgagatc     300

-continued

```
gatcactacc atctcaacaa caatgccttg accaacattg tcaagaaaga ctttggtcaa    360
gtcactcacg agaacagctt gaagtgggat gctactgagc cgagccgcaa tcaattcaac    420
tttgccaacg ccgacgcggt tgtcaacttt gcccaggcca acggcaagct catccgcggc    480
cacaccctcc tctggcactc tcagctgccg cagtgggtgc agaacatcaa cgaccgcaac    540
accttgaccc aggtcatcga gaaccacgtc accacccttg tcactcgcta aagggcaag     600 atcctccact gggacgtcgt taacgagatc tttgccgagg acggctcgct ccgcgacagc    660
gtcttcagcc gcgtcctcgg cgaggacttt gtcggcatcg ccttccgcgc cgcccgcgcc    720
gccgatccca cgccaagct ctacatcaac gactacaacc tcgacattgc caactacgcc     780
aaggtgaccc ggggcatggt cgagaaggtc aacaagtgga tcgcccaggg catcccgatc    840
gacggcatcg gcacccagtg ccacctggcc gggcccggcg ggtggaacac ggccgccggc    900
gtccccgacg ccctcaaggc cctcgccgcg ccaacgtca aggagatcgc catcaccgag     960
ctcgacatcg ccggcgcctc cgccaacgac tacctcaccg tcatgaacgc ctgcctccag   1020
gtctccaagt gcgtcggcat caccgtctgg ggcgtctctg acaaggacag ctggaggtcg   1080
agcagcaacc cgctcctctt cgacagcaac taccagccaa aggcggcata caatgctctg   1140
attaatgcct tgtaa                                                    1155
```

<210> SEQ ID NO 33
<211> LENGTH: 384
<212> TYPE: PRT
<213> ORGANISM: Myceliophthora thermophila

<400> SEQUENCE: 33

```
Met Arg Thr Leu Thr Phe Val Leu Ala Ala Ala Pro Val Ala Val Leu
1               5                   10                  15

Ala Gln Ser Pro Leu Trp Gly Gln Cys Gly Gly Gln Gly Trp Thr Gly
            20                  25                  30

Pro Thr Thr Cys Val Ser Gly Ala Val Cys Gln Phe Val Asn Asp Trp
        35                  40                  45

Tyr Ser Gln Cys Val Pro Gly Ser Ser Asn Pro Pro Thr Gly Thr Thr
    50                  55                  60

Ser Ser Thr Thr Gly Ser Thr Pro Ala Pro Thr Gly Gly Gly Gly Ser
65                  70                  75                  80

Gly Thr Gly Leu His Asp Lys Phe Lys Ala Lys Gly Lys Leu Tyr Phe
                85                  90                  95

Gly Thr Glu Ile Asp His Tyr His Leu Asn Asn Asn Ala Leu Thr Asn
            100                 105                 110

Ile Val Lys Lys Asp Phe Gly Gln Val Thr His Glu Asn Ser Leu Lys
        115                 120                 125

Trp Asp Ala Thr Glu Pro Ser Arg Asn Gln Phe Asn Phe Ala Asn Ala
    130                 135                 140

Asp Ala Val Val Asn Phe Ala Gln Ala Asn Gly Lys Leu Ile Arg Gly
145                 150                 155                 160

His Thr Leu Leu Trp His Ser Gln Leu Pro Gln Trp Val Gln Asn Ile
                165                 170                 175

Asn Asp Arg Asn Thr Leu Thr Gln Val Ile Glu Asn His Val Thr Thr
            180                 185                 190

Leu Val Thr Arg Tyr Lys Gly Lys Ile Leu His Trp Asp Val Val Asn
        195                 200                 205

Glu Ile Phe Ala Glu Asp Gly Ser Leu Arg Asp Ser Val Phe Ser Arg
```

```
                210             215             220
Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
            245                 250                 255

Ala Asn Tyr Ala Lys Val Thr Arg Gly Met Val Glu Lys Val Asn Lys
        260                 265                 270

Trp Ile Ala Gln Gly Ile Pro Ile Asp Gly Ile Gly Thr Gln Cys His
    275                 280                 285

Leu Ala Gly Pro Gly Gly Trp Asn Thr Ala Ala Gly Val Pro Asp Ala
    290                 295                 300

Leu Lys Ala Leu Ala Ala Asn Val Lys Glu Ile Ala Ile Thr Glu
305                 310                 315                 320

Leu Asp Ile Ala Gly Ala Ser Ala Asn Asp Tyr Leu Thr Val Met Asn
            325                 330                 335

Ala Cys Leu Gln Val Ser Lys Cys Val Gly Ile Thr Val Trp Gly Val
        340                 345                 350

Ser Asp Lys Asp Ser Trp Arg Ser Ser Asn Pro Leu Leu Phe Asp
    355                 360                 365

Ser Asn Tyr Gln Pro Lys Ala Ala Tyr Asn Ala Leu Ile Asn Ala Leu
    370                 375                 380

<210> SEQ ID NO 34
<211> LENGTH: 367
<212> TYPE: PRT
<213> ORGANISM: Myceliophthora thermophila

<400> SEQUENCE: 34

Gln Ser Pro Leu Trp Gly Gln Cys Gly Gly Gln Gly Trp Thr Gly Pro
1               5                   10                  15

Thr Thr Cys Val Ser Gly Ala Val Cys Gln Phe Val Asn Asp Trp Tyr
            20                  25                  30

Ser Gln Cys Val Pro Gly Ser Ser Asn Pro Pro Thr Gly Thr Thr Ser
        35                  40                  45

Ser Thr Thr Gly Ser Thr Pro Ala Pro Thr Gly Gly Gly Gly Ser Gly
    50                  55                  60

Thr Gly Leu His Asp Lys Phe Lys Ala Lys Gly Lys Leu Tyr Phe Gly
65                  70                  75                  80

Thr Glu Ile Asp His Tyr His Leu Asn Asn Asn Ala Leu Thr Asn Ile
                85                  90                  95

Val Lys Lys Asp Phe Gly Gln Val Thr His Glu Asn Ser Leu Lys Trp
            100                 105                 110

Asp Ala Thr Glu Pro Ser Arg Asn Gln Phe Asn Phe Ala Asn Ala Asp
        115                 120                 125

Ala Val Val Asn Phe Ala Gln Ala Asn Gly Lys Leu Ile Arg Gly His
    130                 135                 140

Thr Leu Leu Trp His Ser Gln Leu Pro Gln Trp Val Gln Asn Ile Asn
145                 150                 155                 160

Asp Arg Asn Thr Leu Thr Gln Val Ile Glu Asn His Val Thr Thr Leu
                165                 170                 175

Val Thr Arg Tyr Lys Gly Lys Ile Leu His Trp Asp Val Val Asn Glu
            180                 185                 190

Ile Phe Ala Glu Asp Gly Ser Leu Arg Asp Ser Val Phe Ser Arg Val
        195                 200                 205
```

```
Leu Gly Glu Asp Phe Val Gly Ile Ala Phe Arg Ala Arg Ala Ala
    210             215                 220

Asp Pro Asn Ala Lys Leu Tyr Ile Asn Asp Tyr Asn Leu Asp Ile Ala
225             230                 235                 240

Asn Tyr Ala Lys Val Thr Arg Gly Met Val Glu Lys Val Asn Lys Trp
                245                 250                 255

Ile Ala Gln Gly Ile Pro Ile Asp Gly Ile Gly Thr Gln Cys His Leu
            260                 265                 270

Ala Gly Pro Gly Gly Trp Asn Thr Ala Ala Gly Val Pro Asp Ala Leu
        275                 280                 285

Lys Ala Leu Ala Ala Asn Val Lys Glu Ile Ala Ile Thr Glu Leu
    290                 295                 300

Asp Ile Ala Gly Ala Ser Ala Asn Asp Tyr Leu Thr Val Met Asn Ala
305             310                 315                 320

Cys Leu Gln Val Ser Lys Cys Val Gly Ile Thr Val Trp Gly Val Ser
                325                 330                 335

Asp Lys Asp Ser Trp Arg Ser Ser Asn Pro Leu Leu Phe Asp Ser
            340                 345                 350

Asn Tyr Gln Pro Lys Ala Ala Tyr Asn Ala Leu Ile Asn Ala Leu
        355                 360                 365
```

```
<210> SEQ ID NO 35
<211> LENGTH: 1128
<212> TYPE: DNA
<213> ORGANISM: Myceliophthora thermophila

<400> SEQUENCE: 35
atgcatctct cctcgtctct cctcctcctc gccgccttgc cctgggcat cgccggcaag      60
ggcaagggcc acggccacgg ccccatacc gggctccaca ccctcgccaa gcaggccggc     120
ctcaagtact cggctctgc accgactct cccggccagc gtgagcgcgc cggctacgag     180
gacaagtacg cccagtacga ccagatcatg tggaagtcgg gcgagttcgg cctgacgacc    240
ccgaccaacg gccaaaagtg ctgtttact gagcccgagc gtggcgtgtt caacttcacc    300
gagggtgaca tcgtgacgaa cctggcccgg aagcacggtt tcatgcagcg gtgccacgcg    360
ctcgtctggc acagccagct cgcccccttgg gtcgagtcga ccgagtggac gcccgaggag    420
ctgcgccagt cattgtcaa ccacatcacc acgtggccg gctactacaa gggcaagtgc     480
tatgcctggg acgtcgtcaa cgaggccctg aacgaggacg caacctaccg cgagtccgtc    540
ttctacaagg tgctcggcga ggactacatc aagctggcct cgagacggc cgccaaggtc    600
gacccccacg ccaagctcta ctacaacgac tacaacctcg agtcccccag cgccaagacc    660
gagggcgcca gcgcatcgt caagatgctc aaggacgccg gcatccgcat cgacggcgtc    720
ggcctgcagg cccacctcgt cgccgagagc caccccgaccc tcgacgagca catcgatgcc    780
atcaagggct tcaccgagct cggcgtcgag gtcgccctga ccgagctcga catccgcctc    840
tccatcccgg ccaacgccac caacctcgcc agcagaggg aggcgtacaa gaacgtcgtc    900
ggcgcttgcg tccaggttcg cggctgcatt ggcgtggaga tctggacttt ctatgacccc    960
ttcagctggg tccctgccac cttccccggc cagggcgccc cctgctctg gttcgaggac   1020
ttttccaagc acccgcccta cgacggcgtc gtcgaggccc tgaccaacag gaccacgggc   1080
gggtgcaagg gcaagggcaa gggcaaggc aaggtttgga aggcctaa                 1128

<210> SEQ ID NO 36
<211> LENGTH: 375
```

<212> TYPE: PRT
<213> ORGANISM: Myceliophthora thermophila

<400> SEQUENCE: 36

```
Met His Leu Ser Ser Leu Leu Leu Ala Ala Leu Pro Leu Gly
1               5                   10                  15

Ile Ala Gly Lys Gly Lys Gly His Gly His Gly Pro His Thr Gly Leu
            20                  25                  30

His Thr Leu Ala Lys Gln Ala Gly Leu Lys Tyr Phe Gly Ser Ala Thr
        35                  40                  45

Asp Ser Pro Gly Gln Arg Glu Arg Ala Gly Tyr Glu Asp Lys Tyr Ala
    50                  55                  60

Gln Tyr Asp Gln Ile Met Trp Lys Ser Gly Glu Phe Gly Leu Thr Thr
65                  70                  75                  80

Pro Thr Asn Gly Gln Lys Trp Leu Phe Thr Glu Pro Glu Arg Gly Val
                85                  90                  95

Phe Asn Phe Thr Glu Gly Asp Ile Val Thr Asn Leu Ala Arg Lys His
            100                 105                 110

Gly Phe Met Gln Arg Cys His Ala Leu Val Trp His Ser Gln Leu Ala
        115                 120                 125

Pro Trp Val Glu Ser Thr Glu Trp Thr Pro Glu Glu Leu Arg Gln Val
    130                 135                 140

Ile Val Asn His Ile Thr His Val Ala Gly Tyr Tyr Lys Gly Lys Cys
145                 150                 155                 160

Tyr Ala Trp Asp Val Val Asn Glu Ala Leu Asn Glu Asp Gly Thr Tyr
                165                 170                 175

Arg Glu Ser Val Phe Tyr Lys Val Leu Gly Glu Asp Tyr Ile Lys Leu
            180                 185                 190

Ala Phe Glu Thr Ala Ala Lys Val Asp Pro His Ala Lys Leu Tyr Tyr
        195                 200                 205

Asn Asp Tyr Asn Leu Glu Ser Pro Ser Ala Lys Thr Glu Gly Ala Lys
    210                 215                 220

Arg Ile Val Lys Met Leu Lys Asp Ala Gly Ile Arg Ile Asp Gly Val
225                 230                 235                 240

Gly Leu Gln Ala His Leu Val Ala Glu Ser His Pro Thr Leu Asp Glu
                245                 250                 255

His Ile Asp Ala Ile Lys Gly Phe Thr Glu Leu Gly Val Glu Val Ala
            260                 265                 270

Leu Thr Glu Leu Asp Ile Arg Leu Ser Ile Pro Ala Asn Ala Thr Asn
        275                 280                 285

Leu Ala Gln Gln Arg Glu Ala Tyr Lys Asn Val Val Gly Ala Cys Val
    290                 295                 300

Gln Val Arg Gly Cys Ile Gly Val Glu Ile Trp Asp Phe Tyr Asp Pro
305                 310                 315                 320

Phe Ser Trp Val Pro Ala Thr Phe Pro Gly Gln Gly Ala Pro Leu Leu
                325                 330                 335

Trp Phe Glu Asp Phe Ser Lys His Pro Ala Tyr Asp Gly Val Val Glu
            340                 345                 350

Ala Leu Thr Asn Arg Thr Thr Gly Gly Cys Lys Gly Lys Gly Lys Gly
        355                 360                 365

Lys Gly Lys Val Trp Lys Ala
    370                 375
```

<210> SEQ ID NO 37

```
<211> LENGTH: 356
<212> TYPE: PRT
<213> ORGANISM: Myceliophthora thermophila

<400> SEQUENCE: 37

Lys Gly Lys Gly His Gly His Gly Pro His Thr Gly Leu His Thr Leu
1               5                   10                  15

Ala Lys Gln Ala Gly Leu Lys Tyr Phe Gly Ser Ala Thr Asp Ser Pro
            20                  25                  30

Gly Gln Arg Glu Arg Ala Gly Tyr Glu Asp Lys Tyr Ala Gln Tyr Asp
        35                  40                  45

Gln Ile Met Trp Lys Ser Gly Glu Phe Gly Leu Thr Thr Pro Thr Asn
    50                  55                  60

Gly Gln Lys Trp Leu Phe Thr Glu Pro Glu Arg Gly Val Phe Asn Phe
65                  70                  75                  80

Thr Glu Gly Asp Ile Val Thr Asn Leu Ala Arg Lys His Gly Phe Met
                85                  90                  95

Gln Arg Cys His Ala Leu Val Trp His Ser Gln Leu Ala Pro Trp Val
            100                 105                 110

Glu Ser Thr Glu Trp Thr Pro Glu Glu Leu Arg Gln Val Ile Val Asn
        115                 120                 125

His Ile Thr His Val Ala Gly Tyr Tyr Lys Gly Lys Cys Tyr Ala Trp
    130                 135                 140

Asp Val Val Asn Glu Ala Leu Asn Glu Asp Gly Thr Tyr Arg Glu Ser
145                 150                 155                 160

Val Phe Tyr Lys Val Leu Gly Glu Asp Tyr Ile Lys Leu Ala Phe Glu
                165                 170                 175

Thr Ala Ala Lys Val Asp Pro His Ala Lys Leu Tyr Tyr Asn Asp Tyr
            180                 185                 190

Asn Leu Glu Ser Pro Ser Ala Lys Thr Glu Gly Ala Lys Arg Ile Val
        195                 200                 205

Lys Met Leu Lys Asp Ala Gly Ile Arg Ile Asp Gly Val Gly Leu Gln
    210                 215                 220

Ala His Leu Val Ala Glu Ser His Pro Thr Leu Asp Glu His Ile Asp
225                 230                 235                 240

Ala Ile Lys Gly Phe Thr Glu Leu Gly Val Glu Val Ala Leu Thr Glu
                245                 250                 255

Leu Asp Ile Arg Leu Ser Ile Pro Ala Asn Ala Thr Asn Leu Ala Gln
            260                 265                 270

Gln Arg Glu Ala Tyr Lys Asn Val Val Gly Ala Cys Val Gln Val Arg
        275                 280                 285

Gly Cys Ile Gly Val Glu Ile Trp Asp Phe Tyr Asp Pro Phe Ser Trp
    290                 295                 300

Val Pro Ala Thr Phe Pro Gly Gln Gly Ala Pro Leu Leu Trp Phe Glu
305                 310                 315                 320

Asp Phe Ser Lys His Pro Ala Tyr Asp Gly Val Glu Ala Leu Thr
                325                 330                 335

Asn Arg Thr Thr Gly Gly Cys Lys Gly Lys Gly Lys Gly Lys Gly Lys
            340                 345                 350

Val Trp Lys Ala
        355

<210> SEQ ID NO 38
<211> LENGTH: 1242
<212> TYPE: DNA
```

<213> ORGANISM: Artificial Sequence
<220> FEATURE:
<223> OTHER INFORMATION: Synthetic polynucleotide

<400> SEQUENCE: 38

```
atgcactcca aagctttctt ggcagcgctt cttgcgcctg ccgtctcagg gcaactgaac      60
gacctcgccg tcagggctgg actcaagtac tttggtactg ctcttagcga gagcgtcatc     120
aacagtgata tcggtatgc tgccatcctc agcgacaaga gcatgttcgg ccagctcgtc     180
cccgagaatg gcatgaagtg ggatgctact gagccgtccc gtggccagtt caactacgcc     240
tcgggcgaca tcacggccaa cacggccaag aagaatggcc agggcatgcg ttgccacacc     300
atggtctggt acagccagct cccgagctgg gtctcctcgg gctcgtggac cagggactcg     360
ctcacctcgg tcatcgagac gcacatgaac aacgtcatgg ccactacaa gggccaatgc     420
tacgcctggg atgtcatcaa cgaggccatc aatgacgacg gcaactcctg gcgcgacaac     480
gtctttctcc ggacctttgg gaccgactac ttcgccctgt ccttcaacct agccaagaag     540
gccgatcccg ataccaagct gtactacaac gactacaacc tcgagtacaa ccaggccaag     600
acggaccgcg ctgttgagct cgtcaagatg gtccaggccg ccggcgcgcc catcgacggt     660
gtcggcttcc agggccacct cattgtcggc tcgaccccga cgcgctcgca gctggccacc     720
gccctccagc gcttcaccgc gctcggcctc gaggtcgcct acaccgagct cgacatccgc     780
cactcgagcc tgccggcctc ttcgtcggcg ctcgcgaccc agggcaacga cttcgccaac     840
gtggtcggct cttgcctcga caccgccggc tgcgtcggcg tcaccgtctg gggcttcacc     900
gatgcgcact cgtggatccc gaacacgttc cccggccagg cgacgccct gatctacgac     960
agcaactaca caagaagcc cgcgtggacc tcgatctcgt ccgtcctggc cgccaaggcc    1020
accggcgccc cgcccgcctc gtcctccacc accctcgtca ccatcaccac ccctccgccg    1080
gcatccacca ccgcctcctc ctcctccagt gccacgccca cgagcgtccc gacgcagacg    1140
aggtggggac agtgcggcgg catcggatgg acggggccga cccagtgcga gagcccatgg    1200
acctgccaga agctgaacga ctggtactgg cagtgcctgt aa                       1242
```

<210> SEQ ID NO 39
<211> LENGTH: 413
<212> TYPE: PRT
<213> ORGANISM: Myceliophthora thermophila

<400> SEQUENCE: 39

```
Met His Ser Lys Ala Phe Leu Ala Ala Leu Leu Ala Pro Ala Val Ser
1               5                   10                  15

Gly Gln Leu Asn Asp Leu Ala Val Arg Ala Gly Leu Lys Tyr Phe Gly
            20                  25                  30

Thr Ala Leu Ser Glu Ser Val Ile Asn Ser Asp Thr Arg Tyr Ala Ala
        35                  40                  45

Ile Leu Ser Asp Lys Ser Met Phe Gly Gln Leu Val Pro Glu Asn Gly
    50                  55                  60

Met Lys Trp Asp Ala Thr Glu Pro Ser Arg Gly Gln Phe Asn Tyr Ala
65                  70                  75                  80

Ser Gly Asp Ile Thr Ala Asn Thr Ala Lys Lys Asn Gly Gln Gly Met
                85                  90                  95

Arg Cys His Thr Met Val Trp Tyr Ser Gln Leu Pro Ser Trp Val Ser
            100                 105                 110

Ser Gly Ser Trp Thr Arg Asp Ser Leu Thr Ser Val Ile Glu Thr His
        115                 120                 125
```

```
Met Asn Asn Val Met Gly His Tyr Lys Gly Gln Cys Tyr Ala Trp Asp
        130                 135                 140

Val Ile Asn Glu Ala Ile Asn Asp Asp Gly Asn Ser Trp Arg Asp Asn
145                 150                 155                 160

Val Phe Leu Arg Thr Phe Gly Thr Asp Tyr Phe Ala Leu Ser Phe Asn
                165                 170                 175

Leu Ala Lys Lys Ala Asp Pro Asp Thr Lys Leu Tyr Tyr Asn Asp Tyr
                180                 185                 190

Asn Leu Glu Tyr Asn Gln Ala Lys Thr Asp Arg Ala Val Glu Leu Val
            195                 200                 205

Lys Met Val Gln Ala Ala Gly Ala Pro Ile Asp Gly Val Gly Phe Gln
210                 215                 220

Gly His Leu Ile Val Gly Ser Thr Pro Thr Arg Ser Gln Leu Ala Thr
225                 230                 235                 240

Ala Leu Gln Arg Phe Thr Ala Leu Gly Leu Glu Val Ala Tyr Thr Glu
                245                 250                 255

Leu Asp Ile Arg His Ser Ser Leu Pro Ala Ser Ser Ala Leu Ala
                260                 265                 270

Thr Gln Gly Asn Asp Phe Ala Asn Val Val Gly Ser Cys Leu Asp Thr
            275                 280                 285

Ala Gly Cys Val Gly Val Thr Val Trp Gly Phe Thr Asp Ala His Ser
290                 295                 300

Trp Ile Pro Asn Thr Phe Pro Gly Gln Gly Asp Ala Leu Ile Tyr Asp
305                 310                 315                 320

Ser Asn Tyr Asn Lys Lys Pro Ala Trp Thr Ser Ile Ser Ser Val Leu
                325                 330                 335

Ala Ala Lys Ala Thr Gly Ala Pro Pro Ala Ser Ser Ser Thr Thr Leu
            340                 345                 350

Val Thr Ile Thr Thr Pro Pro Ala Ser Thr Ala Ser Ser Ser
            355                 360                 365

Ser Ser Ala Thr Pro Thr Ser Val Pro Thr Gln Thr Arg Trp Gly Gln
370                 375                 380

Cys Gly Gly Ile Gly Trp Thr Gly Pro Thr Gln Cys Glu Ser Pro Trp
385                 390                 395                 400

Thr Cys Gln Lys Leu Asn Asp Trp Tyr Trp Gln Cys Leu
                405                 410

<210> SEQ ID NO 40
<211> LENGTH: 396
<212> TYPE: PRT
<213> ORGANISM: Myceliophthora thermophila

<400> SEQUENCE: 40

Gln Leu Asn Asp Leu Ala Val Arg Ala Gly Leu Lys Tyr Phe Gly Thr
1               5                   10                  15

Ala Leu Ser Glu Ser Val Ile Asn Ser Asp Thr Arg Tyr Ala Ala Ile
                20                  25                  30

Leu Ser Asp Lys Ser Met Phe Gly Gln Leu Val Pro Glu Asn Gly Met
            35                  40                  45

Lys Trp Asp Ala Thr Glu Pro Ser Arg Gly Gln Phe Asn Tyr Ala Ser
        50                  55                  60

Gly Asp Ile Thr Ala Asn Thr Ala Lys Lys Asn Gly Gln Gly Met Arg
65                  70                  75                  80

Cys His Thr Met Val Trp Tyr Ser Gln Leu Pro Ser Trp Val Ser Ser
```

```
                      85                  90                  95
Gly Ser Trp Thr Arg Asp Ser Leu Thr Ser Val Ile Glu Thr His Met
                100                 105                 110
Asn Asn Val Met Gly His Tyr Lys Gly Gln Cys Tyr Ala Trp Asp Val
                115                 120                 125
Ile Asn Glu Ala Ile Asn Asp Gly Asn Ser Trp Arg Asp Asn Val
                130                 135                 140
Phe Leu Arg Thr Phe Gly Thr Asp Tyr Phe Ala Leu Ser Phe Asn Leu
145                 150                 155                 160
Ala Lys Lys Ala Asp Pro Asp Thr Lys Leu Tyr Tyr Asn Asp Tyr Asn
                165                 170                 175
Leu Glu Tyr Asn Gln Ala Lys Thr Asp Arg Ala Val Glu Leu Val Lys
                180                 185                 190
Met Val Gln Ala Ala Gly Ala Pro Ile Asp Gly Val Gly Phe Gln Gly
                195                 200                 205
His Leu Ile Val Gly Ser Thr Pro Thr Arg Ser Gln Leu Ala Thr Ala
                210                 215                 220
Leu Gln Arg Phe Thr Ala Leu Gly Leu Glu Val Ala Tyr Thr Glu Leu
225                 230                 235                 240
Asp Ile Arg His Ser Ser Leu Pro Ala Ser Ser Ala Leu Ala Thr
                245                 250                 255
Gln Gly Asn Asp Phe Ala Asn Val Val Gly Ser Cys Leu Asp Thr Ala
                260                 265                 270
Gly Cys Val Gly Val Thr Val Trp Gly Phe Thr Asp Ala His Ser Trp
                275                 280                 285
Ile Pro Asn Thr Phe Pro Gly Gln Gly Asp Ala Leu Ile Tyr Asp Ser
                290                 295                 300
Asn Tyr Asn Lys Lys Pro Ala Trp Thr Ser Ile Ser Ser Val Leu Ala
305                 310                 315                 320
Ala Lys Ala Thr Gly Ala Pro Pro Ala Ser Ser Thr Thr Leu Val
                325                 330                 335
Thr Ile Thr Thr Pro Pro Pro Ala Ser Thr Ala Ser Ser Ser Ser
                340                 345                 350
Ser Ala Thr Pro Thr Ser Val Pro Thr Gln Thr Arg Trp Gly Gln Cys
                355                 360                 365
Gly Gly Ile Gly Trp Thr Gly Pro Thr Gln Cys Glu Ser Pro Trp Thr
                370                 375                 380
Cys Gln Lys Leu Asn Asp Trp Tyr Trp Gln Cys Leu
385                 390                 395

<210> SEQ ID NO 41
<211> LENGTH: 693
<212> TYPE: DNA
<213> ORGANISM: Myceliophthora thermophila

<400> SEQUENCE: 41
atggtctcct tcaaggcccct cgttctcggc gccgttggcg ccctctcctt cccttttcaac    60 gtcaccgagc tgtccgaggc gcacgcccgg ggcgagaatg tgaccgagct cttgatgtct   120
cgcgccggca cgccgagcca gaccggctgg cacgggggct actacttctc cttctggacc   180
gacaacggcg gcaccgtcaa ctactggaac ggcgacaatg gcagatacgg tgtccagtgg   240
cagaactgcg gcaactttgt cggcggtaag ggatggaacc ccggcgcggc gcggaccatc   300
aacttcagcg gctccttcaa cccgtcgggc aacgggtacc tggccgtgta cgggtggacg   360
```

```
cagaacccgc tgatcgagta ctacatcgtc gagtcgttcg gcacgtacga cccgtcgtcg    420
caggcccagg tcctcggcac cttctaccag gacggcagca actacaagat cgccaagacg    480
acccgctaca accagccctc catcgagggc accagcacct cgaccagtt ctggtccgtc     540 cgcgagaacc accgcaccag cggcagcgtc aacgtcggcg cccacttcgc cgctggcag    600 caggccggcc tccgcctcgg cacccacaac taccaaatca tggccaccga gggctaccag    660
agcagcggct cctccgatat caccgtctgg taa                                693
```

<210> SEQ ID NO 42
<211> LENGTH: 230
<212> TYPE: PRT
<213> ORGANISM: Myceliophthora thermophila

<400> SEQUENCE: 42

Met Val Ser Phe Lys Ala Leu Val Leu Gly Ala Val Ala Leu Ser
1               5                   10                  15

Phe Pro Phe Asn Val Thr Glu Leu Ser Glu Ala His Ala Arg Gly Glu
                20                  25                  30

Asn Val Thr Glu Leu Leu Met Ser Arg Ala Gly Thr Pro Ser Gln Thr
            35                  40                  45

Gly Trp His Gly Gly Tyr Tyr Phe Ser Phe Trp Thr Asp Asn Gly Gly
        50                  55                  60

Thr Val Asn Tyr Trp Asn Gly Asp Asn Gly Arg Tyr Gly Val Gln Trp
65                  70                  75                  80

Gln Asn Cys Gly Asn Phe Val Gly Gly Lys Gly Trp Asn Pro Gly Ala
                85                  90                  95

Ala Arg Thr Ile Asn Phe Ser Gly Ser Phe Asn Pro Ser Gly Asn Gly
                100                 105                 110

Tyr Leu Ala Val Tyr Gly Trp Thr Gln Asn Pro Leu Ile Glu Tyr Tyr
            115                 120                 125

Ile Val Glu Ser Phe Gly Thr Tyr Asp Pro Ser Ser Gln Ala Gln Val
        130                 135                 140

Leu Gly Thr Phe Tyr Gln Asp Gly Ser Asn Tyr Lys Ile Ala Lys Thr
145                 150                 155                 160

Thr Arg Tyr Asn Gln Pro Ser Ile Glu Gly Thr Ser Thr Phe Asp Gln
                165                 170                 175

Phe Trp Ser Val Arg Glu Asn His Arg Thr Ser Gly Ser Val Asn Val
            180                 185                 190

Gly Ala His Phe Ala Arg Trp Gln Gln Ala Gly Leu Arg Leu Gly Thr
        195                 200                 205

His Asn Tyr Gln Ile Met Ala Thr Glu Gly Tyr Gln Ser Ser Gly Ser
    210                 215                 220

Ser Asp Ile Thr Val Trp
225                 230

<210> SEQ ID NO 43
<211> LENGTH: 214
<212> TYPE: PRT
<213> ORGANISM: Myceliophthora thermophila

<400> SEQUENCE: 43

Phe Pro Phe Asn Val Thr Glu Leu Ser Glu Ala His Ala Arg Gly Glu
1               5                   10                  15

Asn Val Thr Glu Leu Leu Met Ser Arg Ala Gly Thr Pro Ser Gln Thr
                20                  25                  30

```
Gly Trp His Gly Gly Tyr Tyr Phe Ser Phe Trp Thr Asp Asn Gly Gly
             35                  40                  45

Thr Val Asn Tyr Trp Asn Gly Asp Asn Gly Arg Tyr Gly Val Gln Trp
     50                  55                  60

Gln Asn Cys Gly Asn Phe Val Gly Gly Lys Gly Trp Asn Pro Gly Ala
 65              70                  75                  80

Ala Arg Thr Ile Asn Phe Ser Gly Ser Phe Asn Pro Ser Gly Asn Gly
                 85                  90                  95

Tyr Leu Ala Val Tyr Gly Trp Thr Gln Asn Pro Leu Ile Glu Tyr Tyr
            100                 105                 110

Ile Val Glu Ser Phe Gly Thr Tyr Asp Pro Ser Ser Gln Ala Gln Val
        115                 120                 125

Leu Gly Thr Phe Tyr Gln Asp Gly Ser Asn Tyr Lys Ile Ala Lys Thr
    130                 135                 140

Thr Arg Tyr Asn Gln Pro Ser Ile Glu Gly Thr Ser Thr Phe Asp Gln
145                 150                 155                 160

Phe Trp Ser Val Arg Glu Asn His Arg Thr Ser Gly Ser Val Asn Val
                165                 170                 175

Gly Ala His Phe Ala Arg Trp Gln Gln Ala Gly Leu Arg Leu Gly Thr
            180                 185                 190

His Asn Tyr Gln Ile Met Ala Thr Glu Gly Tyr Gln Ser Ser Gly Ser
        195                 200                 205

Ser Asp Ile Thr Val Trp
    210

<210> SEQ ID NO 44
<211> LENGTH: 738
<212> TYPE: DNA
<213> ORGANISM: Artificial sequence
<220> FEATURE:
<223> OTHER INFORMATION: Synthetic polynucleotide

<400> SEQUENCE: 44
atggtttctg tcaaggcagt cctcctcctc ggcgccgccg gcaccaccct ggccttcccg      60
ttcaacgcta cccagttcag cgagctcgtt gcccgggccg gcaccccgag cggcaccggc     120
acgcacgacg gcttctacta ctccttctgg accgacggcg gcggcaacgt caactacgag     180
aacggtcctg gcggctccta caccgtccag tggcagaact gcggcaactt gtcggcggc     240 aagggctgga accccggcca ggcccgcacc atcacctact cgggcaccgt cgacttccag     300
ggcggcaacg gctacctggc catctacggc tggacgcaga accgctgat cgagtactac      360 atcgtcgagt cgttcggctc gtacgacccc tcgtcgcagg cccagacttt cggcaccgtc     420
gaggtggacg gcggcaccta cacgctggcc aagacgacgc gcgtcaacca gccctcgatc     480
gagggcacca gcaccttcga ccagttctgg tccgtccgcc agcagcaccg cacctccggc     540
tccgtcgacg tcggcgccca cttcgacgcc tgggccaagg ccggcctcca gctcggcacc     600
cacaactaca gatcgtcgcc accgagggct accagagcag cggctcctct tccatcaccg     660
tccaggccta agagggccct caggcctttg ctctactgcc ctctcctctc ctctgcgctt     720
tccgtaaggg agatctaa                                                  738

<210> SEQ ID NO 45
<211> LENGTH: 245
<212> TYPE: PRT
<213> ORGANISM: Artificial sequence
<220> FEATURE:
<223> OTHER INFORMATION: Synthetic polypeptide
```

<400> SEQUENCE: 45

Met Val Ser Val Lys Ala Val Leu Leu Gly Ala Ala Gly Thr Thr
1               5                   10                  15

Leu Ala Phe Pro Phe Asn Ala Thr Gln Phe Ser Glu Leu Val Ala Arg
            20                  25                  30

Ala Gly Thr Pro Ser Gly Thr Gly Thr His Asp Gly Phe Tyr Tyr Ser
        35                  40                  45

Phe Trp Thr Asp Gly Gly Asn Val Asn Tyr Glu Asn Gly Pro Gly
    50                  55                  60

Gly Ser Tyr Thr Val Gln Trp Gln Asn Cys Gly Asn Phe Val Gly Gly
65              70                  75                  80

Lys Gly Trp Asn Pro Gly Gln Ala Arg Thr Ile Thr Tyr Ser Gly Thr
                85                  90                  95

Val Asp Phe Gln Gly Gly Asn Gly Tyr Leu Ala Ile Tyr Gly Trp Thr
            100                 105                 110

Gln Asn Pro Leu Ile Glu Tyr Tyr Ile Val Glu Ser Phe Gly Ser Tyr
            115                 120                 125

Asp Pro Ser Ser Gln Ala Gln Thr Phe Gly Thr Val Glu Val Asp Gly
            130                 135                 140

Gly Thr Tyr Thr Leu Ala Lys Thr Thr Arg Val Asn Gln Pro Ser Ile
145                 150                 155                 160

Glu Gly Thr Ser Thr Phe Asp Gln Phe Trp Ser Val Arg Gln Gln His
                165                 170                 175

Arg Thr Ser Gly Ser Val Asp Val Gly Ala His Phe Asp Ala Trp Ala
            180                 185                 190

Lys Ala Gly Leu Gln Leu Gly Thr His Asn Tyr Arg Ser Ser Pro Pro
            195                 200                 205

Arg Ala Thr Arg Ala Ala Ala Pro Leu Pro Ser Pro Ser Arg Pro Lys
            210                 215                 220

Arg Ala Leu Arg Pro Leu Leu Tyr Cys Pro Leu Leu Ser Ser Ala Leu
225                 230                 235                 240

Ser Val Arg Glu Ile
                245

<210> SEQ ID NO 46
<211> LENGTH: 227
<212> TYPE: PRT
<213> ORGANISM: Artificial sequence
<220> FEATURE:
<223> OTHER INFORMATION: Synthetic polypeptide

<400> SEQUENCE: 46

Phe Pro Phe Asn Ala Thr Gln Phe Ser Glu Leu Val Ala Arg Ala Gly
1               5                   10                  15

Thr Pro Ser Gly Thr Gly Thr His Asp Gly Phe Tyr Tyr Ser Phe Trp
            20                  25                  30

Thr Asp Gly Gly Gly Asn Val Asn Tyr Glu Asn Gly Pro Gly Gly Ser
        35                  40                  45

Tyr Thr Val Gln Trp Gln Asn Cys Gly Asn Phe Val Gly Gly Lys Gly
    50                  55                  60

Trp Asn Pro Gly Gln Ala Arg Thr Ile Thr Tyr Ser Gly Thr Val Asp
65                  70                  75                  80

Phe Gln Gly Gly Asn Gly Tyr Leu Ala Ile Tyr Gly Trp Thr Gln Asn
                85                  90                  95

```
Pro Leu Ile Glu Tyr Tyr Ile Val Glu Ser Phe Gly Ser Tyr Asp Pro
            100                 105                 110

Ser Ser Gln Ala Gln Thr Phe Gly Thr Val Glu Val Asp Gly Gly Thr
        115                 120                 125

Tyr Thr Leu Ala Lys Thr Thr Arg Val Asn Gln Pro Ser Ile Glu Gly
    130                 135                 140

Thr Ser Thr Phe Asp Gln Phe Trp Ser Val Arg Gln Gln His Arg Thr
145                 150                 155                 160

Ser Gly Ser Val Asp Val Gly Ala His Phe Asp Ala Trp Ala Lys Ala
                165                 170                 175

Gly Leu Gln Leu Gly Thr His Asn Tyr Arg Ser Pro Pro Arg Ala
            180                 185                 190

Thr Arg Ala Ala Ala Pro Leu Pro Ser Pro Ser Arg Pro Lys Arg Ala
        195                 200                 205

Leu Arg Pro Leu Leu Tyr Cys Pro Leu Leu Ser Ser Ala Leu Ser Val
    210                 215                 220

Arg Glu Ile
225
```

```
<210> SEQ ID NO 47
<211> LENGTH: 2046
<212> TYPE: DNA
<213> ORGANISM: Artificial sequence
<220> FEATURE:
<223> OTHER INFORMATION: Synthetic polynucleotide

<400> SEQUENCE: 47
atgataatga tgagactcaa gtcgggactg gccggggcgc tggcctgggg aacgacggcg    60
gcggcggcgg cggcggtggc gagagtggga gccggcgcgg ccgcgaactc gacctactac   120
aacccgatcc tccccggggtg gcactcggac ccgtcgtgcg tgcaggtgga ggggatcttc   180
tactgcgtga cgtcgacctt catctcgttc cccggcctgc ccatctacgc gtcccgggac   240
ctgatcaact ggaagcacgt cagccacgtg tggaaccgcg agtcccagct gcccgggtac   300
agctgggcga cggagggcca gcaggagggc atgtacgcgg cgacgatccg gcaccgcgag   360
ggcgtcttct atgtcatctg cgagtacctg gcgtcggcg caggacgc cggcgtgctc   420
ttccgggcga cggacccgtt cgacgacgcg gcctggagcg acgccctgac cttcgccgcg   480
cccaagatcg acccggacct gttctgggac gacgacggga cggcctacgt ggcgacgcag   540
ggcgtgcagg tgcagcgcat ggacctcgac acgggcgcca tcggcccgcc cgtgccgctg   600
tggaacggga cgggcggggt gtggcccgag ggccgcacga tctaccgccg cgccgaccac   660
ttctacctca tgatcgccga gggcggcacg gccgaggacc acgccatcac catcgcccgc   720
agcgaccggc tgacggggcc ctacgtctcc tgcccgcaca cccgatcct gaccaaccgc   780
ggcacggacg agtacttcca gacggtcggc cacggcgacc tcttccagga cgccgccggc   840
aactggtggg gcgtcgccct ggccacgcgc tccggcccgg agtaccgcgt ctacccgatg   900
gggcgcgaga ccgtgctgtt ccccgtcacc tggcgcgagg gcgactggcc ggtcctgcag   960
cccgtgcgcg cgccatgtc gggctggccg ctgccgccgc cgacgcgcga cctgcccggc  1020
gacgggccct tcaacgcgga cccggacgtg aaggcgatgc cgcggaacct ggtgcactgg  1080
cgggtcccgc gcgagggcgc cttcgcgacc acggcgcgcg ggctccgcgt cgcgctgggg  1140
cgcaaccggc tcgacggctg gccgggggc gccgagccgg ccgccagggc cgtctccttc  1200
gtggggcgcc gccagaccga cagcctcttc accttcagcg aggccggcgt gaccgcgttc  1260
```

```
ctgacccagc tcgccaacct gcagctcggc ctggtcctcc ctggacggcg ggccagctgc   1320
ggctccgctt catcgcgtcg ggccacgtca cgcgataccg cggtgccgga ggactgcacc   1380
gatgtcggca gctgtgacgg cggtgacgac ggcggtgacg gcgggtaccg gttcgcggcc   1440
atgctggcgt ccgacccgga cccggaccgg acccggatcg aggtcggcac cgcgccggcc   1500
gagctgctca gcggcggctc cggctccttc gtcggcaccc tgctcggcgt ctacgccacc   1560
tgcaacgggg ccggggaggg catcgactgc cccgccggca cgcccgacgc ttacttcacc   1620
cggtggaggt acacgggcga gggccagttc tacaccgaga ccgatctcgt cccgcccgac   1680
gagggccagg gcaagggtaa aggtaaaggg aacggtaaag gcaagggcaa cggcaacggc   1740
aacggcaaag ccgccaagag aagcaggttt ccaaggtgga cgccgggtct aaatggcgtc   1800
gttatcccgc ccctgtggat catggaggac gacccggaga cccgctggcc ggcccagaag   1860
cgggctgggg cgggcgggca gagctacgtc ttccgccacg gcaacctgca cacagttcgg   1920
gatgagaatg atgccttcaa gggcgcctct ctctgcgtac cttaccatac ctaccttgcc   1980
aaggtgatcc aggcacttac tctcaacttt gcgcatcttt tcggggcgtg gagactgacg   2040
gtgtag                                                             2046
```

<210> SEQ ID NO 48
<211> LENGTH: 681
<212> TYPE: PRT
<213> ORGANISM: Artificial sequence
<220> FEATURE:
<223> OTHER INFORMATION: Synthetic polypeptide

<400> SEQUENCE: 48

```
Met Ile Met Met Arg Leu Lys Ser Gly Leu Ala Gly Ala Leu Ala Trp
1               5                   10                  15

Gly Thr Thr Ala Ala Ala Ala Ala Val Ala Arg Val Gly Ala Gly
            20                  25                  30

Ala Ala Ala Asn Ser Thr Tyr Tyr Asn Pro Ile Leu Pro Gly Trp His
        35                  40                  45

Ser Asp Pro Ser Cys Val Gln Val Glu Gly Ile Phe Tyr Cys Val Thr
    50                  55                  60

Ser Thr Phe Ile Ser Phe Pro Gly Leu Pro Ile Tyr Ala Ser Arg Asp
65                  70                  75                  80

Leu Ile Asn Trp Lys His Val Ser His Val Trp Asn Arg Glu Ser Gln
                85                  90                  95

Leu Pro Gly Tyr Ser Trp Ala Thr Glu Gly Gln Gln Glu Gly Met Tyr
            100                 105                 110

Ala Ala Thr Ile Arg His Arg Glu Gly Val Phe Tyr Val Ile Cys Glu
        115                 120                 125

Tyr Leu Gly Val Gly Gly Arg Asp Ala Gly Val Leu Phe Arg Ala Thr
    130                 135                 140

Asp Pro Phe Asp Ala Ala Trp Ser Asp Ala Leu Thr Phe Ala Ala
145                 150                 155                 160

Pro Lys Ile Asp Pro Asp Leu Phe Trp Asp Asp Asp Gly Thr Ala Tyr
                165                 170                 175

Val Ala Thr Gln Gly Val Gln Val Gln Arg Met Asp Leu Asp Thr Gly
            180                 185                 190

Ala Ile Gly Pro Pro Val Pro Leu Trp Asn Gly Thr Gly Gly Val Trp
        195                 200                 205

Pro Glu Gly Pro His Ile Tyr Arg Arg Ala Asp His Phe Tyr Leu Met
    210                 215                 220
```

```
Ile Ala Glu Gly Gly Thr Ala Glu Asp His Ala Ile Thr Ile Ala Arg
225                 230                 235                 240

Ser Asp Arg Leu Thr Gly Pro Tyr Val Ser Cys Pro His Asn Pro Ile
            245                 250                 255

Leu Thr Asn Arg Gly Thr Asp Glu Tyr Phe Gln Thr Val Gly His Gly
        260                 265                 270

Asp Leu Phe Gln Asp Ala Ala Gly Asn Trp Trp Gly Val Ala Leu Ala
    275                 280                 285

Thr Arg Ser Gly Pro Glu Tyr Arg Val Tyr Pro Met Gly Arg Glu Thr
290                 295                 300

Val Leu Phe Pro Val Thr Trp Arg Glu Gly Asp Trp Pro Val Leu Gln
305                 310                 315                 320

Pro Val Arg Gly Ala Met Ser Gly Trp Pro Leu Pro Pro Thr Arg
                325                 330                 335

Asp Leu Pro Gly Asp Gly Pro Phe Asn Ala Asp Pro Asp Val Lys Ala
            340                 345                 350

Met Pro Arg Asn Leu Val His Trp Arg Val Pro Arg Glu Gly Ala Phe
        355                 360                 365

Ala Thr Thr Ala Arg Gly Leu Arg Val Ala Leu Gly Arg Asn Arg Leu
370                 375                 380

Asp Gly Trp Pro Gly Gly Ala Glu Pro Ala Ala Arg Ala Val Ser Phe
385                 390                 395                 400

Val Gly Arg Arg Gln Thr Asp Ser Leu Phe Thr Phe Ser Glu Ala Gly
            405                 410                 415

Val Thr Ala Phe Leu Thr Gln Leu Ala Asn Leu Gln Leu Gly Leu Val
            420                 425                 430

Leu Pro Gly Arg Arg Ala Ser Cys Gly Ser Ala Ser Ser Arg Arg Ala
        435                 440                 445

Thr Ser Arg Asp Thr Ala Val Pro Glu Asp Cys Thr Asp Val Gly Ser
    450                 455                 460

Cys Asp Gly Gly Asp Asp Gly Gly Asp Gly Gly Tyr Arg Phe Ala Ala
465                 470                 475                 480

Met Leu Ala Ser Asp Pro Asp Pro Asp Arg Thr Arg Ile Glu Val Gly
                485                 490                 495

Thr Ala Pro Ala Glu Leu Leu Ser Gly Gly Ser Gly Ser Phe Val Gly
            500                 505                 510

Thr Leu Leu Gly Val Tyr Ala Thr Cys Asn Gly Ala Gly Glu Gly Ile
        515                 520                 525

Asp Cys Pro Ala Gly Thr Pro Asp Ala Tyr Phe Thr Arg Trp Arg Tyr
    530                 535                 540

Thr Gly Glu Gly Gln Phe Tyr Thr Glu Thr Asp Leu Val Pro Pro Asp
545                 550                 555                 560

Glu Gly Gln Gly Lys Gly Lys Gly Lys Gly Asn Gly Lys Gly Lys Gly
                565                 570                 575

Asn Gly Asn Gly Asn Gly Lys Ala Ala Lys Arg Ser Arg Phe Pro Arg
            580                 585                 590

Trp Thr Pro Gly Leu Asn Gly Val Val Ile Pro Pro Leu Trp Ile Met
        595                 600                 605

Glu Asp Asp Pro Glu Thr Arg Trp Pro Ala Gln Lys Arg Ala Gly Ala
    610                 615                 620

Gly Gly Gln Ser Tyr Val Phe Arg His Gly Asn Leu His Thr Val Arg
625                 630                 635                 640
```

Asp Glu Asn Asp Ala Phe Lys Gly Ala Ser Leu Cys Val Pro Tyr His
            645                 650                 655

Thr Tyr Leu Ala Lys Val Ile Gln Ala Leu Thr Leu Asn Phe Ala His
            660                 665                 670

Leu Phe Gly Ala Trp Arg Leu Thr Val
        675                 680

<210> SEQ ID NO 49
<211> LENGTH: 666
<212> TYPE: PRT
<213> ORGANISM: Artificial sequence
<220> FEATURE:
<223> OTHER INFORMATION: Synthetic polypeptide

<400> SEQUENCE: 49

Trp Gly Thr Thr Ala Ala Ala Ala Val Ala Arg Val Gly Ala
1               5                   10                  15

Gly Ala Ala Ala Asn Ser Thr Tyr Tyr Asn Pro Ile Leu Pro Gly Trp
            20                  25                  30

His Ser Asp Pro Ser Cys Val Gln Val Glu Gly Ile Phe Tyr Cys Val
        35                  40                  45

Thr Ser Thr Phe Ile Ser Phe Pro Gly Leu Pro Ile Tyr Ala Ser Arg
    50                  55                  60

Asp Leu Ile Asn Trp Lys His Val Ser His Val Trp Asn Arg Glu Ser
65                  70                  75                  80

Gln Leu Pro Gly Tyr Ser Trp Ala Thr Glu Gly Gln Gln Glu Gly Met
                85                  90                  95

Tyr Ala Ala Thr Ile Arg His Arg Glu Gly Val Phe Tyr Val Ile Cys
            100                 105                 110

Glu Tyr Leu Gly Val Gly Gly Arg Asp Ala Gly Val Leu Phe Arg Ala
        115                 120                 125

Thr Asp Pro Phe Asp Asp Ala Ala Trp Ser Asp Ala Leu Thr Phe Ala
    130                 135                 140

Ala Pro Lys Ile Asp Pro Asp Leu Phe Trp Asp Asp Gly Thr Ala
145                 150                 155                 160

Tyr Val Ala Thr Gln Gly Val Gln Val Gln Arg Met Asp Leu Asp Thr
                165                 170                 175

Gly Ala Ile Gly Pro Pro Val Pro Leu Trp Asn Gly Thr Gly Gly Val
            180                 185                 190

Trp Pro Glu Gly Pro His Ile Tyr Arg Arg Ala Asp His Phe Tyr Leu
        195                 200                 205

Met Ile Ala Glu Gly Gly Thr Ala Glu Asp His Ala Ile Thr Ile Ala
    210                 215                 220

Arg Ser Asp Arg Leu Thr Gly Pro Tyr Val Ser Cys Pro His Asn Pro
225                 230                 235                 240

Ile Leu Thr Asn Arg Gly Thr Asp Glu Tyr Phe Gln Thr Val Gly His
                245                 250                 255

Gly Asp Leu Phe Gln Asp Ala Ala Gly Asn Trp Trp Gly Val Ala Leu
            260                 265                 270

Ala Thr Arg Ser Gly Pro Glu Tyr Arg Val Tyr Pro Met Gly Arg Glu
        275                 280                 285

Thr Val Leu Phe Pro Val Thr Trp Arg Glu Gly Asp Trp Pro Val Leu
    290                 295                 300

Gln Pro Val Arg Gly Ala Met Ser Gly Trp Pro Leu Pro Pro Pro Thr
305                 310                 315                 320

```
Arg Asp Leu Pro Gly Asp Gly Pro Phe Asn Ala Asp Pro Asp Val Lys
                325                 330                 335

Ala Met Pro Arg Asn Leu Val His Trp Arg Val Pro Arg Glu Gly Ala
            340                 345                 350

Phe Ala Thr Thr Ala Arg Gly Leu Arg Val Ala Leu Gly Arg Asn Arg
        355                 360                 365

Leu Asp Gly Trp Pro Gly Gly Ala Glu Pro Ala Ala Arg Ala Val Ser
    370                 375                 380

Phe Val Gly Arg Arg Gln Thr Asp Ser Leu Phe Thr Phe Ser Glu Ala
385                 390                 395                 400

Gly Val Thr Ala Phe Leu Thr Gln Leu Ala Asn Leu Gln Leu Gly Leu
                405                 410                 415

Val Leu Pro Gly Arg Arg Ala Ser Cys Gly Ser Ala Ser Ser Arg Arg
            420                 425                 430

Ala Thr Ser Arg Asp Thr Ala Val Pro Glu Asp Cys Thr Asp Val Gly
        435                 440                 445

Ser Cys Asp Gly Gly Asp Gly Gly Asp Gly Tyr Arg Phe Ala
    450                 455                 460

Ala Met Leu Ala Ser Asp Pro Asp Pro Asp Arg Thr Arg Ile Glu Val
465                 470                 475                 480

Gly Thr Ala Pro Ala Glu Leu Leu Ser Gly Ser Gly Ser Phe Val
                485                 490                 495

Gly Thr Leu Leu Gly Val Tyr Ala Thr Cys Asn Gly Ala Gly Glu Gly
            500                 505                 510

Ile Asp Cys Pro Ala Gly Thr Pro Asp Ala Tyr Phe Thr Arg Trp Arg
        515                 520                 525

Tyr Thr Gly Glu Gly Gln Phe Tyr Thr Glu Thr Asp Leu Val Pro Pro
    530                 535                 540

Asp Glu Gly Gln Gly Lys Gly Lys Gly Lys Gly Asn Gly Lys Gly Lys
545                 550                 555                 560

Gly Asn Gly Asn Gly Asn Gly Lys Ala Ala Lys Arg Ser Arg Phe Pro
                565                 570                 575

Arg Trp Thr Pro Gly Leu Asn Gly Val Val Ile Pro Pro Leu Trp Ile
            580                 585                 590

Met Glu Asp Asp Pro Glu Thr Arg Trp Pro Ala Gln Lys Arg Ala Gly
        595                 600                 605

Ala Gly Gly Gln Ser Tyr Val Phe Arg His Gly Asn Leu His Thr Val
    610                 615                 620

Arg Asp Glu Asn Asp Ala Phe Lys Gly Ala Ser Leu Cys Val Pro Tyr
625                 630                 635                 640

His Thr Tyr Leu Ala Lys Val Ile Gln Ala Leu Thr Leu Asn Phe Ala
                645                 650                 655

His Leu Phe Gly Ala Trp Arg Leu Thr Val
            660                 665

<210> SEQ ID NO 50
<211> LENGTH: 1608
<212> TYPE: DNA
<213> ORGANISM: Artificial sequence
<220> FEATURE:
<223> OTHER INFORMATION: Synthetic polynucleotide

<400> SEQUENCE: 50
atggggcgcc taaacgatct catagccctc cttgcactgt tgagcggcag tgccacatcc      60
gctgccgtaa gaaacacggc ttctcaggct cgcgcggcgg aattcaacaa cccggtgctc     120
```

```
tgggaggact atccggacct ggacgtgttc cgggtcgggt cgaccttcta ctactcctcc    180
tccacgttcg cctactcccc ggggctccg gtgctcaagt cgtacgacct ggtgaactgg     240 accccgtca cccactcggt cccgacgctc aactttgggg accgctacaa cctcacgggc     300
ggcacgccgg ccggctacgt caagggcatc tgggcgtcga cgctgcggta ccggcccctcc   360 aacgacaagt tctactggta cggctgcgtc gagttcggca agacgtacat ctggaccagc    420
tccggcacgc gcgcgggcga cagggacggc gaggtggacc ccgccgactg ggtctgggag    480
ccgcacccgc ccatcgaccg gtgctactac gacagcggcc tgttgatcga cgacgacgac    540
aagatgtaca tcgcgtacgg caaccccaag atcgaggtcg ccgagctgtc cgacgacggg    600
ctcaccgagg tctcctcccg ggtcgtctac accccgccgg ccggcaccac catcgagggc    660
tcgcgcatgt acaaggtcgg cgacgcctac tacatcctgg tgacgcggcc ggccgacgcc    720
gagtgggtgc tccggtcgac gtccgggccc tttcggcccg gcggcatggt cgacaccccg    780
gacggccgca gctggtacta cgtcgccttc atggacgcgt acccgggggg ccgcatcccc    840
gtggtcgcgc cgctgcgctg gacggacgac gggtggcccg aggtggtgac ggacgcgcag    900
ggcggctggg gcgccagcta cccggtcccc gtggagacgg gcaagacggt gccggacgac    960
ggctgggagc tggacgagtt caggggcggc cggctgagcc accactggga gtggaaccac    1020
aacccggacc cggcccgctt cgcgctcgcg ggcggggacg agggcgggct ggtgctgcag    1080
gcggcgacgg tgacggagga cctgttcgcg gccaggaaca cgctcacgcg gaggatcagg    1140
ggccccaagt cgagcggcac gttccggctg acgtcagca ggatgcgcga cggcgaccgg     1200
gccggggccg tgctgttccg ggacacggcg gcgtatatcg gcgtgtggaa gcaagggggac   1260 gaggccacca tcgtcgtagt cgacggcctt gagctggctc tgagctcctg gacgaccgtc    1320
tcgaccggga gggtggccga cgggcccg accctgagca gcacgcagga tgtctggctc      1380
cggatcgagg ccgacatcac gcccgcgttc gggaccaaca cggcaaggac cacgactttc    1440
tcgtacagtg tggacggcgg gaagaccttt gtccgtcttg gccggccttt ctcgatgagc    1500
aatacttggc aatactttac gggctacagg ttcggagtct tcaactttgc caccaaggag    1560
cttgggggcg aagtcaaggt caagagcttc cagatgcagc tctgtga               1608
```

<210> SEQ ID NO 51
<211> LENGTH: 535
<212> TYPE: PRT
<213> ORGANISM: Artificial sequence
<220> FEATURE:
<223> OTHER INFORMATION: Synthetic polypeptide

<400> SEQUENCE: 51

```
Met Gly Arg Leu Asn Asp Leu Ile Ala Leu Leu Ala Leu Leu Ser Gly
1               5                   10                  15

Ser Ala Thr Ser Ala Ala Val Arg Asn Thr Ala Ser Gln Ala Arg Ala
            20                  25                  30

Ala Glu Phe Asn Asn Pro Val Leu Trp Glu Asp Tyr Pro Asp Leu Asp
        35                  40                  45

Val Phe Arg Val Gly Ser Thr Phe Tyr Ser Ser Thr Phe Ala
    50                  55                  60

Tyr Ser Pro Gly Ala Pro Val Leu Lys Ser Tyr Asp Leu Val Asn Trp
65                  70                  75                  80

Thr Pro Val Thr His Ser Val Pro Thr Leu Asn Phe Gly Asp Arg Tyr
                85                  90                  95
```

Asn Leu Thr Gly Gly Thr Pro Ala Gly Tyr Val Lys Gly Ile Trp Ala
                100                 105                 110

Ser Thr Leu Arg Tyr Arg Pro Ser Asn Asp Lys Phe Tyr Trp Tyr Gly
        115                 120                 125

Cys Val Glu Phe Gly Lys Thr Tyr Ile Trp Thr Ser Ser Gly Thr Arg
    130                 135                 140

Ala Gly Asp Arg Asp Gly Glu Val Asp Pro Ala Asp Trp Val Trp Glu
145                 150                 155                 160

Pro His Pro Pro Ile Asp Arg Cys Tyr Tyr Asp Ser Gly Leu Leu Ile
                165                 170                 175

Asp Asp Asp Asp Lys Met Tyr Ile Ala Tyr Gly Asn Pro Lys Ile Glu
            180                 185                 190

Val Ala Glu Leu Ser Asp Asp Gly Leu Thr Glu Val Ser Ser Arg Val
        195                 200                 205

Val Tyr Thr Pro Pro Ala Gly Thr Thr Ile Glu Gly Ser Arg Met Tyr
    210                 215                 220

Lys Val Gly Asp Ala Tyr Tyr Ile Leu Val Thr Arg Pro Ala Asp Ala
225                 230                 235                 240

Glu Trp Val Leu Arg Ser Thr Ser Gly Pro Phe Arg Pro Gly Gly Met
                245                 250                 255

Val Asp Thr Pro Asp Gly Arg Ser Trp Tyr Tyr Val Ala Phe Met Asp
            260                 265                 270

Ala Tyr Pro Gly Gly Arg Ile Pro Val Val Ala Pro Leu Arg Trp Thr
        275                 280                 285

Asp Asp Gly Trp Pro Glu Val Val Thr Asp Ala Gln Gly Gly Trp Gly
    290                 295                 300

Ala Ser Tyr Pro Val Pro Val Glu Thr Gly Lys Thr Val Pro Asp Asp
305                 310                 315                 320

Gly Trp Glu Leu Asp Glu Phe Arg Gly Gly Arg Leu Ser His His Trp
                325                 330                 335

Glu Trp Asn His Asn Pro Asp Pro Ala Arg Phe Ala Leu Ala Gly Gly
            340                 345                 350

Asp Glu Gly Gly Leu Val Leu Gln Ala Ala Thr Val Thr Glu Asp Leu
        355                 360                 365

Phe Ala Ala Arg Asn Thr Leu Thr Arg Arg Ile Arg Gly Pro Lys Ser
    370                 375                 380

Ser Gly Thr Phe Arg Leu Asp Val Ser Arg Met Arg Asp Gly Asp Arg
385                 390                 395                 400

Ala Gly Ala Val Leu Phe Arg Asp Thr Ala Ala Tyr Ile Gly Val Trp
                405                 410                 415

Lys Gln Gly Asp Glu Ala Thr Ile Val Val Asp Gly Leu Glu Leu
            420                 425                 430

Ala Leu Ser Ser Trp Thr Thr Val Ser Thr Gly Arg Val Ala Glu Thr
        435                 440                 445

Gly Pro Thr Leu Ser Ser Thr Gln Asp Val Trp Leu Arg Ile Glu Ala
    450                 455                 460

Asp Ile Thr Pro Ala Phe Gly Thr Asn Thr Ala Arg Thr Thr Thr Phe
465                 470                 475                 480

Ser Tyr Ser Val Asp Gly Gly Lys Thr Phe Val Arg Leu Gly Pro Ala
                485                 490                 495

Phe Ser Met Ser Asn Thr Trp Gln Tyr Phe Thr Gly Tyr Arg Phe Gly
            500                 505                 510

Val Phe Asn Phe Ala Thr Lys Glu Leu Gly Gly Glu Val Lys Val Lys

```
                515                 520                 525
Ser Phe Gln Met Gln Pro Leu
    530                 535

<210> SEQ ID NO 52
<211> LENGTH: 513
<212> TYPE: PRT
<213> ORGANISM: Artificial sequence
<220> FEATURE:
<223> OTHER INFORMATION: Synthetic polypeptide

<400> SEQUENCE: 52

Val Arg Asn Thr Ala Ser Gln Ala Arg Ala Ala Glu Phe Asn Asn Pro
1               5                   10                  15

Val Leu Trp Glu Asp Tyr Pro Asp Leu Asp Val Phe Arg Val Gly Ser
            20                  25                  30

Thr Phe Tyr Tyr Ser Ser Thr Phe Ala Tyr Ser Pro Gly Ala Pro
        35                  40                  45

Val Leu Lys Ser Tyr Asp Leu Val Asn Trp Thr Pro Val Thr His Ser
50                  55                  60

Val Pro Thr Leu Asn Phe Gly Asp Arg Tyr Asn Leu Thr Gly Thr
65                  70                  75                  80

Pro Ala Gly Tyr Val Lys Gly Ile Trp Ala Ser Thr Leu Arg Tyr Arg
                85                  90                  95

Pro Ser Asn Asp Lys Phe Tyr Trp Tyr Gly Cys Val Glu Phe Gly Lys
            100                 105                 110

Thr Tyr Ile Trp Thr Ser Ser Gly Thr Arg Ala Gly Asp Arg Asp Gly
        115                 120                 125

Glu Val Asp Pro Ala Asp Trp Val Trp Glu Pro His Pro Ile Asp
130                 135                 140

Arg Cys Tyr Tyr Asp Ser Gly Leu Leu Ile Asp Asp Asp Lys Met
145                 150                 155                 160

Tyr Ile Ala Tyr Gly Asn Pro Lys Ile Glu Val Ala Glu Leu Ser Asp
                165                 170                 175

Asp Gly Leu Thr Glu Val Ser Ser Arg Val Val Tyr Thr Pro Pro Ala
            180                 185                 190

Gly Thr Thr Ile Glu Gly Ser Arg Met Tyr Lys Val Gly Asp Ala Tyr
        195                 200                 205

Tyr Ile Leu Val Thr Arg Pro Ala Asp Ala Glu Trp Val Leu Arg Ser
    210                 215                 220

Thr Ser Gly Pro Phe Arg Pro Gly Gly Met Val Asp Thr Pro Asp Gly
225                 230                 235                 240

Arg Ser Trp Tyr Tyr Val Ala Phe Met Asp Ala Tyr Pro Gly Gly Arg
                245                 250                 255

Ile Pro Val Val Ala Pro Leu Arg Trp Thr Asp Asp Gly Trp Pro Glu
            260                 265                 270

Val Val Thr Asp Ala Gln Gly Gly Trp Gly Ala Ser Tyr Pro Val Pro
        275                 280                 285

Val Glu Thr Gly Lys Thr Val Pro Asp Asp Gly Trp Glu Leu Asp Glu
    290                 295                 300

Phe Arg Gly Gly Arg Leu Ser His His Trp Glu Trp Asn His Asn Pro
305                 310                 315                 320

Asp Pro Ala Arg Phe Ala Leu Ala Gly Gly Asp Glu Gly Gly Leu Val
                325                 330                 335

Leu Gln Ala Ala Thr Val Thr Glu Asp Leu Phe Ala Ala Arg Asn Thr
```

|  |  |  | 340 |  |  |  | 345 |  |  |  | 350 |  |
|---|---|---|---|---|---|---|---|---|---|---|---|---|
| Leu | Thr | Arg | Arg | Ile | Arg | Gly | Pro | Lys | Ser | Ser | Gly | Thr | Phe | Arg | Leu |
|  |  |  |  | 355 |  |  |  |  | 360 |  |  |  |  | 365 |  |

Asp Val Ser Arg Met Arg Asp Gly Asp Arg Ala Gly Ala Val Leu Phe
        370                 375                 380

Arg Asp Thr Ala Ala Tyr Ile Gly Val Trp Lys Gln Gly Asp Glu Ala
385                 390                 395                 400

Thr Ile Val Val Asp Gly Leu Glu Leu Ala Leu Ser Ser Trp Thr
                405                 410                 415

Thr Val Ser Thr Gly Arg Val Ala Glu Thr Gly Pro Thr Leu Ser Ser
            420                 425                 430

Thr Gln Asp Val Trp Leu Arg Ile Glu Ala Asp Ile Thr Pro Ala Phe
        435                 440                 445

Gly Thr Asn Thr Ala Arg Thr Thr Phe Ser Tyr Ser Val Asp Gly
            450                 455                 460

Gly Lys Thr Phe Val Arg Leu Gly Pro Ala Phe Ser Met Ser Asn Thr
465                 470                 475                 480

Trp Gln Tyr Phe Thr Gly Tyr Arg Phe Gly Val Phe Asn Phe Ala Thr
                485                 490                 495

Lys Glu Leu Gly Gly Glu Val Lys Val Lys Ser Phe Gln Met Gln Pro
            500                 505                 510

Leu

<210> SEQ ID NO 53
<211> LENGTH: 1851
<212> TYPE: DNA
<213> ORGANISM: Artificial sequence
<220> FEATURE:
<223> OTHER INFORMATION: Synthetic polynucleotide

<400> SEQUENCE: 53

| atgacgatgc | tcaagtcggc | cctccccgcg | gcgctggccc | tcctcctaac | ggcggccaac | 60 |
| ggccacccctt | ccaggacccc | ggcggcggcg | gcggcggggg | gatgggcacc | gctggcgaat | 120 |
| gggacattcc | ggaacccgat | cctgtacgag | gacttcccgg | acaacgacgt | gtcggtcggg | 180 |
| ccggacgggg | ccttctacct | gtcggcgtcc | aacttccact | tcagccccgg | ggcgcccatc | 240 |
| ctgcggtctt | acgacctggt | cgactgggag | tttgtgggcc | actcgatccc | gcgcctcgac | 300 |
| ttcggcgccg | gctacgacct | gccgccgacg | ggcgagcggg | cgtaccgcgc | gggcacgtgg | 360 |
| gcgtcgacgc | tgcggtaccg | cgagagcacg | gggctctggt | actggatcgg | gtgcaccaac | 420 |
| ttctggcgca | cctgggtctt | caccgccccg | gcgcccgagg | ggccctggac | ccgggcgggc | 480 |
| gacttcggcg | acggcgtgtg | cttctacgac | aacggcctgc | tggtcgacga | cgacgacacc | 540 |
| atgtacgtcg | tctacaccca | cgacggcggc | aagcgggtcc | acgtgaccca | gctgagcgcg | 600 |
| gacgggctga | gcgccgtccg | caccgagacc | gtcctggtgc | cggagcaggc | cggcgtcgac | 660 |
| gccctcgagg | gcaaccgcat | gtacaagatc | gacggccgct | actacatcct | caacgaccac | 720 |
| ccgggcacca | ccgcctacgt | ctggaagtcc | gactcgccct | ggggtcccta | cgagggcaag | 780 |
| gcgctggccg | acaacgtcgc | cagccccctg | cccggcggcg | cgccccgca | ccagggcagc | 840 |
| ctggtgccca | cgccctcggg | cgcctggtac | tttatgtcct | tcacctgggc | ctaccgtcc | 900 |
| ggccgcctgc | ccgtgctggc | ccgatcgag | ttccagccgg | acgggttccc | gaccctcggc | 960 |
| gcctggtact | ttatgtcctt | cacctgggcc | taccgtccg | ccgcctgcc | cgtgctggcc | 1020 |
| ccgatcgagt | tccagccgga | cgggttcccg | accctcgtca | ccgccaagga | caacaacaac | 1080 |

-continued

```
aacaacaaca acaacgcctg gggcgccagc tacccgctgc cgccgctacc gcgccggccg    1140
ctgggctacc cgtggtcgcg ggcgcggtac gacttcagcg cgctcgccga actgccgccc    1200
gcgttcgagt ggaaccacaa cccggacgcg agcaactaca cgctgggagg gaacggcgct    1260
gccggcctga tcctgcgggc cgccaccgtc gcgcccgacg acgacctgta ctcggcgcgc    1320
aacacgctga cgcaccgcgc ccacgggccc ttcccctcgg ccacgctggt cctcgacgtc    1380
gcggacatgg ccgacggcga ccgcgccggg ctggccgcct ccgcgaccg cagtgcctac     1440 atcggcatcc actgctcctc ctcctctgat gagaagaaga agaagacgta cgaggtggtg    1500
gcgcgattca acatgacgct ggacgagtgg ggcagcggcg agacgctcga tctgggcgag    1560
gtggtggagc gggtcgagct ggcctcgggc gtgacgcgcg tgtggctgcg ggcgagcatg    1620
gacgcgcggc ccgacggcga gcggacggcc cggttcgggt acagcgtcga cggggggcgag   1680 accttgcccg gcctggggcc cgcctaccaa ctctacgccg ggtggcccct ctttgtcggc    1740
taccgcttcg ccgtcttcaa ctacgccacc aaggccctcg gcgggagcgt caccgtcctg    1800
agcctcgaga ccgactcggg cgagggtgag cgcgatgccg agcaagcgtg a             1851
```

<210> SEQ ID NO 54
<211> LENGTH: 616
<212> TYPE: PRT
<213> ORGANISM: Artificial sequence
<220> FEATURE:
<223> OTHER INFORMATION: Synthetic polypeptide

<400> SEQUENCE: 54

```
Met Thr Met Leu Lys Ser Ala Leu Pro Ala Ala Leu Ala Leu Leu Leu
1               5                   10                  15

Thr Ala Ala Asn Gly His Pro Ser Arg Thr Pro Ala Ala Ala Ala
            20                  25                  30

Gly Gly Trp Ala Pro Leu Ala Asn Gly Thr Phe Arg Asn Pro Ile Leu
        35                  40                  45

Tyr Glu Asp Phe Pro Asp Asn Asp Val Ser Val Gly Pro Asp Gly Ala
    50                  55                  60

Phe Tyr Leu Ser Ala Ser Asn Phe His Phe Ser Pro Gly Ala Pro Ile
65                  70                  75                  80

Leu Arg Ser Tyr Asp Leu Val Asp Trp Glu Phe Val Gly His Ser Ile
                85                  90                  95

Pro Arg Leu Asp Phe Gly Ala Gly Tyr Asp Leu Pro Pro Thr Gly Glu
            100                 105                 110

Arg Ala Tyr Arg Ala Gly Thr Trp Ala Ser Thr Leu Arg Tyr Arg Glu
        115                 120                 125

Ser Thr Gly Leu Trp Tyr Trp Ile Gly Cys Thr Asn Phe Trp Arg Thr
    130                 135                 140

Trp Val Phe Thr Ala Pro Ala Pro Glu Gly Pro Trp Thr Arg Ala Gly
145                 150                 155                 160

Asp Phe Gly Asp Gly Val Cys Phe Tyr Asp Asn Gly Leu Leu Val Asp
                165                 170                 175

Asp Asp Asp Thr Met Tyr Val Val Tyr Thr His Asp Gly Gly Lys Arg
            180                 185                 190

Val His Val Thr Gln Leu Ser Ala Asp Gly Leu Ser Ala Val Arg Thr
        195                 200                 205

Glu Thr Val Leu Val Pro Glu Gln Ala Gly Val Asp Ala Leu Glu Gly
    210                 215                 220
```

Asn Arg Met Tyr Lys Ile Asp Gly Arg Tyr Tyr Ile Leu Asn Asp His
225                 230                 235                 240

Pro Gly Thr Thr Ala Tyr Val Trp Lys Ser Asp Ser Pro Trp Gly Pro
            245                 250                 255

Tyr Glu Gly Lys Ala Leu Ala Asp Asn Val Ala Ser Pro Leu Pro Gly
        260                 265                 270

Gly Gly Ala Pro His Gln Gly Ser Leu Val Pro Thr Pro Ser Gly Ala
    275                 280                 285

Trp Tyr Phe Met Ser Phe Thr Trp Ala Tyr Pro Ser Gly Arg Leu Pro
290                 295                 300

Val Leu Ala Pro Ile Glu Phe Gln Pro Asp Gly Phe Pro Thr Leu Gly
305                 310                 315                 320

Ala Trp Tyr Phe Met Ser Phe Thr Trp Ala Tyr Pro Ser Gly Arg Leu
            325                 330                 335

Pro Val Leu Ala Pro Ile Glu Phe Gln Pro Asp Gly Phe Pro Thr Leu
        340                 345                 350

Val Thr Ala Lys Asp Asn Asn Asn Asn Asn Asn Asn Ala Trp Gly
            355                 360                 365

Ala Ser Tyr Pro Leu Pro Pro Leu Pro Arg Arg Pro Leu Gly Tyr Pro
    370                 375                 380

Trp Ser Arg Ala Arg Tyr Asp Phe Ser Ala Leu Ala Glu Leu Pro Pro
385                 390                 395                 400

Ala Phe Glu Trp Asn His Asn Pro Asp Ala Ser Asn Tyr Thr Leu Gly
                405                 410                 415

Gly Asn Gly Ala Ala Gly Leu Ile Leu Arg Ala Ala Thr Val Ala Pro
            420                 425                 430

Asp Asp Asp Leu Tyr Ser Ala Arg Asn Thr Leu Thr His Arg Ala His
            435                 440                 445

Gly Pro Phe Pro Ser Ala Thr Leu Val Leu Asp Val Ala Asp Met Ala
    450                 455                 460

Asp Gly Asp Arg Ala Gly Leu Ala Ala Phe Arg Asp Arg Ser Ala Tyr
465                 470                 475                 480

Ile Gly Ile His Cys Ser Ser Ser Asp Glu Lys Lys Lys Thr
            485                 490                 495

Tyr Glu Val Val Ala Arg Phe Asn Met Thr Leu Asp Glu Trp Gly Ser
        500                 505                 510

Gly Glu Thr Leu Asp Leu Gly Glu Val Val Glu Arg Val Glu Leu Ala
        515                 520                 525

Ser Gly Val Thr Arg Val Trp Leu Arg Ala Ser Met Asp Ala Arg Pro
530                 535                 540

Asp Gly Glu Arg Thr Ala Arg Phe Gly Tyr Ser Val Asp Gly Gly Glu
545                 550                 555                 560

Thr Phe Ala Gly Leu Gly Pro Ala Tyr Gln Leu Tyr Ala Gly Trp Pro
            565                 570                 575

Phe Phe Val Gly Tyr Arg Phe Ala Val Phe Asn Tyr Ala Thr Lys Ala
        580                 585                 590

Leu Gly Gly Ser Val Thr Val Leu Ser Leu Glu Thr Asp Ser Gly Glu
        595                 600                 605

Gly Glu Arg Asp Ala Glu Gln Ala
        610                 615

<210> SEQ ID NO 55
<211> LENGTH: 595
<212> TYPE: PRT

<213> ORGANISM: Artificial sequence
<220> FEATURE:
<223> OTHER INFORMATION: Synthetic polypeptide

<400> SEQUENCE: 55

```
His Pro Ser Arg Thr Pro Ala Ala Ala Ala Gly Gly Trp Ala Pro
1               5                   10                  15

Leu Ala Asn Gly Thr Phe Arg Asn Pro Ile Leu Tyr Glu Asp Phe Pro
                20                  25                  30

Asp Asn Asp Val Ser Val Gly Pro Asp Gly Ala Phe Tyr Leu Ser Ala
            35                  40                  45

Ser Asn Phe His Phe Ser Pro Gly Ala Pro Ile Leu Arg Ser Tyr Asp
    50                  55                  60

Leu Val Asp Trp Glu Phe Val Gly His Ser Ile Pro Arg Leu Asp Phe
65                  70                  75                  80

Gly Ala Gly Tyr Asp Leu Pro Pro Thr Gly Glu Arg Ala Tyr Arg Ala
                85                  90                  95

Gly Thr Trp Ala Ser Thr Leu Arg Tyr Arg Glu Ser Thr Gly Leu Trp
                100                 105                 110

Tyr Trp Ile Gly Cys Thr Asn Phe Trp Arg Thr Trp Val Phe Thr Ala
                115                 120                 125

Pro Ala Pro Glu Gly Pro Trp Thr Arg Ala Gly Asp Phe Gly Asp Gly
            130                 135                 140

Val Cys Phe Tyr Asp Asn Gly Leu Leu Val Asp Asp Asp Thr Met
145                 150                 155                 160

Tyr Val Val Tyr Thr His Asp Gly Gly Lys Arg Val His Val Thr Gln
                165                 170                 175

Leu Ser Ala Asp Gly Leu Ser Ala Val Arg Thr Glu Thr Val Leu Val
            180                 185                 190

Pro Glu Gln Ala Gly Val Asp Ala Leu Glu Gly Asn Arg Met Tyr Lys
        195                 200                 205

Ile Asp Gly Arg Tyr Tyr Ile Leu Asn Asp His Pro Gly Thr Thr Ala
    210                 215                 220

Tyr Val Trp Lys Ser Asp Ser Pro Trp Gly Pro Tyr Glu Gly Lys Ala
225                 230                 235                 240

Leu Ala Asp Asn Val Ala Ser Pro Leu Pro Gly Gly Ala Pro His
                245                 250                 255

Gln Gly Ser Leu Val Pro Thr Pro Ser Gly Ala Trp Tyr Phe Met Ser
            260                 265                 270

Phe Thr Trp Ala Tyr Pro Ser Gly Arg Leu Pro Val Leu Ala Pro Ile
            275                 280                 285

Glu Phe Gln Pro Asp Gly Phe Pro Thr Leu Gly Ala Trp Tyr Phe Met
        290                 295                 300

Ser Phe Thr Trp Ala Tyr Pro Ser Gly Arg Leu Pro Val Leu Ala Pro
305                 310                 315                 320

Ile Glu Phe Gln Pro Asp Gly Phe Pro Thr Leu Val Thr Ala Lys Asp
                325                 330                 335

Asn Asn Asn Asn Asn Asn Asn Ala Trp Gly Ala Ser Tyr Pro Leu
                340                 345                 350

Pro Pro Leu Pro Arg Arg Pro Leu Gly Tyr Pro Trp Ser Arg Ala Arg
            355                 360                 365

Tyr Asp Phe Ser Ala Leu Ala Glu Leu Pro Pro Ala Phe Glu Trp Asn
        370                 375                 380

His Asn Pro Asp Ala Ser Asn Tyr Thr Leu Gly Gly Asn Gly Ala Ala
```

```
                385                 390                 395                 400
        Gly Leu Ile Leu Arg Ala Ala Thr Val Ala Pro Asp Asp Leu Tyr
                        405                 410                 415

Ser Ala Arg Asn Thr Leu Thr His Arg Ala His Gly Pro Phe Pro Ser
                    420                 425                 430

Ala Thr Leu Val Leu Asp Val Ala Asp Met Ala Asp Gly Asp Arg Ala
                        435                 440                 445

Gly Leu Ala Ala Phe Arg Asp Arg Ser Ala Tyr Ile Gly Ile His Cys
                    450                 455                 460

Ser Ser Ser Ser Asp Glu Lys Lys Lys Thr Tyr Glu Val Val Ala
        465                 470                 475                 480

Arg Phe Asn Met Thr Leu Asp Glu Trp Gly Ser Gly Glu Thr Leu Asp
                        485                 490                 495

Leu Gly Glu Val Val Glu Arg Val Glu Leu Ala Ser Gly Val Thr Arg
                    500                 505                 510

Val Trp Leu Arg Ala Ser Met Asp Ala Arg Pro Asp Gly Glu Arg Thr
                    515                 520                 525

Ala Arg Phe Gly Tyr Ser Val Asp Gly Gly Glu Thr Phe Ala Gly Leu
                    530                 535                 540

Gly Pro Ala Tyr Gln Leu Tyr Ala Gly Trp Pro Phe Val Gly Tyr
        545                 550                 555                 560

Arg Phe Ala Val Phe Asn Tyr Ala Thr Lys Ala Leu Gly Gly Ser Val
                        565                 570                 575

Thr Val Leu Ser Leu Glu Thr Asp Ser Gly Glu Gly Glu Arg Asp Ala
                    580                 585                 590

Glu Gln Ala
                595

<210> SEQ ID NO 56
<211> LENGTH: 348
<212> TYPE: DNA
<213> ORGANISM: Myceliophthora thermophila

<400> SEQUENCE: 56
atgctgaacc tatcccacac cgagcacact ctctttcgcc ctctcccccct ttccctccct      60 catcaccacc accaccacca cttcattgtc ggccgccgcc cgcccgaggc gctgcgcggc     120
gccatcacgc gccacatccg cgccgtcgcc ggctactacc gcggccgctg ctacgcctgg     180
gacgtggtca acgaggcgct cgacgaggac ggcacctacc gcaagagcct cttctacaac     240
gtcctcggcg acgagtacat ccgcatcgtc aagaccttcg agaagctgat ccgcgagaag     300
ccaaagccgg gcttcaagcg caagaggaaa accgtagcag caaactaa                  348

<210> SEQ ID NO 57
<211> LENGTH: 115
<212> TYPE: PRT
<213> ORGANISM: Myceliophthora thermophila

<400> SEQUENCE: 57

Met Leu Asn Leu Ser His Thr Glu His Thr Leu Phe Arg Pro Leu Pro
1               5                  10                  15

Leu Ser Leu Pro His His His His His His Phe Ile Val Gly Arg
                20                  25                  30

Arg Pro Pro Glu Ala Leu Arg Gly Ala Ile Thr Arg His Ile Arg Ala
            35                  40                  45

Val Ala Gly Tyr Tyr Arg Gly Arg Cys Tyr Ala Trp Asp Val Val Asn
```

|  | 50 |  |  |  | 55 |  |  |  | 60 |  |  |  |  |
|---|---|---|---|---|---|---|---|---|---|---|---|---|---|

Glu Ala Leu Asp Glu Asp Gly Thr Tyr Arg Lys Ser Leu Phe Tyr Asn
65                70                    75                    80

Val Leu Gly Asp Glu Tyr Ile Arg Ile Val Lys Thr Phe Glu Lys Leu
                    85                    90                    95

Ile Arg Glu Lys Pro Lys Pro Gly Phe Lys Arg Lys Arg Lys Thr Val
            100                    105                    110

Ala Ala Asn
      115

<210> SEQ ID NO 58
<211> LENGTH: 2466
<212> TYPE: DNA
<213> ORGANISM: Artificial sequence
<220> FEATURE:
<223> OTHER INFORMATION: Synthetic polynucleotide

<400> SEQUENCE: 58

```
atggaggagg aagcgactcc aagaccccaa tcgagtatcg tgcagatgca gaggcacatg      60
ctcaactcgc gctggcatgc caggcgtttg ccaacaaac cccacggcgt cttcccaagc     120
ttggatggac atctaaggac ctacaccaag gatatccgac cagccccgac ctggcgggtc     180
ggacaatggc tcgtggccga gggcgtacaa gtccaatacg ccgaggaagt ataccgaatc     240
actcccacgg cctcgggcaa gggaatcagc ctcttgtgcc cgacgcgcaa gatcttgaac     300
cgtgggaaca ctctgaacct ggcaacgctc agcatcgaca tcgagccggc ttttgatggc     360
gtcctctctg tcgagaccac ccactggcaa ggcgccgtcc gtcgcggacc cgacttcgac     420
ctcttccccg ccggccggcc cgaggtggac gccaaggtga ccaagacgga gagcggcacc     480
accctgtcgt ccgggacgct ctcggcgaca gtcagcggca gccgcacga gttcgagatc     540
gccttccatc cgaccggggg caagaagccc ctgaccaccc tgctcaaccg gtcagtcggc     600
ctggcctaca cgcccgcccc gagcacgccc atgcagctgg ccgacatgcg caacttccgc     660
cactacatct tcacccagac caccctcgcc gtcggcgagt ccatccacgg gctcggcgag     720
cgcttcgggc ccttcaacaa ggtcggccag agggtcgagc tgtggaacgc ggacgggggc     780
acctcgtccg accaggcgta caagaacgtg ggcttctgga tgagctcgcg cggctacggt     840
gtcttcgtcg acactcccgg gcgcgtcgag ctcgagatcg ggagcgagcg tgctgccgg     900
ctccagacga gcgtcgaggg gcagcggctc cgctggttca tcatctacgg ccctccccg     960
cgcgacatcc tgcgccggta ctcggtcctc accggagccc ccggcagcgt gcccagctgg    1020
tccttcggcc tgtggctcag cacgtccttc accacctcgt acgacgagga gacggtcaac    1080
agcttcctgg ccggcatgag ggcgcgcgac ataccgtcg aggtcttcca cttcgactgc    1140
ttctggctca aggcgttcca gtggtgcgac ttcgagttcg accgcgacat gttcccggac    1200
ccgaggggcc agatcgggcg cctcaaggcc ggcggcctcg tcaagaaggt ctgcgtctgg    1260
acgaacccgt acctgggcca ggcgtccccc gtcttcgccg aggccgcggc caggggctac    1320
ctgctccggc gcaggaacgg cgacgtcttc cagtgggacc tgtggcagac gggcatgggc    1380
atcgtcgact tcaccaaccc ggacgcccgc gcctggttcg ccgcctgtct cgaccgcctc    1440
ttcgacacgg gcgtcgactg catcaagacc gactttggcg agcgcatccc ctccgaggat    1500
gtgcagtggt cgacccttc ggtcgacccg agcggatgc acaactacta cgccttcatc    1560
tacaacaagc tcgtctacga ggccctgcag aggcgttacg cgccaacga ggccgtcctg    1620
ttcgcccgcg ccgccaccgc cggctgccag cggttccccc tcacctgggg cggcgactgc    1680
```

-continued

```
gagtcgaccc ccgaggccat ggccgagtcg ctacgcggtg gtttgtccct cggcctgtcc   1740
gggttcgcct tctggagcgt cgacattggc ggcttcgagg ggtcgccgcc tccctggatc   1800
tacaagcgct gggtcgcctt cggcctcctc tgctcccact cgcgcctgca cggctccaac   1860
tcgtaccggg tccctggac ggtcgacggc gacgaccagt ccgaggaggg atgctccgcc   1920
acgctgcgca gtggaccca tctcaaggct cgcctgatgc cctacctctt ctcccaggcg   1980
caggagagcg tccggggcgg gctcccgctc agcctgaggg ccatgtgcat cgagttcccc   2040
gacgacccga ccgcctggac cctcgatcgc cagttcatgc tcggcgacgg cctcctcgtc   2100
gcccccgtct tcgaggagga cggcaccgtc gagttctacc tgcccagggg caagtggacc   2160
aacttcttca ccggcgaggt caaggagggc cccggctggt cgccgagac ccacgggttc   2220 ggcaccctgc cgctctacgt ccggcccaac acgctcctgg ttctgggcaa ggaaggagag   2280
acgaggaccg tgtacgacta cacgagcgac gtcgaggtga gggcgtattt tgccagtgac   2340
agcgccagcg ccgtgctggt cgacgccgag ggcaagactg taggtaccct gcgtgtcaag   2400
gacggggaga ttatcggaaa ggaactgcta tctggcaact cggtcatcaa tgtcgtgagc   2460
tcctga                                                              2466
```

<210> SEQ ID NO 59
<211> LENGTH: 821
<212> TYPE: PRT
<213> ORGANISM: Artificial sequence
<220> FEATURE:
<223> OTHER INFORMATION: Synthetic polypeptide

<400> SEQUENCE: 59

```
Met Glu Glu Glu Ala Thr Pro Arg Pro Gln Ser Ser Ile Val Gln Met
1               5                   10                  15

Gln Arg His Met Leu Asn Ser Arg Trp His Ala Arg Arg Leu Ala Asn
                20                  25                  30

Lys Pro His Gly Val Phe Pro Ser Leu Asp Gly His Leu Arg Thr Tyr
            35                  40                  45

Thr Lys Asp Ile Arg Pro Ala Pro Thr Trp Arg Val Gly Gln Trp Leu
        50                  55                  60

Val Ala Glu Gly Val Gln Val Gln Tyr Ala Glu Glu Val Tyr Arg Ile
65                  70                  75                  80

Thr Pro Thr Ala Ser Gly Lys Gly Ile Ser Leu Leu Cys Pro Thr Arg
                85                  90                  95

Lys Ile Leu Asn Arg Gly Asn Thr Leu Asn Leu Ala Thr Leu Ser Ile
                100                 105                 110

Asp Ile Glu Pro Ala Phe Asp Gly Val Leu Ser Val Glu Thr Thr His
            115                 120                 125

Trp Gln Gly Ala Val Arg Arg Gly Pro Asp Phe Asp Leu Phe Pro Ala
        130                 135                 140

Gly Arg Pro Glu Val Asp Ala Lys Val Thr Lys Thr Glu Ser Gly Thr
145                 150                 155                 160

Thr Leu Ser Ser Gly Thr Leu Ser Ala Thr Val Ser Gly Lys Pro His
                165                 170                 175

Glu Phe Glu Ile Ala Phe His Pro Thr Gly Gly Lys Lys Pro Leu Thr
            180                 185                 190

Thr Leu Leu Asn Arg Ser Val Gly Leu Ala Tyr Thr Pro Ala Pro Ser
        195                 200                 205

Thr Pro Met Gln Leu Ala Asp Met Arg Asn Phe Arg His Tyr Ile Phe
```

```
              210                 215                 220
Thr Gln Thr Thr Leu Ala Val Gly Glu Ser Ile His Gly Leu Gly Glu
225                 230                 235                 240

Arg Phe Gly Pro Phe Asn Lys Val Gly Gln Arg Val Glu Leu Trp Asn
                245                 250                 255

Ala Asp Gly Gly Thr Ser Ser Asp Gln Ala Tyr Lys Asn Val Gly Phe
                260                 265                 270

Trp Met Ser Ser Arg Gly Tyr Gly Val Phe Val Asp Thr Pro Gly Arg
            275                 280                 285

Val Glu Leu Glu Ile Gly Ser Glu Arg Cys Cys Arg Leu Gln Thr Ser
290                 295                 300

Val Glu Gly Gln Arg Leu Arg Trp Phe Ile Ile Tyr Gly Pro Ser Pro
305                 310                 315                 320

Arg Asp Ile Leu Arg Arg Tyr Ser Val Leu Thr Gly Ala Pro Gly Ser
                325                 330                 335

Val Pro Ser Trp Ser Phe Gly Leu Trp Leu Ser Thr Ser Phe Thr Thr
            340                 345                 350

Ser Tyr Asp Glu Glu Thr Val Asn Ser Phe Leu Ala Gly Met Arg Ala
            355                 360                 365

Arg Asp Ile Pro Val Glu Val Phe His Phe Asp Cys Phe Trp Leu Lys
            370                 375                 380

Ala Phe Gln Trp Cys Asp Phe Glu Phe Asp Arg Asp Met Phe Pro Asp
385                 390                 395                 400

Pro Arg Gly Gln Ile Gly Arg Leu Lys Ala Gly Gly Leu Val Lys Lys
                405                 410                 415

Val Cys Val Trp Thr Asn Pro Tyr Leu Gly Gln Ala Ser Pro Val Phe
                420                 425                 430

Ala Glu Ala Ala Arg Gly Tyr Leu Leu Arg Arg Arg Asn Gly Asp
                435                 440                 445

Val Phe Gln Trp Asp Leu Trp Gln Thr Gly Met Gly Ile Val Asp Phe
            450                 455                 460

Thr Asn Pro Asp Ala Arg Ala Trp Phe Ala Ala Cys Leu Asp Arg Leu
465                 470                 475                 480

Phe Asp Thr Gly Val Asp Cys Ile Lys Thr Asp Phe Gly Glu Arg Ile
                485                 490                 495

Pro Ser Glu Asp Val Gln Trp Phe Asp Pro Ser Val Asp Pro Glu Arg
                500                 505                 510

Met His Asn Tyr Tyr Ala Phe Ile Tyr Asn Lys Leu Val Tyr Glu Ala
            515                 520                 525

Leu Gln Arg Arg Tyr Gly Ala Asn Glu Ala Val Leu Phe Ala Arg Ala
530                 535                 540

Ala Thr Ala Gly Cys Gln Arg Phe Pro Leu Thr Trp Gly Gly Asp Cys
545                 550                 555                 560

Glu Ser Thr Pro Glu Ala Met Ala Glu Ser Leu Arg Gly Gly Leu Ser
                565                 570                 575

Leu Gly Leu Ser Gly Phe Ala Phe Trp Ser Val Asp Ile Gly Gly Phe
            580                 585                 590

Glu Gly Ser Pro Pro Trp Ile Tyr Lys Arg Trp Val Ala Phe Gly
            595                 600                 605

Leu Leu Cys Ser His Ser Arg Leu His Gly Ser Asn Ser Tyr Arg Val
            610                 615                 620

Pro Trp Thr Val Asp Gly Asp Asp Gln Ser Glu Glu Gly Cys Ser Ala
625                 630                 635                 640
```

Thr Leu Arg Lys Trp Thr His Leu Lys Ala Arg Leu Met Pro Tyr Leu
            645                 650                 655

Phe Ser Gln Ala Gln Glu Ser Val Arg Gly Gly Leu Pro Leu Ser Leu
        660                 665                 670

Arg Ala Met Cys Ile Glu Phe Pro Asp Asp Pro Thr Ala Trp Thr Leu
    675                 680                 685

Asp Arg Gln Phe Met Leu Gly Asp Gly Leu Leu Val Ala Pro Val Phe
690                 695                 700

Glu Glu Asp Gly Thr Val Glu Phe Tyr Leu Pro Arg Gly Lys Trp Thr
705                 710                 715                 720

Asn Phe Phe Thr Gly Glu Val Lys Glu Gly Pro Gly Trp Phe Ala Glu
                725                 730                 735

Thr His Gly Phe Gly Thr Leu Pro Leu Tyr Val Arg Pro Asn Thr Leu
            740                 745                 750

Leu Val Leu Gly Lys Glu Gly Glu Thr Arg Thr Val Tyr Asp Tyr Thr
        755                 760                 765

Ser Asp Val Glu Val Arg Ala Tyr Phe Ala Ser Asp Ser Ala Ser Ala
    770                 775                 780

Val Leu Val Asp Ala Glu Gly Lys Thr Val Gly Thr Leu Arg Val Lys
785                 790                 795                 800

Asp Gly Glu Ile Ile Gly Lys Glu Leu Leu Ser Gly Asn Ser Val Ile
                805                 810                 815

Asn Val Val Ser Ser
            820

<210> SEQ ID NO 60
<211> LENGTH: 2553
<212> TYPE: DNA
<213> ORGANISM: Artificial sequence
<220> FEATURE:
<223> OTHER INFORMATION: Synthetic polynucleotide

<400> SEQUENCE: 60
atggccagca gccggtaccg gtacacgttc ccgaggaatc cgaaggccaa tccgaaggcc    60
gtcgtgacag gcggcaaggg atcctcttac tatcgcttca ccctcctcac cgaacggttg   120
atccgttacg agtggtccga ggacggaggc ttcgaggatc gcgcgtccac gttcgcggta   180
ttcagatact ttgatgcccc gcagtaccgc gttgtcgaga caaacgacag tctcgagatc   240
atcacggact actttcacct cacctatgac aagaagaagt tctcatcgga aggactttcc   300
gtcagagtcg gctccgacct ctggaattac gacggcaaga gttatggaga cctgggcggc   360
accgcccgga ccctagacgg cgcctatggc cgcgtggacc tggaaccggg tgtgctctcg   420
cgcaaagctt atgcggttct cgacgacagc aagtctatgc tctttgacga cgacgggtgg   480
attgccattc gcgagccggg ccgcattgac ggttacgtgt ttgcctacag cggcgagcac   540
aaggccgcca tcagggactt ctaccgcctc tccgggcgtc agccggtgct ccccgctgg   600 gtgctgggga actggtggtc caggtaccac gcatactcgg ccgacgaata catcgagctt   660
atggaccact tcaaacgcga aggaatcccg ctcacgacga gcatcgtgga tatggactgg   720
caccgggttg acgacgtccc gcccaagtac ggctcaggat ggacgggcta cagctggaac   780
cgcaagctgt tcccggaccc cgagggggttc ctgcaggagc tgcgtaatcg gaacctgaaa   840
gtggccctca cgaccaccc ggcggacggc atcggggcgt atgaggatct gtacccggcg   900
gtggccaagg ccctgaatca cgacacgtcg cgagaggaac cgatcaagtt tgactgcacc   960

-continued

```
gatcgcaagt tcatggacgc ctacttcgac gttctgaagc tcagccttga gaagcagggc    1020
gtcatgttct ggtggatcga ctggcagcaa ggcaccggca gcaagctccc cagcgtagac    1080
ccgctgtggg tgctcaatca ctaccactac ctcaccagta agcgcaacgc gaaagacatc    1140
caacgtccca tcacattctc ccgctacgcc ggcgccggtg cccatcggta cccgatcggc    1200
ttctcgggcg acacgcagac gacttgggaa ggtctcgagt tccagcccga gtttaccgca    1260
acggcatcca acatcggcta tggctggtgg agccacgaca tcggcgggca ttggggcggc    1320
gtccgctcca accagctgac ggtccgctgg gtccagctgg gctgcttctc cccgatcctg    1380
cggctgcact cgaacaagag cccgtggaac tcgagagagc cgtggaacta cgaggacgag    1440
gcgcacagga tcatgaagga cttcctcatc ctgcgccacc gcctcatccc cttcctctac    1500
accatgaaca tccgggccag ctacgagagc gagccgctca tccagcccat gtactggaat    1560
cacccgaagg acgaagaggc ctacacggtg ccgacgcagt actacttcgg gccggacctc    1620
ctcgtggccc ccatcacgtc tcccaacagc accgtcaccc tgatgggccg cgtgcgcgcc    1680
tggctgccgc cgggccggta cgtcgacctg ttctacccgc acctggtcta cgacggcggc    1740
cggtacatgc acctgcaccg cgacctgtcg cagatccccg tgctcgcgcg ggagggcacc    1800
atcgtgccgc tggacacgac gcccaggacg ggccacggcg ccgcgcggcc gaccgagatc    1860
accctcctcc tcgtcgtcgg ccgggacgcg cactttgagc tggtcgagga gccggagcag    1920
caggaccacc atcgccacgg cggcggcgac gacggcgatg accaaccccc gctcagcgcg    1980
ttcgcccgga ccccatctc gtggtcgcag gcggacggcg tgctcaccat cgggccggag    2040
tggaacggcg ccgggcccg ccgctggcgg cagtggaacg tcaagctggt cgggcacacc    2100
aacacggacg tgcaggcgca ggtgcccggg ttccgggtca cgcgcgacgt cgaggcgggg    2160
tgcacgacgg tggcgctcgg caacgtgcac cggtggcagc agccgcacca gcgggacggc    2220
ggcgggttcg agatctcgct ggggcgcgac ctgcagctgg acgtggtgga cgtgcgcgcg    2280
cgcgccttcg aggtcctgca ccgggccgag atggggtacg aggccaagga ccccgtctgg    2340
gacgtcttca cgtccggcga cgcggtgcag acgcgggtgc agcggctggc ggcgctcgac    2400
gtcgacgccg cgctcaagaa cgccctcatg gaggtctggg cggccgacgg gcgggccgag    2460
ggcagcgcgg cgggctacga gacctgggtg gacgtgaagg cgtgcgcggg agacgcggtc    2520
gaggaggcgc tcaaggagta cgttatcgtg tga                                 2553
```

<210> SEQ ID NO 61
<211> LENGTH: 850
<212> TYPE: PRT
<213> ORGANISM: Artificial sequence
<220> FEATURE:
<223> OTHER INFORMATION: Synthetic polypeptide

<400> SEQUENCE: 61

```
Met Ala Ser Ser Arg Tyr Arg Tyr Thr Phe Pro Arg Asn Pro Lys Ala
1               5                   10                  15

Asn Pro Lys Ala Val Val Thr Gly Gly Lys Gly Ser Ser Tyr Tyr Arg
            20                  25                  30

Phe Thr Leu Leu Thr Glu Arg Leu Ile Arg Tyr Glu Trp Ser Glu Asp
        35                  40                  45

Gly Gly Phe Glu Asp Arg Ala Ser Thr Phe Ala Val Phe Arg Tyr Phe
    50                  55                  60

Asp Ala Pro Gln Tyr Arg Val Val Glu Thr Asn Asp Ser Leu Glu Ile
65                  70                  75                  80
```

-continued

```
Ile Thr Asp Tyr Phe His Leu Thr Tyr Asp Lys Lys Phe Ser Ser
             85                  90                  95

Glu Gly Leu Ser Val Arg Val Gly Ser Asp Leu Trp Asn Tyr Asp Gly
            100                 105                 110

Lys Ser Tyr Gly Asp Leu Gly Gly Thr Ala Arg Thr Leu Asp Gly Ala
            115                 120                 125

Tyr Gly Arg Val Asp Leu Glu Pro Gly Val Leu Ser Arg Lys Ala Tyr
            130                 135                 140

Ala Val Leu Asp Asp Ser Lys Ser Met Leu Phe Asp Asp Asp Gly Trp
145                 150                 155                 160

Ile Ala Ile Arg Glu Pro Gly Arg Ile Asp Gly Tyr Val Phe Ala Tyr
                165                 170                 175

Ser Gly Glu His Lys Ala Ala Ile Arg Asp Phe Tyr Arg Leu Ser Gly
            180                 185                 190

Arg Gln Pro Val Leu Pro Arg Trp Leu Gly Asn Trp Trp Ser Arg
            195                 200                 205

Tyr His Ala Tyr Ser Ala Asp Glu Tyr Ile Glu Leu Met Asp His Phe
            210                 215                 220

Lys Arg Glu Gly Ile Pro Leu Thr Thr Ser Ile Val Asp Met Asp Trp
225                 230                 235                 240

His Arg Val Asp Asp Val Pro Pro Lys Tyr Gly Ser Gly Trp Thr Gly
                245                 250                 255

Tyr Ser Trp Asn Arg Lys Leu Phe Pro Asp Pro Glu Gly Phe Leu Gln
            260                 265                 270

Glu Leu Arg Asn Arg Asn Leu Lys Val Ala Leu Asn Asp His Pro Ala
            275                 280                 285

Asp Gly Ile Arg Ala Tyr Glu Asp Leu Tyr Pro Ala Val Ala Lys Ala
290                 295                 300

Leu Asn His Asp Thr Ser Arg Glu Glu Pro Ile Lys Phe Asp Cys Thr
305                 310                 315                 320

Asp Arg Lys Phe Met Asp Ala Tyr Phe Asp Val Leu Lys Leu Ser Leu
                325                 330                 335

Glu Lys Gln Gly Val Met Phe Trp Trp Ile Asp Trp Gln Gln Gly Thr
            340                 345                 350

Gly Ser Lys Leu Pro Ser Val Asp Pro Leu Trp Val Leu Asn His Tyr
            355                 360                 365

His Tyr Leu Thr Ser Lys Arg Asn Ala Lys Asp Ile Gln Arg Pro Ile
            370                 375                 380

Thr Phe Ser Arg Tyr Ala Gly Ala Gly Ala His Arg Tyr Pro Ile Gly
385                 390                 395                 400

Phe Ser Gly Asp Thr Gln Thr Thr Trp Glu Gly Leu Glu Phe Gln Pro
                405                 410                 415

Glu Phe Thr Ala Thr Ala Ser Asn Ile Gly Tyr Gly Trp Trp Ser His
            420                 425                 430

Asp Ile Gly Gly His Trp Gly Val Arg Ser Asn Gln Leu Thr Val
            435                 440                 445

Arg Trp Val Gln Leu Gly Cys Phe Ser Pro Ile Leu Arg Leu His Ser
450                 455                 460

Asn Lys Ser Pro Trp Asn Ser Arg Glu Pro Trp Asn Tyr Glu Asp Glu
465                 470                 475                 480

Ala His Arg Ile Met Lys Asp Phe Leu Ile Leu Arg His Arg Leu Ile
                485                 490                 495

Pro Phe Leu Tyr Thr Met Asn Ile Arg Ala Ser Tyr Glu Ser Glu Pro
```

```
                 500                 505                 510
Leu Ile Gln Pro Met Tyr Trp Asn His Pro Lys Asp Glu Glu Ala Tyr
            515                 520                 525

Thr Val Pro Thr Gln Tyr Tyr Phe Gly Pro Asp Leu Leu Val Ala Pro
            530                 535                 540

Ile Thr Ser Pro Asn Ser Thr Val Thr Leu Met Gly Arg Val Arg Ala
545                 550                 555                 560

Trp Leu Pro Pro Gly Arg Tyr Val Asp Leu Phe Tyr Pro His Leu Val
                565                 570                 575

Tyr Asp Gly Gly Arg Tyr Met His Leu His Arg Asp Leu Ser Gln Ile
            580                 585                 590

Pro Val Leu Ala Arg Glu Gly Thr Ile Val Pro Leu Asp Thr Thr Pro
            595                 600                 605

Arg Thr Gly His Gly Ala Ala Arg Pro Thr Glu Ile Thr Leu Leu Leu
            610                 615                 620

Val Val Gly Arg Asp Ala His Phe Glu Leu Val Glu Glu Pro Glu Gln
625                 630                 635                 640

Gln Asp His His Arg His Gly Gly Asp Gly Asp Asp Gln Pro
                645                 650                 655

Pro Leu Ser Ala Phe Ala Arg Thr Pro Ile Ser Trp Ser Gln Ala Asp
                660                 665                 670

Gly Val Leu Thr Ile Gly Pro Glu Trp Asn Gly Ala Gly Ala Arg Arg
                675                 680                 685

Trp Arg Gln Trp Asn Val Lys Leu Val Gly His Thr Asn Thr Asp Val
    690                 695                 700

Gln Ala Gln Val Pro Gly Phe Arg Val Thr Arg Asp Val Glu Gly Gly
705                 710                 715                 720

Cys Thr Thr Val Ala Leu Gly Asn Val His Arg Trp Gln Gln Pro His
                725                 730                 735

Gln Arg Asp Gly Gly Gly Phe Glu Ile Ser Leu Gly Arg Asp Leu Gln
            740                 745                 750

Leu Asp Val Val Asp Val Arg Ala Arg Ala Phe Glu Val Leu His Arg
            755                 760                 765

Ala Glu Met Gly Tyr Glu Ala Lys Asp Pro Val Trp Asp Val Phe Thr
            770                 775                 780

Ser Gly Asp Ala Val Gln Thr Arg Val Gln Arg Leu Ala Ala Leu Asp
785                 790                 795                 800

Val Asp Ala Ala Leu Lys Asn Ala Leu Met Glu Val Trp Ala Ala Asp
                805                 810                 815

Gly Arg Ala Glu Gly Ser Ala Ala Gly Tyr Glu Thr Trp Val Asp Val
            820                 825                 830

Lys Ala Cys Ala Gly Asp Ala Val Glu Glu Ala Leu Lys Glu Tyr Val
            835                 840                 845

Ile Val
    850

<210> SEQ ID NO 62
<211> LENGTH: 1614
<212> TYPE: DNA
<213> ORGANISM: Myceliophthora thermophila

<400> SEQUENCE: 62
atgccgcagg ttcgaaaccc catcctcccc ggcttcaacc ccgacccttc catcctccgg      60
gttggggatg actactacat cgccacttca acctttgagt ggtacccggg tgttcagatc     120
```

```
caccactcca tggacctcgc aaactgggaa cttgtcaccc gtcccctaaa ccgcaagagc    180
caactggata tgcgaggaga tccggacagc tgcggcatct gggctccctg cctgacgcat    240
gacggcgaca ggttctggct ggtatacacg gacgtcaaac gcaaggacgg ctcgttcaag    300
gacgcacaca actacatcgt cagtgcgccc gccatcgagg tccctggtc ggaccccttc     360
tatgtcaact cgtccgggtt cgaccccctcg ctcttccatg acgacgacgg ccggaagtgg   420
ttcgtcaaca tgatgtggga ccaccgcagc cgcccgcgaa cctttgccgg catcgcgctg    480
caagagttcg accccaaggc cgggaagctg gttgggccgc gcaagaacat ttaccaaggc    540
accgacctgg gcctcgtcga gggcccgcac ttgtacaagc gcaacgggtg gtactatctc    600
ctgacagcag agggcgggac tggctatgag catgcctgca ccctcgcccg gtctcggaac    660
atctggggcc cgtacgaaga tcacccgcag aagtacatct tgacgtctaa ggaccacccg    720
cacgcagccc tgcagcgagc cggccacggc gacatcgtcg acaccccccga cgggcgtacc   780
tacgtcgttc acctgaccgg ccggcccatc acgcagttcc gccgctgtgt cttggggcgc    840
gagacggcca tccaggaggc ctactggggc gacgacgact ggctctacgt caagaacggc    900
cctgtgccca gcctgttcgt ggacctcccg gccgcccgca acgacgacga ctactgggcc    960
gagaagaggt acacgttcga ggcgggcctg cacaaggact ccagtggct gcgcacgccc    1020
gagacggacc gcatcttcag gacggacaac gggaagttga cgctcatcgg ccgcgagtcc   1080
atcggctcct ggttcgagca ggccctggtc gcccggcgcc agacgcactt ctcgtacgac    1140
gccgagaccg tcatcgactt caagcctgcc gacgagcgcc agttcgccgg cctgacggcc    1200
tattactgcc gctacaactt cttctacctg accgtcacgg cccactcgga cggccggcgg    1260
gagctgctca tcatggcctc cgaggcctcc tggcccctcg cgccctccg gtccccttat     1320
ccgggacccg tccagatccc caacgagggc aaggtccggc tcgcgctcaa gatcagggc    1380
aaggagctgc agttctacta cgctctcgag ggcgaagagc taaaacagat tgggcccgta    1440
ttcgacgcta gcatcgtttc tgacgagtgc ggcggccacc agaagcacgg cagcttcacg    1500
ggcgcccttcg tcggcgtggc tgcttccgac atcaacggta ctgctgccga ggcgaccttt    1560
gactactttg tgtacaagcc cgtgcaccat gagagtgacc ggtacgagat ttaa          1614

<210> SEQ ID NO 63
<211> LENGTH: 537
<212> TYPE: PRT
<213> ORGANISM: Myceliophthora thermophila

<400> SEQUENCE: 63

Met Pro Gln Val Arg Asn Pro Ile Leu Pro Gly Phe Asn Pro Asp Pro
1               5                   10                  15

Ser Ile Leu Arg Val Gly Asp Asp Tyr Tyr Ile Ala Thr Ser Thr Phe
                20                  25                  30

Glu Trp Tyr Pro Gly Val Gln Ile His His Ser Met Asp Leu Ala Asn
            35                  40                  45

Trp Glu Leu Val Thr Arg Pro Leu Asn Arg Lys Ser Gln Leu Asp Met
        50                  55                  60

Arg Gly Asp Pro Asp Ser Cys Gly Ile Trp Ala Pro Cys Leu Thr His
65                  70                  75                  80

Asp Gly Asp Arg Phe Trp Leu Val Tyr Thr Asp Val Lys Arg Lys Asp
                85                  90                  95

Gly Ser Phe Lys Asp Ala His Asn Tyr Ile Val Ser Ala Pro Ala Ile
                100                 105                 110
```

Glu Gly Pro Trp Ser Asp Pro Phe Tyr Val Asn Ser Ser Gly Phe Asp
            115                 120                 125

Pro Ser Leu Phe His Asp Asp Gly Arg Lys Trp Phe Val Asn Met
130                 135                 140

Met Trp Asp His Arg Ser Arg Pro Arg Thr Phe Ala Gly Ile Ala Leu
145                 150                 155                 160

Gln Glu Phe Asp Pro Lys Ala Gly Lys Leu Val Gly Pro Arg Lys Asn
                165                 170                 175

Ile Tyr Gln Gly Thr Asp Leu Gly Leu Val Glu Gly Pro His Leu Tyr
            180                 185                 190

Lys Arg Asn Gly Trp Tyr Tyr Leu Leu Thr Ala Glu Gly Gly Thr Gly
        195                 200                 205

Tyr Glu His Ala Cys Thr Leu Ala Arg Ser Arg Asn Ile Trp Gly Pro
    210                 215                 220

Tyr Glu Asp His Pro Gln Lys Tyr Ile Leu Thr Ser Lys Asp His Pro
225                 230                 235                 240

His Ala Ala Leu Gln Arg Ala Gly His Gly Asp Ile Val Asp Thr Pro
                245                 250                 255

Asp Gly Arg Thr Tyr Val Val His Leu Thr Gly Arg Pro Ile Thr Gln
            260                 265                 270

Phe Arg Arg Cys Val Leu Gly Arg Glu Thr Ala Ile Gln Glu Ala Tyr
        275                 280                 285

Trp Gly Asp Asp Asp Trp Leu Tyr Val Lys Asn Gly Pro Val Pro Ser
    290                 295                 300

Leu Phe Val Asp Leu Pro Ala Ala Arg Asn Asp Asp Tyr Trp Ala
305                 310                 315                 320

Glu Lys Arg Tyr Thr Phe Glu Ala Gly Leu His Lys Asp Phe Gln Trp
                325                 330                 335

Leu Arg Thr Pro Glu Thr Asp Arg Ile Phe Arg Thr Asp Asn Gly Lys
            340                 345                 350

Leu Thr Leu Ile Gly Arg Glu Ser Ile Gly Ser Trp Phe Glu Gln Ala
        355                 360                 365

Leu Val Ala Arg Arg Gln Thr His Phe Ser Tyr Asp Ala Glu Thr Val
    370                 375                 380

Ile Asp Phe Lys Pro Ala Asp Glu Arg Gln Phe Ala Gly Leu Thr Ala
385                 390                 395                 400

Tyr Tyr Cys Arg Tyr Asn Phe Phe Tyr Leu Thr Val Thr Ala His Ser
                405                 410                 415

Asp Gly Arg Arg Glu Leu Leu Ile Met Ala Ser Glu Ala Ser Trp Pro
            420                 425                 430

Leu Gly Ala Leu Arg Ser Pro Tyr Pro Gly Pro Val Gln Ile Pro Asn
        435                 440                 445

Glu Gly Lys Val Arg Leu Ala Leu Lys Ile Arg Gly Lys Glu Leu Gln
    450                 455                 460

Phe Tyr Tyr Ala Leu Glu Gly Glu Leu Lys Gln Ile Gly Pro Val
465                 470                 475                 480

Phe Asp Ala Ser Ile Val Ser Asp Glu Cys Gly Gly His Gln Lys His
                485                 490                 495

Gly Ser Phe Thr Gly Ala Phe Val Gly Val Ala Ala Ser Asp Ile Asn
            500                 505                 510

Gly Thr Ala Ala Glu Ala Thr Phe Asp Tyr Phe Val Tyr Lys Pro Val
        515                 520                 525

His His Glu Ser Asp Arg Tyr Glu Ile
    530                 535

<210> SEQ ID NO 64
<211> LENGTH: 984
<212> TYPE: DNA
<213> ORGANISM: Myceliophthora thermophila

<400> SEQUENCE: 64

```
atggcgcccc tcatcaccaa catcttcacg gccgacccgt cggcccacgt cttcgagggc      60
aagctcttca tacccgtc gcacgatcgc gagacggaca tcaagttcaa cgacgacggc     120
gaccagtacg acatggtcga ctaccacgta ttcagcaccg agtcgctgga cccggccgcc     180
cccgtgaccg accacggcgt cgtgctccgg gccgaagacg tcccctgggt gtccaagcag     240
ctctgggccc ccgacgccgc ctacaaggac ggcaggtact acctctactt ccccgcccgc     300
gacaagcagg gcgtcttccg catcggcgtc gccgtcggcg accgccccga gggccccttc     360
accccccgacc cggagcccat ccgggacagc tacagcatcg acccggccgt cttcgtcgac     420
gacgacggcc gggcctacat gtactttggc gggctctggg cggccagct gcagtgctac     480
cagaagggca acggcatctt cgaccccgag tggctgggc ccaggagcc ctcgggcgag     540
ggcgtccggg cgctggggcc gcgcgtcgcc cggctggcgg acgacatgcg ccagttcgcc     600
agcgaggtga aggagatttc gatcctggcg cccgagacgg cgagccgat cgcggccgac     660
gaccacgacc gccgcttctt cgaggccgcc tggatgcaca gtacgacgg caagtactac     720
ttcagctact ccaccggcga cacccactac ctcgtctacg ccgtcggcga cagcccctac     780
gggcccttca cctacgccgg ccgcatcctc gagcccgtcc tcggctggac cacgcaccac     840
tccatcgtcg agttccacgg ccgctggtgg ctcttccacc acgactgcga gctcagcggc     900
ggagtcgacc acctgcgctc cgtcaaggtc aaggagatct tctacgacaa ggacggcaag     960
attgtcactg aaaagcccga atag                                           984
```

<210> SEQ ID NO 65
<211> LENGTH: 327
<212> TYPE: PRT
<213> ORGANISM: Myceliophthora thermophila

<400> SEQUENCE: 65

Met Ala Pro Leu Ile Thr Asn Ile Phe Thr Ala Asp Pro Ser Ala His
1               5                   10                  15

Val Phe Glu Gly Lys Leu Phe Ile Tyr Pro Ser His Asp Arg Glu Thr
            20                  25                  30

Asp Ile Lys Phe Asn Asp Asp Gly Asp Gln Tyr Asp Met Val Asp Tyr
        35                  40                  45

His Val Phe Ser Thr Glu Ser Leu Asp Pro Ala Ala Pro Val Thr Asp
    50                  55                  60

His Gly Val Val Leu Arg Ala Glu Asp Val Pro Trp Val Ser Lys Gln
65                  70                  75                  80

Leu Trp Ala Pro Asp Ala Ala Tyr Lys Asp Gly Arg Tyr Tyr Leu Tyr
                85                  90                  95

Phe Pro Ala Arg Asp Lys Gln Gly Val Phe Arg Ile Gly Val Ala Val
            100                 105                 110

Gly Asp Arg Pro Glu Gly Pro Phe Thr Pro Asp Pro Glu Pro Ile Arg
        115                 120                 125

Asp Ser Tyr Ser Ile Asp Pro Ala Val Phe Val Asp Asp Gly Arg
    130                 135                 140

Ala Tyr Met Tyr Phe Gly Gly Leu Trp Gly Gly Gln Leu Gln Cys Tyr
145                 150                 155                 160

Gln Lys Gly Asn Gly Ile Phe Asp Pro Glu Trp Leu Gly Pro Arg Glu
            165                 170                 175

Pro Ser Gly Glu Gly Val Arg Ala Leu Gly Pro Arg Val Ala Arg Leu
        180                 185                 190

Ala Asp Asp Met Arg Gln Phe Ala Ser Glu Val Lys Glu Ile Ser Ile
            195                 200                 205

Leu Ala Pro Glu Thr Gly Glu Pro Ile Ala Ala Asp Asp His Asp Arg
210                 215                 220

Arg Phe Phe Glu Ala Ala Trp Met His Lys Tyr Asp Gly Lys Tyr Tyr
225                 230                 235                 240

Phe Ser Tyr Ser Thr Gly Asp Thr His Tyr Leu Val Tyr Ala Val Gly
            245                 250                 255

Asp Ser Pro Tyr Gly Pro Phe Thr Tyr Ala Gly Arg Ile Leu Glu Pro
            260                 265                 270

Val Leu Gly Trp Thr Thr His His Ser Ile Val Glu Phe His Gly Arg
        275                 280                 285

Trp Trp Leu Phe His His Asp Cys Glu Leu Ser Gly Val Asp His
        290                 295                 300

Leu Arg Ser Val Lys Val Lys Glu Ile Phe Tyr Asp Lys Asp Gly Lys
305                 310                 315                 320

Ile Val Thr Glu Lys Pro Glu
            325

<210> SEQ ID NO 66
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 66
tgatcctctt ccgtcatggt taccctcact cgcctggcg                              39

<210> SEQ ID NO 67
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 67
tcgtttactt acttatcagc cgctgacggt gtactggga                              39

<210> SEQ ID NO 68
<211> LENGTH: 37
<212> TYPE: DNA
<213> ORGANISM: Artificial sequence
<220> FEATURE:
<223> OTHER INFORMATION: Synthetic polynucleotide

<400> SEQUENCE: 68
tgatcctctt ccgtcatgtt cttcgcttct ctgctgc                                37

<210> SEQ ID NO 69
<211> LENGTH: 39
<212> TYPE: DNA
<213> ORGANISM: Artificial sequence
<220> FEATURE:

<223> OTHER INFORMATION: Synthetic polynucleotide

<400> SEQUENCE: 69
tcgtttactt acttatcaat ccctaaactg ctccaatgg                          39

<210> SEQ ID NO 70
<211> LENGTH: 43
<212> TYPE: DNA
<213> ORGANISM: Artificial sequence
<220> FEATURE:
<223> OTHER INFORMATION: Synthetic polynucleotide

<400> SEQUENCE: 70
tgtgctgatc ctcttccgtc atgaaggcct ctgtatcatg cct                     43

<210> SEQ ID NO 71
<211> LENGTH: 41
<212> TYPE: DNA
<213> ORGANISM: Artificial sequence
<220> FEATURE:
<223> OTHER INFORMATION: Synthetic polynucleotide

<400> SEQUENCE: 71
gaggttcgtt tacttactta ttacctgtgc ctcccctgg c                       41

<210> SEQ ID NO 72
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 72
tacaatcaac tatcaactat taactatatc gtaatacaca atgaaggcct ctgtatcatg   60

<210> SEQ ID NO 73
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 73
gcggcgcccc cggcgccttg ctgaccaggt tttgcagctt                         40

<210> SEQ ID NO 74
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 74
aagctgcaaa acctggtcag caaggcgccg ggggcgccgc                         40

<210> SEQ ID NO 75
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 75
tcagaacctc cttcagagag gttcgtttac ttacttatta cctgtgcctc ccctggcgg    60